(12) United States Patent
Fujita et al.

(10) Patent No.: US 11,065,306 B2
(45) Date of Patent: Jul. 20, 2021

(54) METHODS FOR TREATING HYPOPHOSPHATASIA IN CHILDREN

(71) Applicant: Alexion Pharmaceuticals, Inc., Boston, MA (US)

(72) Inventors: Kenji Fujita, Millburn, NJ (US); Dawn Phillips, Chapel Hill, NC (US)

(73) Assignee: Alexion Pharmaceuticals, Inc., Boston, MA (US)

(*) Notice: Subject to any disclaimer, the term of this patent is extended or adjusted under 35 U.S.C. 154(b) by 5 days.

(21) Appl. No.: 16/083,186

(22) PCT Filed: Sep. 1, 2016

(86) PCT No.: PCT/US2016/049983
§ 371 (c)(1),
(2) Date: Sep. 7, 2018

(87) PCT Pub. No.: WO2017/155569
PCT Pub. Date: Sep. 14, 2017

(65) Prior Publication Data
US 2019/0099473 A1  Apr. 4, 2019

Related U.S. Application Data

(60) Provisional application No. 62/305,450, filed on Mar. 8, 2016.

(51) Int. Cl.
*A61K 38/46* (2006.01)
*A61P 19/08* (2006.01)
*C12N 9/16* (2006.01)

(52) U.S. Cl.
CPC ............ *A61K 38/465* (2013.01); *A61P 19/08* (2018.01); *C12N 9/16* (2013.01); *C12Y 301/03001* (2013.01)

(58) Field of Classification Search
CPC .................................................. A61K 38/465
See application file for complete search history.

(56) References Cited

U.S. PATENT DOCUMENTS

| | | |
|---|---|---|
| 5,336,759 A | 8/1994 | Matsuo et al. |
| 5,338,830 A | 8/1994 | Matsuo et al. |
| 5,340,920 A | 8/1994 | Matsuo et al. |
| 5,352,770 A | 10/1994 | Matsuo |
| 5,428,130 A | 6/1995 | Capon et al. |
| 5,434,133 A | 7/1995 | Tanaka et al. |

(Continued)

FOREIGN PATENT DOCUMENTS

| | | |
|---|---|---|
| EP | 0478797 B1 | 4/1995 |
| EP | 0769554 A2 | 4/1997 |

(Continued)

OTHER PUBLICATIONS

Kishnani et al., Endocrine Abstracts 29: OC8.1 (2012).*

(Continued)

*Primary Examiner* — Erin M. Bowers
(74) *Attorney, Agent, or Firm* — Clark & Elbing LLP

(57) ABSTRACT

The disclosure features methods for treating hypophosphatasia (HPP) in a patient (e.g., a child having HPP) exhibiting physical impairments, disability in activities of daily living (ADL), pain, and/or delayed motor development by administering a soluble alkaline phosphatase (sALP) to the patient.

27 Claims, 34 Drawing Sheets

Specification includes a Sequence Listing.

(56) References Cited

U.S. PATENT DOCUMENTS

| | | |
|---|---|---|
| 5,583,108 A | 12/1996 | Wei et al. |
| 5,665,704 A | 9/1997 | Lowe et al. |
| 5,714,147 A | 2/1998 | Capon et al. |
| 5,767,239 A | 6/1998 | Immer et al. |
| 5,846,932 A | 12/1998 | Lowe et al. |
| 5,948,761 A | 9/1999 | Seilhamer et al. |
| 5,973,134 A | 10/1999 | Matsuo et al. |
| 6,020,168 A | 2/2000 | Matsuo et al. |
| 6,028,055 A | 2/2000 | Lowe et al. |
| 6,034,231 A | 3/2000 | Tanaka et al. |
| 6,290,952 B1 | 9/2001 | Poelstra et al. |
| 6,406,697 B1 | 6/2002 | Capon et al. |
| 6,407,211 B1 | 6/2002 | Burnett, Jr. et al. |
| 6,420,384 B2 | 7/2002 | Weigele et al. |
| 6,436,386 B1 | 8/2002 | Roberts et al. |
| 6,455,495 B1 | 9/2002 | Orgel et al. |
| 6,458,579 B2 | 10/2002 | Hopwood et al. |
| 6,525,022 B1 | 2/2003 | Lowe et al. |
| 6,541,610 B1 | 4/2003 | Smith |
| 6,743,425 B2 | 6/2004 | Nakao |
| 6,790,649 B1 | 9/2004 | Crine et al. |
| 6,818,619 B2 | 11/2004 | Burnett, Jr. et al. |
| 6,830,885 B1 | 12/2004 | Lanctot et al. |
| 6,849,714 B1 | 2/2005 | Bridon et al. |
| 6,887,470 B1 | 5/2005 | Bridon et al. |
| 6,905,689 B2 | 6/2005 | Schneidinger et al. |
| 6,946,484 B2 | 9/2005 | Adams et al. |
| 7,026,293 B2 | 4/2006 | Kitakaze |
| 7,033,997 B2 | 4/2006 | Forssmann et al. |
| 7,070,974 B1 | 7/2006 | Desgroseillers et al. |
| 7,105,539 B2 | 9/2006 | Gravel et al. |
| 7,179,903 B2 | 2/2007 | McArthur et al. |
| 7,256,253 B2 | 8/2007 | Bridon et al. |
| 7,271,149 B2 | 9/2007 | Glaesner et al. |
| 7,276,481 B2 | 10/2007 | Golembo et al. |
| 7,341,838 B2 | 3/2008 | Buechler et al. |
| 7,365,091 B2 | 4/2008 | Gravel et al. |
| 7,384,917 B2 | 6/2008 | Burnett, Jr. et al. |
| 7,399,466 B2 | 7/2008 | Boileau |
| 7,414,107 B2 | 8/2008 | Larsen |
| 7,425,531 B2 | 9/2008 | Lanctot et al. |
| 7,427,498 B2 | 9/2008 | Crine et al. |
| 7,470,668 B2 | 12/2008 | Lanctot et al. |
| 7,488,713 B2 | 2/2009 | Vesely |
| 7,527,939 B2 | 5/2009 | Davey et al. |
| 7,563,769 B2 | 7/2009 | Bogin et al. |
| 7,625,564 B2 | 12/2009 | Wang et al. |
| 7,642,243 B2 | 1/2010 | Nakao et al. |
| 7,648,962 B2 | 1/2010 | James et al. |
| 7,662,773 B2 | 2/2010 | James et al. |
| 7,678,391 B2 | 3/2010 | Graham et al. |
| 7,732,406 B2 | 6/2010 | Mitrovic et al. |
| 7,736,653 B2 | 6/2010 | Kim et al. |
| 7,754,852 B2 | 7/2010 | Burnett, Jr. et al. |
| 7,763,712 B2 | 7/2010 | Crine et al. |
| 7,803,769 B2 | 9/2010 | Sullivan et al. |
| 7,803,901 B2 | 9/2010 | Burnett, Jr. et al. |
| 7,825,092 B2 | 11/2010 | Vesely |
| 7,846,900 B2 | 12/2010 | Vesely |
| 7,858,560 B2 | 12/2010 | Koster et al. |
| 7,919,591 B2 | 4/2011 | Sheffer et al. |
| 7,943,126 B2 | 5/2011 | Tomatsu et al. |
| 7,960,529 B2 | 6/2011 | Crine et al. |
| 8,058,242 B2 | 11/2011 | Alewood et al. |
| 8,691,208 B2 | 4/2014 | Tomatsu et al. |
| 9,266,939 B2 | 2/2016 | Crine et al. |
| 9,908,932 B2 | 3/2018 | Malanson et al. |
| 9,988,620 B2 | 6/2018 | Crine et al. |
| 10,000,532 B2 | 6/2018 | Crine et al. |
| 10,052,366 B2 | 8/2018 | Crine et al. |
| 10,449,236 B2 | 10/2019 | Marozsan et al. |
| 2002/0183276 A1 | 12/2002 | Millan et al. |
| 2003/0158132 A1 | 8/2003 | Kovesdi |
| 2004/0023916 A1 | 2/2004 | Millan et al. |
| 2004/0077537 A1 | 4/2004 | Schreiner |
| 2004/0234518 A1 | 11/2004 | Crine et al. |
| 2005/0113286 A1 | 5/2005 | Schreiner et al. |
| 2005/0142217 A1 | 6/2005 | Adams et al. |
| 2005/0202442 A1 | 9/2005 | Morris et al. |
| 2005/0244904 A1 | 11/2005 | Ng |
| 2005/0276796 A1 | 12/2005 | Tomatsu et al. |
| 2006/0014687 A1 | 1/2006 | Crine et al. |
| 2006/0019890 A1 | 1/2006 | Kapoun et al. |
| 2006/0074009 A1 | 4/2006 | James et al. |
| 2006/0110359 A1 | 5/2006 | Sanchez-Ramos et al. |
| 2006/0172929 A1 | 8/2006 | Rappold-Hoerbrand et al. |
| 2006/0228710 A1 | 10/2006 | Morris et al. |
| 2007/0041972 A1 | 2/2007 | Rother et al. |
| 2007/0042957 A1 | 2/2007 | Burnett et al. |
| 2007/0081984 A1 | 4/2007 | Tomatsu et al. |
| 2007/0081986 A1 | 4/2007 | Tomatsu et al. |
| 2007/0197434 A1 | 8/2007 | Nakao et al. |
| 2007/0281887 A1 | 12/2007 | Pan |
| 2007/0292966 A1 | 12/2007 | Prickett et al. |
| 2007/0293418 A1 | 12/2007 | Larsen |
| 2008/0032933 A1 | 2/2008 | Burnett et al. |
| 2008/0081768 A1 | 4/2008 | Watt et al. |
| 2008/0085862 A1 | 4/2008 | Kim et al. |
| 2008/0113411 A1 | 5/2008 | Sheffer et al. |
| 2008/0113412 A1 | 5/2008 | Sheffer et al. |
| 2008/0125574 A1 | 5/2008 | Sheffer et al. |
| 2008/0153747 A1 | 6/2008 | Alewood et al. |
| 2008/0161243 A1 | 7/2008 | Rosen et al. |
| 2008/0181903 A1 | 7/2008 | Bhaskar et al. |
| 2008/0182299 A1 | 7/2008 | Colocaru et al. |
| 2008/0194481 A1 | 8/2008 | Rosen et al. |
| 2008/0194682 A1 | 8/2008 | Golembo et al. |
| 2008/0227713 A1 | 9/2008 | Protter |
| 2008/0293632 A1 | 11/2008 | Rappold-Hoerbrand et al. |
| 2008/0312142 A1 | 12/2008 | Nakao et al. |
| 2009/0011997 A1 | 1/2009 | Peri et al. |
| 2009/0023652 A1 | 1/2009 | Bell et al. |
| 2009/0053192 A1 | 2/2009 | Millan et al. |
| 2009/0069243 A1 | 3/2009 | Burnett, Jr. et al. |
| 2009/0092582 A1 | 4/2009 | Bogin et al. |
| 2009/0142347 A1 | 6/2009 | Millan |
| 2009/0170756 A1 | 7/2009 | Burnett, Jr. et al. |
| 2009/0221803 A1 | 9/2009 | Dall'Acqua et al. |
| 2009/0238814 A1 | 9/2009 | Tomatsu et al. |
| 2009/0240031 A1 | 9/2009 | Immer et al. |
| 2009/0247462 A1 | 10/2009 | Bogin et al. |
| 2009/0252729 A1 | 10/2009 | Farrington et al. |
| 2009/0258018 A1 | 10/2009 | Medich et al. |
| 2009/0275506 A1 | 11/2009 | Bakis et al. |
| 2009/0325195 A1 | 12/2009 | Davey et al. |
| 2010/0008979 A1 | 1/2010 | Tomatsu et al. |
| 2010/0055150 A1 | 3/2010 | Golembo et al. |
| 2010/0093678 A1 | 4/2010 | Della-Fera et al. |
| 2010/0160212 A1 | 6/2010 | Sheffer et al. |
| 2010/0168443 A1 | 7/2010 | Geysen |
| 2010/0184680 A1 | 7/2010 | Bevec |
| 2010/0197574 A1 | 8/2010 | Chen et al. |
| 2010/0204094 A1 | 8/2010 | Simari et al. |
| 2010/0204109 A1 | 8/2010 | Bevec |
| 2010/0204446 A1 | 8/2010 | Forssmann |
| 2010/0209958 A1 | 8/2010 | Nakao et al. |
| 2010/0216714 A1 | 8/2010 | James et al. |
| 2010/0221234 A1 | 9/2010 | Crine et al. |
| 2010/0240125 A1 | 9/2010 | Crine et al. |
| 2010/0249017 A1 | 9/2010 | Bevec et al. |
| 2010/0260706 A1 | 10/2010 | Bogin et al. |
| 2010/0261248 A1 | 10/2010 | Kim et al. |
| 2010/0297021 A1 | 11/2010 | Wendt et al. |
| 2010/0297119 A1* | 11/2010 | Crine .................. A61P 1/02 424/134.1 |
| 2010/0305031 A1 | 12/2010 | Wakabayashi et al. |
| 2010/0305051 A1 | 12/2010 | Burnett, Jr. et al. |
| 2010/0310561 A1 | 12/2010 | Canada et al. |
| 2010/0311660 A1 | 12/2010 | Simari et al. |
| 2010/0317600 A1 | 12/2010 | Immer et al. |
| 2010/0331256 A1 | 12/2010 | Wendt et al. |
| 2011/0152194 A1 | 6/2011 | Burnett, Jr. et al. |
| 2011/0250187 A1 | 10/2011 | Tomatsu et al. |
| 2011/0269684 A1 | 11/2011 | Burnett, Jr. et al. |

(56) References Cited

U.S. PATENT DOCUMENTS

| | | |
|---|---|---|
| 2011/0300143 A1 | 12/2011 | Sly et al. |
| 2012/0088771 A1 | 4/2012 | Millan |
| 2012/0164142 A1 | 6/2012 | Crine et al. |
| 2013/0108635 A1 | 5/2013 | Crine et al. |
| 2013/0323244 A1 | 12/2013 | Crine et al. |
| 2014/0193388 A1 | 7/2014 | Velders et al. |
| 2014/0194484 A1 | 7/2014 | Coats et al. |
| 2015/0353633 A1 | 12/2015 | Kakkis et al. |
| 2016/0052968 A1 | 2/2016 | Crine et al. |
| 2016/0097100 A1 | 4/2016 | Trent et al. |
| 2017/0175094 A1 | 6/2017 | Hatch |
| 2017/0360899 A1 | 12/2017 | Marozsan et al. |
| 2018/0230445 A1 | 8/2018 | Jaluria et al. |

FOREIGN PATENT DOCUMENTS

| | | |
|---|---|---|
| EP | 0771875 B1 | 5/1997 |
| EP | 0466174 B1 | 6/1997 |
| EP | 0475394 B1 | 6/1997 |
| EP | 0466175 B1 | 1/1998 |
| EP | 0477971 B1 | 1/1998 |
| EP | 0475290 B1 | 12/1998 |
| EP | 0475291 B1 | 12/1998 |
| EP | 0497368 B1 | 6/2002 |
| EP | 1492567 | 9/2003 |
| EP | 1502604 A1 | 2/2005 |
| EP | 1623994 A2 | 2/2006 |
| EP | 1759001 B1 | 3/2007 |
| EP | 1759710 A1 | 3/2007 |
| EP | 1985697 A1 | 10/2008 |
| EP | 2158319 | 3/2010 |
| EP | 2158319 B1 | 12/2011 |
| JP | H0870875 A | 3/1996 |
| JP | 2000-327583 A | 11/2000 |
| JP | 2002-541776 A | 12/2002 |
| JP | 2007-511209 A | 5/2007 |
| JP | 2010-501026 A | 1/2010 |
| JP | 2010-526543 A | 8/2010 |
| JP | 2010-530222 A | 9/2010 |
| JP | 2011-504506 A | 2/2011 |
| WO | WO-92/20371 A1 | 11/1992 |
| WO | WO-94/20534 A1 | 9/1994 |
| WO | WO-95/05456 A1 | 2/1995 |
| WO | WO-95/13296 A1 | 5/1995 |
| WO | WO-95/33769 A1 | 12/1995 |
| WO | WO-98/17690 A1 | 4/1998 |
| WO | WO-98/35703 A2 | 8/1998 |
| WO | WO-99/46283 A1 | 9/1999 |
| WO | WO-00/18954 A2 | 4/2000 |
| WO | WO-00/50580 A2 | 8/2000 |
| WO | WO-00/53755 A2 | 9/2000 |
| WO | WO-00/64486 A2 | 11/2000 |
| WO | WO-00/69900 A2 | 11/2000 |
| WO | WO-01/36620 A2 | 5/2001 |
| WO | WO-01/44284 A2 | 6/2001 |
| WO | WO-01/80890 A2 | 11/2001 |
| WO | WO-02/15918 A2 | 2/2002 |
| WO | WO-02/47871 A1 | 6/2002 |
| WO | WO-02/067639 A1 | 8/2002 |
| WO | WO-02/068579 A2 | 9/2002 |
| WO | WO-02/074234 A2 | 9/2002 |
| WO | WO-03/074082 A1 | 9/2003 |
| WO | WO-03/079979 A2 | 10/2003 |
| WO | WO-03/092581 A2 | 11/2003 |
| WO | WO-03/094835 A2 | 11/2003 |
| WO | WO-2004/011498 A2 | 2/2004 |
| WO | WO-2004/022579 A2 | 3/2004 |
| WO | WO-2004/046194 A2 | 6/2004 |
| WO | WO-2004/047871 A2 | 6/2004 |
| WO | WO-2004/062555 A2 | 7/2004 |
| WO | WO-2004/074320 A2 | 9/2004 |
| WO | WO-2004/094460 A2 | 11/2004 |
| WO | WO-2005/000095 A2 | 1/2005 |
| WO | WO-2005/007809 A2 | 1/2005 |
| WO | WO-2005/042034 A1 | 5/2005 |
| WO | WO-2005/047337 A2 | 5/2005 |
| WO | WO-2005/070446 A1 | 8/2005 |
| WO | WO-2005/072055 A2 | 8/2005 |
| WO | WO-2005/094890 A1 | 10/2005 |
| WO | WO-2005/098490 A1 | 10/2005 |
| WO | WO-2005/103263 A1 | 11/2005 |
| WO | WO-2005/110435 A1 | 11/2005 |
| WO | WO-2006/005140 A2 | 1/2006 |
| WO | WO-2006/026663 A1 | 3/2006 |
| WO | WO-2006/039480 A2 | 4/2006 |
| WO | WO-2006/060641 A2 | 6/2006 |
| WO | WO-2006/110743 A1 | 10/2006 |
| WO | WO-2006/116260 A2 | 11/2006 |
| WO | WO-2007/041645 A2 | 4/2007 |
| WO | WO-2007/071295 A1 | 6/2007 |
| WO | WO-2007/097923 A2 | 8/2007 |
| WO | WO-2007/130113 A2 | 11/2007 |
| WO | WO-2008/021872 A1 | 2/2008 |
| WO | WO-2008/030558 A2 | 3/2008 |
| WO | WO-2008/031045 A2 | 3/2008 |
| WO | WO-2008/053362 A2 | 5/2008 |
| WO | WO-2008/058016 A2 | 5/2008 |
| WO | WO-2008/079995 A2 | 7/2008 |
| WO | WO-2008/088422 A2 | 7/2008 |
| WO | WO-2008/109903 A1 | 9/2008 |
| WO | WO-2008/136611 A1 | 11/2008 |
| WO | WO-2008/138131 A1 | 11/2008 |
| WO | WO-2008/154226 A1 | 12/2008 |
| WO | WO-2009/006520 A1 | 1/2009 |
| WO | WO-2009/006732 A9 | 1/2009 |
| WO | WO-2009/015011 A1 | 1/2009 |
| WO | WO-2009/023270 A2 | 2/2009 |
| WO | WO-2009/033680 A2 | 3/2009 |
| WO | WO-2009/033724 A1 | 3/2009 |
| WO | WO-2009/033796 A1 | 3/2009 |
| WO | WO-2009/033807 A2 | 3/2009 |
| WO | WO-2009/034134 A2 | 3/2009 |
| WO | WO-2009/036448 A2 | 3/2009 |
| WO | WO-2009/040030 A1 | 4/2009 |
| WO | WO-2009/040031 A2 | 4/2009 |
| WO | WO-2009/040083 A2 | 4/2009 |
| WO | WO-2009/046861 A1 | 4/2009 |
| WO | WO-2009/058322 A1 | 5/2009 |
| WO | WO-2009/067639 A2 | 5/2009 |
| WO | WO-2009/086126 A2 | 7/2009 |
| WO | WO-2009/090553 A2 | 7/2009 |
| WO | WO-2009/142307 A1 | 11/2009 |
| WO | WO-2009/149161 A9 | 12/2009 |
| WO | WO-2009/156481 A1 | 12/2009 |
| WO | WO-2009/158035 A2 | 12/2009 |
| WO | WO-2010/002583 A2 | 1/2010 |
| WO | WO-2010/011096 A2 | 1/2010 |
| WO | WO-2010/048308 A2 | 4/2010 |
| WO | WO-2010/078325 A2 | 7/2010 |
| WO | WO-2010/082804 A2 | 7/2010 |
| WO | WO-2010/117760 A2 | 10/2010 |
| WO | WO-2010/129655 A2 | 11/2010 |
| WO | WO-2010/135541 A2 | 11/2010 |
| WO | WO-2011/130229 A1 | 10/2011 |
| WO | WO-2011/134084 A1 | 11/2011 |
| WO | WO-2012/088608 A1 | 7/2012 |
| WO | WO-2012/099851 A2 | 7/2012 |
| WO | WO-2013/058833 A1 | 4/2013 |
| WO | WO-2013/059491 A1 | 4/2013 |
| WO | WO-2013/071262 A1 | 5/2013 |
| WO | WO-2015/112015 A1 | 7/2015 |
| WO | WO-2015/112017 A1 | 7/2015 |
| WO | WO-2016/007873 A1 | 1/2016 |
| WO | WO-2016/090251 A1 | 6/2016 |
| WO | WO-2016/123342 A2 | 8/2016 |
| WO | WO-2017/031114 A1 | 2/2017 |
| WO | WO-2017/058822 A1 | 4/2017 |
| WO | WO-2017/074466 A1 | 5/2017 |
| WO | WO-2017/155569 A1 | 9/2017 |
| WO | WO-2017/171871 A1 | 10/2017 |
| WO | WO-2017/173395 A1 | 10/2017 |
| WO | WO-2017/173413 A1 | 10/2017 |

(56) References Cited

FOREIGN PATENT DOCUMENTS

| WO | WO-2017/214130 A1 | 12/2017 |
|---|---|---|
| WO | WO-2018/004517 A1 | 1/2018 |
| WO | WO-2018/035420 A1 | 2/2018 |

OTHER PUBLICATIONS

Ali et al., "Isolation and characterization of calcifying matrix vesicles from epiphyseal cartilage," Proc Natl Acad Sci USA. 67(3):1513-1520 (1970).
Anderson et al., "Pyrophosphate stimulation of calcium uptake into cultured embryonic bones. Fine structure of matrix vesicles and their role in calcification," Dev Biol. 34:211-227 (1973).
Anderson et al., "Sustained osteomalacia of long bones despite major improvement in other hypophosphatasia-related mineral deficits in tissue nonspecific alkaline phosphatase/nucleotide pyrophosphatase phosphodiesterase 1 double-deficient mice," Am J Pathol. 166(6):1711-1720 (2005).
Anderson et al., "The role of matrix vesicles in growth plate development and biomineralization," Front Biosci. 10:822-837 (2005).
Beertsen et al., "Root development in mice lacking functional tissue non-specific alkaline phosphatase gene: Inhibition of acellular cementum formation," J Dent Res. 78(6):1221-1229 (1999) (10 pages).
Bennett et al., "Extracellular domain-IgG fusion proteins for three human natriuretic peptide receptors," J Biol Chem. 266(34):23060-23067 (1991).
Bernard, "Ultrastructural localization of alkaline phosphatase in initial intramembranous osteogenesis," Clin Orthop Relat Res. 135:218-225 (1978).
Bonilla, "Pharmacokinetics of immunoglobulin administered via intravenous or subcutaneous routes," Immunol Allergy Clin N Am. 28:803-819 (2008).
Byers et al., "Effect of enzyme replacement therapy on bone formation in a feline model of mucopolysaccharidosis type VI," Bone. 21(5):425-431 (1997).
Cameron et al., "Minireview: Natriuretic peptides during development of the fetal heart and circulation," Endocrinology. 144(6):2191-2194 (2003).
Clemens et al., "Pharmacokinetics and biological actions of subcutaneously administered human brain natriuretic peptide," J Pharmacol Exp Ther. 287(1):67-71 (1998).
Declaration of Dr. Philippe Crine for EP 08757088.3, executed Jan. 14, 2011 (6 pages).
Engel et al., "Characterization of the hormone binding site of natriuretic peptide receptor-C," FEBS Lett. 360:169-172 (1995).
Extended European Search Report for European Application No. 08757088.3, dated Jun. 21, 2010 (6 pages).
Farley et al., "Effects of tunicamycin, mannosamine, and other inhibitors of glycoprotein processing on skeletal alkaline phosphatase in human osteoblast-like cells," Calcif Tissue Int. 76:63-74 (2005).
Fedde et al., "Alkaline phosphatase knock-out mice recapitulate the metabolic and skeletal defects of infantile hypophosphatasia," available in PMC Mar. 7, 2011, published in final edited form as: J Bone Miner Res. 14(12):2015-2026 (1999) (19 pages).
Garg, "Investigation of the role of FcRn in the absorption, distribution, and elimination of monoclonal antibodies," Dissertation: State University of New York at Buffalo, 2007 (Abstract only) (2 pages).
Greenberg et al., "A homoallelic Gly$^{317}$ to Asp mutation in ALPL causes the perinatal (lethal) form of hypophosphatasia in Canadian mennonites," Genomics. 17:215-217 (1993).
Harmey et al., "Concerted regulation of inorganic pyrophosphate and osteopontin by Akp2, Enpp1, and Ank," Am J Pathol. 164(4):1199-1209 (2004).
Harmey et al., "Elevated skeletal osteopontin levels contribute to the hypophosphatasia phenotype in Akp2$^{-/-}$ mice," J Bone Miner Res. 21(9):1377-1386 (2006).

Hawrylak et al., "The solubilization of tetrameric alkaline phosphatase from human liver and its conversion into various forms by phosphatidylinositol phospholipase C or proteolysis," J Biol Chem. 263(28):14368-14373 (1988).
Henthorn et al., "Different missense mutations at the tissue-nonspecific alkaline phosphatase gene locus in autosomal recessively inherited forms of mild and severe hypophosphatasia," Proc Natl Acad Sci USA. 89:9924-9928 (1992).
Hessle et al., "Tissue-nonspecific alkaline phosphatase and plasma cell membrane glycoprotein-1 are central antagonistic regulators of bone mineralization," Proc Natl Acad Sci USA. 99(14): 9445-9449 (2002).
Jansonius, "Structure, evolution and action of vitamin $B_6$-dependent enzymes," Curr Opin Struct Biol. 8:759-769 (1998).
Jin et al., "Novel analog of atrial natriuretic peptide selective for receptor-A produces increased diuresis and natriuresis in rats," J Clin Invest. 98(4):969-976 (1996).
Johnson et al., "Matrix vesicle plasma cell membrane glycoprotein-1 regulates mineralization by murine osteoblastic MC3T3 cells," J Bone Miner Res. 14(6):883-892 (1999).
Kochendoerfer, "Protein & peptide drug delivery—third international conference: Minimally invasive delivery methods," Sep. 22-23, Philadelphia, PA. IDrugs. 6(11):1043-1045 (2003).
Kostenuik et al., "Infrequent delivery of a long-acting PTH-Fc fusion protein has potent anabolic effects on cortical and cancellous bone," J Bone Miner Res. 22(10):1534-1547 (2007).
Mahmood et al., "Selection of the first-time dose in humans: comparison of different approaches based on interspecies scaling of clearance," J Clin Pharmacol. 43:692-697 (2003).
Millan, "Mammalian Alkaline Phosphatases," Wiley-WCH Verlag GmbH & Co., Weinheim, Germany, 1-322 (2006).
Morris et al., "Immunolocalization of alkaline phosphatase in osteoblasts and matrix vesicles of human fetal bone," Bone Miner. 19:287-298 (1992).
Nasu et al., "Aberrant interchain disulfide bridge of tissue-nonspecific alkaline phosphatase with an Arg433 to Cys substitution associated with severe hypophosphatasia," FEBS Journal. 273:5612-5624 (2006).
NCBI Protein Database Accession No. AAF64516. Retrieved on Apr. 16, 2013 (2 pages).
NCBI Protein Database Accession No. AAC33858. Retrieved on Apr. 16, 2013 (1 page).
NCBI Protein Database Accession No. AAH21289. Retrieved on Apr. 16, 2013 (2 pages).
NCBI Protein Database Accession No. AAH66116. Retrieved on Apr. 16, 2013 (2 pages).
NCBI Protein Database Accession No. AAH90861. Retrieved on Apr. 16, 2013 (2 pages).
NCBI Protein Database Accession No. AAI10910. Retrieved on Apr. 16, 2013 (2 pages).
NCBI Protein Database Accession No. AAI26166. Retrieved on Apr. 16, 2013 (2 pages).
NCBI Protein Database Accession No. AAI18209. Retrieved on Apr. 17, 2013 (2 pages).
NCBI Protein Database Accession No. AAN64273. Retrieved on Apr. 16, 2013 (1 page).
NCBI Protein Database Accession No. NP_000469. Retrieved on Apr. 16, 2013 (3 pages).
NCBI Protein Database Accession No. NP_001623. Retrieved on Apr. 16, 2013 (3 pages).
NCBI Protein Database Accession No. NP_001036028. Retrieved on Apr. 16, 2013 (2 pages).
NCBI Protein Database Accession No. NP_001253798.1, downloaded on Apr. 17, 2013. (2 pages).
NCBI Protein Database Accession No. NP_112603. Retrieved on Apr. 16, 2013 (3 pages).
NCBI Protein Database Accession No. P05186. Retrieved on Apr. 16, 2013 (19 pages).
NCBI Protein Database Accession No. P05187. Retrieved on Apr. 16, 2013 (10 pages).
NCBI Protein Database Accession No. P08289. Retrieved on Apr. 16, 2013 (5 pages).

(56) References Cited

OTHER PUBLICATIONS

NCBI Protein Database Accession No. P09487. Retrieved on Apr. 16, 2013 (4 pages).
NCBI Protein Database Accession No. P09242. Retrieved on Apr. 16, 2013 (6 pages).
NCBI Protein Database Accession No. P09923. Retrieved on Apr. 16, 2013 (6 pages).
NCBI Protein Database Accession No. P10696. Retrieved on Apr. 16, 2013 (7 pages).
NCBI Protein Database Accession No. Q29486. Retrieved on Apr. 16, 2013 (3 pages).
NCBI Protein Database Accession No. Q9N0V0. Retrieved on Apr. 16, 2013 (1 page).
Nosjean et al., "Human tissue non-specific alkaline phosphatases: sugar-moiety-induced enzymic and antigenic modulations and genetic aspects," Biochem J. 321:297-303 (1997).
Ramachandran et al., "Treatment of an anabolic bone deficiency in neurofibromatosis with bone morphogenetic proteins and its potential application for congenital pseudarthrosis of the tibia," J Bone Joint Surg Br. 91-B (Suppl. 1), Abstract 137 (2009).
Srinivas et al., "Assessment of dose proportionality, absolute bioavailability, and immunogenicity response of CTLA4lg (BMS-188667), a novel immunosuppressive agent, following subcutaneous and intravenous administration to rats," Pharmaceutical Res. 14(7): 911-916 (1997).
Tye et al., "Delineation of the hydroxyapatite-nucleating domains of bone sialoprotein," J Biol Chem. 278(10):7949-7955 (2003).
Urlaub et al., "Deletion of the diploid dihydrofolate reductase locus from cultured mammalian cells," Cell. 33:405-412 (1983).
Wang et al., "A mouse model for achondroplasia produced by targeting fibroblast growth factor receptor 3," Proc Natl Acad Sci USA. 96:4455-4460 (1999).
Wang et al., "Structure-based chemical modification strategy for enzyme replacement treatment of phenylketonuria," Mol Genet Metab. 86:134-140 (2005).
Weiss et al., "A missense mutation in the human liver/bone/kidney alkaline phosphatase gene causing a lethal form of hypophosphatasia," Proc Natl Acad Sci USA. 85:7666-7669 (1988).
Whyte et al., "Enzyme-replacement therapy in life-threatening hypophosphatasia," N Engl J Med. 366(10):904-13 (2012).
Whyte et al., "Markedly increased circulating pyridoxal-5'-phosphate levels in hypophosphatasia," J Clin Invest. 76:752-756 (1985).
Wroblewski et al., "Pharmacokinetics, metabolic stability, and subcutaneous bioavailability of a genetically engineered analog of DcR3, flint [DcR3(R218Q)], in cynomolgus monkeys and mice," Drug Metab Dispos. 31(4):502-507 (2003).
Yamamoto et al., "Long term phenotypic correction of severe infantile hypophosphatasia in a mouse model by neonatal injection of lentiviral vector," Mol Ther. 17:S67-S68, Abstract 171 (2009).
Zierhut et al., "Population PK-PD model for Fc-osteoprotegerin in healthy postmenopausal women," J Pharmacokinet Pharmacodyn. 35:379-399 (2008).
Zurutuza et al., "Correlations of genotype and phenotype in hypophosphatasia," Hum Mol Genet. 8(6):1039-1046 (1999).
International Preliminary Report on Patentability for International Patent Application No. PCT/CA2011/050258, dated Nov. 15, 2012 (9 pages).
International Search Report and Written Opinion for International Patent Application No. PCT/US2012/039004, dated Nov. 2, 2012 (22 pages).
Invitation to Pay Additional Fees for International Patent Application No. PCT/US2012/039004, dated Aug. 29, 2012 (2 pages).
Oikawa et al., "Enzyme replacement therapy on hypophosphatasia mouse model," J Inherit Metab Dis. 9 pages (2013).
Whyte et al., "Infantile hypophosphatasia: normalization of circulating bone alkaline phosphatase activity followed by skeletal remineralization. Evidence for an intact structural gene for tissue nonspecific alkaline phosphatase," J Pediatr. 108(1):82-8 (1986).

Achord et al., "Human beta-glucuronidase: in vivo clearance and in vitro uptake by a glycoprotein recognition system on reticuloendothelial cells," Cell 15(1):269-278 (1978).
Anderson et al., "Matrix vesicles in osteomalacic hypophosphatasia bone contain apatite-like mineral crystals," Am J Pathol. 151(6):1555-61 (1997).
Barton et al., "Replacement therapy for inherited enzyme deficiency—macrophage-targeted glucocerebrosidase for Gaucher's disease," N Engl J Med. 324(21):1464-70 (1991) (abstract only).
Bernardi, "Chromatography of proteins on hydroxyapatite," Methods Enzymol. 27:471-9 (1973).
Boskey et al., "Matrix vesicles promote mineralization in a gelatin gel," Calcif Tissue Int 60(3):309-15 (1997).
Ciancaglini et al., "Contribution of matrix vesicles and alkaline phosphatase to ectopic bone formation," Braz. J Med Biol Res. 39(5):603-10 (2006).
Crawley et al., "Enzyme replacement therapy in a feline model of Maroteaux-Lamy Syndrome," J Clin Invest. 97(8):1864-73 (1996).
Di Mauro et al., "Kinetic characterization of hypophosphatasia mutations with physiological substrates," J Bone Miner Res. 17(8):1383-91 (2002).
Dumont et al., "Monomeric Fc fusions: impact on pharmacokinetic and biological activity of protein therapeutics," BioDrugs. 20(3):151-60 (2006).
Eng et al., "Safety and efficacy of recombinant human alpha-galactosidase A replacement therapy in Fabry's disease," N Engl J Med. 345(1):9-16 (2001).
Gilbert et al., "Chimeric peptides of statherin and osteopontin that bind hydroxyapatite and mediate cell adhesion," J Biol Chem. 275(21):16213-8 (2000).
Guo et al., "Protein tolerance to random amino acid change," Proc Natl Acad Sci USA. 101(25):9205-9210 (2004).
Henthorn et al., "Missense mutations of the tissue-nonspecific alkaline phosphatase gene in hypophosphatasia," Clin Chem. 38(12):2501-5 (1992).
Hosain et al., "Targeted delivery of antineoplastic agent to bone: biodistribution studies of technetium-99m-labeled gem-bisphosphonate conjugate of methotrexate," J Nucl Med. 37(1):105-7 (1996).
Kakkis et al., "Enzyme-replacement therapy in mucopolysaccharidosis I," N Engl J Med. 344(3):182-8 (2001).
Kaufmann et al., "Influence of low temperature on productivity, proteome and protein phosphorylation of CHO cells," Biotechnol Bioeng. 63(5):573-82 (1999).
Millán et al., "Enzyme replacement therapy for murine hypophosphatasia," J Bone Miner Res. 23(6): 777-87 (2008).
Murray, "Lectin-specific targeting of lysosomal enzymes to reticuloendothelial cells," Methods Enzymol. 149:25-42 (1987).
Oda et al., "A general method for rapid purification of soluble versions of glycosylphosphatidylinositol-anchored proteins expressed in insect cells: an application for human tissue-nonspecific alkaline phosphatase," J Biochem. 126(4):694-9 (1999).
Pedersen et al., "Removal of N-terminal polyhistidine tags from recombinant proteins using engineered aminopeptidases," Protein Expr Purif. 15(3):389-400 (1999).
Salih et al., "Identification of the phosphorylated sites of metabolically 32P-labeled osteopontin from cultured chicken osteoblasts," J Biol Chem. 272(21):13966-73 (1997).
Sands et al., "Enzyme replacement therapy for murine mucopolysaccharidosis type VII," J Clin Invest. 93(6):2324-31 (1994).
Sekido et al., "Novel drug delivery system to bone using acidic oligopeptide: pharmacokinetic characteristics and pharmacological potential," J Drug Target. 9(2):111-21 (2001).
Sturtz et al., "A study of the delivery-targeting concept applied to antineoplasic drugs active on human osteosarcoma. I. Synthesis and biological activity in nude mice carrying human osteosarcoma xenografts of gem-bisphosphonic methotrexate analogues," Eur J Med Chemistry. 27:825-33 (1992).
Tomatsu, Declaration Under 37 C.F.R. § 1.132 for U.S. Appl. No. 11/484,870, dated Jun. 1, 2009 (3 pages).
Uludag et al., "Bone affinity of a bisphosphonate-conjugated protein in vivo," Biotechnol Prog. 16(6):1115-8 (2000).

(56) References Cited

OTHER PUBLICATIONS

Waymire et al., "Mice lacking tissue non-specific alkaline phosphatase die from seizures due to defective metabolism of vitamin B-6," Nat Genet. 11(1):45-51 (1995).
Weinberg, "An overview of infliximab, etanercept, efalizumab, and alefacept as biologic therapy for psoriasis," Clin Ther. 25(10):2487-505 (2003).
Weiss et al., "Isolation and characterization of a cDNA encoding a human liver/bone/kidney-type alkaline phosphatase," Proc Natl Acad Sci USA. 83(19):7182-6 (1986).
Weiss et al., "Structure of the human liver/bone/kidney alkaline phosphatase gene," J Biol Chem. 263(24):12002-10 (1988).
Weninger et al., "Biochemical and morphological effects of human hepatic alkaline phosphatase in a neonate with hypophosphatasia," Acta Paediatr Scand. Suppl. 360:154-160 (1989).
Whyte et al., "Infantile hypophosphatasia: enzyme replacement therapy by intravenous infusion of alkaline phosphatase-rich plasma from patients with Paget bone disease," J Pediatr. 101(3):379-86 (1982).
Whyte et al., "Enzyme replacement therapy for infantile hypophosphatasia attempted by intravenous infusions of alkaline phosphatase-rich Paget plasma: results in three additional patients," J Pediatr. 105(6):926-33 (1984).
Whyte et al., "Alkaline phosphatase: placental and tissue-nonspecific isoenzymes hydrolyze phosphoethanolamine, inorganic pyrophosphate, and pyridoxal 5'-phosphate. Substrate accumulation in carriers of hypophosphatasia corrects during pregnancy," J Clin Invest. 95(4):1440-5 (1995).
Whyte, "Hypophosphatasia," in The Metabolic and Molecular Bases of Inherited Disease (8th ed.), pp. 5313-5329, 2001 (McGraw-Hill Book Company) (epub pp. 1-41).
Whyte, "Heritable Forms of Rickets and Osteomalacia," in Connective Tissues and Its Heritable Disorders, pp. 765-787, 2002 (eds. R.M. Royce and B. Steinmann, Wiley-Liss, Inc. Hoboken).
Whyte et al., "Marrow cell transplantation for infantile hypophosphatasia," J Bone Miner Res. 18(4):624-36 (2003).
Yamamoto et al., "Prolonged survival and phenotypic correction of Akp2(-/-) hypophosphatasia mice by lentiviral gene therapy," J Bone Miner Res. 26(1):135-42 (2011).
Communication from Examining Division for European Application No. EP 05 73 9065.0, dated Jun. 18, 2009 (6 pages).
Communication from Examining Division for European Application No. EP 05 73 9065.0, dated Jun. 11, 2010 (5 pages).
Office Action for U.S. Appl. No. 12/793,517, dated Aug. 16, 2010 (9 pages).
Office Action for U.S. Appl. No. 13/071,445, dated Feb. 6, 2012 (12 pages).
Supplementary European Search Report for European Application No. EP 05 73 9065 (date of completion of search Nov. 7, 2008, dated Dec. 2, 2008) (3 pages).
Choe et al., "Substrate profiling of cysteine proteases using a combinatorial peptide library identifies functionally unique specificities," J Biol Chem. 281(18):12824-12832 (2006).
Official Action for Japanese Application No. 2013-544989, dated Oct. 27, 2015 (3 pages).
Harris, "The human alkaline phosphatases: what we know and what we don't know," Clin Chim Acta. 186:133-50 (1989).
De la Croix Ndong et al., "Asfotase-alpha improves bone growth, mineralization and strength in mouse models of neurofibromatosis type-1," Nat Med. 20(8):904-10 (2014) (10 pages).
International Search Report and Written Opinion for International Patent Application No. PCT/US2016/047166, dated Nov. 7, 2016 (15 pages).
Ratner, "Alexion pays big for Synageva's rare disease drug candidate," Nat Biotechnol. 33(7):679 (2015).
Addison et al., "Pyrophosphate inhibits mineralization of osteoblast cultures by binding to mineral, up-regulating osteopontin, and inhibiting alkaline phosphatase activity," J Biol Chem. 282(21):15872-15883 (2007).

Advisory Action for U.S. Appl. No. 11/484,870, dated Dec. 20, 2007 (4 pages).
Altarescu et al., "The efficacy of enzyme replacement therapy in patients with chronic neuronopathic Gaucher's disease," J Pediatr. 138(4):539-547 (2001).
Anderson et al., "Impaired calcification around matrix vesicles of growth plate and bone in alkaline phosphatase-deficient mice," *Am J Pathol.* 164:841-847 (2004).
Barranger et al., "Lessons learned from the development of enzyme therapy for Gaucher disease," J Inherit Metab Dis. 24(Supp 2):89-96 (2001).
Bobé et al., "Fas-mediated liver damage in MRL hemopoietic chimeras undergoing lpr-mediated graft-versus-host disease," J Immunol. 159:4197-4204 (1997).
Boskey, "Amorphous calcium phosphate: The contention of bone," J Dent Res. 76:1433-1436 (1997).
Campbell et al., "Insulin-like growth factor (IGF)-binding protein-5-(201-218) region regulates hydroxyapatite and IGF-I binding," Am J Physiol. 273:E1005-1013 (1997).
Cleland et al., "Emerging protein delivery methods," Curr Opin Biotechnol. 12:212-219 (2001).
Communication from Examining Division for European Application No. EP 08 757 088.3, dated Apr. 20, 2011 (4 pages).
Data Sheet for pFUSE-SEAP-hFC "Plasmid designed for the expression of a SEAP-Fc Fusion protein," Invivogen, San Diego, CA (4 pages) (1989).
Extended European Search Report for European Application No. 11774253.6, dated Oct. 14, 2013 (8 pages).
Extended European Search Report for European Application No. EP 11 00 0196.3, dated Jun. 22, 2011 (6 pages).
Extended European Search Report for European Application No. EP 11 00 4496.3, dated Aug. 26, 2011 (7 pages).
Fujisaki et al., "Osteotropic Drug Delivery System (ODDS) based on bisphosphonic prodrug. IV effects of osteotropic estradiol on bone mineral density and uterine weight in ovariectomized rats," J Drug Target. 5(2):129-138 (1997) (11 pages).
Fujisawa et al., "Acidic amino acid-rich sequences as binding sites of osteonectin to hydroxyapatite crystals," Biochim Biophys Acta. 1292:53-60 (1996).
Furbish et al., "Uptake and distribution of placental glucocerebrosidase in rat hepatic cells and effects of sequential deglycosylation," Biochim Biophys Acta. 673:425-434 (1981).
Halling Linder et al., "Glycosylation differences contribute to distinct catalytic properties among bone alkaline phosphatase isoforms," available in PMC Nov. 1, 2010, published in final edited form as: Bone. 45(5):987-993 (2009) (17 pages).
Hardy et al., "Dissection of a carboxy-terminal region of the yeast regulatory protein RAP1 with effects on both transcriptional activation and silencing," Mol Cell Biol. 12(3):1209-1217 (1992).
Hult et al., "Engineered enzymes for improved organic synthesis," Curr Opin Biotechnol. 14:395-400 (2003).
Hunter et al., "Modulation of crystal formation by bone phosphoproteins: structural specificity of the osteopontin-mediated inhibition of hydroxyapatite formation," Biochem J. 300:723-728 (1994).
Ikezawa, "Glycosylphosphatidylinositol (GPI)-anchored proteins," *Biol Pharm Bull.* 25(4):409-417 (2002).
International Search Report and Written Opinion for International Patent Application No. PCT/CA2005/000615, dated Aug. 18, 2005 (14 pages).
International Search Report and Written Opinion for International Patent Application No. PCT/CA2008/000923, dated Sep. 12, 2008 (11 pages).
International Search Report and Written Opinion for International Patent Application No. PCT/CA2011/050258, dated Jul. 29, 2011 (14 pages).
Kasugai et al., "Selective drug delivery system to bone: small peptide $(Asp)_6$ conjugation," J Bone Miner Res. 15(5):936-943 (2000).
Leone et al., "Allosteric modulation of pyrophosphatase activity of rat osseous plate alkaline phosphatase by magnesium ions," Int J Biochem Cell Biol. 30:89-97 (1998).
Meyer, "Can biological calcification occur in the presence of pyrophosphate?" Arch Biochem Biophys. 231:1-8 (1984).

(56) References Cited

OTHER PUBLICATIONS

Michigami et al., "Common mutations F310L and T1559del in the tissue-nonspecific alkaline phosphatase gene are related to distinct phenotypes in Japanese patients with hypophosphatasia," Eur J Pediatr. 164:277-282 (2005).
Moss et al., "Association of inorganic-pyrophosphatase activity with human alkaline-phosphatase preparations," Biochem J. 102:53-57 (1967).
Murshed et al., "Unique coexpression in osteoblasts of broadly expressed genes accounts for the spatial restriction of ECM mineralization to bone," Genes Dev. 19:1093-1104 (2005).
Narisawa et al., "Abnormal vitamin B6 metabolism in alkaline phosphatase knock-out mice causes multiple abnormalities, but not the impaired bone mineralization,"J Pathol. 193:125-133 (2001).
Narisawa et al., "Inactivation of two mouse alkaline phosphatase genes and establishment of a model of infantile hypophosphatasia," Dev Dyn. 208:432-446 (1997).
NCBI Protein Database Accession No. NP_001622. Retrieved on Apr. 16, 2013 (3 pages).
NCBI Protein Database Accession No. NP_031457. Retrieved on Apr. 16, 2013 (3 pages).
NCBI Protein Database Accession No. NP_037191. Retrieved on Apr. 16, 2013 (3 pages).
NCBI Protein Database Accession No. NP_776412. Retrieved on Apr. 17, 2013 (2 pages).
NCBI Protein Database Accession No. NP_789828. Retrieved on Apr. 16, 2013 (3 pages).
NCBI Protein Database Accession No. P01857. Retrieved on Apr. 18, 2013 (7 pages).
NCBI Protein Database Accession No. Q6PYX1. Retrieved on Oct. 15, 2013 (2 pages).
Ngo et al., Computational complexity, protein structure prediction, and the levinthal paradox. *The Protein Folding Problem and Tertiary Structure Prediction*. Merz et al. (ed.), 433, 492-495 (1994).
Nishioka et al., "Enhancement of drug delivery to bone: characterization of human tissue-nonspecific alkaline phosphatase tagged with an acidic oligopeptide," Mol Genet Metab. 88:244-255 (2006).
Office Action for U.S. Appl. No. 11/111,664, dated Dec. 4, 2008 (7 pages).
Office Action for U.S. Appl. No. 11/111,664, dated May 14, 2008 (8 pages).
Office Action for U.S. Appl. No. 11/111,664, dated Oct. 4, 2007 (11 pages).
Office Action for U.S. Appl. No. 11/484,870, dated Aug. 11, 2009 (15 pages).
Office Action for U.S. Appl. No. 11/484,870, dated Feb. 2, 2009 (16 pages).
Office Action for U.S. Appl. No. 11/484,870, dated Jan. 25, 2007 (15 pages).
Office Action for U.S. Appl. No. 11/484,870, dated Jul. 5, 2007 (13 pages).
Office Action for U.S. Appl. No. 11/484,870, dated Jun. 25, 2008 (16 pages).
Office Action for U.S. Appl. No. 11/484,870, dated Oct. 1, 2007 (12 pages).
Office Action for U.S. Appl. No. 12/405,920, dated Aug. 9, 2010 (7 pages).
Office Action for U.S. Appl. No. 12/405,920, dated Dec. 17, 2009 (14 pages).
Office Action for U.S. Appl. No. 13/071,445, dated May 25, 2012 (14 pages).
Official Notification and Search Report for Eurasian Patent Application No. 201291138, dated May 17, 2013 (3 pages).
Patti et al., "Critical residues in the ligand-binding site of the *Staphylococcus aureus* collagen-binding adhesin (MSCRAMM)," J Biol Chem. 270(20):12005-12011 (1995).
Reply to Final Office Action for U.S. Appl. No. 13/071,445, dated Oct. 25, 2012 (14 pages).
Reply to Office Action for U.S. Appl. No. 11/111,664, dated Sep. 10, 2008 (32 pages).

Restriction Requirement for U.S. Appl. No. 12/599,679, dated Jun. 12, 2012 (5 pages).
Rezende et al., "Inorganic pyrophosphate-phosphohydrolytic activity associated with rat osseous plate alkaline phosphatase," Cell Mol Biol. 44(2):293-302 (1998).
Rowe et al., "MEPE, a new gene expressed in bone marrow and tumors causing osteomalacia," Genomics. 67:54-68 (2000).
Russell et al., "Inorganic pyrophosphate in plasma in normal persons and in patients with hypophosphatasia, osteogenesis imperfecta, and other disorders of bone," J Clin Invest. 50:961-969 (1971).
Sharom et al., "Glycosylphosphatidylinositol-anchored proteins: structure, function, and cleavage by phosphatidylinositol-specific phospholipase C," Biochem Cell Biol. 80:535-549 (2002).
Shull et al., "Enzyme replacement in a canine model of Hurler syndrome," Proc Natl Acad Sci USA. 91:12937-12941 (1994).
Spears et al., "Deoxyuridylate effects on thymidylate synthase-5-fluorodeoxyuridylate-folate ternary complex formation," Biochem Pharmacol. 38(18):2985-2993 (1989).
Stahl et al., "Evidence for receptor-mediated binding of glycoproteins, glycoconjugates, and lysosomal glycosidases by alveolar macrophages," Proc Natl Acad Sci USA. 75(3):1399-1403 (1978).
Symersky et al., "Structure of the collagen-binding domain from a *Staphylococcus aureus* adhesin," Nat Struct Biol. 4(10):833-838 (1997).
Tomatsu, Declaration Under 37 C.F.R. § 1.132 for U.S. Appl. No. 11/484,870, dated Nov. 27, 2007 (2 pages).
Whyte, "Hypophosphatasia and the role of alkaline phosphatase in skeletal mineralization," Endocr Rev. 15(4):439-461 (1994).
Whyte, "Hypophosphatasia: Nature's window on alkaline phosphatase function in man," *Principles of Bone Biology*, 2nd ed., Bilezikian, Raisz, and Rodan. 2:1229-1248 (2002).
Yadav et al., "Dose response of bone-targeted enzyme replacement for murine hypophosphatasia," available in PMC Aug. 1, 2012, published in final edited form as: Bone. 49(2):250-6 (2011) (20 pages).
Yokogawa et al., "Selective delivery of estradiol to bone by aspartic acid oligopeptide and its effects on ovariectomized mice," Endocrinology. 142(3):1228-1233 (2001).
Young et al., "Structure, expression, and regulation of the major noncollagenous matrix proteins of bone," Clin Orthop Relat Res. 281:275-294 (1992).
Orimo, "The mechanism of mineralization and the role of alkaline phosphatase in health and disease," J Nippon Med Sch. 77(1):4-12 (2010).
Attwood, "The Babel of Bioinformatics," Genomics. 290(5491):471-3 (2000).
Skolnick et al., "From genes to protein structure and function: novel applications of computational approaches in the genomic era," Trends Biotechnol. 18(1):34-9 (2000).
Bocciardi et al., "Overexpression of the C-type natriuretic peptide (CNP) is associated with overgrowth and bone anomalies in an individual with balanced t(2;7) translocation," Hum Mutat. 28(7):724-731 (2007).
Brenner et al., "Diverse biological actions of atrial natriuretic peptide," Physiol Rev. 70(3):665-699 (1990).
Chen et al., "Gly369Cys mutation in mouse FGFR3 causes achondroplasia by affecting both chondrogenesis and osteogenesis," J Clin Invest. 104(11):1517-1525 (1999).
Chusho et al., "Dwarfism and early death in mice lacking C-type natriuretic peptide," Proc Natl Acad Sci USA. 98(7):4016-4021 (2001).
Daggubati et al., "Adrenomedullin, endothelin, neuropeptide Y, atrial, brain, and C-natriuretic prohormone peptides compared as early heart failure indicators," Cardiovasc Res. 36:246-255 (1997).
De Plater et al., "The natriuretic peptide (OVCNP-39) from platypus (*Ornithorhynchus anatinus*) venom relaxes the isolated rat uterus and promotes oedema and mast cell histamine release," Toxicon. 36(3):847-857 (1998).
Furuya et al., "Structural requirements of C-natriuretic peptide for elevation of cyclic GMP in cultured vascular smooth muscle cells," Biochem Biophys Res Commun. 183(3):964-969 (1992).

(56) References Cited

OTHER PUBLICATIONS

Hagiwara et al., "Autocrine regulation of rat chondrocyte proliferation by natriuretic peptide C and its receptor, natriuretic peptide receptor-B," J Biol Chem. 269(14):10729-10733 (1994).
Hagiwara et al., "cGMP produced in response to ANP and CNP regulates proliferation and differentiation of osteoblastic cells," Am J Physiol. 270:C1311-C1318 (1996).
Horton et al., "Achondroplasia," Lancet. 370:162-172, 2007.
Inoue et al., "Four functionally distinct C-type natriuretic peptides found in fish reveal evolutionary history of the natriuretic peptide system," Proc Natl Acad Sci USA. 100(17):10079-10084 (2003).
International Search Report and Written Opinion for International Patent Application No. PCT/CA2011/050807, dated Apr. 13, 2012 (18 pages).
International Search Report for International Patent Application No. PCT/US2012/060869, dated Mar. 25, 2013 (5 pages).
Invitation to Pay Additional Fees for International Patent Application No. PCT/CA2011/050807, dated Feb. 13, 2012 (2 pages).
Kalra et al., "The role of C-type natriuretic peptide in cardiovascular medicine," Eur Heart J. 22:997-1007 (2001).
Lo et al., "High level expression and secretion of Fc-X fusion proteins in mammalian cells," Protein Eng. 11(6):495-500 (1998).
Mericq et al., "Regulation of fetal rat bone growth by C-type natriuretic peptide and cGMP," Pediatr Res. 47(2):189-193 (2000) (9 pages).
Miyazawa et al., "Cyclic GMP-dependent protein kinase II plays a critical role in C-type natriuretic peptide-mediated endochondral ossification," Endocrinology. 143(9):3604-3610 (2002).
Nakao et al., "The pharmacokinetics of alpha-human atrial natriuretic polypeptide in healthy subjects," Eur J Clin Pharmacol. 31:101-103 (1986).
NCBI Protein Database Accession No. XP_001109717. Retrieved on Apr. 17, 2013 (1 page).
Pfeifer et al., "Intestinal secretory defects and dwarfism in mice lacking cGMP-dependent protein kinase II," Science. 274:2082-2086 (1996).
Potter et al., "Natriuretic peptides, their receptors, and cyclic guanosine monophosphate-dependent signaling functions," Endocr Rev. 27(1):47-72 (2006).
Shukla et al., "RNA interference and inhibition of MEK-ERK signaling prevent abnormal skeletal phenotypes in a mouse model of craniosynostosis," Nat Genet. 39(9):1145-1150 (2007).
Suda et al., "C-type natriuretic peptide as an autocrine/paracrine regulator of osteoblast: evidence for possible presence of bone natriuretic peptide system," Biochem Biophys Res Commun. 223:1-6 (1996).
Takano et al., "Molecular evolution of shark C-type natriuretic peptides," Zoolog Sci. 11:451-454 (1994).
Tamura et al., "Critical roles of the guanylyl cyclase B receptor in endochondral ossification and development of female reproductive organs," Proc Natl Acad Sci USA. 101(49):17300-17305 (2004).
Teixeira et al., "Nitric oxide, C-type natriuretic peptide and cGMP as regulators of endochondral ossification," Dev Biol. 319:171-178 (2008).
Tsuji et al., "A loss-of-function mutation in natriuretic peptide receptor 2 (Npr2) gene is responsible for disproportionate dwarfism in cn/cn mouse," J Biol Chem. 280(14):14288-14292 (2005).
Wang et al., "Mice lacking Nf1 in osteochondroprogenitor cells display skeletal dysplasia similar to patients with neurofibromatosis type 1," Hum Mol Genet. 20(20):3910-3924 (2011).
Williams et al., "Solute transport in growth plate cartilage: In vitro and in vivo," Biophys J. 93(3):1039-1050 (2007).
Yasoda et al., "Natriuretic peptide regulation of endochondral ossification. Evidence for possible roles of the C-type natriuretic peptide/guanylyl cyclase-B pathway," J Biol Chem. 273(19):11695-11700 (1998).
Yasoda et al., "Systemic administration of C-type natriuretic peptide as a novel therapeutic strategy for skeletal dysplasias," Endocrinology. 150(7):3138-3144 (2009).

Yoder et al., "Reduced ability of C-type natriuretic peptide (CNP) to activate natriuretic peptide receptor B (NPR-B) causes dwarfism in lbab -/- mice," Peptides. 29(9):1575-1581 (2008).
Farnum et al., "In vivo delivery of fluoresceinated dextrans to the murine growth plate: imaging of three vascular routes by multiphoton microscopy," available in PMC Oct. 28, 2008, published in final edited form as: Anat Rec A Discov Mol Cell Evol Biol. 288(1):91-103 (2006) (22 pages).
Husain et al., "Fc site-specific labeling of immunoglobulins with calf intestinal alkaline phosphatase," Bioconjug Chem. 5(5):482-90 (1994).
Mayer, "Microbiology and immunology on-line: Immunoglobulins: structure and function" <http://pathmicro.med.sc.edu/mayer/IgStruct2000.htm>, University of South Carolina School of Medicine, 12 pages (2009).
Yasoda et al., "Overexpression of CNP in chondrocytes rescues achondroplasia through a MAPK-dependent pathway," Nat Med. 10(1):80-86 (2004).
EBI Blast for Accession No. ATD17216. Entered Oct. 16, 2008 (1 page).
Supplementary European Search Report for European Patent Application No. 11853820.6, dated Mar. 25, 2014 (3 pages).
International Preliminary Report on Patentability for International Patent Application No. PCT/US2012/060869, dated Apr. 22, 2014 (7 pages).
International Preliminary Report on Patentability for International Patent Application No. PCT/US2012/039004, dated Apr. 22, 2014 (8 pages).
Siris et al., "Paget's disease of bone," Trends Endocrinol Metab. 2(6):207-12 (1991).
European Search Report for European Patent Application No. 12842640.0, dated Mar. 13, 2015 (7 pages).
Lee et al., "Disturbed osteoblastic differentiation of fibrous hamartoma cell from congenital pseudarthrosis of the tibia associated with neurofibromatosis type I," Clin Orthop Surg. 3(3):230-7 (2011).
Schindeler et al., "Modeling bone morphogenetic protein and bisphosphonate combination therapy in wild-type and Nf1 haploinsufficient mice," J Orthop Res. 26(1):65-74 (2008).
Nahabet et al., "Postnatal Pancraniosynostosis in a Patient With Infantile Hypophosphatasia," Cleft Palate Craniofac J. 53(6):741-4 (2016).
International Search Report and Written Opinion for International Patent Application No. PCT/US2015/058498, dated Jan. 22, 2016 (12 pages).
Kosnik-Infinger et al., "Enzyme replacement therapy for congenital hypophosphatasia allows for surgical treatment of related complex craniosynostosis: a case series," Neurosurg Focus. 38(5):E10 (2015) (8 pages).
Mornet et al., "Identification of fifteen novel mutations in the tissue-nonspecific alkaline phosphatase (TNSALP) gene in European patients with severe hypophosphatasia," Eur J Hum Genet. 6(4):308-14 (1998).
Alexion Pharma International, "Strensiq Product Monograph," <http://alexionpharma.ca/documents/Strensiq-PM-asfotase-alfa-14Aug2015.aspx>, Prepared Aug. 14, 2015 (32 pages).
Madson et al., "Asfotase alfa: sustained efficacy and tolerability in children with hypophosphatasia treated for 5 years," ESPE Abstracts. 84:FC2.4 (2015) (2 pages).
International Search Report and Written Opinion for International Patent Application No. PCT/US2016/025721, dated Aug. 17, 2016 (18 pages).
Invitation to Pay Additional Fees for International Patent Application No. PCT/US2016/015366, dated Jun. 1, 2016 (7 pages).
Phillips et al., "A modified performance-oriented mobility assessment tool for assessing clinically relevant gait impairments and change in children with hypophosphatasia: development and validation," Bone Abstracts. 4 P136 (2015).
Highlights of Prescribing Information for Strensiq™ Alexion Pharmaceuticals, Inc., available <http://www.alexion.com/Documents/strensiq_pi-10-2015.aspx>, 2015 (19 pages).
Phillips et al., "Gait assessment in children with childhood hypophosphatasia: impairments in muscle strength and physical

(56) References Cited

OTHER PUBLICATIONS function," The Endocrine Society's 97th Annual Meeting & Expo, Mar. 5-8, 2015, San Diego, California (2 pages).
"View of NCT02235493 on Nov. 19, 2015," ClinicalTrials.gov archive, Nov. 19, 2015 (4 pages).
Hofmann et al., "Improvement in bone manifestations and respiratory status in infants and young children with HPP treated with asfotase alfa: an update on the ENB-010-10 trial," 7th International Conference on Children's Bone Health, Jun. 27-30, Austria, Salzburg. Bone Abstracts. 4: OC18 (2015) (3 pages).
Epps, "Application No. 125513Orig1s000 Medical Review(s)," Center for Drug Evaluation and Research, <http://www.accessdata.fda.gov/drugsatfda_docs/nda/2015/125513Orig1s000MedR.pdf>, Oct. 20, 2015 (254 pages).
International Search Report and Written Opinion for International Patent Application No. PCT/US2016/039595, dated Feb. 21, 2017 (16 pages).
Liu et al., "Tissue-nonspecific alkaline phosphatase deficiency causes abnormal craniofacial bone development in the Alpl(-/-) mouse model of infantile hypophosphatasia," available in PMC Oct. 1, 2015, published in final edited form as: Bone. 67:81-94 (2014) (30 pages).
Appeal Brief as Filed in U.S. Appl. No. 12/638,527, dated Oct. 9, 2015 (101 pages).
Reply Brief as Filed in U.S. Appl. No. 12/638,527, dated Apr. 22, 2016 (4 pages).
Examiner's Answer to Appeal Brief for U.S. Appl. No. 12/638,527, dated Feb. 23, 2016 (9 pages).
Phillips et al., "Significantly improved muscle strength, running speed, and agility in children with hypophosphatasia treated with asfotase alfa," Endocrine Society's 97th Annual Meeting and Expo, Mar. 5-8, San Diego, CA. Abstract OR29-4 (2015) (2 pages).
Millán et al., "Alkaline phosphatase and hypophosphatasia," Calcif Tissue Int. 98(4):398-416 (2016).
Kishnani et al., "Biochemical and physical function outcomes in adolescents and adults with hypophosphatasia treated with asfotase alfa for up to 4 years: interim results from a phase II study," Endocrine Society's 98th Annual Meeting and Expo, Apr. 1-4, Boston, MA. Abstract OR26-3 (2016) (2 pages).
International Search Report and Written Opinion for International Patent Application No. PCT/US2017/025590, dated Jun. 29, 2017 (18 pages).
Iqbal et al., "Recurrent Metatarsal Fractures in Postmenopausal Woman With Low Serum Alkaline Phosphatase: A Rare Diagnosis Not to Miss," J Investig Med High Impact Case Rep. 5(3):1-3 (2017).
Ahn et al., "Idiopathic calcium pyrophosphate dihydrate (CPPD) crystal deposition disease in a young male patient: a case report," J Korean Med Sci. 18(6):917-20 (2003).
Cahill et al., "Infantile hypophosphatasia: transplantation therapy trial using bone fragments and cultured osteoblasts,"J. Clin Endocrinol Metab. 92(8): 2923-30 (2007).
Glass et al., "The infant skull: a vault of information," Radiographics. 24(2):507-22 (2004).
Herasse et al., "Molecular study of three cases of odontohypophosphatasia resulting from heterozygosity for mutations in the tissue non-specific alkaline phosphatase gene," J Med Genet. 40(8):605-9 (2003).
Ishida et al., "Tissue-nonspecific alkaline phosphatase with an Asp(289)→Val mutation fails to reach the cell surface and undergoes proteasome-mediated degradation," J Biochem. 134(1):63-70 (2003).
Mornet, "Hypophosphatasia," Orphanet J Rare Dis. 2:(40) (2007) (8 pages).
Spentchian et al., "Severe hypophosphatasia: characterization of fifteen novel mutations in the ALPL gene," Hum Mutat. 22(1) (2003) (5 pages).
Takinami et al., "The mutant (F310L and V365I) tissue-nonspecific alkaline phosphatase gene from hypophosphatasia," J Med Dent Sci. 51(1):67-74 (2004).
Sawai et al., "Severe perinatal hypophosphatasia due to homozygous deletion of T at nucleotide 1559 in the tissue nonspecific alkaline phosphatase gene,". Prenat Diagn. 23(9):743-6 (2003).
Wickramasinghe et al., "A case of hypophosphatasia," Ceylon Med J. 48(3):94-5 (2003).
Yamamoto et al., "A successful treatment with pyridoxal phosphate for West syndrome in hypophosphatasia," Pediatr Neurol. 30(3):216-8 (2004).
International Preliminary Report on Patentability for International Patent Application No. PCT/US2016/015366, dated Aug. 10, 2017 (10 pages).
International Search Report and Written Opinion for International Patent Application No. PCT/US2017/047527, dated Nov. 6, 2017 (10 pages).
Millán et al., "Hypophosphatasia—pathophysiology and treatment," available in PMC Sep. 22, 2014, published in final edited form as: Actual Osteol. 8(3):164-182 (2012) (21 pages).
Padidela et al., "P1-118: Management of Tracheobronchomalacia During Asfotase Alfa Treatment in Infants with Perinatal-Onset Hypophosphatasia: A Case Series," European Society for Paediatric Endocrinology (ESPE), Paris, France, Sep. 10-12, 2016 (1 page).
Mornet et al., "Structural evidence for a functional role of human tissue nonspecific alkaline phosphatase in bone mineralization," J Biol Chem. 276(33):31171-8 (2001).
Bhattacharyya et al., "Hypophosphatasia and the risk of atypical femur fractures: a case-control study," BMC Muscoloskelet Disord. 17:332 (2016) (4 pages).
Bishop, "Asfotase alfa for hypophosphatasia," Horizon Scanning Centre. National Institute for Health Research. http://www.hsric.nihr.ac.uk/topics/asfotase-alfa-for-hypophosphatasia/download, retrieved Oct. 20, 2013 (9 pages).
Bishop et al., "Transformative therapy in hypophosphatasia," Arch Dis Child. 101(6):514-5 (2016).
Bishop, "Clinical management of hypophosphatasia," Clin Cases Miner Bone Metab. 12(2):170-3 (2015).
Durussel et al., "Bone mineralization-dependent craniosynostosis and craniofacial shape abnormalities in the mouse model of infantile hypophosphatasia," Dev Dyn. 245(2):175-82 (2016).
Braunstein, "Multiple fractures, pain, and severe disability in a patient with adult-onset hypophosphatasia," Bone Rep. 4:1-4 (2015).
Bloch-Zupan, "Hypophosphatasia: diagnosis and clinical signs—a dental surgeon perspective," Int J Paediatr Dent. 26(6):426-438 (2016).
Kishnani et al., "Monitoring guidance for patients with hypophosphatasia treated with asfotase alfa," Mol Genet Metab. 122(1-2):4-17 (2017).
Güzel Nur et al., "Pyridoxine-responsive seizures in infantile hypophosphatasia and a novel homozygous mutation in ALPL gene," J Clin Res Pediatr Endocrinol. 8(3):360-4 (2016).
Gasque et al., "Improvement of the skeletal and dental hypophosphatasia phenotype in Alpl -/- mice by administration of soluble (nontargeted) chimeric alkaline phosphatase," Available in PMC Mar. 1, 2016, published in final edited form as: Bone. 72:137-147 (2015) (25 pages).
Fodor et al., "Differencial diagnosis of the low alkaline phosphatase activities," Orv Hetil. 158(26): 1003-1007 (2017) (Article in Hungarian) (English Abstract included).
McKiernan et al., "Clinical and radiographic findings in adults with persistent hypophosphatasemia," J Bone Miner Res. 29(7):1651-60 (2014).
Martos-Moreno et al., "Hypophosphatasia: clinical manifestations, diagnostic recommendations and therapeutic options," An Pediatr (Barc). S1695-4033(17)30223-0 (2017) (11 pages) (Article in Spanish) (English Abstract included).
Kulikova et al., "Hypophosphatasia: the clinical description of 3 cases of the disease with the molecular-genetic verification of the diagnosis," Problems of Endocrinology. 61(3):37-42 (2015) (Article in Russian) (English Abstract included).
Orimo, "Pathophysiology of hypophosphatasia and the potential role of asfotase alfa," Ther Clin Risk Manag. 12:777-86 (2016).
Morrow, "Expensive new biologic helps children fight hypophosphatasia," Manag Care. 24(12) (2015) (7 pages).

(56) References Cited

OTHER PUBLICATIONS

Mornet et al., "Hypophosphatasia," GeneReviews. https://www.ncbi.nlm.nih.gov/books/NBK1150/, retrieved Dec. 6, 2017, initially published Nov. 20, 2007, last updated Feb. 4, 2016 (25 pages).
Mori et al., "Case series: odontohypophosphatasia or missed diagnosis of childhood/adult-onset hypophosphatasia?—Call for a long-term follow-up of premature loss of primary teeth," Bone Rep. 5:228-232 (2016).
Remde et al., "Successful asfotase alfa treatment in an adult dialysis patient with childhood-onset hypophosphatasia," J Endoc Soc. 1(9):1188-93 (2017).
Panesar, "Hypophosphatasia: a rare disorder," US Pharm. 42(5) (2017) (8 pages).
Padidela et al., "Enzyme-replacement therapy in life-threatening perinatal hypophosphatasia in a premature infant," Endocrine Abstracts. 33:P9 (2013) (1 page).
Sotillo et al., "Signs and symptoms of hypophosphatasia," Dimensions of Dental Hygiene. 15(4):44-47 (2017) (6 pages).
Simm et al., "Successful use of enzyme replacement therapy in infantile hypophosphatasia," J Paediatr Child Health. 53(9):925-926 (2017).
Sheikh et al., "A newborn with no bones: neonatal hypophosphatasia with respiratory distress," J Pediatr. 188:306 (2017).
Saglam et al., "Clinical and genetic findings of Turkish hypophosphatasia cases," J Clin Res Pediatr Endocrinol. 9(3):229-236 (2017).
Whyte et al., "Asfotase alfa treatment improves survival for perinatal and infantile hypophosphatasia," J Clin Endocrinol Metab. 101(1):334-42 (2016) (17 pages).
Wang et al., "Current concepts in odontohypophosphatasia form of hypophosphatasia and report of two cases," BMC Oral Health. 16(1):70 (2016) (8 pages).
Taketani et al., "Ex vivo expanded allogeneic mesenchymal stem cells with bone marrow transplantation improved osteogenesis in infants with severe hypophosphatasia," Cell Transplant. 24(10):1931-43 (2015).
Belachew et al., "Infantile hypophosphatasia secondary to a novel compound heterozygous mutation presenting with pyridoxine-responsive seizures," JIMD Rep. 11:17-24 (2013).
Whyte et al., "Asfotase alfa therapy for children with hypophosphatasia," JCI Insight. 1(9):e85971 (2016) (11 pages).
Whyte, "Hypophosphatasia: enzyme replacement therapy brings new opportunities and new challenges," J Bone Miner Res. 32(4):667-675 (2017).
Alexion Third Quarter 2017 Earnings Call, "http://files.shareholder.com/downloads/ALXN/5636824573x0x961197/3B361D6E-80E2-463E-B0E5-3EAD7FC5B9D0/Alexion_Q3_2017_Earnings_Slides.pdf" (43 pages).
Urlaub et al., "Isolation of Chinese hamster cell mutants deficient in dihydrofolate reductase activity," Proc Natl Acad Sci U S A. 77(7):4216-20 (1980).
Graham et al., "Characteristics of a human cell line transformed by DNA from human adenovirus type 5," J Gen Virol. 36(1):59-72 (1977).
Mather, "Establishment and characterization of two distinct mouse testicular epithelial cell lines," Biol Reprod. 23(1):243-52 (1980).
Le Du et al., "Crystal structure of alkaline phosphatase from human placenta at 1.8 Å resolution. Implication for a substrate specificity," J Biol Chem. 276(12):9158-65 (2001) (9 pages).
Stec et al., "A revised mechanism for the alkaline phosphatase reaction involving three metal ions," J Mol Biol. 299(5):1303-11 (2000).
Alexion, "Highlights of Prescribing Information" for Strensiq®, 2018 (8 pages).
European Collection of Authenticated Cell Cultures (ECACC) Accession No. 85110503. Retrieved May 2, 2018 (3 pages).
UniProtKB Accession No. P05186. Retrieved May 2, 2018 (19 pages).
UniProtKB Accession No. P01857. Retrieved May 2, 2018 (13 pages).
Belkhouribchia et al., "Case Report: Osteomalacia with low alkaline phosphatase: a not so rare condition with important consequences," BMJ Case Rep. doi: 10.1136/bcr-2015-212827 (2016) (4 pages).
Berkseth et al., "Clinical spectrum of hypophosphatasia diagnosed in adults," Bone. 54(1):21-7 (2013).
Bianchi, "Hypophosphatasia: an overview of the disease and its treatment," Osteoporos Int. 26(12):2743-57; DOI 10.1007/s00198-015-3272-1 (2015) (15 pages).
Bobryshev et al., "Role of bone-type tissue-nonspecific alkaline phosphatase and PHOSPO1 in vascular calcification," Curr Pharm Des. 20(37):5821-8 (2014).
Bowden et al., "Asfotase alfa treatment for 1 year in a 16 year-old male with severe childhood hypophosphatasia," Osteoporos Int. 29(2):511-5; DOI: 10.1007/s00198-017-4267-x (2018) (5 pages).
Briot et al., "Adult hypophosphatasia," Curr Opin Rheumatol. 28(4):448-51 (2016).
Buchet et al., "Multisystemic functions of alkaline phosphatases," Methods Mol Biol. 1053:27-51 (2013).
Deeb et al., "Could alerting physicians for low alkaline phosphatase levels be helpful in early diagnosis of hypophosphatasia?," J Clin Res Pediatr Endocrinol. 10(1):19-24 (2018).
Hofmann et al., "Recombinant enzyme replacement therapy in hypophosphatasia," Subcell Biochem. 76:323-41 (2015).
Hofmann et al., "Asfotase alfa: enzyme replacement for the treatment of bone disease in hypophosphatasia," Drugs Today (Barc). 52(5):271-85 (2016).
Kitaoka et al., "Safety and efficacy of treatment with asfotase alfa in patients with hypophosphatasia: results from a Japanese clinical trial," Clin Endocrinol (Oxf). 87(1):10-19 (epub pp. 1-10) (2017).
Linglart et al., "Hypophosphatasia," Curr Osteoporos Rep. 14(3):95-105; DOI 10.1007/s11914-016-0309-0 (2016) (11 pages).
Mornet, "Hypophosphatasia," Metabolism. 82:142-155; DOI: 10.1016/j.metabol.2017.08.013 (2018) (30 pages).
Mornet, "Molecular genetics of hypophosphatasia and phenotype-genotype correlations," Subcell Biochem. 76:25-43 (2015).
Okazaki et al., "Lethal hypophosphatasia successfully treated with enzyme replacement from day 1 after birth," Eur J Pediatr. 175(3):433-7; DOI 10.1007/s00431-015-2641-2 (2016) (5 pages).
Park et al., "First Korean case of infantile hypophosphatasia with novel mutation in ALPL and literature review," Ann Clin Lab Sci. 46(3):302-7 (2016).
Phillips et al., "Physical therapy management of infants and children with hypophosphatasia," Mol Genet Metab. 119(1-2):14-9 (2016).
Rockman-Greenberg, "Hypophosphatasia," Pediatr Endocrinol Rev. 10 Suppl 2:380-8 (2013) (Abstract only).
Rodriguez et al., "Respiratory mechanics in an infant with perinatal lethal hypophosphatasia treated with human recombinant enzyme replacement therapy," Pediatr Pulmonol. 47(9):917-22 (2012).
Saraff et al., "A diagnostic algorithm for children with low alkaline phosphatase activities: lessons learned from laboratory screening for hypophosphatasia," J Pediatr. 172:181-6 (2016) (7 pages).
Sather, "008-case study: 3 year old female with hypophosphatasia, treated with asfotase alfa replacement," Journal of Pediatric Nursing. 34:104 (2017).
Schmidt et al., "Hypophosphatasia: What is currently available for treatment?" Internist (Berl). 57(12):1145-1154 (2016) (Article in German) (English abstract).
Schmidt et al., "Clinical, radiographic and biochemical characteristics of adult hypophosphatasia," Osteoporos Int. 28(9):2653-2662 (2017).
Scott, "Asfotase alfa in perinatal/infantile-onset and juvenile-onset hypophosphatasia: a guide to its use in the USA," BioDrugs. 30(1):41-8 (2016).
Scott, "Asfotase alfa: a review in paediatric-onset hypophosphatasia," Drugs. 76(2):255-62 (2016).
Shapiro et al., "Hypophosphatasia in adults: clinical assessment and treatment considerations," J Bone Miner Res. 32(10):1977-1980 (2017).
Siller et al., "Alkaline phosphatase: discovery and naming of our favorite enzyme," J Bone Miner Res. 33(2):362-4 (2018).

(56) References Cited

OTHER PUBLICATIONS

Takahashi et al., "Parental serum alkaline phosphatase activity as an auxiliary tool for prenatal diagnosis of hypophosphatasia," Prenat Diagn. 37(5):491-6 (2017).
Tenorio et al., "Molecular and clinical analysis of ALPL in a cohort of patients with suspicion of hypophosphatasia," Am J Med Genet A. 173(3):601-10 (2017).
Tsiantouli et al., "Hypophosphatasia," Rev Med Suisse. 13(559):855-8 (2017) (Article in French) (English Abstract Included).
Weber et al., "Burden of disease in adult patients with hypophosphatasia: Results from two patient-reported surveys," Metabolism. 65(10):1522-30 (2016).
Whyte, "Hypophosphatasia—aetiology, nosology, pathogenesis, diagnosis and treatment," Nat Rev Endocrinol. 12(4):233-46 (2016).
Whyte, "Hypophosphatasia: an overview for 2017," Bone. 102:15-25 (2017).
Whyte et al., "Hypophosphatasia: natural history study of 101 affected children investigated at one research center," Bone. 93:125-138 (2016).
Whyte et al., "Hypophosphatasia: validation and expansion of the clinical nosology for children from 25 years experience with 173 pediatric patients," Bone. 75:229-39 (2015).
International Search Report and Written Opinion for International Patent Application No. PCT/US2016/054013, dated Dec. 13, 2016 (19 pages).
Seefried et al., "Pharmacodynamic results from a phase 2a, randomized, multicenter, open-label, dose-ranging study of asfotase alfa in adults with pediatric hypophosphatasia," 100th Annual Meeting and Expo of the Endocrine Society, Mar. 17-20, 2018, Chicago, IL. (1 page).
International Search Report and Written Opinion for International Patent Application No. PCT/US2018/020859, mailed Jun. 19, 2018 (14 pages).
López-Delgado et al., "Abnormal bone turnover in individuals with low serum alkaline phosphatase," Osteoporosis Int. 29(9):2147-2150; doi: 10.1007/s00198-018-4571-0 (Supplementary information included) (2018) (6 pages).
Matsumoto et al., "Rescue of severe infantile hypophosphatasia mice by AAV-mediated sustained expression of soluble alkaline phosphatase," Hum Gene Ther. 22(11):1355-64 (2011).
Hofmann et al., "Clinical aspects of hypophosphatasia: an update," Clinic Rev Bone Miner Metab. 11(2):60-70 (2013).
Taketani et al., "Clinical and genetic aspects of hypophosphatasia in Japanese patients," Arch Dis Child. 99(3):211-5 (2014) (6 pages).
Whyte, "Physiological role of alkaline phosphatase explored in hypophosphatasia," Ann N Y Acad Sci. 1192:190-200 (2010).
Hofmann et al., "Compound heterozygosity of two functional null mutations in the ALPL gene associated with deleterious neurological outcome in an infant with hypophosphatasia," Bone. 55:150-7 (2013).
De Roo et al., "Infantile hypophosphatasia without bone deformities presenting with severe pyridoxine-resistant seizures," Molecular Genetics and Metabolism 111(3):404-7 (2014).
International Search Report and Written Opinion for International Patent Application No. PCT/US2015/064003, dated Mar. 31, 2016 (13 pages).
Lazdunski et al., "Structure-function relationships for some metalloalkaline phosphatases of *E. coli*," Eur J Biochem. 8(4):510-7 (1969).
Bobyr et al., "High-resolution analysis of Zn(2+) coordination in the alkaline phosphatase superfamily by EXAFS and x-ray crystallography," J Mol Biol. 415(1):102-17 (2012).
International Search Report and Written Opinion for International Patent Application No. PCT/US2017/036133, dated Aug. 24, 2017 (10 pages).
International Search Report and Written Opinion for International Patent Application No. PCT/US2018/025206, dated Jul. 3, 2018 (25 pages).
Kishnani et al., "OR26-3 Biochemical and Physical Function Outcomes in Adolescents and Adults with Hypophosphatasia Treated with Asfotase Alfa for up to 4 Years: Interim Results from a Phase II Study," ENDO 2016, Boston, MA, Apr. 3, 2016 (22 pages).
International Search Report and Written Opinion for International Patent Application No. PCT/US2017/025618, dated Jul. 11, 2017 (22 pages).
Li et al., "Standard reference for the six-minute-walk test in healthy children aged 7 to 16 years," Am J Respir Crit Care Med. 176(2):174-80 (2007).
Park et al., "Ex vivo assessment of contractility, fatigability and alternans in isolated skeletal muscles," J Vis Exp. 69:e4198 (2012) (8 pages).
Phillips et al., "FRI-224: Improved activities of daily living and physical function, with decreased pain, in children with hypophosphatasia treated for three years with asfotase alfa: results from the childhood health assessment questionnaire and the pediatric outcomes data collection instrument," The Endocrine Society's 97th Annual Meeting & Expo, San Diego, California, Mar. 5-8, 2015 (1 page).
Whyte et al., "Hypophosphatasia: Enzyme replacement therapy (asfotase alfa) decreases TNSALP substrate accumulation and improves functional outcomes in affected adolescents and adults," Bull Group Int Rech Sci Stomatol Odontol. 51(1):35 (2012).
Sugano et al., "Successful gene therapy in utero for lethal murine hypophosphatasia," Hum Gene Ther. 23(4):399-406 (2012).
International Search Report and Written Opinion for International Patent Application No. PCT/US2015/039973, dated Oct. 5, 2015 (12 pages).
Johnson et al., "Motor proficiency in children with neurofibromatosis type 1," Pediatr Phys Ther. 22(4):344-8 (2010).
Gates et al., "Effects of age, sex, and comorbidities on the pediatric outcomes data collection instrument (PODCI) in the general population," J Pediatr Orthop. 35(2):203-9 (2015).
International Search Report and Written Opinion for International Patent Application No. PCT/US2016/049983, dated Nov. 29, 2016 (12 pages).
International Search Report and Written Opinion for International Patent Application No. PCT/US2016/015366, dated Aug. 9, 2016 (14 pages).
Extended European Search Report for European Application No. 18173111.8, dated Aug. 21, 2018 (9 pages).
"Highly Specialised Technology Evaluation: Asfotase alfa for treating paediatric-onset hypophosphatasia [ID 758]," Oct. 21, 2015, <https://www.nice.org.uk/guidance/hst6/documents/committee-papers-8>, (99 pages).
Tomazos et al., "Determination of the Minimal Clinically Important Difference in the Six-Minute Walk Test for Patients with Hypophosphatasia," European Society for Paediatric Endocrinology, 55th Annual ESPE, Paris, France, Sep. 10-12, 2016, <http://abstracts.eurospe.org/hrp/0086/hrp0086FC2.5.htm>, (4 pages).
International Search Report and Written Opinion for International Application No. PCT/US18/26868, dated Sep. 7, 2018 (30 pages).
Sequence 4, U.S. Appl. No. 12/599,679, Retrieved Nov. 17, 2018 (2 pages).
Agochukwu et al., "Hearing loss in syndromic craniosynostoses: introduction and consideration of mechanisms," available in PMC Aug. 13, 2014, published in final edited form as: Am J Audiol. 23(2): 135-41 (2014) (13 pages).
Balasubramaniam et al., "Perinatal hypophosphatasia presenting as neonatal epileptic encephalopathy with abnormal neurotransmitter metabolism secondary to reduced co-factor pyridoxal-5'-phosphate availability," J Inherit Metab Dis. 33(Suppl 3):S25-33 (2010).
Barcia et al., "Infantile hypophosphatasia: treatment options to control hypercalcemia, hypercalciuria, and chronic bone demineralization," J Pediatr. 130(5):825-8 (1997).
Barvencik et al., "Skeletal mineralization defects in adult hypophosphatasia—a clinical and histological analysis," Osteoporosis Int. 22(10):2667-75 (2011).
Baumgartner-Sigl et al., "Pyridoxine-responsive seizures as the first symptom of infantile hypophosphatasia caused by two novel missense mutations (c.677T>C, p.M226T; c.1112C>T, p.T371I) of the tissue-nonspecific alkaline phosphatase gene," Bone. 40(6):1655-61 (2007).

(56) References Cited

OTHER PUBLICATIONS

Beck et al., "Whole-body MRI in the childhood form of hypophosphatasia," Rheumatol Int. 31(10):1315-20 (2011).
Beederman et al., "Molecular basis of cranial suture biology and disease: osteoblastic and osteoclastic perspectives," Genes Dis. 1(1):120-5 (2014).
Boulet et al., "A population-based study of craniosynostosis in metropolitan Atlanta, 1989-2003," Am J Med Genet A. 146A(8): 984-91 (2008).
Chan et al., "Endoscope-assisted versus open repair of craniosynostosis: a comparison of perioperative cost and risk," J Craniofac Surg. 24(1): 170-4 (2013).
Choi et al., "Craniosynostosis in growing children: pathophysiological changes and neurosurgical problems," J Korean Neurosurg Soc. 59(3):197-203 (2016).
Chong et al., "Minimally invasive suturectomy and postoperative helmet therapy: advantages and limitations," J Korean Neurosurg Soc. 59(3):227-32 (2016).
Clarke, "Normal bone anatomy and physiology," Clin J Am Soc Nephrol. 3 Suppl 3: S131-9 (2008).
Colantonio et al., "Closing the gaps in pediatric laboratory reference intervals: a CALIPER database of 40 biochemical markers in a healthy and multiethnic population of children," Clin Chem. 58(5):854-68 (2012).
Collmann et al., "Neurosurgical aspects of childhood hypophosphatasia," Childs Nerv Syst. 25(2):217-23 (2009).
Czerwinski et al., "Major morbidity and mortality rates in craniofacial surgery: an analysis of 8101 major procedures," Plast Reconstr Surg. 126(1):181-6 (2010).
Eade et al., "Pyrophosphate arthropathy in hypophosphatasia," Ann Rheum Dis. 40(2):164-70 (1981).
Esparza et al., "Complications in the surgical treatment of craniosynostosis and craniofacial syndromes: apropos of 306 transcranial procedures," Childs Nerv Syst. 24(12):1421-30 (2008).
Esparza et al., "Surgical treatment of isolated and syndromic craniosynostosis. Results and complications in 283 consecutive cases," Neurocirugia. 19(6):509-29 (2008).
Fraser, "Hypophosphatasia," Am J Med. 22(5):730-46 (1957).
Garber et al., "Comparing outcomes and cost of 3 surgical treatments for sagittal synostosis: a retrospective study including procedure-related cost analysis," Neurosurgery. 81(4):680-7 (2017).
Ginelliová et al., "Sudden death associated with syndromic craniosynostosis," Forensic Sci Med Pathol. 12(4):506-9 (2016).
Greenwood et al., "Familial incidence and associated symptoms in a population of individuals with nonsyndromic craniosynostosis," Genet Med. 16(4):302-10 (2014).
Guañabens et al., "Calcific periarthritis as the only clinical manifestation of hypophosphatasia in middle-aged sisters," J Bone Miner Res. 29(4):929-34 (2014).
Herring, "Mechanical influences on suture development and patency," Front Oral Biol. 12:41-56 (2008).
Hollis et al., "Current concepts in hypophosphatasia: case report and literature review," Int J Paediatr Dent. 23(3):153-159 (2013).
Hwang et al., "Update of diagnostic evaluation of craniosynostosis with a focus on pediatric systematic evaluation and genetic studies," J Korean Neurosurg Soc. 59(3):214-8 (2016).
Johnson et al., "Craniosynostosis," Eur J Hum Genet. 19(4):369-76 (2011).
Kabbani et al., "Craniosynostosis," Am Fam Physician. 69(12):2863-70 (2004).
Katsianou et al., "Signaling mechanisms implicated in cranial sutures pathophysiology: craniosynostosis," BBA Clin. 6:165-76 (2016).
Khanna et al., "Pictorial essay: The many faces of craniosynostosis," retrieved from <www.ncbi.nlm.nih.gov/pmc/articles/PMC3056371/> on Sep. 10, 2017, Indian J Radiol Imaging. 21(1):49-56 (2011) (8 pages).
Kim et al., "Craniosynostosis: Updates in radiologic diagnosis," J Korean Neurosurg Soc. 59(3):219-26 (2016).

Kozlowski et al., "Hypophosphatasia. Review of 24 Cases," Pediatr Radiol. 5(2):103-17 (1976).
Krakow et al., "Clinical and radiographic delineation of Bent Bone Dysplasia-FGFR2 type or Bent Bone Dysplasia with Distinctive Clavicles and Angel-shaped Phalanges," Am J Med Genet A. 170(10):2652-61 (2016).
Mathijssen, "Guideline for care of patients with the diagnoses of craniosynostosis: working group on craniosynostosis," J Craniofac Surg. 26(6):1735-807 (2015).
Merrill et al., "Bent bone dysplasia-FGFR2 type, a distinct skeletal disorder, has deficient canonical FGF signaling," Am J Hum Genet. 90(3):550-7 (2012).
Millán, "The role of phosphatases in the initiation of skeletal mineralization," Calcif Tissue Int. 93(4):299-306 (2013).
Miller et al., "Ultrasound diagnosis of craniosynostosis," Cleft Palate Craniofac J. 39(1):73-80 (2002).
Millichap, "Cognitive Development of Children with Craniosynostosis," Pediatr Neurol Briefs. 29(6):47 (2015).
Mohn et al., "Hypophosphatasia in a child with widened anterior fontanelle: lessons learned from late diagnosis and incorrect treatment," Acta Paediatr. 100(7):e43-6 (2011).
Mornet et al., "A molecular-based estimation of the prevalence of hypophosphatasia in the European population," Ann Hum Genet. 75(3):439-45 (2011).
Nakamura-Utsunomiya et al., "Clinical characteristics of perinatal lethal hypophosphatasia: a report of 6 cases," Clin Pediatr Endocrinol. 19(1):7-13 (2010).
Oginni et al., "Radiological and biochemical resolution of nutritional rickets with calcium," Arch Dis Child. 88(9):812-17 (2003).
Opperman, "Cranial sutures as intramembranous bone growth sites," Dev Dyn. 219(4):472-85 (2000).
Reginato et al., "Musculoskeletal manifestations of osteomalacia and rickets," Best Pract Res Clin Rheumatol. 17(6):1063-80 (2003).
Rodgers et al., "Spring assisted cranioplasty for the correction of non-syndromic scaphocephaly: a quantitative analysis of 100 consecutive cases," Plast Reconstr Surg. 140(1):125-34 (2017).
Rottgers et al., "Outcomes of endoscopic suturectomy with post-operative helmet therapy in bilateral coronal craniosynostosis," J Neurosurg Pediatr. 18(3):281-6 (2016).
Rozovsky et al., "Cranial ultrasound as a first-line imaging examination for craniosynostosis," Pediatrics. 137(2):e20152230 (2016) (9 pages).
Sabbagh et al., "Hypophosphatemia leads to rickets by impairing caspase-mediated apoptosis of hypertrophic chondrocytes," Proc Natl Acad Sci U S A. 102(27):9637-42 (2005).
Sakamoto et al., "Physiological changes and clinical implications of syndromic craniosynostosis," J Korean Neurosurg Soc. 59(3):204-13 (2016).
Salva et al., "Signaling networks in joint development," Dev Dyn. 246(4):262-74 (2017).
Seshia et al., "Myopathy with hypophosphatasia," Arch Dis Child. 65(1):130-1 (1990).
Shah et al., "Sudden infant death in a patient with FGFR3 P250R mutation," Am J Med Genet A. 140A(24):2794-6 (2006).
Sharma et al., "Bilateral femoral neck fractures in a young patient suffering from hypophosphatasia, due to a first time epileptic seizure," J Orthop Case Rep. 5(3):66-8 (2015).
Sharma, "Craniosynostosis," Indian J Plast Surg. 46(1):18-27 (2013).
Silver et al., "Pulmonary hypoplasia in neonatal hypophosphatasia," Pediatr Pathol. 8(5):483-93 (1988) (12 pages).
Thacher et al., "Radiographic scoring method for the assessment of the severity of nutritional rickets," J Trop Pediatr. 46(3):132-9 (2000).
Thurner et al., "Osteopontin deficiency increases bone fragility but preserves bone mass," Bone. 46(6):1564-73 (2010).
Tokumaru et al., "Skull base and calvarial deformities: association with intracranial changes in craniofacial syndromes," Am J Neuroradiol. 17(4):619-30 (1996).
Watanabe et al., "Prevalence of c. 1559delT in ALPL, a common mutation resulting in the perinatal (lethal) form of hypophosphatasia in Japanese and effects of the mutation on heterozygous carriers," J Hum Genet. 56(2):166-8 (2011).

(56) References Cited

OTHER PUBLICATIONS

Whyte et al., "Adult hypophosphatasia with chondrocalcinosis and arthropathy: variable penetrance of hypophosphatasemia in a large Oklahoma kindred," Am J Med. 72(4):631-41 (1982).
Whyte et al., "Adult hypophosphatasia treated with teriparatide," J Clin Endocrinol Metab. 92(4):1203-8 (2007).
Whyte et al., "Rickets and osteomalacia," Medicine. 37(9):483-8 (2009).
Zaleckas et al., "Diagnosis and treatment of craniosynostosis: Vilnius team experience," Acta Med Litu. 22(2):111-21 (2015).
Anderson, "Mechanism of Mineral Formation in Bone," *Pathology Reviews*. Emanuel Rubin and Ivan Damjanov (eds.), 13-23 (1990).
Whyte, Chapter 73: Hypophosphatasia: Nature's Window on Alkaline Phosphatase Function in Humans, *Principles of Bone Biology*, vol. 1, Third Edition. John P. Bilezikian, Lawrence G. Raisz and T. John Martin (eds.), 1573-98 (2008).
Whyte, Chapter 22: Hypophosphatasia, *Genetics of Bone Biology and Skeletal Disease*. Rajesh V. Thakker, Michael P. Whyte, John A. Eisman and Takashi Igarashi (eds.), 337-360 (2013).
Del Angel et al., "Birth prevalence estimation of severe Hypophosphatasia in European populations using large-scale protein-coding genetic variation databases," American Society of Human Genetics 66th Annual Meeting, Oct. 18-22, Vancouver, Canada. Poster abstract 1670T (2016) (2 pages).
Rockman-Greenberg et al., "Hypophosphatasia: Enzyme Replacement with ENB-0040, a Bone-Targeted Human Recombinant Tissue Nonspecific Alkaline Phosphatase (TNSALP) Fusion Protein," American College of Medical Genetics, 16th Annual Clinical Genetics Meeting, Mar. 25-29, Tampa, Florida (2009) (1 page).
Simmons, "Best Practices In: Recognizing and Diagnosing Hypophosphatasia," Clinical Endocrinology News. <https://www.mdedge.com/sites/default/files/issues/articles/Alexion_10_11_Final_Web.pdf>, published Sep. 30, 2013, retrieved on Mar. 27, 2019 (8 pages).
Weber et al., "Burden of disease in children with hypophosphatasia: results from patient-reported surveys," 7th International Conference on Children's Bone Health, Jun. 27-30, Salzburg, Austria. *Bone Abstracts*. 4: P119 (2015) (3 pages).
Whyte et al., "Asfotase alfa: Sustained Efficacy and Tolerability in Infants and Young Children with Life-Threatening Hypophosphatasia," 2014 Pediatric Academic Societies and Asian Society for Pediatric Research Joint Meeting, May 3-6, Vancouver, BC, Canada. Poster 69 (2014) (1 page).
Whyte et al., "Hypophosphatasia: A Retrospective Natural History Study of the Severe Perinatal and Infantile Forms," 2014 European Calcified Tissue Society Congress, May 17-20, Prague, Czech Republic. Poster P364 (2014) (1 page).
Whyte et al., "A retrospective, multi-national, non-interventional, natural history study of the childhood form of hypophosphatasia," ENDO 2015: The Endocrine Society Annual Meeting, Mar. 5-8, San Diego, California. Abstract LB-OR01-4 (2015) (2 pages).
Stoll et al., "Severe hypophosphatasia due to mutations in the tissue-nonspecific alkaline phosphatase (TNSALP) gene," Genet Couns. 13(3):289-95 (2002).
Mornet, "Hypophosphatasia," Best Pract Res Clin Rheumatol. 22(1):113-27 (2008).
Kajdic et al., "Craniosynostosis—Recognition, clinical characteristics, and treatment," Bosn J Basic Med Sci. 18(2):110-6 (2018).
Dortschy et al., "Bevölkerungsbezogene verteilungswerte ausgewählter laborparameter aus der studie zur gesundheit von kindern und jugendlichen in Deutschland (KiGGS)," Robert Koch Institute (2009) (136 pages).
Communication pursuant to Rule 164(2)(b) and Article 94(3) EPC for European Patent Application 16707571.2, dated Feb. 26, 2019 (12 pages).

Fong et al., "Hypocalcemia: Updates in diagnosis and management for primary care," Can Fam Physician. 58(2):158-62 (2012).
Makras et al., "Medical treatment of Hypercalcaemia," Hormones. 8(2):83-95 (2009).
Official Action for Russian Patent Application No. 2017123540, dated Jul. 8, 2019 (15 pages).
Di Rocco et al., "Craniosynostosis and hypophosphatasia," Arch Pediatr. 24(5S2):5S89-5S92 (2017).
Official Action for Japanese Application No. 2017-539393, dated Sep. 17, 2019 (7 pages).
Whyte et al., "Natural history of perinatal and infantile hypophosphatasia: a retrospective study," J Pediatr. 209:116-124.e4 (2019) (13 pages).
Leung et al., "Outcome of perinatal hypophosphatasia in manitoba mennonites: a retrospective cohort analysis," JIMD Rep. 11:73-78 (2013).
Taketani et al., Chapter 9: Hypophosphatasia, Human Pathobiochemistry. T. Oohashi et al. (eds.), 91-100 (2019).
Morrison et al., "Mitigation of tracheobronchomalacia with 3D-printed personalized medical devices in pediatric patients," available in PMC Apr. 29, 2016, published in final edited form as: Sci Transl Med. 7(285):285ra264 (2015) (23 pages).
Whyte et al., "Asfotase alfa for infants and young children with hypophosphatasia: 7 year outcomes of a single-arm, open-label, phase 2 extension trial," Lancet Diabetes Endocrinol. 7(2):93-105 (2019) (52 pages).
Mornet, "The tissue nonspecific alkaline phosphatase gene mutations database," <http://www.sesep.uvsq.fr/03_hypo_mutations.php>, accessed Oct. 9, 2019 (14 pages).
Hancarova et al., "Hypophosphatasia due to uniparental disomy," Bone. 81:765-766 (2015) (2 pages).
Carden et al., "Tracheomalacia and tracheobronchomalacia in children and adults: an in-depth review," Chest. 127(3):984-1005 (2005).
Murgu et al., "Tracheobronchomalacia and excessive dynamic airway collapse," Respirology. 11(4):388-406 (2006).
Abrams et al. "Calcium and Vitamin D Requirements of Enterally Fed Preterm Infants," Pediatrics. 131(5): e1676-e1683 (2013) (9 pages).
International Search Report and Written Opinion for International Application No. PCT/US2019/045963, dated Jan. 30, 2020 (26 pages).
Li et al., "Timing of the initiation of bisphosphonates after surgery for fracture healing: a systematic review and meta-analysis of randomized controlled trials," Osteoporos Int. 26(2):431-41 (2015) (11 pages).
Park et al., "The effect of alendronate loaded biphasic calcium phosphate scaffolds on bone regeneration in a rat tibial defect model," Int J Mol Sci. 16(11):26738-53 (2015) (17 pages).
Rodionova et al. "Hypophosphatasia in adults: clinical cases and literature review," Osteoporosis and Bone Diseases. 18(2):25-7 (2015) (4 pages).
Search Report and Translation for Russian Application No. 2018109368, dated Feb. 5, 2020 (4 pages).
Wang et al. "The effects of tissue-non-specific alkaline phosphatase gene therapy on craniosynostosis and craniofacial morphology in the FGFR2$^{c342Y/+}$ mouse model of Crouzon craniosynostosis," Orthod Craniofac Res. 18 Suppl. 1:196-206 (2015).
Whyte et al., "Hypophosphatasia (HPP) in children: enzyme replacement therapy (EzRT) using bone-targeted, tissue-nonspecific alkaline phosphatase (TNSALP)," Ann Neurol. 68(Suppl 14):S70 Abstract WIP-28 (2010) (1 page).
International Preliminary Report on Patentability for International Patent Application No. PCT/US2016/049983, dated Sep. 11, 2018 (9 pages).

\* cited by examiner

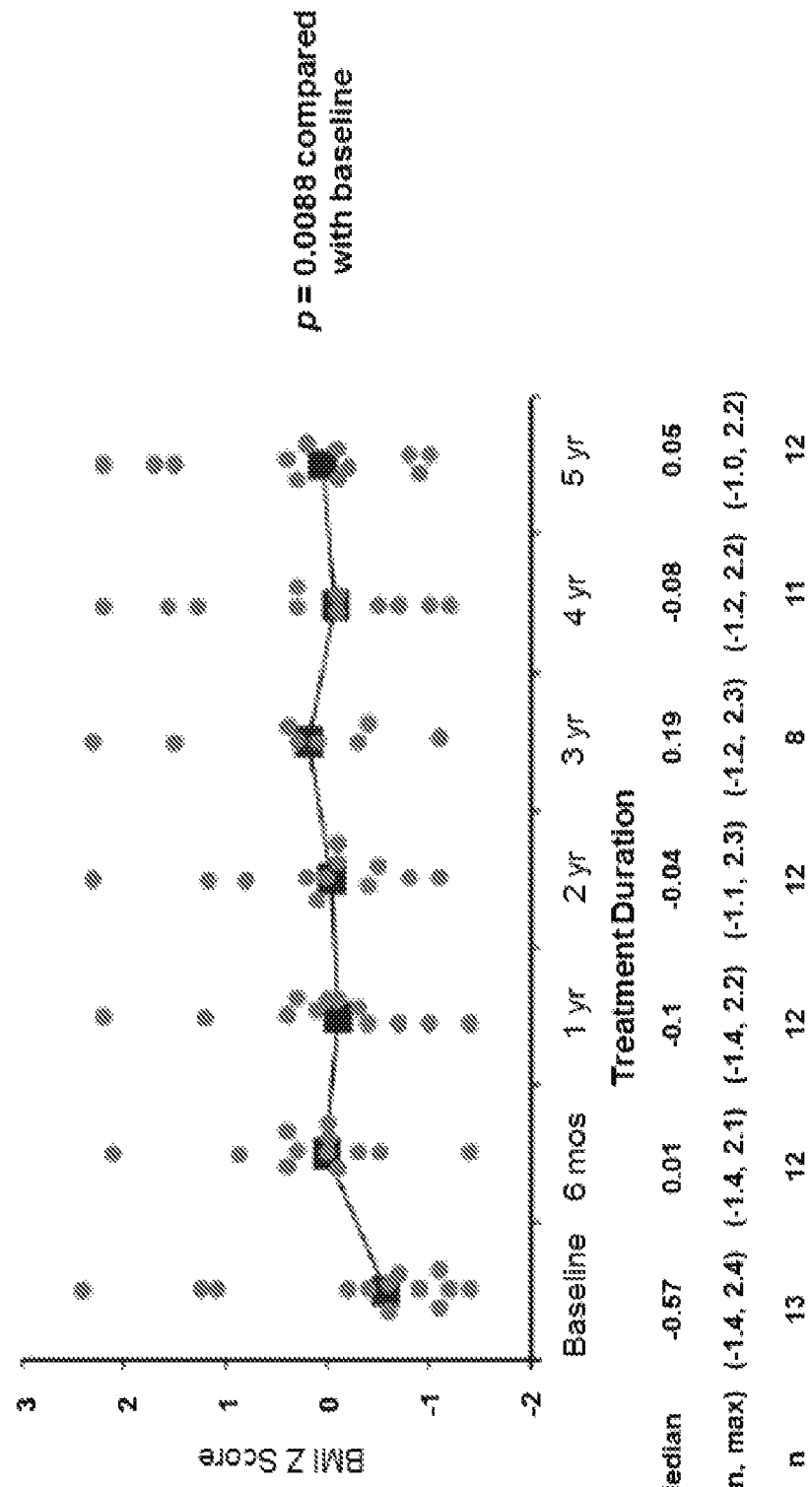

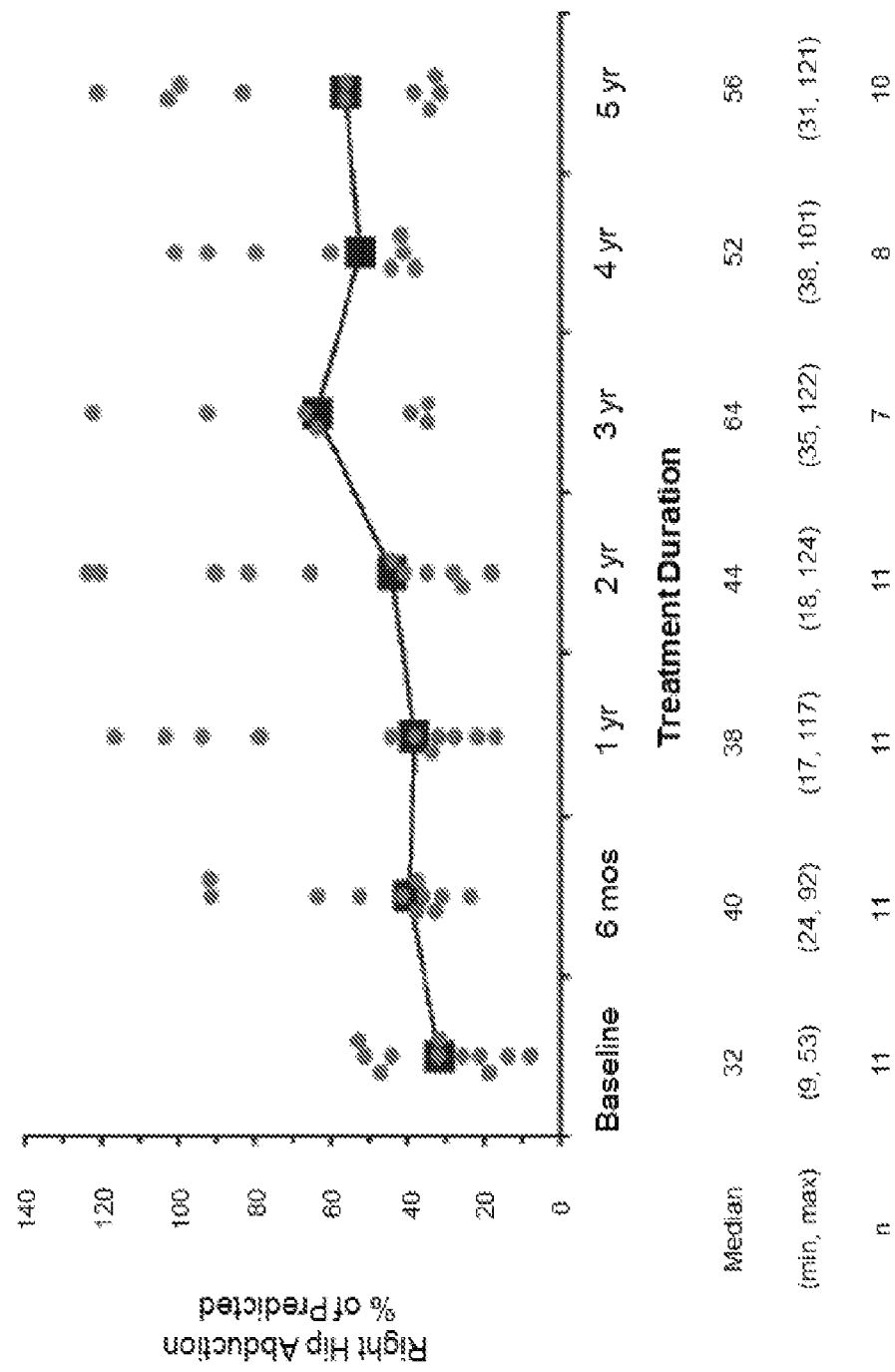

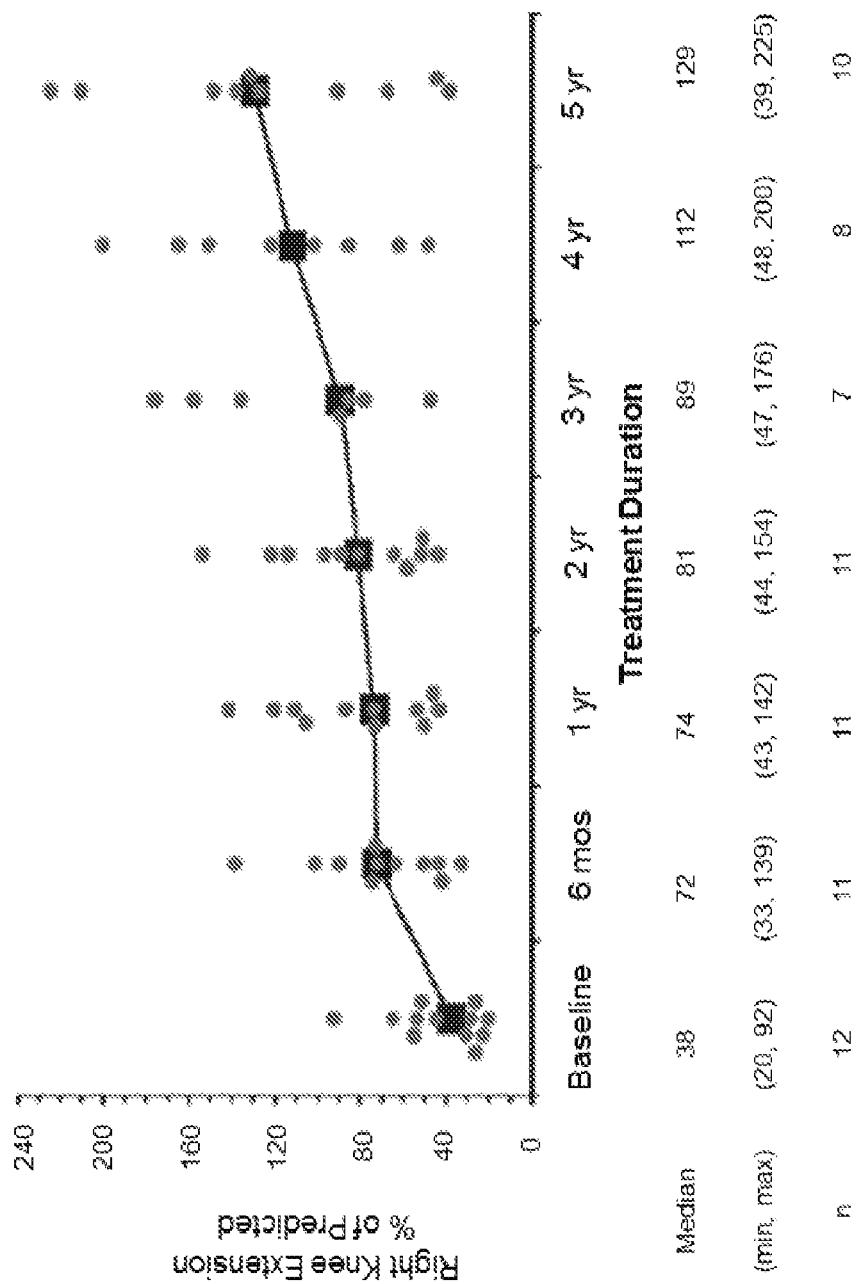

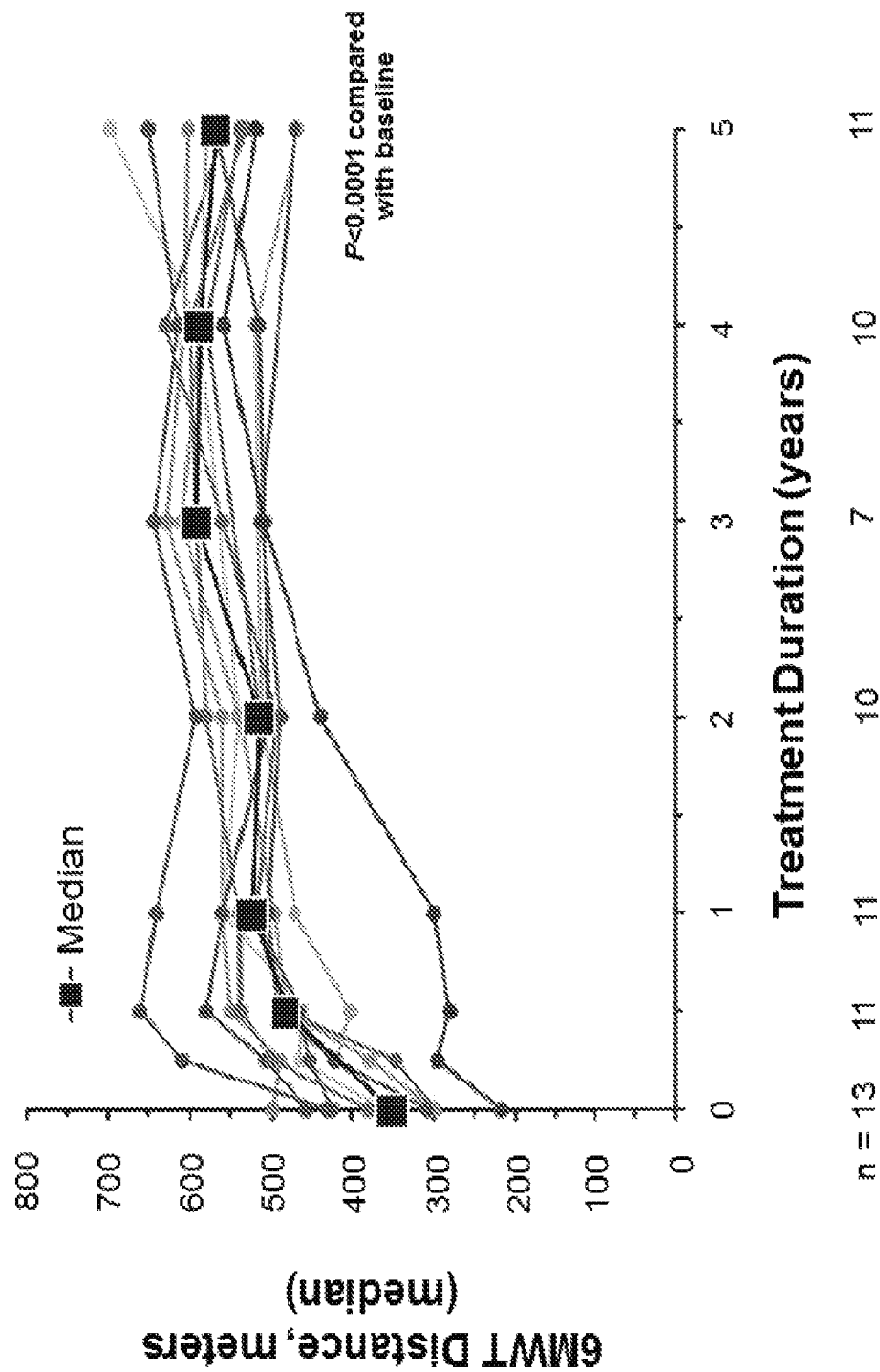

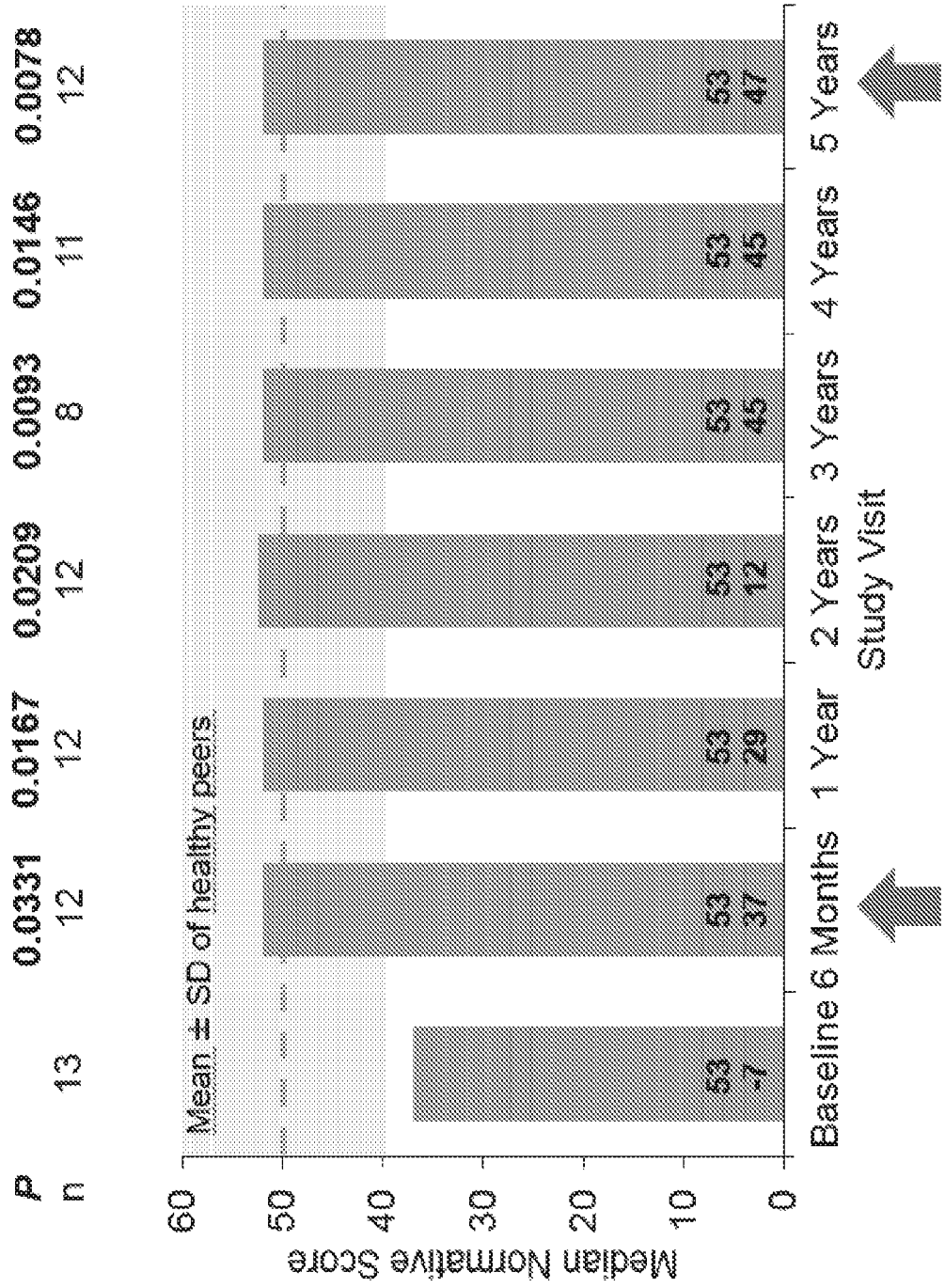

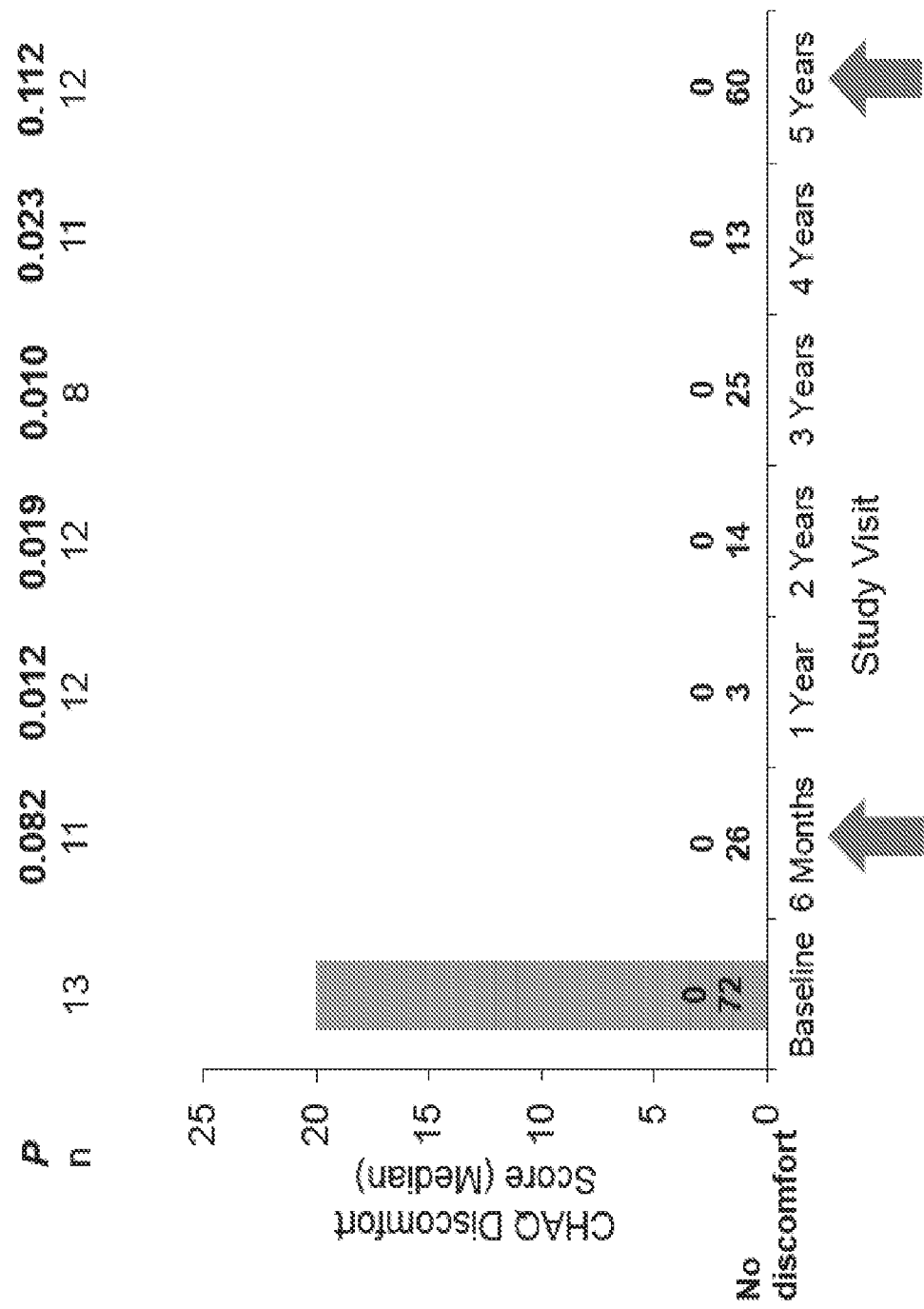

METHODS FOR TREATING HYPOPHOSPHATASIA IN CHILDREN

FIELD

The disclosure relates to methods for treating hypophosphatasia (HPP).

BACKGROUND

Hypophosphatasia (HPP) is a rare, heritable skeletal disease with an incidence of 1 per 100,000 births for the most severe forms of the disease. HPP is often fatal when observed at birth, having an infant mortality rate of ~70%. Severely affected patients often die in infancy from respiratory insufficiency due to progressive chest deformity.

The disorder results from loss-of-function mutations in the gene coding for tissue-nonspecific alkaline phosphatase (TNALP). HPP leads to a remarkable range of symptoms and severity, from rickets (osteomalacia) to almost complete absence of bone mineralization in utero. Most patients exhibit the characteristics of skeletal changes, short stature, painful lower limbs, gait disturbance, and premature shedding of teeth. For instance, infantile symptoms of HPP can include inadequate weight gain, the appearance of rickets, impaired skeletal mineralization, progressive skeletal demineralization, rib fractures, and chest deformity, while childhood symptoms of HPP can include short stature and skeletal deformities, such as bowed legs and enlarged wrists, knees, and ankles as a result of flared metaphyses. Due to physical impairments associated with HPP, patients afflicted with HPP often exhibit a decreased ability or inability to perform routine activities that healthy patients perform on a daily basis without requiring assistance.

Notably, the treatment of HPP, particularly the physical impairments associated with HPP, for an extended period of time, is unknown. Furthermore, the efficacy of HPP treatments to alleviate pain associated with HPP is unknown. Thus, there exists a need for methods that can be used to treat HPP in patients, such as children having HPP, for extended durations so that these patients can live with decreased physical impairments and decreased pain.

SUMMARY

The disclosure relates to methods to identify children having hypophosphatasia (HPP; e.g., children of about 5 to about 12 years of age having HPP) for treatment with a soluble alkaline phosphatase (sALP; such as TNALP, for example the sALP polypeptide of SEQ ID NO: 1 or a polypeptide variant having at least 95% sequence identity to the sequence of SEQ ID NO: 1, e.g., asfotase alfa). Exemplary tests useful in the methods include (1) the Bruininks-Oseretsky Test of Motor Proficiency $2^{nd}$ Edition (BOT-2), (2) the Childhood Health Assessment Questionnaire (CHAQ), (3) the Pediatric Outcomes Data Collection Instrument (PODCI), (4) the Six Minute Walk Test (6MWT), (5) the Bayley Scales of Infant and Toddler Development, $3^{rd}$ Edition (BSID-III), and (6) the Peabody Developmental Motor Scales, 2nd Edition (PDMS-2).

The methods further include the use of one or more of the described tests (e.g., the BOT-2, the CHAQ, the 6MWT, the BSID-III, and/or the PDMS-2) singly or in combination to assess treatment efficacy using a sALP (such as TNALP, for example the sALP polypeptide of SEQ ID NO: 1 or a polypeptide variant having at least 95% sequence identity to the sequence of SEQ ID NO: 1, e.g., asfotase alfa) for a patient having HPP (e.g., a child of about 5 to about 12 years of age having HPP), in which improvements relative to a certain test score demonstrate that the sALP is effective for treating HPP. Additionally, methods may further include changing the dosage and/or frequency of sALP in order to determine the effective amount of the sALP to administer to a child having HPP (e.g., a child of about 5 to about 12 years of age).

A first aspect features a method of treating HPP in a child of about 5 to about 12 years of age having an average Bruininks-Oseretsky Test of Motor Proficiency $2^{nd}$ Edition (BOT-2) score of less than about 10 (e.g., an average BOT-2 strength score, an average BOT-2 running speed and agility score, and/or an average BOT-2 composite strength and agility score), which includes administering a soluble alkaline phosphatase (sALP) to the child at a dosage providing about 6 mg/kg/week of the sALP (e.g., asfotase alfa). The sALP may have an amino acid sequence with at least 95% sequence identity to the amino acid sequence of SEQ ID NO: 1. Administration of the sALP (e.g., asfotase alfa; SEQ ID NO: 1) results in an average increase in the BOT-2 strength score to about 10 to about 20 after a period of at least four years (e.g., at least five years, at least six years, at least seven years, at least eight years, at least nine years, at least ten years, or more than ten years (e.g., for the lifetime of the patient)).

The method includes using the BOT-2 score (e.g., an average BOT-2 strength score, an average BOT-2 running speed and agility score, and/or an average BOT-2 composite strength and agility score) to assess the child having HPP prior to administration of the sALP such as TNALP, for example the sALP polypeptide of SEQ ID NO: 1 or a polypeptide variant having at least 95% sequence identity to the sequence of SEQ ID NO: 1, e.g., asfotase alfa).

In particular, the method can feature treating HPP in a child of about 5 to about 12 years of age having an average BOT-2 strength score of less than 10, which includes administering a soluble alkaline phosphatase (sALP) to the child at a dosage providing about 6 mg/kg/week of the sALP (e.g., asfotase alfa). The sALP includes an amino acid sequence having at least 95% sequence identity to the amino acid sequence of SEQ ID NO: 1. Administration of the sALP (e.g., asfotase alfa; SEQ ID NO: 1) results in an average increase in the BOT-2 strength score to about 10 to about 20 after a period of at least four years (e.g., at least five years, at least six years, at least seven years, at least eight years, at least nine years, at least ten years, or more than ten years (e.g., for the lifetime of the patient)).

The average BOT-2 strength score of the child of the first aspect may be determined relative to a BOT-2 strength score of a child without HPP. In particular, the average BOT-2 strength score of the child may be determined from measurements of activities selected from the group consisting of sit-ups, V-ups, standing long jump, wall sit, and push-ups.

The child having an average BOT-2 strength score of less than 10 exhibits physical impairments relative to the child without HPP. Furthermore, the child exhibits a decrease in physical impairments after administration of the sALP (e.g., asfotase alfa; SEQ ID NO: 1), in which the decrease in physical impairments is sustained throughout administration of the sALP (e.g., asfotase alfa; SEQ ID NO: 1) to the child. Additionally, the average BOT-2 strength score of the child increases to about 12 to about 16 after treatment with the sALP.

Additionally, the method can feature treating HPP in a child of about 5 to about 12 years of age having an average BOT-2 running speed and agility score of less than 5 by administering a sALP (e.g., asfotase alfa; SEQ ID NO: 1) to the child at a dosage providing about 6 mg/kg/week of the sALP. The sALP may have an amino acid sequence with at least 95% sequence identity to the amino acid sequence of SEQ ID NO: 1. Administration of the sALP (e.g., asfotase alfa; SEQ ID NO: 1) results in an average increase in the BOT-2 running speed and agility score to about 5 to about 20 after a period of at least four years (e.g., at least five years, at least six years, at least seven years, at least eight years, at least nine years, at least ten years, or more than ten years (e.g., for the lifetime of the patient)).

The average BOT-2 running speed and agility score of the child of the second aspect may be determined relative to a BOT-2 running speed and agility score of a child without HPP. In particular, the average BOT-2 running speed and agility score of the child may be determined from measurements of activities selected from the group consisting of stepping over a balance beam, shuttle run, two-legged side hop, and one-legged side hop.

The child having an average BOT-2 running speed and agility score of less than 5 exhibits physical impairments relative to the child without HPP. Furthermore, the child exhibits a decrease in physical impairments after administration of the sALP (e.g., asfotase alfa; SEQ ID NO: 1), in which the decrease in physical impairments is sustained throughout administration of the sALP to the child. Additionally, the average BOT-2 running speed and agility score of the child increases to about 9 to about 13 after treatment with the sALP.

A second aspect features a method of treating HPP in a child of about 5 to about 12 years of age having an average Childhood Health Assessment Questionnaire (CHAQ) disability index and/or discomfort score of greater than about 0.8 by administering a sALP (e.g., asfotase alfa; SEQ ID NO: 1) to the child at a dosage providing about 6 mg/kg/week of the sALP (e.g., asfotase alfa; SEQ ID NO: 1). The sALP may be an amino acid sequence with at least 95% sequence identity to the amino acid sequence of SEQ ID NO: 1. Administration of the sALP (e.g., asfotase alfa; SEQ ID NO: 1) results in an average decrease in the CHAQ disability index and/or discomfort score to about 0 to equal to or less than about 0.5 after a period of at least four (e.g., at least five years, at least six years, at least seven years, at least eight years, at least nine years, at least ten years, or more than ten years (e.g., for the lifetime of the patient)). The method includes using the CHAQ disability index and/or discomfort score to assess the child having HPP prior to administration of the sALP such as TNALP, for example the sALP polypeptide of SEQ ID NO: 1 or a polypeptide variant having at least 95% sequence identity to the sequence of SEQ ID NO: 1, e.g., asfotase alfa).

Additionally, the average CHAQ disability index and/or discomfort score of the child may be determined relative to a CHAQ disability index and/or discomfort score of a child without HPP. The child having an average CHAQ disability index and/or discomfort score of greater than 0.5 exhibits disability in activities of daily living (ADL) and pain relative to the child without HPP. For instance, the child exhibits an increase in ADL after administration of the sALP (e.g., asfotase alfa; SEQ ID NO: 1). The increase in ADL may be sustained throughout administration of the sALP (e.g., asfotase alfa; SEQ ID NO: 1) to the child. For example, administration of the sALP (e.g., asfotase alfa; SEQ ID NO: 1) to the child results in a decrease in pain, as determined using the CHAQ disability index and/or discomfort score. The decrease in pain is sustained throughout administration of the sALP to the child. Furthermore, the average CHAQ disability index and/or discomfort score of the child may decrease to about 0 to equal to or less than about 0.25.

A third aspect features a method of treating HPP in a child of about 5 to about 12 years of age having an average Pediatric Outcomes Data Collection Instrument (PODCI) transfer and mobility, sports and physical functioning, and/or pain score of less than about 40 by administering a sALP to the child at a dosage providing about 6 mg/kg/week of the sALP (e.g., asfotase alfa; SEQ ID NO: 1). The sALP may have an amino acid sequence with at least 95% sequence identity to the amino acid sequence of SEQ ID NO: 1. Administration of the sALP (e.g., asfotase alfa; SEQ ID NO: 1) results in an average increase in the PODCI transfer and mobility, sports and physical functioning, and/or pain score to about 40 to about 50 after a period of at least four years (e.g., at least five years, at least six years, at least seven years, at least eight years, at least nine years, at least ten years, or more than ten years (e.g., for the lifetime of the patient)). The method includes using the PODCI transfer and mobility, sports and physical functioning, and/or pain score to assess the child having HPP prior to administration of the sALP such as TNALP, for example the sALP polypeptide of SEQ ID NO: 1 or a polypeptide variant having at least 95% sequence identity to the sequence of SEQ ID NO: 1, e.g., asfotase alfa).

Additionally, the average PODCI transfer and mobility, sports and physical functioning, and/or pain score of the child of the third aspect may be determined relative to a PODCI transfer and mobility, sports and physical functioning, and/or pain score of a child without HPP. The child having an average PODCI transfer and mobility, sports and physical functioning, and/or pain score of less than 40 exhibits disability in ADL and pain relative to the child without HPP. For instance, administration of the sALP (e.g., asfotase alfa; SEQ ID NO: 1) to the child results in an increase in ADL, as determined using the PODCI transfer and mobility, sports and physical functioning, and/or pain score. The increase in ADL is sustained throughout administration of the sALP to the child. For example, the child may also exhibit a decrease in pain after administration of the sALP (e.g., asfotase alfa; SEQ ID NO: 1). The decrease in pain is sustained throughout administration of the sALP to the child.

A fourth aspect features a method of treating HPP in a child of about 5 to about 12 years of age by administering a sALP to the child at a dosage providing about 6 mg/kg/week of the sALP (e.g., asfotase alfa; SEQ ID NO: 1). The sALP can have an amino acid sequence with at least 95% sequence identity to the amino acid sequence of SEQ ID NO: 1. Administration of the sALP for a treatment period of at least one year (e.g., at least two years, at least three years, at least four years, at least five years, at least six years, at least seven years, at least eight years, at least nine years, at least ten years, or more than ten years (e.g., for the lifetime of the patient)) results in an average increase in a Six Minute Walk Test (6MWT) distance of the child relative to the 6MWT distance of the child prior to administration of the sALP.

For example, the average increase in the 6MWT distance is about 20 meters or greater (e.g., about 20 meters, about 25 meters, about 30 meters, about 35 meters, about 40 meters, about 45 meters, about 50 meters, about 55 meters, about 60 meters, about 65 meters, about 70 meters, about 75 meters, about 80 meters, about 85 meters, about 90 meters, about 95 meters, about 100 meters, or greater). The child can also exhibit an improvement in rickets as determined by the Rickets Severity Scale (RSS) after administration of the sALP. Additionally, the child can exhibit an increase in ADL after administration of the sALP, in which the ADL is determined by a CHAQ disability index score or a PODCI global function, transfer and mobility, or sports and physical functioning scale score.

In any of the above aspects, the child of about 5 to about 12 years of age exhibited an average Bayley Scales of Infant and Toddler Development, 3$^{rd}$ Edition (BSID-III) scaled score of less than about 2 at about 3 years of age or less than 3 years of age. Administration of the sALP (e.g., asfotase alfa; SEQ ID NO: 1) results in an average increase in the BSID-III scaled score to greater than about 5 after a five year period. The average BSID-III scaled score of the child may be determined relative to an average BSID-III scaled score of a child without HPP. In particular, the child having an average BSID-III scaled score of less than 2 exhibits delayed motor development relative to a child without HPP. For instance, the child exhibits an increase in motor development after administration of the sALP (e.g., asfotase alfa; SEQ ID NO: 1), in which the increase in motor development is sustained throughout administration of the sALP to the child, e.g., the average BSID-III scaled score increases to about 5 to about 7.

The average BSID-III scaled score of the child may be determined from measurements of activities selected from the group consisting of prehension, perceptual-motor integration, motor planning and speed, visual tracking, reaching, object grasping, object manipulation, functional hand skills, responses to tactile information, movement of the limbs and torso, static positioning, dynamic movement, balance, and motor planning.

In any of the above aspects, the child of about 5 to about 12 years of age exhibits an average Peabody Developmental Motor Scales, 2nd Edition (PDMS-2) standard score of about 5 at about 3 years of age or less than 3 years of age. Administration of the sALP (e.g., asfotase alfa; SEQ ID NO: 1) results in an average increase in the PDMS-2 standard score to about 7 after a period of at least four years. The average PDMS-2 standard score of the child may be determined relative to a PDMS-2 standard score of a child without HPP. In particular, the child having an average PDMS-2 standard score of about 5 exhibits delayed motor development relative to the child without HPP. For instance, the child exhibits an increase in motor development after administration of the sALP (e.g., asfotase alfa; SEQ ID NO: 1). The increase in motor development is sustained throughout administration of the sALP to the child.

For example, the average PDMS-2 standard score of the child may be determined from measurements of activities selected from the group consisting of crawling, walking, running, hopping, jumping forward, reflexes, balance, object manipulation, grasping, and visual-motor integration.

In any of the above aspects, the sALP (e.g., asfotase alfa; SEQ ID NO: 1) is formulated for daily or weekly administration, e.g., the sALP (e.g., asfotase alfa; SEQ ID NO: 1) is formulated for administration twice a week, three time a week, four times a week, five times a week, six times a week, or seven times a week. For example, the sALP (e.g., asfotase alfa; SEQ ID NO: 1) is formulated at a dosage of 2 mg/kg for administration three times a week, the sALP (e.g., asfotase alfa; SEQ ID NO: 1) is formulated at a dosage of 1 mg/kg for administration six times a week, or the sALP (e.g., asfotase alfa; SEQ ID NO: 1) is formulated at a dosage of 3 mg/kg for administration three times a week.

For any of the above aspects, the sALP (e.g., asfotase alfa; SEQ ID NO: 1) is administered for at least five years, at least six years, at least seven years, at least eight years, at least nine years, at least ten years, or for more than ten years (e.g., the sALP is administered for the lifetime of the patient).

In any of the above aspects, the sALP (e.g., asfotase alfa) includes or consists of the amino acid sequence of SEQ ID NO: 1.

For any of the above aspects, the method may further include determining sALP activity (e.g., asfotase alfa activity). The determination of sALP activity may include measuring at least one of phosphoethanolamine (PEA), inorganic pyrophosphate (PPi), and/or pyridoxal 5'-phosphate (PLP) in a serum and/or blood sample from the child.

In any of the above aspects, the sALP (e.g., asfotase alfa; SEQ ID NO: 1) is administered in an amount that is therapeutically effective to treat at least one symptom of HPP (e.g., rickets, premature loss of deciduous teeth, incomplete bone mineralization, elevated blood and/or urine levels of inorganic pyrophosphate (PR), elevated blood and/or urine levels of phosphoethanolamine (PEA), elevated blood and/or urine levels of pyridoxal 5'-phosphate (PLP), hypomineralization, rachitic ribs, hypercalciuria, short stature, skeletal deformity, waddling gait, bone pain, bone fracture, HPP-related seizure, inadequate weight gain, and/or calcium pyrophosphate dihydrate crystal deposition).

For any of the above aspects, the sALP (e.g., asfotase alfa; SEQ ID NO: 1) may be administered at an initial dosage of about 3 mg/kg/week and then increased to a dosage of about 6 mg/kg/week or more. Furthermore, the dosage may be increased to about 6 mg/kg/week or more after about three months to about nine months. Additionally, the dosage may be increased to about 9 mg/kg/week.

For any of the above aspects, the child may exhibit symptoms of HPP at birth or after birth (e.g., at five years of age or older).

In any of the above aspects, the child exhibits tolerability to administration of the sALP (e.g., asfotase alfa; SEQ ID NO: 1). For instance, the tolerability includes a lack or decreased incidence of adverse events selected from the group consisting of injection site erythema, decrease in hemoglobin, pyrexia, pneumonia, upper respiratory tract infection, craniosynostosis, otitis media, vomiting, constipation, diarrhea, tooth loss, nasopharyngitis, rash, dental carries, and irritability.

In any of the above aspects, the child may be one that does not exhibit serum calcium and/or phosphorus levels below the age-adjusted normal range. Additionally, the child may be one that does not exhibit symptoms of a treatable form of rickets. Furthermore, the child may be one that has not previously received treatment with a bisphosphonate.

For any of the above aspects, the method further includes performing radiographs of the child to determine an average Radiographic Global Impression of Change (RGI-C) score, in which the child exhibits an average RG1-C score of less than 2 prior to administration of the sALP (e.g., asfotase alfa; SEQ ID NO: 1). In particular, the average RGI-C score of the child may be determined relative to an average RGI-C score of a child without HPP. Preferably, the child exhibits increased bone density after administration of the sALP (e.g., asfotase alfa; SEQ ID NO: 1). The increase in bone density is sustained throughout administration of the sALP. For instance, the child exhibits an average RGI-C score of greater than 2.

For any of the above aspects, the method further includes determining weight and/or length of the child, in which a Z-score is determined from the weight and/or length of the child. Preferably, the child exhibits an improved Z-score for weight and/or length after administration of the sALP (e.g., asfotase alfa; SEQ ID NO: 1).

In any of the above aspects, the sALP (e.g., asfotase alfa; SEQ ID NO: 1) is formulated in a pharmaceutical composition, e.g., with a pharmaceutically acceptable carrier. For example, the pharmaceutically acceptable carrier is saline. The pharmaceutically acceptable carrier may include sodium chloride and sodium phosphate (e.g., the pharmaceutically acceptable carrier may contain about 150 mM sodium chloride and about 25 mM sodium phosphate).

In any of the above aspects, the pharmaceutical composition is formulated for subcutaneous, intramuscular, intravenous, oral, nasal, sublingual, intrathecal, or intradermal administration. In particular, the pharmaceutical composition is formulation for subcutaneous administration.

For any of the above aspects, the sALP (e.g., asfotase alfa; SEQ ID NO: 1) is physiologically active toward PEA, PPi, and PLP. For example, the sALP (e.g., asfotase alfa; SEQ ID NO: 1) is catalytically competent to improve skeletal mineralization in bone. Preferably, the sALP (e.g., asfotase alfa; SEQ ID NO: 1) is the soluble extracellular domain of an alkaline phosphatase.

In any of the above aspects, the child has not previously been administered the sALP (e.g., asfotase alfa; SEQ ID NO: 1).

Additionally, the child may have been continuously treated with the sALP (e.g., asfotase alfa; SEQ ID NO: 1), according to the treatment regimens described herein for a period of days (e.g., 1, 2, 3, 4, 5, 6, 7, 8, 9, 10, 15, 20, 25, 30, or more days), weeks (e.g., 1, 2, 3, 4, 5, 6, 7, 8, 9, 10, 15, 20, 25, 30, 35, 45, 50, or more weeks), months (e.g., 1, 2, 3, 4, 5, 6, 7, 8, 9, 10, 11, or 12 months), or years (e.g., 1, 2, 3, 4, 5, 6, 7, 8, 9, 10, 15, 20, 25, 30, or more years). Alternatively, the child may have been continuously treated with the sALP (e.g., asfotase alfa; SEQ ID NO: 1) for a period of days, weeks, months, or years, and then treatment with the sALP was discontinued for a period of days (e.g., 1, 2, 3, 4, 5, 6, 7, 8, 9, 10, 15, 20, 25, 30, or more days), weeks (e.g., 1, 2, 3, 4, 5, 6, 7, 8, 9, 10, 15, 20, 25, 30, 35, 45, 50, or more weeks), months (e.g., 1, 2, 3, 4, 5, 6, 7, 8, 9, 10, 11, or 12 months), or years (e.g., 1, 2, 3, 4, 5, 6, 7, 8, 9, 10, 15, 20, 25, 30, or more years).

Definitions

As used herein, "a" or "an" means "at least one" or "one or more" unless otherwise indicated. In addition, the singular forms "a", "an", and "the" include plural referents unless the context clearly dictates otherwise.

As used herein, "about" refers to an amount that is ±10% of the recited value and is preferably ±5% of the recited value, or more preferably ±2% of the recited value.

As used herein, "at least" refers to an amount that is ≤10% of the recited value and is preferably ≤5% of the recited value, or more preferably ≤2% of the recited value.

By "asfotase alfa" is meant a human TNALP (hTNALP) fusion protein formulated for the treatment of HPP. Asfotase alfa (STRENSIQ®, Alexion Pharmaceuticals, Inc.) is a fusion protein including a soluble glycoprotein of two identical polypeptide chains, in which each polypeptide chain includes amino acid residues 1-726 of SEQ ID NO: 1. The structure of each polypeptide chain includes the catalytic domain of hTNALP, the human immunoglobulin $G_1$ Fc domain, and a deca-aspartate peptide used as a bone targeting domain (the structure hTNALP-Fc-$D_{10}$). The two polypeptide chains are covalently linked by two disulfide bonds. Asfotase alfa has been approved under the trade name STRENSIQ® in the United States, Europe, Japan, Canada, Israel, Australia, and Korea.

As used herein, "average" refers to a numerical value expressing the mean or median of a data set. The mean of a data set is calculated by dividing the sum of the values in the set by their number. The median of a date set is calculated by determining the middle value in a list of odd numbers or by determining the mean of the two data values in the middle in a list of even numbers.

The terms "Bayley Scales of Infant and Toddler Development, $3^{rd}$ Edition" or "BSID-III" as used herein refer to a standardized series of measurements used to assess the motor (fine and gross), language (receptive and expressive), and cognitive development of patients, e.g., infants and toddlers. See Bayley, (2006). *Bayley scales of infant and toddler development: administration manual*. San Antonio, Tex.: Harcourt Assessment, hereby incorporated by reference in its entirety. In particular, the BSID-III is designed to assess infants and young children. The BSID-III measurements include a series of developmental play tasks to be administered to the patient. Raw scores of successfully completed items are converted to scaled scores. The scaled scores are then used to determine the patient's performance compared to healthy, age-adjusted patients. The BSID-III can also include the Social-Emotional Adaptive Behavior Questionnaire, which is completed by the parent/guardian, to establish the range of adaptive behaviors of the patient. For example, measurements for determining the BSID-III score (e.g., the BSID-III gross motor function score) can include prehension, perceptual-motor integration, motor planning and speed, visual tracking, reaching, object grasping, object manipulation, functional hand skills, responses to tactile information, movement of the limbs and torso, static positioning, dynamic movement, balance, and motor planning. These patient measurements are then converted into a BSID-III scaled score (e.g., the BSID-III gross motor function scaled score) ranging from 0 to 14, in which scores of about 7 to about 13 are considered the normal range of healthy patients.

The term "bone-targeting moiety," as used herein, refers to an amino acid sequence of between 1 and 50 amino acid residues in length having a sufficient affinity to the bone matrix, such that the bone-targeting moiety, singularly, has an in vivo binding affinity to the bone matrix that is about $10^{-6}$ M to about $10^{-15}$ M (e.g., $10^{-7}$ M, $10^{-8}$ M, $10^{-9}$ M, $10^{-10}$ M, $10^{-11}$ M, $10^{-12}$ M, $10^{-13}$ M, $10^{-14}$ M, or $10^{-15}$ M).

The terms "Bruininks-Oseretsky Test of Motor Proficiency $2^{nd}$ Edition" or "BOT-2," as used herein, refer to the second edition of a standardized test of gross and fine motor performance for patients, e.g., from about 4 to about 21 years of age. See Bruininks, R. H. (2005). *Bruininks-Oscretsky Test of Motor Proficiency, (BOT-2)*. Minneapolis, Minn.: Pearson Assessment, hereby incorporated by reference in its entirety. The BOT-2 is administered individually to assess gross and fine motor skills of a range of patients. In particular, the BOT-2 can be used to evaluate physical impairments and mobility restrictions in patients having HPP. The BOT-2 provides composite BOT-2 scores in the following areas: strength, running speed and agility, fine motor precision, fine motor integration, manual dexterity, bilateral coordination, balance, and upper-limb coordination. For example, a BOT-2 strength score can be determined by having a patient perform sit-ups, v-ups, standing long jump, wall sit, and push-ups. A running speed and agility score can be determined by having a patient step over a balance beam or perform a shuttle run, two-legged side hop, or one-legged side hop. Both BOT-2 strength and BOT-2 running speed and agility scores range from 0 to 25, in which a score of about 10 to 20 is considered representative of healthy patients.

The terms "Childhood Health Assessment Questionnaire" or "CHAQ," as used herein refer to a questionnaire that is used to assess the health status (e.g., ability to perform activities of daily living (ADLs) and incidence of pain) of patients of 1 to 19 years of age, such as patients with HPP. For a description of the CHAQ test and index, see Bruce & Fries (*J. Rheumatol.* 30(1): 167-178, 2003), hereby incorporated by reference in its entirety. The CHAQ may be administered by interview or self-report for children greater than 8 years of age. The CHAQ includes eight sub-scales for dressing/grooming, arising, eating, walking, hygiene, reach, grip, and activities. The range of scores within each category is from 0 to 3, in which a score of 0 indicates without any difficulty; a score of 1 indicates with some difficulty; a score of 2 indicates with much difficulty; and a score of 3 indicates that the patient is unable to perform the activity. The CHAQ index may also be used to determine the presence and severity of pain.

By "extracellular domain" is meant any functional extracellular portion of the native protein, e.g., alkaline phosphatase. In particular, the extracellular domain lacks the signal peptide.

By "Fc" is meant a fragment crystallizable region of an immunoglobulin, e.g., IgG-1, IgG-2, IgG-3, IgG-3 or IgG-4, including the CH2 and CH3 domains of the immunoglobulin heavy chain. Fc may also include any portion of the hinge region joining the Fab and Fc regions. The Fc can be of any mammal, including human, and may be post-translationally modified (e.g., by glycosylation). In a non-limiting example, Fc can be the fragment crystallizable region of human IgG-1 having the amino acid sequence of SEQ ID NO: 20.

By "fragment" is meant a portion of a polypeptide or nucleic acid molecule that contains, preferably, at least 10%, 20%, 30%, 40%, 50%, 60%, 70%, 75%, 80%, 85%, 90%, 95%, 96%, 97%, 98%, 99%, or more of the entire length of the reference nucleic acid molecule or polypeptide. A fragment may contain, e.g., 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 400, 500, 600, 700, or more amino acid residues, up to the entire length of the polypeptide. Exemplary sALP fragments have amino acid residues 18-498, 18-499, 18-500, 18-501, 18-502, 18-503, 18-504, 18-505, 18-506, 18-507, 18-508, 18-509, 18-510, 18-511, or 18-512 of a ALP (e.g., SEQ ID NOs: 2-6), and may include additional C-terminal and/or N-terminal portions.

The terms "hypophosphatasia" or "HPP," as used herein, refer to a rare, heritable skeletal disorder caused by, e.g., one or more loss-of-function mutations in the ALPL (alkaline phosphatase, liver/bone/kidney) gene, which encodes tissue-nonspecific alkaline phosphatase (TNALP). HPP may be further characterized as infantile HPP, childhood HPP, perinatal HPP (e.g., benign perinatal HPP or lethal perinatal HPP), or odonto-HPP.

The term "HPP phenotype," as used herein, refers to any one of rickets (defect in growth plate cartilage), osteomalacia, elevated blood and/or urine levels of inorganic pyrophosphate (PP;), phosphoethanolamine (PEA), or pyridoxal 5'-phosphate (PLP), seizure, bone pains, and calcium pyrophosphate dihydrate crystal deposition (CPPD) in joints leading to chondrocalcinosis, craniosynostosis, and premature death. Without being so limited, a HPP phenotype can be documented by one or more of growth retardation with a decrease of long bone length (including but not limited to femur, tibia, humerus, radius, and/or ulna), a decrease of the mean density of total bone and a decrease of bone mineralization in bones such as femur, tibia, ribs and metatarsi, and phalange, a decrease in teeth mineralization, and a premature loss of deciduous teeth (e.g., aplasia, hypoplasia, or dysplasia of dental cementum). Without being so limited, correction or prevention of bone mineralization defect may be observed by one or more of the following: an increase of long bone length, an increase of mineralization in bone and/or teeth, a correction of bowing of the legs, a reduction of bone pain and a reduction of CPPD crystal deposition in joints.

By "naïve patient" is meant a patient having HPP (e.g., a child) that has never received treatment with a sALP such as TNALP, for example the sALP polypeptide of SEQ ID NO: 1 or a polypeptide variant having at least 95% sequence identity to the sequence of SEQ ID NO: 1, e.g., asfotase alfa).

By "pain" as used herein refers to physical suffering or discomfort caused by HPP, such as bone pain. For instance, symptoms of pain can include, e.g., soreness, tightness, or stiffness. The severity of pain can vary between patients (e.g., chronic pain or acute pain). In particular, chronic pain refers to pain that lasts longer than three to six months or pain that extend beyond the expected period of healing. In contrast, acute pain refers to pain that typically lasts less than three to six months. As described herein, therapeutic compositions (e.g., including a sALP, such as asfotase alfa) can be administered to a patient suffering from pain (e.g., bone pain) in an amount sufficient to relieve or at least partially relieve the symptoms of pain (e.g., discomfort, soreness, tightness, or stiffness) and its complications (e.g., fatigue, sleeplessness, weakened immune system, depression, anxiety, stress, irritability, or disability).

The terms "peptide," "polypeptide," and "protein" are used interchangeably and refer to any chain of two or more natural or unnatural amino acid residues, regardless of post-translational modification (e.g., glycosylation or phosphorylation), constituting all or part of a naturally-occurring or non-naturally occurring polypeptide or peptide, as is described herein.

By "pharmaceutically acceptable carrier" or "pharmaceutically acceptable excipient" is meant at least one carrier or excipient, respectively, which is physiologically acceptable to the treated patient while retaining the therapeutic properties of the compound with which it is administered. One exemplary pharmaceutically acceptable carrier substance is physiological saline. For instance, the pharmaceutically acceptable carrier can include sodium chloride (e.g., 150 mM sodium chloride) and sodium phosphate (e.g., 25 mM sodium phosphate). Other physiologically acceptable carriers and their formulations are known to those skilled in the art and described, e.g., in Remington's Pharmaceutical Sciences (20th edition), A. Gennaro, Ed., 2000, Lippincott, Williams & Wilkins, Philadelphia, Pa.

By "pharmaceutical composition" is meant a composition containing a polypeptide or nucleic acid molecule as described herein formulated with at least one pharmaceutically acceptable excipient, diluent, or carrier. The pharmaceutical composition may be manufactured or sold with the approval of a governmental regulatory agency as part of a therapeutic regimen for the treatment or prevention of a disease or event in a patient. Pharmaceutical compositions can be formulated, for example, for subcutaneous administration, intravenous administration (e.g., as a sterile solution free of particulate emboli and in a solvent system suitable for intravenous use), for oral administration (e.g., a tablet, capsule, caplet, gelcap, or syrup), or any other formulation described herein, e.g., in unit dosage form.

The term "physical impairments," as used herein, refers to a physiological condition, such as bone weakness and muscle weakness, associated with HPP that can restrict or eliminate, e.g., ambulation, functional endurance, and ability to perform activities of daily living (ADL) of a patient. In particular, physical impairments may restrict or eliminate a patient's ability to perform ADL, which are routine activities that healthy patients perform on a daily basis without requiring assistance, such as functional mobility or transferring (e.g., walking), bathing and showering, dressing, self-feeding, and personal hygiene and grooming. As described herein, therapeutic compositions (e.g., compositions including a sALP, such as asfotase alfa) can be administered to a patient to decrease the severity and/or frequency of physical impairments associated with an HPP phenotype.

The terms "Pediatric Outcomes Data Collection Instrument" or "PODCI," as used herein, refer to a questionnaire used to assess overall health, incidence of pain, and ability to perform ADLs of patients under 19 years of age, particularly in patients with chronic health disorders, such as patients with HPP. For a description of the PODCI, see Plint et al. (J. Pediatr. Orthop. 23(6): 788-790, 2003), hereby incorporated by reference in its entirety. The questionnaire may be completed by the patient or by a parent/guardian of the patient with knowledge of the patient's condition. The eight scales generated from the PODCI include the following: 1) the upper extremity and physical function scale to measure difficulty encountered in performing daily personal care and student activities; 2) the transfer and basic mobility scale to measure difficulty experienced in performing routine motion and motor activities in daily activities; 3) the sports/physical functioning scale to measure difficulty or limitations encountered in participating in more active activities or sports; 4) the pain/comfort scale to measure the level of pain experienced during the past week; 5) the treatment expectations scale to measure the long term expectations of treatment; 6) the happiness scale to measure overall satisfaction with personal looks and sense of similarity to friends and others of own age; 7) the satisfaction with symptoms scale to measure the patients acceptance of current limitations should this be a life-long state; and 8) the global functioning scale, which is a general combined scale calculated from the first four scales listed above. Standardized scores are generated from a series of questions in the PODCI and converted to a 0 to 100 scale, in which 0 represents significant disability and 100 represents less disability.

The terms "Peabody Developmental Motor Scales, 2nd Edition" or "PDMS-2," as used herein, refer to an early childhood motor development program that provides an assessment of gross and fine motor skills in patients from birth throughout childhood (e.g., infants and children). For a description of the PDMS-2 scales, see van Hartingsveldt, et al. (Occup. Ther. Int 12(1): 1-13, 2005), hereby incorporated by reference in its entirety. The PDMS-2 is composed of six subtests that measure interrelated motor abilities of early development. The six subtests include the following: 1) the locomotor subtest to measures a patient's ability to move from one place to another (measurements include crawling, walking, running, hopping, and jumping forward); 2) the reflexes subtest to measure a patients ability to automatically react to environmental events; 3) the stationary subtest to measure a patient's ability to sustain control of his or her body within the center of gravity and retain equilibrium; 4) the object manipulation subtest to measure a patient's ability to manipulate an object, such as catching, throwing, and kicking a ball; 5) the grasping subtest to measure a patient's ability to use his or her hands, such as the ability to hold an object with one hand and actions involving the controlled use of the fingers of both hands; and 6) the visual-motor integration subtest to measure a patient's ability to use his or her visual perceptual skills to perform complex eye-hand coordination tasks, such as reaching and grasping for an object, building with blocks, and copying designs. The PDMS-2 measurements for each subtest is converted into a PDMS-2 score, such as the PDMS-2 locomotor standard score ranging from 0 to 13, in which the range of health patients is from about 7 to about 13.

The terms "sALP," "soluble alkaline phosphatase," and "extracellular domain of an alkaline phosphatase" are used interchangeably and refer to a soluble, non-membrane-bound alkaline phosphatase or a domain, biologically active fragment, or biologically active variant thereof. sALPs include, for example, an alkaline phosphatase lacking a C-terminal glycolipid anchor (GPI signal sequence, e.g., polypeptides including or consisting of the amino acid residues 18-502 of a human TNALP (SEQ ID NOs: 2, 3, 4, 5, or 6)). In particular, a TNALP may include, e.g., a polypeptide including or consisting of amino acid residues 1-485 of SEQ ID NO: 1, such as asfotase alfa, or a polypeptide variant having at least 95% sequence identity to the amino acid residues 1-485 of SEQ ID NO: 1. sALPs further include, for example, mammalian orthologs of human TNALP, such as a rhesus TNALP (SEQ ID NO: 7), a rat TNALP (SEQ ID NO: 8), a canine TNALP (SEQ ID NO: 9), a porcine TNALP (SEQ ID NO: 10), a murine TNALP (SEQ ID NO: 11), a bovine TNALP (SEQ ID NOs: 12-14), or a feline TNALP (SEQ ID NO: 15). sALPs also include soluble, non-membrane-bound forms of human PALP (e.g., polypeptides including or consisting of amino acid residues 18-502 of SEQ ID NOs: 16 or 17), GCALP (e.g., polypeptides including or consisting of amino acid residues 18-502 of SEQ ID NO: 18), and IALP (e.g., polypeptides including or consisting of amino acid residues 18-502 of SEQ ID NO: 19), and additional variants and analogs thereof that retain alkaline phosphatase activity, e.g., the ability to hydrolyze $PP_i$. A sALP, in particular, lacks the N-terminal signal peptide (e.g., aa 1-17 of SEQ ID NOs: 2-6, 8, 11-13, or 15 or aa 1-25 of SEQ ID NO: 7).

By "sALP polypeptide" is meant a polypeptide having the structure A-sALP-B, wherein sALP is as defined herein and each of A and B is absent or is an amino acid sequence of at least one amino acid (e.g., any sALP fusion polypeptide described herein (for example the sALP fusion polypeptide of SEQ ID NO: 1 or a polypeptide variant having at least 95% sequence identity to the sequence of SEQ ID NO: 1, e.g., asfotase alfa).

By "signal peptide" is meant a short peptide (5-30 amino acids long) at the N-terminus of a polypeptide that directs a polypeptide towards the secretory pathway (e.g., the extracellular space). The signal peptide is typically cleaved during secretion of the polypeptide. The signal sequence may direct the polypeptide to an intracellular compartment or organelle, e.g., the Golgi apparatus. A signal sequence may be identified by homology, or biological activity, to a peptide with the known function of targeting a polypeptide to a particular region of the cell. One of ordinary skill in the art can identify a signal peptide by using readily available software (e.g., Sequence Analysis Software Package of the Genetics Computer Group, University of Wisconsin Biotechnology Center, 1710 University Avenue, Madison, Wis.

53705, BLAST, or PILEUP/PRETTYBOX programs). A signal peptide can be one that is, for example, substantially identical to amino acid residues 1-17 of SEQ ID NOs: 2-6 or amino acid residues 1-25 of SEQ ID NO: 7.

As used herein, when a polypeptide or nucleic acid sequence is referred to as having "at least X % sequence identity" to a reference sequence, wherein "X" is a real number, it is meant that at least X percent of the amino acid residues or nucleotides in the polypeptide or nucleic acid are identical to those of the reference sequence when the sequences are optimally aligned. An optimal alignment of sequences can be determined in various ways that are within the skill in the art, for instance, the Smith Waterman alignment algorithm (Smith et al., *J. Mol. Biol.* 147:195-7, 1981) and BLAST (Basic Local Alignment Search Tool; Altschul et al., *J. Mol. Biol.* 215: 403-10, 1990). These and other alignment algorithms are accessible using publicly available computer software such as "Best Fit" (Smith and Waterman, Advances in Applied Mathematics, 482-489, 1981) as incorporated into GeneMatcher Plus (Schwarz and Dayhoff, Atlas of Protein Sequence and Structure, Dayhoff, M. O., Ed pp 353-358, 1979), BLAST, BLAST-2, BLAST-P, BLAST-N, BLAST-X, WU-BLAST-2, ALIGN, ALIGN-2, CLUSTAL, Megalign (DNASTAR), or other software/hardware for alignment. In addition, those skilled in the art can determine appropriate parameters for measuring alignment, including any algorithms needed to achieve optimal alignment over the length of the sequences being compared.

The term "patient" refers to a mammal, including, but not limited to, a human or a non-human mammal, such as a bovine, equine, canine, ovine, or feline.

As used herein, "Six Minute Walk Test" and "6MWT" refer to a standardized test to assess walking ability of a patient (e.g., a child having HPP), in particular, the ability of the patient to lift and set down each foot in turn. See the American Thoracic Society statement: guidelines for the six-minute walk test (*American Journal of Respiratory and Critical Care Medicine*, 166(1):111-7, 2002), hereby incorporated by reference in its entirety. The 6MWT is determined from the distance (e.g., in meters) that a patient walks on a flat, hard surface in a period of six minutes. The 6MWT distance can then be compared to the 6MWT distance of the patient at baseline, the 6MWT distance of an untreated subject (e.g., an untreated subject of about the same age, height, and/or gender), or the 6MWT distance of a healthy subject (e.g., a healthy subject of about the same age, height, and/or gender) and expressed as a percentage to determine the 6MWT value.

By "therapeutically effective amount" is meant an amount of a polypeptide or nucleic acid molecule described herein that is sufficient to substantially improve, treat, prevent, delay, suppress, or arrest at least one symptom of HPP. A therapeutically effective amount of a composition described herein may depend on the severity of the disorder being treated and the condition, weight, and general state of the patient and can be determined by an ordinarily-skilled artisan with consideration of such factors. A therapeutically effective amount of a composition described herein can be administered to a patient in a single dose or in multiple doses administered over a period of time.

By "treating," "treat," or "treatment" is meant the medical management of a patient with the intent to cure, ameliorate, stabilize, reduce the likelihood of, or prevent HPP and/or management of a patient exhibiting or likely to have HPP, e.g., by administering a pharmaceutical composition. This term includes active treatment, that is, treatment directed specifically toward the improvement or associated with the cure of a disease, pathological condition, disorder, or event, and also includes causal treatment, that is, treatment directed toward removal of the cause of the associated disease, pathological condition, disorder, or event. In addition, this term includes palliative treatment, that is, treatment designed for the relief or improvement of at least one symptom rather than the curing of the disease, pathological condition, disorder, or event; symptomatic treatment, that is, treatment directed toward constitutional symptoms of the associated disease, pathological condition, disorder, or event; preventative treatment, that is, treatment directed to minimizing or partially or completely inhibiting the development of the associated disease, pathological condition, disorder, or event, e.g., in a patient who is not yet ill, but who is susceptible to, or otherwise at risk of, a particular disease, pathological condition, disorder, or event; and supportive treatment, that is, treatment employed to supplement another specific therapy directed toward the improvement of the associated disease, pathological condition, disorder, or event.

Other features and advantages of the present disclosure will be apparent from the following Detailed Description, the drawings, and the claims.

BRIEF DESCRIPTION OF THE DRAWINGS

FIGS. 6A-6C are graphs showing growth during treatment of HPP children with asfotase alfa over a time period of 5 years. Growth was assessed for weight Z-scores (FIG. 6A), height Z-scores (FIG. 6B), and body mass index (BMI) Z-scores (FIG. 6C). For all graphs, individual dots indicate individual patient scores at each time point. Median, min, max, and n values are shown below each panel. P-values at 5 years are from a Wilcoxon signed-rank test.

FIGS. 7A-7D are graphs showing right hip abduction (FIG. 7A), right hip extension (FIG. 7B), right knee flexion (FIG. 7C), and right knee extension (FIG. 7D) of HPP children after administration of asfotase alfa over a time period of 5 years. Values are expressed as a percentage of the predicted value for healthy children. For all graphs, individual dots indicate individual patient scores at each time point. Median, min, max, and n values are shown below each panel.

FIGS. 8A-8B are graphs showing individual and median 6MWT values (FIG. 8A) and the percent predicted 6MWT distance median (FIG. 8B) of HPP children administered asfotase alfa over a time period of 5 years. Median, min, max, and n values are shown. Individual dots indicate individual patient scores at each time point. Gray area represents the normal range for the 6MWT distance. P≤0.0005 by paired t test for the mean difference between each time point and baseline.

FIGS. 12A-12B are graphs of the Pediatric Outcomes Data Collection Instrument (PODCI) median normative scores for transfer and basic mobility (FIG. 12A) and sports/physical functioning (FIG. 12B) of HPP patients administered asfotase alfa over a time period of 5 years. PODCI disability index scores at baseline, 6 months, 1 year, 2 years, 3 years, 4 years, and 5 years are shown. Maximum and median PODCI scores at each time interval are shown in bold. Arrows indicate the initial phase and extension phase, respectively, of treatment with asfotase alfa.

FIGS. 13A-13B are graphs of the median CHAQ discomfort score (FIG. 13A) and median PODCI score (FIG. 13B) of HPP patients after administration of asfotase alfa over a time period of 5 years. Average CHAQ and PODCI scores at baseline, 6 months, 1 year, 2 years, 3 years, 4 years, and 5 years are shown. Maximum and median CHAQ and PODCI scores at each time interval are shown in bold. Arrows indicate the initial phase and extension phase, respectively, of treatment with asfotase alfa.

DETAILED DESCRIPTION

Figure 1:
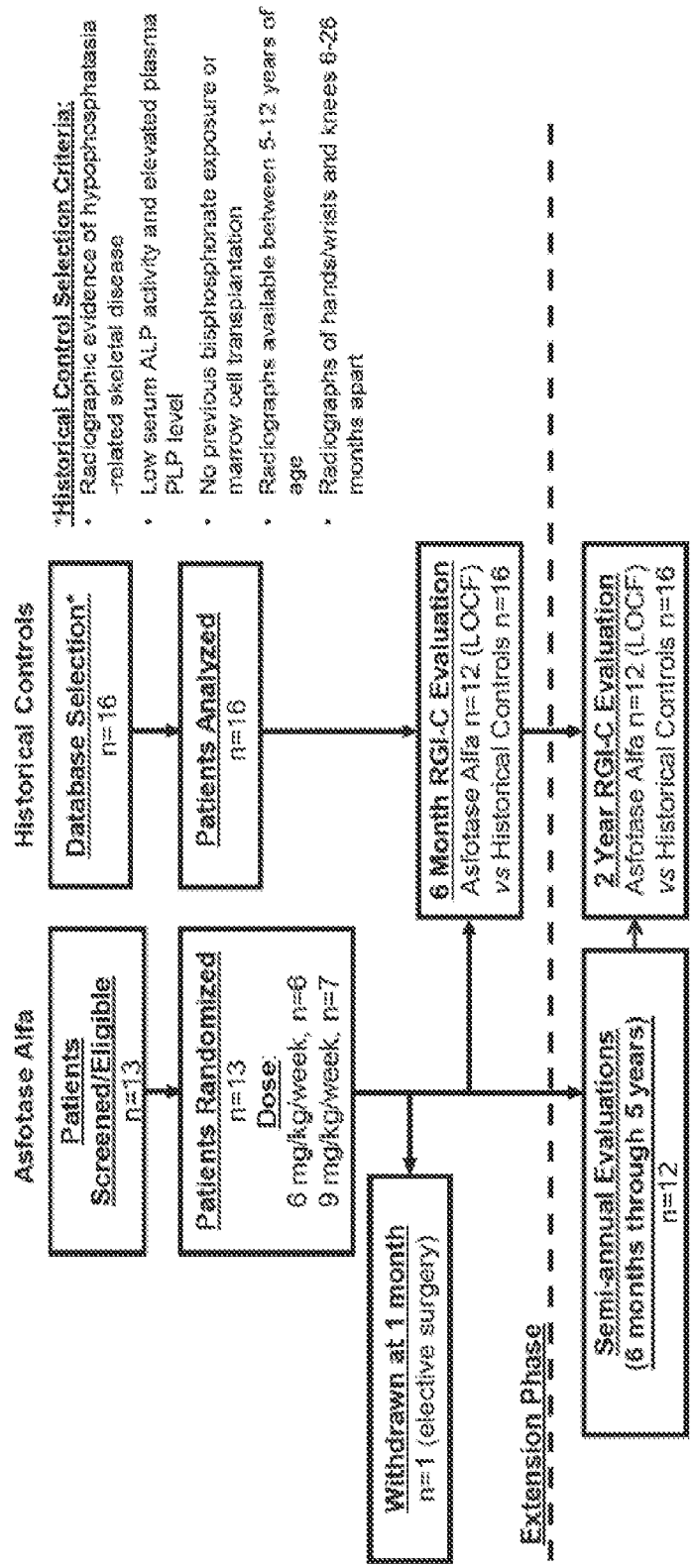
FIG. 1 is an image showing the study design for administering asfotase alfa to children with hypophosphatasia (HPP) over a time period of 5 years, including an initial phase of treatment with asfotase alfa, from baseline to 6 months, and an extension phase of treatment with asfotase alfa (from 6 months of treatment to 5 or more years of treatment). During the 6 month initial phase involving 13 participants, 1 child withdrew for elective surgery after 1 month of treatment. The remaining 12 were assessed up to 5 years (60 months) of treatment and continue on study. Data were pooled across these 2 phases for analysis. The radiographic findings were contrasted to 2 year experience with 16 historical control patients. LOCF, last observation carried forward.

We have discovered that asfotase alfa (SEQ ID NO: 1) can be used effectively to treat hypophosphatasia (HPP), its symptoms, and physical impairments associated therewith in a child with HPP (e.g., a child of about 5 to about 12 years of age having HPP) for an extended period of time (e.g., at least four years, at least five years, at least six years, at least seven years, at least eight years, at least nine years, at least ten years, or more than ten years (e.g., for the lifetime of the patient)). In particular, asfotase alfa (SEQ ID NO: 1) can be administered to treat children with HPP exhibiting physical impairments (e.g., bone or muscle weakness) and/or pain (e.g., bone or muscle pain). Furthermore, the child having HPP (e.g., a child of about 5 to about 12 years of age having HPP) can be a naïve patient that has not have previously received treatment with asfotase alfa (SEQ ID NO: 1).

Methods for administering asfotase alfa (SEQ ID NO: 1) to a child with HPP (e.g., a child of about 5 to about 12 years of age with HPP) having an average Bruininks-Oseretsky Test of Motor Proficiency 2$^{nd}$ Edition (BOT-2) score indicative of physical impairments (e.g, an average BOT-2 score of less than about 10 in one or more BOT-2 score areas of strength, running speed and agility, fine motor precision, fine motor integration, manual dexterity, bilateral coordination, balance, and upper-limb coordination) are described. For example, asfotase alfa (SEQ ID NO: 1) can be administered to a child with HPP (e.g., a child of about 5 to about 12 years of age having HPP) having an average BOT-2 strength score of less than about 10 and/or an average BOT-2 running speed and agility score of less than about 5. Similarly, methods for administering asfotase alfa (SEQ ID NO: 1) to a child (e.g., a child of about 5 to about 12 years of age having HPP) having a Six Minute Walk Test (6MWT) distance that is indicative of decreased walking ability, e.g., relative to a healthy patient, are also described.

Methods for administering asfotase alfa (SEQ ID NO: 1) to a child (e.g., a child of about 5 to about 12 years of age having HPP) having an average Childhood Health Assessment Questionnaire (CHAQ) index score indicative of disability in activities of daily living (ADL) and pain (e.g., an an average CHAQ index score of greater than about 0.8) are also described. Likewise, methods for administering asfotase alfa (SEQ ID NO: 1) to a child (e.g., a child of about 5 to about 12 years of age having HPP) having an average Pediatric Outcomes Data Collection Instrument (PODCI) score indicative of disability in activities of daily living (ADL) and pain (e.g., an average PODCI score of less than about 40) are also described.

Additionally, methods for administering asfotase alfa (SEQ ID NO: 1) to a child (e.g., a child of about 5 to about 12 years of age having HPP) that exhibited an average Bayley Scales of Infant and Toddler Development, 3$^{rd}$ Edition (BSID-III) score indicative of delayed motor development (e.g., an average BSID-III scaled score of less than 2) at about 3 years of age or less than 3 years of age are described. Likewise, methods for administering asfotase alfa (SEQ ID NO: 1) to a child (e.g., a child of about 5 to about 12 years of age having HPP) that exhibited an average Peabody Developmental Motor Scales, 2nd Edition (PDMS-2) standard score indicative of delayed motor development (e.g., an average PDMS-2 standard score of about 5) at about 3 years of age or less than 3 years of age are described.

Methods for administering asfotase alfa (SEQ ID NO: 1) to a child (e.g., a child of about 5 to about 12 years of age having HPP) having one or more (e.g., two, three, four, or five) scores selected from the average BOT-2 score, average CHAQ index score, average PODCI score, average 6MWT distance, average BSID-III score, and average PDMS-2 standard score are further described. Alternatively, the child (e.g., a child of about 5 to about 12 years of age having HPP) may not have an average BOT-2 score, average CHAQ index score, average PODCI score, average 6MWT distance, average BSID-III score, or average PDMS-2 standard score, and instead exhibits symptoms of physical impairments, pain, and/or development delay as described. Moreover, the child may have a 6MWT distance that is indicative of impairments in walking ability.

In any of these methods, asfotase alfa (SEQ ID NO: 1) may be administered to the child (e.g., a child of about 5 to about 12 years of age having HPP) for an extended period of time, e.g., at least four years, at least five years, at least six years, at least seven years, at least eight years, at least nine years, at least ten years, or more than ten years (e.g., for the lifetime of the patient). Furthermore, given the results described herein using asfotase alfa, other sALPs (such as TNALP, for example the sALP polypeptide of SEQ ID NO: 1 or a polypeptide variant having at least 95% sequence identity to the sequence of SEQ ID NO: 1, e.g., asfotase alfa) are useful for treating a child having HPP (e.g., a child of about 5 to about 12 years of age having HPP) for an extended period of time, e.g., at least four years, at least five years, at least six years, at least seven years, at least eight years, at least nine years, at least ten years, or more than ten years (e.g., for the lifetime of the patient) as described.

Methods of Treatment

Provided herein are methods for treating a child having HPP (e.g., a child of about 5 to about 12 years of age having HPP). Children having HPP can be treated by administering a sALP (such as TNALP, for example the sALP polypeptide of SEQ ID NO: 1 or a polypeptide variant having at least 95% sequence identity to the sequence of SEQ ID NO: 1, e.g., asfotase alfa) across a range of ages, e.g., about 5 to about 12 years of age, about 6 to about 7 years of age, about 6 to about 8 years of age, about 7 to about 9 years of age, about 8 to about 10 years of age, about 8 to about 9 years of age, about 9 to about 11 years of age, about 10 to about 11 years of age, about 10 to about 12 years of age, about 11 to about 12 years of age, about 5 to about 10 years of age, about 5 to about 8 years of age, about 5 to about 6 years of age, or about 5 to about 11 years of age.

Children (e.g., children of about 5 to about 12 years of age) can be diagnosed with HPP prior to administration of a sALP (such as TNALP, for example the sALP polypeptide of SEQ ID NO: 1 or a polypeptide variant having at least 95% sequence identity to the sequence of SEQ ID NO: 1, e.g., asfotase alfa). A child having HPP (e.g., a child of about 5 to about 12 years of age having HPP) can exhibit, e.g., physical impairments, disability in ADL, pain, and/or delayed motor development, relative to a child without HPP (e.g., a child of about 5 to about 12 years of age without HPP). Additionally, the child having HPP (e.g., a child of about 5 to about 12 years of age having HPP) can be a naïve patient that has not have previously received treatment with a sALP (such as TNALP, for example the sALP polypeptide of SEQ ID NO: 1 or a polypeptide variant having at least 95% sequence identity to the sequence of SEQ ID NO: 1, e.g., asfotase alfa).

The method involves administering a sALP (such as TNALP, for example the sALP polypeptide of SEQ ID NO: 1 or a polypeptide variant having at least 95% sequence identity to the sequence of SEQ ID NO: 1, e.g., asfotase alfa) to a child having HPP (e.g., a child of about 5 to about 12 years of age having HPP), such as administering a sALP for a period of least four years (e.g., at least five years, at least six years, at least seven years, at least eight years, at least nine years, at least ten years, or more than ten years). In particular, a sALP, such as asfotase alfa, can be administered to a child (e.g., a child of about 5 to about 12 years of age) previously determined to have an average BOT-2 strength score of less than 10, an average BOT-2 running speed and agility score of less than 5, an average CHAQ index score greater than about 0.8, an average PODCI score of less than about 40, and/or an average 6MWT distance less than 80% of the predicted 6MWT distance for a period of least four years (e.g., at least five years, at least six years, at least seven years, at least eight years, at least nine years, at least ten years, or more than ten years).

Alternatively, the sALP (such as TNALP, for example the sALP polypeptide of SEQ ID NO: 1 or a polypeptide variant having at least 95% sequence identity to the sequence of SEQ ID NO: 1, e.g., asfotase alfa) can be administered to the patient having HPP (e.g., a child, particularly a child of about 5 to about 12 years of age or an infant, particularly an infant of about 3 years of age or less than 3 years of age such as 6 months, 1 year of age, and 2-years of age) prior to determination of such scores (e.g., the BOT-2 strength score, BOT-2 running speed and agility score, the CHAQ index score, a 6MWT distance, the BSID-III scaled score, and/or the PDMS-2 standard score) to allow for, e.g., an increase in activities of ADL, a decrease in pain, and/or improved motor development.

Additionally, each of the described scores (e.g., the BOT-2 strength score, BOT-2 running speed and agility score, the CHAQ index score, the 6MWT distance, the BSID-III scaled score, and/or the PDMS-2 standard score) of a patient having HPP (e.g., a child of about 5 to about 12 years of age having HPP) can be used singly or in combination to assess treatment efficacy using a sALP (such as TNALP, for example the sALP polypeptide of SEQ ID NO: 1 or a polypeptide variant having at least 95% sequence identity to the sequence of SEQ ID NO: 1, e.g., asfotase alfa), in which improvements relative to a certain test score demonstrate that the sALP is effective for treating HPP. For example, when administration of a sALP to a child having HPP (e.g., a child of about 5 to about 12 years of age) results in an average increase in the BOT-2 strength score to about 10 or greater than about 10, in which the child previously had an average BOT-2 strength score of less than about 10, then the sALP treatment is effective at treating, e.g., physical impairments associated with HPP. Alternatively, when administration of a sALP does not result in an average increase in the BOT-2 strength score to about 10 or greater than about 10, the dosage and/or frequency of sALP administration can be changed in order to determine the effective amount of the sALP for the child having HPP (e.g., a child of about 5 to about 12 years of age). For instance, the dosage of the sALP such as TNALP, for example the sALP polypeptide of SEQ ID NO: 1 or a polypeptide variant having at least 95% sequence identity to the sequence of SEQ ID NO: 1, e.g., asfotase alfa) can be increased from, e.g., about 3 mg/kg/week to about 6 mg/kg/week or about 6 mg/kg/week to about 9 mg/kg/wk.

Hypophosphatasia in Children

Asfotase alfa is administered, as described herein, to treat, e.g., perinatal HPP, infantile HPP, childhood HPP, and odonto-HPP. In particular, patients having childhood HPP (e.g., children of about 5 to about 12 years of age having HPP) or infantile HPP (e.g., infants of about 3 years of age or less than 3 years of age) can be treated with a sALP (such as TNALP, for example the sALP polypeptide of SEQ ID NO: 1 or a polypeptide variant having at least 95% sequence identity to the sequence of SEQ ID NO: 1, e.g., asfotase alfa) for a period of at least one year (e.g., at least five years, at least six years, at least seven years, at least eight years, at least nine years, at least ten years, or more than ten years (e.g., the lifetime of the patient)).

In preferred embodiments, an HPP phenotype, e.g., perinatal HPP, infantile HPP, childhood HPP, and odontohypophosphatasia, is treated with a sALP (such as TNALP, for example the sALP polypeptide of SEQ ID NO: 1 or a polypeptide variant having at least 95% sequence identity to the sequence of SEQ ID NO: 1, e.g., asfotase alfa). For instance, the methods are useful for treating a perinatal HPP patient, such as a patient with increased respiratory compromise due to hypoplastic and rachitic disease of the chest; diminished ossification of the skull; diminished ossification and height of vertebral bodies; and/or absent ossification of the humeral, radial, and ulnar metaphyses with marked metaphyseal irregularity; fragmentation and fraying. The methods are also useful for treating patients exhibiting symptoms of infantile HPP, including, but not limited to, inadequate weight gain, the appearance of rickets, impaired skeletal mineralization, progressive skeletal demineralization, rib fractures, and chest deformity. A patient with childhood HPP, such as patients exhibiting symptoms such as premature loss of deciduous teeth (e.g., as a result of aplasia, hypoplasia, or dysplasia of dental cementum) and rickets, which causes short stature and skeletal deformities, such as bowed legs and enlarged wrists, knees, and ankles as a result of flared metaphyses, are treated with the methods described herein.

Accordingly, the methods are useful for alleviating any of the symptoms of HPP described herein, particularly when the sALP (such as TNALP, for example the sALP polypeptide of SEQ ID NO: 1 or a polypeptide variant having at least 95% sequence identity to the sequence of SEQ ID NO: 1, e.g., asfotase alfa) is administered for a period of at least four years (e.g., at least five years, at least six years, at least seven years, at least eight years, at least nine years, at least ten years, or more than ten years (e.g., for the lifetime of the patient)). Non-limiting examples of HPP symptoms that can be treated with a sALP for a period of at least four years (e.g., at least five years, at least six years, at least seven years, at least eight years, at least nine years, at least ten years, or more than ten years (e.g., for the lifetime of the patient)) include elevated blood and/or urine levels of inorganic pyrophosphate (PR), elevated blood and/or urine levels of phosphoethanolamine (PEA), elevated blood and/or urine levels of pyridoxal 5'-phosphate (PLP), hypomineralization, rachitic ribs, hypercalciuria, bone pain, bone fracture, HPP-related seizure, inadequate weight gain, and/or calcium pyrophosphate dihydrate crystal deposition.

A patient (e.g., a child, particularly a child of about 5 to about 12 years of age, or an infant, particularly an infant of about 3 years of age or less than 3 years of age) with a mutation in TNALP can also be treated with a sALP (such as TNALP, for example the sALP polypeptide of SEQ ID NO: 1 or a polypeptide variant having at least 95% sequence identity to the sequence of SEQ ID NO: 1, e.g., asfotase alfa), e.g., to alleviate pain, increase ADL, and/or improve motor development. Missense mutations at a variety of positions in TNALP, including the enzyme's active site vicinity, homodimer interface, crown domain, amino-terminal arm, and calcium-binding site, have all been found to affect its catalytic activity. In addition, missense, nonsense, frame-shift, and splice site mutations have also been shown to lead to aberrant mutant proteins or intracellular trafficking defects that lead to subnormal activity on the cell surface. Accordingly, the methods can be used to treat patients with different mutation in TNALP (e.g., missense mutations, frame-shift, nonsense, and splicing mutations).

For instance, the presence of a mutation in TNALP can be detected in a sample from the patient (e.g., a child, particularly a child of about 5 to about 12 years of age, or an infant, particularly an infant of about 3 years of age or less than 3 years of age) prior to or after treatment (such as TNALP, for example the sALP polypeptide of SEQ ID NO: 1 or a polypeptide variant having at least 95% sequence identity to the sequence of SEQ ID NO: 1, e.g., asfotase alfa). Additionally, a parent of the patient and/or a fetal sample (e.g., fetal nucleic acid obtained from maternal blood, placental, and/or fetal samples) can be tested by methods known in the art for a mutation in TNALP. Traditional management of HPP has also included symptomatic treatment of the phenotypic manifestations of the disease, e.g., treating hypercalcemia with dietary restriction or calciuretics and orthopedic stabilization of fractures. Accordingly, these treatments (e.g., dietary restriction, calciuretics, and orthopedic stabilization of fractures) can be used with a sALP (such as TNALP, for example the sALP polypeptide of SEQ ID NO: 1 or a polypeptide variant having at least 95% sequence identity to the sequence of SEQ ID NO: 1, e.g., asfotase alfa) administered for a period of at least four years (e.g., at least five years, at least six years, at least seven years, at least eight years, at least nine years, at least ten years, or more than ten years (e.g., for the lifetime of the patient)), such as to decrease physical impairments, increase ADL, alleviate pain, and/or improve motor development.

Exemplary tests useful in the methods include (1) the Bruininks-Oseretsky Test of Motor Proficiency $2^{nd}$ Edition (BOT-2), (2) the Childhood Health Assessment Questionnaire (CHAQ), (3) the Pediatric Outcomes Data Collection Instrument (PODCI), (4) the Six Minute Walk Test (6MWT), (5) the Bayley Scales of Infant and Toddler Development, $3^{rd}$ Edition (BSID-III), and (6) the Peabody Developmental Motor Scales, 2nd Edition (PDMS-2), which are described in further detail below.

Bruininks-Oseretsky Test of Motor Proficiency $2^{nd}$ Edition (BOT-2)

Children with HPP (e.g., children of about 5 to about 12 years of age) can be identified for treatment with a sALP (such as TNALP, for example the sALP polypeptide of SEQ ID NO: 1 or a polypeptide variant having at least 95% sequence identity to the sequence of SEQ ID NO: 1, e.g., asfotase alfa) using the Bruininks-Oseretsky Test of Motor Proficiency 2nd Edition (BOT-2), which is described in Bruininks, R. H. (2005). *Bruininks-Oseretsky Test of Motor Proficiency*, (BOT-2), Minneapolis, Minn.: Pearson Assessment, hereby incorporated by reference in its entirety. In particular, the BOT-2 can be used to evaluate physical impairments and mobility restrictions in a child having HPP (e.g., children of about 5 to about 12 years of age having HPP) to generate a BOT-2 score for the child.

The BOT-2 includes a range of tests to evaluate physical impairments of a child (e.g., a child of about 5 to about 12 years of age), which can be performed with, e.g., a kit including the tests. The BOT-2 provides composite BOT-2 scores in the following areas: strength, running speed and agility, fine motor precision, fine motor integration, manual dexterity, bilateral coordination, balance, and upper-limb coordination. For example, the child having HPP (e.g., a child of about 5 to about 12 years of age having HPP) can perform sit-ups, v-ups, standing long jump, wall sit, and/or push-ups to determine the BOT-2 strength score; the child having HPP (e.g., a child of about 5 to about 12 years of age having HPP) can step over a balance beam and/or perform a shuttle run, two-legged side hop, and/or one-legged side hop to determine the BOT-2 running speed and agility score; the child having HPP (e.g., a child of about 5 to about 12 years of age having HPP) can cut out a circle and/or connect dots to determine the BOT-2 fine motor precision score; the child having HPP (e.g., a child of about 5 to about 12 years of age having HPP) can copy a star and/or copy a square to determine the BOT-2 fine motor integration score; the child having HPP (e.g., a child of about 5 to about 12 years of age having HPP) can transfer pennies, sort cards, and/or string blocks to determine the manual dexterity score; the child having HPP (e.g., a child of about 5 to about 12 years of age having HPP) can tap his or her foot and finger and/or perform jumping jacks to determine the BOT-2 bilateral coordination score; the child having HPP (e.g., a child of about 5 to about 12 years of age having HPP) can walk forward on a line and/or stand on one leg on a balance beam to determine the BOT-2 balance score; and the child having HPP (e.g., a child of about 5 to about 12 years of age having HPP) can throw a ball at a target and/or catch a tossed ball to determine the BOT-2 upper-limb coordination score.

A child having HPP (e.g., a child of about 5 to about 12 years of age having HPP) could perform tests in one or more of described areas (strength, running speed and agility, fine motor precision, fine motor integration, manual dexterity, bilateral coordination, balance, and upper-limb coordination) to generate a BOT-2 score indicative of physical impairments in the child. Within each BOT-2 area (strength, running speed and agility, fine motor precision, fine motor integration, manual dexterity, bilateral coordination, balance, and upper-limb coordination), a child having HPP could perform one or more tests to determine the BOT-2 score of the child, e.g., the child could perform one or more of sit-ups, v-ups, standing long jump, wall sit, and push-ups to determine the BOT-2 strength score. Thus, only one test (e.g., one test selected from the group of sit-ups, v-ups, standing long jump, wall sit, and push-ups) can be performed to determine the BOT-2 score (e.g., a BOT-2 strength score) of a child having HPP.

Each of the BOT-2 scores (strength, running speed and agility, fine motor precision, fine motor integration, manual dexterity, bilateral coordination, balance, and upper-limb coordination) of the patient having HPP (e.g., a child of about 5 to about 12 years of age having HPP) can be compared to the BOT-2 score of patients without HPP (e.g., children of about 5 to about 12 years of age without HPP) to, e.g., determine the standard deviation of the BOT-2 score. Each of the BOT-2 scores (e.g., strength, running speed and agility, fine motor precision, fine motor integration, manual dexterity, bilateral coordination, balance, and upper-limb coordination) of the patient having HPP (e.g., a child of about 5 to about 12 years of age having HPP) can be compared to the BOT-2 score of other HPP patients (e.g., children of about 5 to about 12 years of age having HPP) to, e.g., determine the average BOT-2 score for the HPP patient.

BOT-2 scores (e.g., strength, running speed and agility, fine motor precision, fine motor integration, manual dexterity, bilateral coordination, balance, and upper-limb coordination scores) range from about 0 to equal to or less than about 25, in which a score of about 10 to about 20 is considered representative of healthy patients (e.g., patients without HPP). Patients with an average BOT-2 score (e.g., strength, running speed and agility, fine motor precision, fine motor integration, manual dexterity, bilateral coordination, balance, and upper-limb coordination scores) of less than about 10 can be treated with a sALP (such as TNALP, for example the sALP polypeptide of SEQ ID NO: 1 or a polypeptide variant having at least 95% sequence identity to the sequence of SEQ ID NO: 1, e.g., asfotase alfa), such as by administering a sALP for a period of at least four years (e.g., at least five years, at least six years, at least seven years, at least eight years, at least nine years, at least ten years, or more than ten years (e.g., for the lifetime of the patient)).

For example, HPP patients (e.g., a child of about 5 to about 12 years of age having HPP) with a BOT-2 strength score of less than 10 (e.g, about 0, about 1, about 2, about 3, about 4, about 5, about 6, about 7, about 8, about 9, or about 10) can be treated with a sALP (such as TNALP, for example the sALP polypeptide of SEQ ID NO: 1 or a polypeptide variant having at least 95% sequence identity to the sequence of SEQ ID NO: 1, e.g., asfotase alfa) for a period of at least four years (e.g., at least five years, at least six years, at least seven years, at least eight years, at least nine years, at least ten years, or more than ten years (e.g., for the lifetime of the patient)). Likewise, HPP patients (e.g., a child of about 5 to about 12 years of age having HPP) with a BOT-2 running speed and agility score of less than 10 (e.g, about 0, about 1, about 2, about 3, about 4, about 5, about 6, about 7, about 8, about 9, or about 10) can then be treated with a sALP (such as TNALP, for example the sALP polypeptide of SEQ ID NO: 1 or a polypeptide variant having at least 95% sequence identity to the sequence of SEQ ID NO: 1, e.g., asfotase alfa) for a period of at least four years (e.g., at least five years, at least six years, at least seven years, at least eight years, at least nine years, at least ten years, or more than ten years (e.g., for the lifetime of the patient)).

The methods can result in an improvement in the BOT-2 score (e.g., strength, running speed and agility, fine motor precision, fine motor integration, manual dexterity, bilateral coordination, balance, and/or upper-limb coordination score) of a HPP patient (e.g., a child of about 5 to about 12 years of age having HPP). For example, treatment with a sALP (such as TNALP, for example the sALP polypeptide of SEQ ID NO: 1 or a polypeptide variant having at least 95% sequence identity to the sequence of SEQ ID NO: 1, e.g., asfotase alfa), such as treatment with a sALP for a period of at least four years (e.g., at least five years, at least six years, at least seven years, at least eight years, at least nine years, at least ten years, or more than ten years (e.g., for the lifetime of the patient)), can result in an average increase in the BOT-2 strength score to about 10 to about 20 (e.g. about 10, about 11, about 12, about 13, about 14, about 15, about 16, about 17, about 18, about 19, or about 20). Additionally, treatment with a sALP (such as TNALP, for example the sALP polypeptide of SEQ ID NO: 1 or a polypeptide variant having at least 95% sequence identity to the sequence of SEQ ID NO: 1, e.g., asfotase alfa), such as treatment with a sALP for a period of a period of at least four years (e.g., at least five years, at least six years, at least seven years, at least eight years, at least nine years, at least ten years, or more than ten years (e.g., for the lifetime of the patient)), can result in an average increase in the BOT-2 running speed and agility score to about 5 to about 20 (e.g. about 5, about 6, about 7, about 8, about 9, about 10, about 11, about 12, about 13, about 14, about 15, about 16, about 17, about 18, about 19, or about 20).

The increase in the BOT-2 score (e.g., strength, running speed and agility, fine motor precision, fine motor integration, manual dexterity, bilateral coordination, balance, and/or upper-limb coordination score) can be sustained throughout administration of the sALP (such as TNALP, for example the sALP polypeptide of SEQ ID NO: 1 or a polypeptide variant having at least 95% sequence identity to the sequence of SEQ ID NO: 1, e.g., asfotase alfa), e.g., for a period of a period of at least four years (e.g., at least five years, at least six years, at least seven years, at least eight years, at least nine years, at least ten years, or more than ten years (e.g., for the lifetime of the patient)). Likewise, the decrease in physical impairments after administration of the sALP can be sustained throughout administration of the sALP (such as TNALP, for example the sALP polypeptide of SEQ ID NO: 1 or a polypeptide variant having at least 95% sequence identity to the sequence of SEQ ID NO: 1, e.g., asfotase alfa), e.g., a period of at least four years (e.g., at least five years, at least six years, at least seven years, at least eight years, at least nine years, at least ten years, or more than ten years (e.g., for the lifetime of the patient)).

The BOT-2 scores (strength, running speed and agility, fine motor precision, fine motor integration, manual dexterity, bilateral coordination, balance, and upper-limb coordination scores) of a patient having HPP (e.g., a child of about 5 to about 12 years of age having HPP) can be used singly or in combination to assess treatment efficacy using a sALP (such as TNALP, for example the sALP polypeptide of SEQ ID NO: 1 or a polypeptide variant having at least 95% sequence identity to the sequence of SEQ ID NO: 1, e.g., asfotase alfa), in which improvements relative to a certain test score demonstrate that the sALP is effective for treating physical impairments associated with HPP. For example, when administration of a sALP to a child having HPP (e.g., a child of about 5 to about 12 years of age) results in an average increase in the BOT-2 running speed and agility score to about 5 or greater than about 5, in which the child previously had an average BOT-2 running speed and agility score of less than about 5, then the sALP is considered to be effective at, e.g., treating physical impairments associated with HPP.

Additionally, within each BOT-2 area (strength, running speed and agility, fine motor precision, fine motor integration, manual dexterity, bilateral coordination, balance, and upper-limb coordination), a child having HPP could perform one or more tests to determine the BOT-2 score of the child. For instance, the child having HPP could perform one or more of sit-ups, v-ups, standing long jump, wall sit, and push-ups to determine the BOT-2 strength score, to determine the BOT-2 strength score and assess the treatment efficacy of sALP administration. The child having HPP could perform one or more of balance beam, a shuttle run, two-legged side hop, and/or one-legged side hop to determine the BOT-2 running speed and agility score and assess the treatment efficacy of sALP administration. The child having HPP can cut out a circle and/or connect dots to determine the BOT-2 fine motor precision score and assess the treatment efficacy of sALP administration. The child having HPP can copy a star and/or copy a square to determine the BOT-2 fine motor integration score and assess the treatment efficacy of sALP administration. The child having HPP could perform one or more of transferring pennies, sorting cards, and stringing blocks to determine the BOT-2 manual dexterity score and assess the treatment efficacy of sALP administration. The child having HPP can tap his or her foot and finger and/or perform jumping jacks to determine the BOT-2 bilateral coordination score and assess the treatment efficacy of sALP administration. The child having HPP can walk forward on a line and/or stand on one leg on a balance beam to determine the BOT-2 balance score and assess the treatment efficacy of sALP administration. The child having HPP can throw a ball at a target and/or catch a tossed ball to determine the BOT-2 upper-limb coordination score and assess the treatment efficacy of sALP administration.

Alternatively, when administration of a sALP does not result in an average increase in the BOT-2 running speed and agility score to greater than about 5, the dosage and/or frequency of sALP administration can be changed in order to determine the effective amount of the sALP for the child having HPP (e.g., a child of about 5 to about 12 years of age). For instance, the dosage of the sALP (such as TNALP, for example the sALP polypeptide of SEQ ID NO: 1 or a polypeptide variant having at least 95% sequence identity to the sequence of SEQ ID NO: 1, e.g., asfotase alfa) can be increased from, e.g., about 3 mg/kg/week to about 6 mg/kg/week or about 6 mg/kg/week to about 9 mg/kg/wk.

Childhood Health Assessment Questionnaire (CHAQ)

Children with HPP (e.g., children of about 5 to about 12 years of age) can be identified for treatment with a sALP (such as TNALP, for example the sALP polypeptide of SEQ ID NO: 1 or a polypeptide variant having at least 95% sequence identity to the sequence of SEQ ID NO: 1, e.g., asfotase alfa) using the Childhood Health Assessment Questionnaire (CHAQ). The CHAQ can be administered to evaluate the health status of children having HPP (e.g., children of about 5 to about 12 years of age having HPP) to generate a CHAQ index score for the child, as is described in Bruce & Fries (*J. Rheumatol.* 30(1): 167-178, 2003) and Klepper (*Arthritis & Rheumatism,* 49: S5-S14, 2003), hereby incorporated by reference in their entirety. The CHAQ includes eight categories of questions for dressing/grooming, arising, eating, walking, hygiene, reach, grip, and activities, in which a parent or guardian records the amount of difficulty the child with HPP (e.g., a child of about 5 to about 12 years of age having HPP) has in performing the respective activities. The range of scores within each category is from 0 to 3, in which a score of 0 indicates without any difficulty; a score of 1 indicates with some difficulty; a score of 2 indicates with much difficulty; and a score of 3 indicates that the child is unable to perform the activity.

Children with HPP (e.g., children of about 5 to about 12 years of age) with an average CHAQ index score (e.g., indicative of disability in activities of daily living (ADL) and/or pain) greater than about 0.8 (e.g., about 0.8, about 1, about 1.2, about 1.4, about 1.6, about 1.8, about 2.0, about 2.2, about 2.4, about 2.6, about 2.8, or about 3.0) can be treated by administering a sALP (such as TNALP, for example the sALP polypeptide of SEQ ID NO: 1 or a polypeptide variant having at least 95% sequence identity to the sequence of SEQ ID NO: 1, e.g., asfotase alfa). In particular, children with an average CHAQ index score of greater than about 0.8 can be treated by administering a sALP (such as TNALP, for example the sALP polypeptide of SEQ ID NO: 1 or a polypeptide variant having at least 95% sequence identity to the sequence of SEQ ID NO: 1, e.g., asfotase alfa) for a period of at least four years (e.g., at least five years, at least six years, at least seven years, at least eight years, at least nine years, at least ten years, or more than ten years (e.g., for the lifetime of the children)). Furthermore, a child having HPP could be asked one or more questions in one or more of the eight categories (dressing/grooming, arising, eating, walking, hygiene, reach, grip, and activities) to arrive at an average CHAQ index score, and if the average CHAQ index score is greater than about 0.8, the child can be treated by administering a sALP.

The CHAQ index score of a child having HPP (e.g., a child of about 5 to about 12 years of age having HPP) can be compared to the CHAQ index score of children without HPP (e.g., children of about 5 to about 12 years of age without HPP) to, e.g., determine the standard deviation of the CHAQ index score. Additionally, the CHAQ index score of a child having HPP (e.g., a child of about 5 to about 12 years of age having HPP) can be compared to the CHAQ index score of other children having HPP (e.g., children of about 5 to about 12 years of age without HPP) to, e.g., determine the standard deviation of the CHAQ index score.

The methods can result in an improvement in the CHAQ index score (e.g., indicative of disability in ADL and/or pain) of the child having HPP (e.g., a child of about 5 to about 12 years of age having HPP). For example, treatment with a sALP (such as TNALP, for example the sALP polypeptide of SEQ ID NO: 1 or a polypeptide variant having at least 95% sequence identity to the sequence of SEQ ID NO: 1, e.g., asfotase alfa), such as treatment with a sALP for a period of at least four years (e.g., at least five years, at least six years, at least seven years, at least eight years, at least nine years, at least ten years, or more than ten years (e.g., for the lifetime of the patient)) can result in an average decrease in the CHAQ index score to about 0 to equal to or less than about 0.5 (e.g. about 0, about 0.1, about 0.2, about 0.4, or about 0.5).

The increase in the CHAQ index score of the child having HPP (e.g., a child of about 5 to about 12 years of age having HPP) can be sustained throughout administration of the sALP (such as TNALP, for example the sALP polypeptide of SEQ ID NO: 1 or a polypeptide variant having at least 95% sequence identity to the sequence of SEQ ID NO: 1, e.g., asfotase alfa), e.g., for a period of at least four years (e.g., at least five years, at least six years, at least seven years, at least eight years, at least nine years, at least ten years, or more than ten years (e.g., for the lifetime of the patient)). Likewise, the increase in ADL and/or decrease in pain of the child having HPP (e.g., a child of about 5 to about 12 years of age having HPP) can be sustained throughout administration of the sALP (such as TNALP, for example the sALP polypeptide of SEQ ID NO: 1 or a polypeptide variant having at least 95% sequence identity to the sequence of SEQ ID NO: 1, e.g., asfotase alfa), e.g., a period of at least four years (e.g., at least five years, at least six years, at least seven years, at least eight years, at least nine years, at least ten years, or more than ten years (e.g., for the lifetime of the patient)).

The CHAQ index score of a child having HPP (e.g., a child of about 5 to about 12 years of age having HPP) can be used to assess treatment efficacy using a sALP (such as TNALP, for example the sALP polypeptide of SEQ ID NO: 1 or a polypeptide variant having at least 95% sequence identity to the sequence of SEQ ID NO: 1, e.g., asfotase alfa), in which improvements relative to a certain test score demonstrate that the sALP is effective for treating, e.g., disability in activities of daily living (ADL) and pain associated with HPP. In particular, a child having HPP could be asked one or more questions in one or more of the eight categories (dressing/grooming, arising, eating, walking, hygiene, reach, grip, and activities) to arrive at an average CHAQ index score and to assess treatment efficacy of sALP administration. For example, when administration of a sALP to a child having HPP (e.g., a child of about 5 to about 12 years of age) results in an average decrease in the CHAQ index score to equal to or less than about 0.5, in which the child previously had an average CHAQ index score of greater than about 0.8, then the sALP is effective at treating, e.g., disability in activities of daily living (ADL) and pain associated with HPP. Alternatively, when administration of a sALP does not result in an average decrease in the CHAQ index score to equal to or less than about 0.5, the dosage and/or frequency of sALP administration can be changed in order to determine the effective amount of the sALP for the child having HPP (e.g., a child of about 5 to about 12 years of age). For instance, the dosage of the sALP (such as TNALP, for example the sALP polypeptide of SEQ ID NO: 1 or a polypeptide variant having at least 95% sequence identity to the sequence of SEQ ID NO: 1, e.g., asfotase alfa) can be increased from, e.g., about 3 mg/kg/week to about 6 mg/kg/week or about 6 mg/kg/week to about 9 mg/kg/wk.

Pediatric Outcomes Data Collection Instrument (PODCI)

Certain patients with HPP (e.g., children of about 5 to about 12 years of age having HPP) can be identified for treatment with a sALP (such as TNALP, for example the sALP polypeptide of SEQ ID NO: 1 or a polypeptide variant having at least 95% sequence identity to the sequence of SEQ ID NO: 1, e.g., asfotase alfa) using the Pediatric Outcomes Data Collection Instrument (PODCI). The PODCI can be administered to evaluate the health status of children having HPP under about 19 years of age (e.g., children of about 5 to about 12 years of age having HPP) to generate a PODCI score for the patient, as is described in Plint et al. (*J. Pediatr. Orthop.* 23(6): 788-790, 2003). The PODCI includes eight categories of questions that can be completed by the patient or by a parent/guardian of the HPP patient. Categories that can be used to determine the PODCI of a HPP patient (e.g., a child of about 5 to about 12 years of age having HPP) include the following: 1) the upper extremity and physical function scale to measure difficulty encountered in performing daily personal care and student activities; 2) the transfer and basic mobility scale to measure difficulty experienced in performing routine motion and motor activities in daily activities; 3) the sports/physical functioning scale to measure difficulty or limitations encountered in participating in more active activities or sports; 4) the pain/comfort scale to measure the level of pain experienced during the past week; 5) the treatment expectations scale to measure the long term expectations of treatment; 6) the happiness scale to measure overall satisfaction with personal looks and sense of similarity to friends and others of own age; 7) the satisfaction with symptoms scale to measure the patient's acceptance of current limitations should this be a life-long state; and 8) the global functioning scale, which is a general combined scale calculated from the first four scales listed above. In each of the categories, a standardized score is determined for the HPP patient (e.g., a child of about 5 to about 12 years of age having HPP) and then converted to a 0 to 100 scale, in which 0 represents significant disability and 100 represents less disability.

HPP patients (e.g., children of about 5 to about 12 years of age having HPP) with an average PODCI score (e.g., indicative of disability in ADL and/or pain) less than about 40 (e.g., about 5, about 10, about 15, about 20, about 25, about 30, about 35, or about 39) can be treated by administering a sALP (such as TNALP, for example the sALP polypeptide of SEQ ID NO: 1 or a polypeptide variant having at least 95% sequence identity to the sequence of SEQ ID NO: 1, e.g., asfotase alfa). In particular, patients (e.g., children of about 5 to about 12 years of age having HPP) with an average PODCI score of less than 40 can be treated by administering a sALP for a period of at least four years (e.g., at least five years, at least six years, at least seven years, at least eight years, at least nine years, at least ten years, or more than ten years (e.g., for the lifetime of the patient)). Furthermore, a child having HPP could be asked one or more questions in one or more of the eight scales described above (e.g., transfer and basic mobility, sports/physical functioning, and the pain/comfort scale) to arrive at an average PODCI score, and if the average PODCI score is greater than less than 40, the child can be treated by administering a sALP.

The methods described herein can result in an increase in the PODCI score (e.g., indicative of disability in ADL and/or pain) of the HPP patient (e.g., children of about 5 to about 12 years of age having HPP). For example, treatment with a sALP (such as TNALP, for example the sALP polypeptide of SEQ ID NO: 1 or a polypeptide variant having at least 95% sequence identity to the sequence of SEQ ID NO: 1, e.g., asfotase alfa), such as treatment with a sALP for a period of at least four years (e.g., at least five years, at least six years, at least seven years, at least eight years, at least nine years, at least ten years, or more than ten years (e.g., for the lifetime of the patient)), can result in an average increase in the PODCI score to about 40 to about 50 (e.g. about 40, about 41, about 42, about 43, about 44, about 45, about 46, about 47, about 48, about 49, or about 50).

The increase in the PODCI score can be sustained throughout administration of the sALP (such as TNALP, for example the sALP polypeptide of SEQ ID NO: 1 or a polypeptide variant having at least 95% sequence identity to the sequence of SEQ ID NO: 1, e.g., asfotase alfa), e.g., for a period of at least four years (e.g., at least five years, at least six years, at least seven years, at least eight years, at least nine years, at least ten years, or more than ten years (e.g., for the lifetime of the patient)). Likewise, the increase in ADL and/or decrease in pain can be sustained throughout administration of the sALP (such as TNALP, for example the sALP polypeptide of SEQ ID NO: 1 or a polypeptide variant having at least 95% sequence identity to the sequence of SEQ ID NO: 1, e.g., asfotase alfa), e.g., a period of at least four years (e.g., at least five years, at least six years, at least seven years, at least eight years, at least nine years, at least ten years, or more than ten years (e.g., for the lifetime of the patient)).

The PODCI score of a patient having HPP (e.g., a child of about 5 to about 12 years of age having HPP) can be used to assess treatment efficacy using a sALP (such as TNALP, for example the sALP polypeptide of SEQ ID NO: 1 or a polypeptide variant having at least 95% sequence identity to the sequence of SEQ ID NO: 1, e.g., asfotase alfa), in which improvements relative to a certain test score demonstrate that the sALP is effective for treating, e.g., disability in activities of daily living (ADL) and pain associated with HPP. In particular, a child having HPP could be asked one or more questions in one or more of the eight scales (the upper extremity and physical function scale, the transfer and basic mobility scale, the sports/physical functioning scale, the pain/comfort scale, the treatment expectations scale, the happiness scale, the satisfaction with symptoms scale, and the global functioning scale) to arrive at an average PODCI score and to assess treatment efficacy of sALP administration.

For example, when administration of a sALP to a child having HPP (e.g., a child of about 5 to about 12 years of age) results in an average increase in the PODCI score to about 40 or greater than about 40, in which the child previously had an average PODCI score of less than about 40, then the sALP is effective at treating, e.g., disability in activities of daily living (ADL) and pain associated with HPP. Alternatively, when administration of a sALP does not result in an average increase in the PODCI score to about 40 or greater than about 40, the dosage and frequency of sALP administration can be changed in order to determine the effective amount of the sALP for the child having HPP (e.g., a child of about 5 to about 12 years of age). For instance, the dosage of the sALP (such as TNALP, for example the sALP polypeptide of SEQ ID NO: 1 or a polypeptide variant having at least 95% sequence identity to the sequence of SEQ ID NO: 1, e.g., asfotase alfa) can be increased from, e.g., about 3 mg/kg/week to about 6 mg/kg/week or about 6 mg/kg/week to about 9 mg/kg/wk.

Six Minute Walk Test (6MWT)

Children with HPP (e.g., children with HPP of about 5 to about 12 years of age) can be identified for treatment with a sALP (such as TNALP, for example the sALP fusion polypeptide of SEQ ID NO: 1 or a polypeptide variant having at least 95% sequence identity to the sequence of SEQ ID NO: 1, e.g., asfotase alfa) using the 6MWT. In particular, the 6MWT can be used to evaluate walking ability in children with HPP (e.g., children with HPP of about 5 to about 12 years of age) to determine the 6MWT distance for the child prior to or after administration of a sALP.

The 6MWT can be performed indoors or outdoors using a flat, straight, enclosed corridor (e.g., of about 30 meters in length) with a hard surface. A stopwatch or other timer can be used to track the time and a mechanical counter or other device can be used to determine the distance (e.g., in meters) that the HPP patient (e.g., a child with HPP of about 5 to about 12 years of age) walks. For instance, the length of the corridor can be marked every three meters to determine the number of meters walked by the HPP patient, with the turnaround point at 30 meters and the starting line also marked. The distance walked by the patient in six minutes (the 6MWT distance) can then be compared to the predicted number of meters walked, e.g., by an untreated or healthy subject of about the same age, the same gender, and/or the same height, and expressed as a percentage value to generate the 6MWT value of the patient. The 6MWT distance of the patient (e.g., the child having HPP) can also be compared to the 6MWT distance of the patient at baseline.

HPP patients (e.g., a child with HPP of about 5 to about 12 years of age) with an average 6MWT distance of less than about 80% of the predicted 6MWT distance can be treated with a sALP (such as TNALP, for example the sALP fusion polypeptide of SEQ ID NO: 1 or a polypeptide variant having at least 95% sequence identity to the sequence of SEQ ID NO: 1, e.g., asfotase alfa), such as by administering a sALP for a period of at least one year (e.g., at least two years, at least three years, at least four years, at least five years, at least six years, at least seven years, at least eight years, at least nine years, at least ten years, or longer than ten years, such as for the lifetime of the patient). For example, an HPP patient with an average 6MWT of less than about 80% of the predicted 6MWT distance (e.g., about 35%, about 40%, about 45%, about 50%, about 55%, about 60%, about 65%, about 70%, or about 75% of the predicted 6MWT distance) can be treated with a sALP for a period of at least one year (e.g., at least two years, at least three years, at least four years, at least five years, at least six years, at least seven years, at least eight years, at least nine years, at least ten years, or longer than ten years, such as for the lifetime of the patient).

The methods can result in an improvement in the 6MWT distance of a HPP patient (e.g., a child with HPP of about 5 to about 12 years of age). For example, treatment with a sALP (such as TNALP, for example the sALP fusion polypeptide of SEQ ID NO: 1 or a polypeptide variant having at least 95% sequence identity to the sequence of SEQ ID NO: 1, e.g., asfotase alfa), such as treatment with a sALP for a period of at least one year (e.g., at least two years, at least three years, at least four years, at least five years, at least six years, at least seven years, at least eight years, at least nine years, at least ten years, or longer than ten years, such as for the lifetime of the patient), can result in an average increase in the 6MWT distance of about 20 meters or more (e.g., about 20 meters, about 25 meters, about 30 meters, about 35 meters, about 40 meters, about 45 meters, about 50 meters, about 55 meters, about 60 meters, about 65 meters, about 70 meters, about 75 meters, about 80 meters, about 85 meters, about 90 meters, about 95 meters, about 100 meters, or more). Likewise, treatment with a sALP can result in an average increase in the 6MWT value to about 50% or greater of the predicted 6MWT value (e.g., the predicted number of meters walked by a healthy subject of about the same age, the same gender, and/or the same height expressed as a percentage value) of the patient (e.g. about 55%, about 60%, about 65%, about 70%, about 75%, about 80%, about 85%, about 90%, about 95%, or more of the predicted 6MWT value).

The increase in the 6MWT distance of the HPP patient (e.g., a child with HPP of about 5 to about 12 years of age) can be sustained throughout administration of the sALP (such as TNALP, for example the sALP fusion polypeptide of SEQ ID NO: 1 or a polypeptide variant having at least 95% sequence identity to the sequence of SEQ ID NO: 1, e.g., asfotase alfa), e.g., for a period of at least one year (e.g., at least two years, at least three years, at least four years, at least five years, at least six years, at least seven years, at least eight years, at least nine years, at least ten years, or longer than ten years, such as for the lifetime of the patient). For instance, the 6MWT value increases by about 20 meters and/or to greater than about 80% of the predicted 6MWT distance of the patient and remains at ±10% of the increased 6MWT distance during treatment with the sALP (e.g., asfotase alfa).

Likewise, the improvement in walking ability of the HPP patient can be sustained throughout administration of the sALP, e.g., for a period of at least one year (e.g., at least two years, at least three years, at least four years, at least five years, at least six years, at least seven years, at least eight years, at least nine years, at least ten years, or longer than ten years, such as for the lifetime of the patient). For instance, the HPP patient exhibits decreased reliance on an assistive device for walking, such as a wheelchair, a wheeled walker, a cane, or an orthotic during treatment with the sALP.

Alternatively, when administration of a sALP does not result in an average increase in the 6MWT distance by about 20 meters relative to baseline, the dosage and/or frequency of sALP administration can be changed in order to determine the effective amount of the sALP for the HPP patient (e.g., a child with HPP of about 5 to about 12 years of age). Likewise, when administration of a sALP does not result in an average increase in the 6MWT distance to greater than 80% of the predicted 6MWT distance (e.g., of an untreated subject having HPP of about the same age, same gender, and/or height), the dosage and/or frequency of sALP administration can be changed in order to determine the effective amount of the sALP for the HPP patient (e.g., a child with HPP of about 5 to about 12 years of age). For instance, the dosage of the sALP (such as TNALP, for example the sALP fusion polypeptide of SEQ ID NO: 1 or a polypeptide variant having at least 95% sequence identity to the sequence of SEQ ID NO: 1, e.g., asfotase alfa) can be increased from, e.g., about 2.1 mg/kg/week or about 3.5 mg/kg/week to about 6 mg/kg/week or about 9 mg/kg/week.

Bayley Scales of Infant and Toddler Development, $3^{rd}$ Edition (BSID-III)

Children with HPP (e.g., children of about 5 to about 12 years of age) can be identified for treatment with a sALP (such as TNALP, for example the sALP polypeptide of SEQ ID NO: 1 or a polypeptide variant having at least 95% sequence identity to the sequence of SEQ ID NO: 1, e.g., asfotase alfa) using the Bayley Scales of Infant and Toddler Development, 3$^{rd}$ Edition (BSID-III). The BSID-III can be administered to evaluate the health status of HPP patients from birth to generate a BSID-III score for the patient, as is described in Bayley. (2006). *Bayley scales of infant and toddler development: administration manual*. San Antonio, Tex.: Harcourt Assessment. The BSID-III includes a series of developmental play tasks that can be administered to the HPP patient (e.g., infants of about three years of age or less having HPP) to determine the raw BSID-III score. For example, categories for determining the BSID-III score of an HPP patient (e.g., infants of about three years of age or less having HPP) can include prehension, perceptual-motor integration, motor planning and speed, visual tracking, reaching, object grasping, object manipulation, functional hand skills, responses to tactile information, movement of the limbs and torso, static positioning, dynamic movement, balance, and motor planning. The BSID-III measurements are then converted to scaled BSID-III scores, which can be used to determine the HPP patient's performance compared to healthy, age-adjusted patients. The BSID-III scaled score of a patient (e.g., a patient with HPP) can range from 0 to 14, in which scores of about 7 to about 13 are considered the normal range of healthy patients.

A child having HPP (e.g., a child of about 5 to about 12 years of age having HPP) could perform tests in one or more of described categories (prehension, perceptual-motor integration, motor planning and speed, visual tracking, reaching, object grasping, object manipulation, functional hand skills, responses to tactile information, movement of the limbs and torso, static positioning, dynamic movement, balance, and motor planning) as an infant (e.g., at about 3 years of age or less than 3 years of age) to generate a BSID-III score indicative of delayed motor development. Children having HPP with an average BSID-III score in one or more of the described categories (prehension, perceptual-motor integration, motor planning and speed, visual tracking, reaching, object grasping, object manipulation, functional hand skills, responses to tactile information, movement of the limbs and torso, static positioning, dynamic movement, balance, and motor planning) less than about 2 as an infant can be treated by administering a sALP (such as TNALP, for example the sALP polypeptide of SEQ ID NO: 1 or a polypeptide variant having at least 95% sequence identity to the sequence of SEQ ID NO: 1, e.g., asfotase alfa). In particular, children having HPP with an average BSID-III score of less than about 2 as an infant can be treated by administering a sALP for a period of at least four years (e.g., at least five years, at least six years, at least seven years, at least eight years, at least nine years, at least ten years, or more than ten years (e.g., for the lifetime of the patient)).

The methods can result in an improvement in the average BSID-III score (e.g., indicative of delayed motor development) of the HPP patient. For example, treatment with a sALP (such as TNALP, for example the sALP polypeptide of SEQ ID NO: 1 or a polypeptide variant having at least 95% sequence identity to the sequence of SEQ ID NO: 1, e.g., asfotase alfa), such as treatment with a sALP for a period of at least four years (e.g., at least five years, at least six years, at least seven years, at least eight years, at least nine years, at least ten years, or more than ten years (e.g., for the lifetime of the patient)) can result in an average increase in the BSID-III score to greater than about 5 (e.g., about 5, about 6, about 7, about 8, about 9, about 10, about 11, about 12, or about 13).

The increase in the BSID-III score can be sustained throughout administration of the sALP (such as TNALP, for example the sALP polypeptide of SEQ ID NO: 1 or a polypeptide variant having at least 95% sequence identity to the sequence of SEQ ID NO: 1, e.g., asfotase alfa), e.g., for a period of at least four years (e.g., at least five years, at least six years, at least seven years, at least eight years, at least nine years, at least ten years, or more than ten years (e.g., for the lifetime of the patient)). Likewise, the increase in motor development can be sustained throughout administration of the sALP (such as TNALP, for example the sALP polypeptide of SEQ ID NO: 1 or a polypeptide variant having at least 95% sequence identity to the sequence of SEQ ID NO: 1, e.g., asfotase alfa), e.g., for a period of at least four years (e.g., at least five years, at least six years, at least seven years, at least eight years, at least nine years, at least ten years, or more than ten years (e.g., for the lifetime of the patient)).

The BSID-III score of a patient having HPP (e.g., a child of about 5 to about 12 years of age having HPP) can be used to assess treatment efficacy using a sALP (such as TNALP, for example the sALP polypeptide of SEQ ID NO: 1 or a polypeptide variant having at least 95% sequence identity to the sequence of SEQ ID NO: 1, e.g., asfotase alfa), in which improvements relative to a certain test score demonstrate that the sALP is effective for treating, e.g., delayed motor development associated with HPP. In particular, a child having HPP could perform tests in one or more of described categories (prehension, perceptual-motor integration, motor planning and speed, visual tracking, reaching, object grasping, object manipulation, functional hand skills, responses to tactile information, movement of the limbs and torso, static positioning, dynamic movement, balance, and motor planning) as an infant (e.g., at about three years of age or less having HPP) to arrive at an average BSID-III score and to assess treatment efficacy of sALP administration.

For example, when administration of a sALP to a child having HPP (e.g., a child of about 5 to about 12 years of age) results in an average increase in the BSID-III scaled score to greater than about 5, in which the child previously had an average BSID-III scaled score of less than about 2 as an infant (e.g., at about 3 years of age or less than 3 years of age), then the sALP is effective at treating, e.g., delayed motor development associated with HPP. Alternatively, when administration of a sALP does not result in an average increase in the BSID-III scaled score to greater than about 5, the dosage and/or frequency of sALP administration can be changed in order to determine the effective amount of the sALP for the child having HPP (e.g., a child of about 5 to about 12 years of age). For instance, the dosage of the sALP (such as TNALP, for example the sALP polypeptide of SEQ ID NO: 1 or a polypeptide variant having at least 95% sequence identity to the sequence of SEQ ID NO: 1, e.g., asfotase alfa) can be increased from, e.g., about 3 mg/kg/week to about 6 mg/kg/week or about 6 mg/kg/week to about 9 mg/kg/wk.

Peabody Developmental Motor Scales, 2nd Edition (PDMS-2)

Children with HPP (e.g., children of about 5 to about 12 years of age) can be identified for treatment with a sALP (such as TNALP, for example the sALP polypeptide of SEQ ID NO: 1 or a polypeptide variant having at least 95% sequence identity to the sequence of SEQ ID NO: 1, e.g., asfotase alfa) using the Peabody Developmental Motor Scales, 2nd Edition (PDMS-2). The PDMS-2 can be administered to evaluate the health status of HPP patients from birth to generate a PDMS-2 score for the patient, as is described in van Hartingsveldt, et al. (*Occup. Ther. Int.* 12(1): 1-13, 2005). The PDMS-2 includes six categories of subtests to measure motor skills of patients, such as a patient having HPP (e.g., infants and children having HPP).

In particular, PDMS-2 measurements can be determined from the following subtests: 1) the locomotor subtest to measure a child's (e.g., a child having HPP of about 5 years of age or less than 5 years of age) ability to move from one place to another (measurements include crawling, walking, running, hopping, and jumping forward); 2) the reflexes subtest to measure a child's (e.g., a child having HPP of about 5 years of age or less than 5 years of age) ability to automatically react to environmental events; 3) the stationary subtest to measure a child's (e.g., a child having HPP of about 5 years of age or less than 5 years of age) ability to sustain control of his or her body within the center of gravity and retain equilibrium; 4) the object manipulation subtest to measure a child's (e.g., a child having HPP of about 5 years of age or less than 5 years of age) ability to manipulate an object, such as catching, throwing, and kicking a ball; 5) the grasping subtest to measure a child's (e.g., a child having HPP of about 5 years of age or less than 5 years of age) ability to use his or her hands, such as the ability to hold an object with one hand and actions involving the controlled use of the fingers of both hands; and 6) the visual-motor integration subtest to measure a child's (e.g., a child having HPP of about 5 years of age or less than 5 years of age) ability to use his or her visual perceptual skills to perform complex eye-hand coordination tasks, such as reaching and grasping for an object, building with blocks, and copying designs. The PDMS-2 measurement can be determined for one or more of these categories for children with HPP (e.g., children of about 5 years of age or less than 5 years of age) and then converted into a PDMS-2 score, such as the PDMS-2 locomotor standard score ranging from 0 to 13, in which the range of healthy patients (e.g., patients without HPP) is from about 7 to about 13.

Children with HPP (e.g., children of about 5 to about 12 years of age) with an average PDMS-score (e.g., indicative of delayed motor development) of about 5 at 5 years of age or less than 5 years of age can be treated by administering a sALP (such as TNALP, for example the sALP polypeptide of SEQ ID NO: 1 or a polypeptide variant having at least 95% sequence identity to the sequence of SEQ ID NO: 1, e.g., asfotase alfa). In particular, children having HPP with an average PDMS-score in one or more of the described categories (locomotor, reflexes, stationary, object manipulation, grasping, and visual-motor) of about 5 at 5 years of age or less than 5 years of age can be treated by administering a sALP (such as TNALP, for example the sALP polypeptide of SEQ ID NO: 1 or a polypeptide variant having at least 95% sequence identity to the sequence of SEQ ID NO: 1, e.g., asfotase alfa).

The methods described herein can result in an improvement in the PDMS-2 score (e.g., indicative of delayed motor development) of the HPP patient (e.g., children of about 5 to about 12 years of age). For example, treatment with a sALP (such as TNALP, for example the sALP polypeptide of SEQ ID NO: 1 or a polypeptide variant having at least 95% sequence identity to the sequence of SEQ ID NO: 1, e.g., asfotase alfa), such as treatment with a sALP for a period of at least four years (e.g., at least five years, at least six years, at least seven years, at least eight years, at least nine years, at least ten years, or more than ten years (e.g., for the lifetime of the patient)) can result in an average increase in the PDMS-2 score to about 7 to about 13 (e.g., about 7, about 8, about 9, about 10, about 11, about 12, or about 13).

The increase in the PDMS-2 score can be sustained throughout administration of the sALP (such as TNALP, for example the sALP polypeptide of SEQ ID NO: 1 or a polypeptide variant having at least 95% sequence identity to the sequence of SEQ ID NO: 1, e.g., asfotase alfa), e.g., for a period of at least four years (e.g., at least five years, at least six years, at least seven years, at least eight years, at least nine years, at least ten years, or more than ten years (e.g., for the lifetime of the patient)). Likewise, the increase in motor development can be sustained throughout administration of the sALP (such as TNALP, for example the sALP polypeptide of SEQ ID NO: 1 or a polypeptide variant having at least 95% sequence identity to the sequence of SEQ ID NO: 1, e.g., asfotase alfa) for a period of at least four years (e.g., at least five years, at least six years, at least seven years, at least eight years, at least nine years, at least ten years, or more than ten years (e.g., for the lifetime of the patient)).

The PDMS-2 score of a child having HPP (e.g., a child of about 5 to about 12 years of age having HPP) can be used to assess treatment efficacy using a sALP (such as TNALP, for example the sALP polypeptide of SEQ ID NO: 1 or a polypeptide variant having at least 95% sequence identity to the sequence of SEQ ID NO: 1, e.g., asfotase alfa), in which improvements relative to a certain test score demonstrate that the sALP is effective for treating, e.g., delayed motor development associated with HPP. In particular, a child having HPP could perform tests in one or more of described categories (locomotor, reflexes, stationary, object manipulation, grasping, and visual-motor) at about 5 years of age or less than 5 years of age to arrive at an average PDMS-2 score and to assess treatment efficacy of sALP administration.

For example, when administration of a sALP to a child having HPP (e.g., a child of about 5 to about 12 years of age) results in an average increase in the PDMS-2 standard score to about 7, in which the child previously had an average PDMS-2 standard score of about 5, then the sALP is effective at treating, e.g., delayed motor development associated with HPP. Alternatively, when administration of a sALP does not result in an average increase in the PDMS-2 standard score to about 7, the dosage and/or frequency of sALP administration can be changed in order to determine the effective amount of the sALP for the child having HPP (e.g., a child of about 5 to about 12 years of age). For instance, the dosage of the sALP (such as TNALP, for example the sALP polypeptide of SEQ ID NO: 1 or a polypeptide variant having at least 95% sequence identity to the sequence of SEQ ID NO: 1, e.g., asfotase alfa) can be increased from, e.g., about 3 mg/kg/week to about 6 mg/kg/week or about 6 mg/kg/week to about 9 mg/kg/wk.

Alkaline Phosphatase

Asfotase alfa is a human TNALP (hTNALP; SEQ ID NO: 1) fusion protein formulated for the treatment of HPP. In particular, asfotase alfa (SEQ ID NO: 1) can be used effectively to treat hypophosphatasia (HPP), its symptoms, and physical impairments associated therewith in a child with HPP (e.g., a child of about 5 to about 12 years of age having HPP) for an extended period of time (e.g., at least four years, at least five years, at least six years, at least seven years, at least eight years, at least nine years, at least ten years, or more than ten years (e.g., for the lifetime of the patient)).

Given the results described herein, the present disclosure is not limited to a particular alkaline phosphatase (ALP) or nucleic acid sequence encoding an ALP. Alkaline phosphatases encompass a group of enzymes that catalyze the cleavage of a phosphate moiety (e.g., hydrolysis of pyrophosphate, PR). There are four known mammalian alkaline phosphatase (ALP) isozymes: tissue nonspecific alkaline phosphatase (TNALP; described further below), placental alkaline phosphatase (PLALP) (e.g., Accession Nos. P05187, NP_112603, and NP_001623), germ cell alkaline phosphatase (GALP) (e.g., Accession No. P10696), and intestinal alkaline phosphatase (IALP) (e.g., Accession Nos. P09923 and NP_001622). In addition to the exemplary ALPs discussed above, this disclosure also provides any polypeptide having the identical or similar catalytic site structure and/or enzymatic activity of ALP for treating HPP patients, such as children with HPP (e.g., children of about 5 to about 12 years of age having HPP) or infants with HPP (e.g., infants of about 3 years of age or less than 3 years of age). Bone delivery conjugates including sALP are further described in PCT publication Nos: WO 2005/103263 and WO 2008/138131.

TNALPs that can be used according to the methods described herein include, e.g., human TNALP (Accession Nos. NP_000469, AAI10910, AAH90861, AAH66116, AAH21289, and AAI26166); rhesus TNALP (Accession No. XP_01109717); rat TNALP (Accession No. NP_037191); dog TNALP (Accession No. AAF64516); pig TNALP (Accession No. AAN64273), mouse (Accession No. NP_031457), cow TNALP (Accession Nos. NP_789828, NP_776412, AAM 8209, and AAC33858), and cat TNALP (Accession No. NP_001036028). In particular, TNALP can be a recombinant human TNALP (e.g., SEQ ID NO: 1, asfotase alfa; see U.S. Pat. Nos. 7,763,712 and 7,960,529, incorporated herein by reference in their entirety) used for the treatment of HPP patients, such as children with HPP (e.g., children of about 5 to about 12 years of age having HPP) or infants with HPP (e.g., infants of about 3 years of age or less than 3 years of age). The TNALP can also be one that exhibits at least about 95% sequence identity to the polypeptide or nucleic acid sequence of the above-noted TNALPs.

Soluble Alkaline Phosphatase

The ALPs of the present invention include soluble (e.g., extracellular or non-membrane-bound) forms of any of the alkaline phosphatases described herein. The sALP of the invention can be, for example, a soluble form of human tissue non-specific alkaline phosphatase (human TNALP (hTNALP)). The present disclosure is not limited to a particular sALP and can include any sALP polypeptide that is physiologically active toward, e.g., phosphoethanolamine (PEA), inorganic pyrophosphate (PPi), and pyridoxal 5'-phosphate (PLP). In particular, a sALP of the present invention is catalytically competent to improve skeletal mineralization in bone. The present invention further includes nucleic acids encoding the sALPs described herein that can be used to treat the conditions described herein, e.g., HPP, such as children with HPP (e.g., children of about 5 to about 12 years of age having HPP) or infants with HPP (e.g., infants of about 3 years of age or less than 3 years of age).

TNALP is a membrane-bound protein anchored by a glycolipid moiety at the C-terminal (Swiss-Prot, P05186). This glycolipid anchor (GPI) is added post-translationally after the removal of a hydrophobic C-terminal end, which serves both as a temporary membrane anchor and as a signal for the addition of the GPI. While the GPI anchor is located in the cell membrane, the remaining portions of TNALP are extracellular. In particular, TNALP (e.g., human TNALP (hTNALP)) can be engineered to replace the first amino acid of the hydrophobic C-terminal sequence (an alanine) with a stop codon, thereby producing an engineered hTNALP that contains all amino acid residues of the native anchored form of TNALP and lacks the GPI membrane anchor. One skilled in the art will appreciate that the position of the GPI membrane anchor will vary in different ALPs and can include, e.g., the last 10, 12, 14, 16, 18, 20, 21, 22, 23, 24, 25, 26, 27, 28, 29, 30, 32, 34, 36, 38, 40, 45, 50, or more amino acid residues on the C-terminus of the polypeptide. Recombinant sTNALP can include, e.g., amino acids 1 to 502 (18 to 502 when secreted), amino acids 1 to 501 (18 to 501 when secreted), amino acids 1 to 504 (18 to 504 when secreted), amino acids 1 to 505 (18-505 when secreted), or amino acids 1 to 502. Thus, the C-terminal end of the native ALP can be truncated by certain amino acids without affecting ALP activity.

In addition to the C-terminal GPI anchor, TNALP also has an N-terminal signal peptide sequence. The N-terminal signal peptide is present on the synthesized protein when it is synthesized, but cleaved from TNALP after translocation into the ER. The sALPs of the invention include both secreted (i.e., lacking the N-terminal signal) and non-secreted (i.e., having the N-terminal signal) forms thereof. One skilled in the art will appreciate that the position of the N-terminal signal peptide will vary in different alkaline phosphatases and can include, for example, the first 5, 8, 10, 11, 12, 13, 14, 15, 16, 17, 18, 19, 20, 21, 22, 23, 24, 25, 27, 30, or more amino acid residues on the N-terminus of the polypeptide. One of skill in the art can predict the position of a signal sequence cleavage site, e.g., by an appropriate computer algorithm such as that described in Bendtsen et al. (*J. Mol. Biol.* 340(4):783-795, 2004) and available on the Web at www.cbs.dtu.dk/services/SignalP/.

The present invention also includes sALP consensus sequences derived from the extracellular domain of ALP isozymes (e.g., TNALP, PALP, GCALP, IALP, etc.). Thus, similar to sTNALP discussed above, the present disclosure also provides other soluble human ALP isozymes, i.e., without the peptide signal, preferably comprising the extracellular domain of the ALPs. The sALPs of the invention also include polypeptide sequences satisfying a consensus sequence derived from the ALP extracellular domain of human ALP isozymes and of mammalian TNALP orthologs (human, mouse, rat, cow, cat, and dog) or a consensus derived from the ALP extracellular domain of just mammalian TNALP orthologs (human, mouse, rat, cow, cat, and dog). The sALPs of the invention also include those which satisfy similar consensus sequences derived from various combinations of these TNALP orthologs or human ALP isozymes. Such consensus sequences are given, for example, in WO 2008/138131.

sALPs of the present invention can include not only the wild-type sequence of the sALPs described above, but any polypeptide having at least 50% (e.g., 55%, 60%, 65%, 70%, 75%, 80%, 85%, 86%, 87%, 88%, 89%, 90%, 91%, 92%, 93%, 94%, 95%, 96%, 97%, 98%, 99%, or more) sequence identity to these alkaline phosphatases (e.g., SEQ ID NOs: 1-24; for example the sALP polypeptide of SEQ ID NO: 1 or a polypeptide variant having at least 95% sequence identity to the sequence of SEQ ID NO: 1, e.g., asfotase alfa). Examples of mutations that can be introduced into an ALP sequence are described in US Publication No. 2013/0323244, hereby incorporated by reference in its entirety. A sALP can optionally be glycosylated at any appropriate one or more amino acid residues. In addition, an sALP can have at least 50% (e.g., 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more) sequence identity to any of the sALPs described herein (such as TNALP, for example the sALP polypeptide of SEQ ID NO: 1 or a polypeptide variant having at least 95% sequence identity to the sequence of SEQ ID NO: 1, e.g., asfotase alfa). A sALP can have 1, 2, 3, 4, 5, 6, 7, 8, 9, 10, or more additions, deletions, or substitutions relative to any of the sALPs described herein (such as TNALP, for example the sALP polypeptide of SEQ ID NO: 1 or a polypeptide variant having at least 95% sequence identity to the sequence of SEQ ID NO: 1, e.g., asfotase alfa).

sALP Fusion Polypeptides

Any of the sALPs and linkers described herein can be combined in a sALP polypeptide, e.g., a sALP polypeptide of A-sALP-B, wherein each of A and B is absent or is an amino acid sequence of at least one amino acid (such as TNALP, for example the sALP polypeptide of SEQ ID NO: 1 or a polypeptide variant having at least 95% sequence identity to the sequence of SEQ ID NO: 1, e.g., asfotase alfa). When present, A and/or B can be any linker described herein. In some sALP polypeptides, A is absent, B is absent, or A and B are both absent. The sALP polypeptides of the invention can optionally include an Fc region to provide an sALP fusion polypeptide, as described herein. The sALP polypeptide can optionally include a bone-targeting moiety, as described herein. In some sALP polypeptides, a linker, e.g., a flexible linker, can be included between the bone-targeting moiety and the sALP, such as a dipeptide sequence (e.g., leucine-lysine or aspartic acid-isoleucine). Further exemplary Fc regions, linkers, and bone-targeting moieties are described below.

Any of the sALPs, linkers, and Fc regions described herein can be combined in a fusion polypeptide, e.g., a recombinant fusion polypeptide, which includes the structure Z-sALP-Y-spacer-X-$W_n$-V, Z-$W_n$-X-spacer-Y-sALP-V, Z-sALP-Y-$W_n$-X-spacer-V, and Z-$W_n$-X-sALP-Y-spacer-V (such as TNALP, for example the sALP polypeptide of SEQ ID NO: 1 or a polypeptide variant having at least 95% sequence identity to the sequence of SEQ ID NO: 1, e.g., asfotase alfa). In particular, the structure can be Z-sALP-Y-spacer-X-$W_n$-V or Z-$W_n$-X-spacer-Y-sALP-V. The sALP can be the full-length or functional fragments of ALPs, such as the soluble, extracellular domain of the ALP, as is described herein (e.g., TNALP, PALP, GCALP and IALP). Any one of X, Y, Z, and V and/or the spacer can be absent or an amino acid sequence of at least one amino acid. $W_n$ can be a bone-targeting moiety, e.g., having a series of consecutive Asp or Glu residues, in which n=1 to 50, e.g., n=3-30, e.g., 5-15, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 36, 38, 39, 40, 41, 42, 43, 44, 45, 46, 47, 48, 49, or 50. The bone-targeting moiety, if present, can be positioned anywhere in the fusion polypeptide, e.g., at or near the N-terminal or C-terminal end, and/or in the linker region. For instance, the bone-targeting moiety is at the C-terminal end. sALP polypeptides and fusion polypeptides can also not include a bone-targeting moiety.

sALP fusion polypeptides of the present invention can be of the structure hTNALP-Fc-$D_{10}$. In particular, sALP fusion polypeptides can include an amino acid sequence of SEQ ID NO: 1 or a polypeptide variant having at least 95% sequence identity to the sequence of SEQ ID NO: 1, e.g., asfotase alfa.

Useful spacers include, but are not limited to, polypeptides comprising a Fc, and hydrophilic and flexible polypeptides able to alleviate the repulsive forces caused by the presence of the terminal highly negatively charged peptide (e.g., $W_n$). For example, a sALP can be a fusion polypeptide including an Fc region of an immunoglobulin at the N-terminal or C-terminal domain. An immunoglobulin molecule has a structure that is well known in the art. It includes two light chains (~23 kD each) and two heavy chains (~50-70 kD each) joined by inter-chain disulfide bonds. Immunoglobulins are readily cleaved proteolytically (e.g., by papain cleavage) into Fab (containing the light chain and the VH and CH1 domains of the heavy chain) and Fc (containing the CH2 and CH3 domains of the heavy chain, along with adjoining sequences). Useful Fc fragments as described herein include the Fc fragment of any immunoglobulin molecule, including IgG, IgM, IgA, IgD, or IgE, and their various subclasses (e.g., IgG-1, IgG-2, IgG-3, IgG-4, IgA-1, IgA-2), from any mammal (e.g., human). For instance, the Fc fragment is human IgG-1. The Fc fragments of the invention can include, for example, the CH2 and CH3 domains of the heavy chain and any portion of the hinge region. The Fc region can optionally be glycosylated at any appropriate one or more amino acid residues known to those skilled in the art. In particular, the Fc fragment of the fusion polypeptide has the amino acid sequence of SEQ ID NO: 20, or has at least 50% (e.g., 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more) sequence identity to SEQ ID NO: 20. Engineered, e.g., non-naturally occurring, Fc regions can be utilized in the methods of the invention, e.g., as described in International Application Pub. No. WO2005/007809, which is hereby incorporated by reference. An Fc fragment as described herein can have 1, 2, 3, 4, 5, 6, 7, 8, 9, 10, 11, 12, 13, 14, 15, 16, 17, 18, 19, 20, 25, 30, 35, 40, 50, or more additions, deletions, or substitutions relative to any of the Fc fragments described herein.

The sALP fusion polypeptides described herein (such as TNALP, for example the sALP polypeptide of SEQ ID NO: 1 or a polypeptide variant having at least 95% sequence identity to the sequence of SEQ ID NO: 1, e.g., asfotase alfa) can include a peptide linker region between the Fc fragment. In addition, a peptide linker region can be included between the Fc fragment and the optional bone-targeting moiety. The linker region can be of any sequence and length that allows the sALP to remain biologically active, e.g., not sterically hindered. Exemplary linker lengths are between 1 and 200 amino acid residues, e.g., 1-5, 6-10, 11-15, 16-20, 21-25, 26-30, 31-35, 36-40, 41-45, 46-50, 51-55, 56-60, 61-65, 66-70, 71-75, 76-80, 81-85, 86-90, 91-95, 96-100, 101-110, 111-120, 121-130, 131-140, 141-150, 151-160, 161-170, 171-180, 181-190, or 191-200 amino acid residues. For instance, linkers include or consist of flexible portions, e.g., regions without significant fixed secondary or tertiary structure. Exemplary flexible linkers are glycine-rich linkers, e.g., containing at least 50%, 60%, 65%, 70%, 75%, 80%, 85%, 90%, 95%, or even 100% glycine residues. Linkers can also contain, e.g., serine residues. In some cases, the amino acid sequence of linkers consists only of glycine and serine residues. A linker can optionally be glycosylated at any appropriate one or more amino acid residues. Additionally, a linker as described herein can include any other sequence or moiety, attached covalently or non-covalently. The linker can also be absent, in which the Fc fragment and the sALP are fused together directly, with no intervening residues. Certain Fc-sALP or sALP-Fc fusion polypeptides can be viewed, according to the present disclosure, either as 1) having no linker, or as 2) having a linker which corresponds to a portion of the sALP. For example, Fc fused directly to hsTNALP (1-502) can be viewed, e.g., either as having no linker, in which the hsTNALP is amino acids 1-502, or as having a 17-amino acid linker, in which the hsTNALP (18-502).

Additional amino acid residues can be introduced into the polypeptide according to the cloning strategy used to produce the fusion polypeptides. For instance, the additional amino acid residues do not provide an additional GPI anchoring signal so as to maintain the polypeptide in a soluble form. Furthermore, any such additional amino acid residues, when incorporated into the polypeptide of the invention, do not provide a cleavage site for endoproteases of the host cell. The likelihood that a designed sequence would be cleaved by the endoproteases of the host cell can be predicted as described, e.g., by Ikezawa (*Biol. Pharm. Bull.* 25:409-417, 2002).

The sALPs and sALP fusion polypeptides of the invention (such as TNALP, for example the sALP polypeptide of SEQ ID NO: 1 or a polypeptide variant having at least 95% sequence identity to the sequence of SEQ ID NO: 1, e.g., asfotase alfa) can be associated into dimers or tetramers. For example, two sALP-Fc monomers can covalently be linked through two disulfide bonds located in the hinge regions of the Fc fragments. Additionally, the polypeptide or fusion polypeptide of the invention (e.g., a sALP polypeptide or fusion polypeptide) can be glycosylated or PEGylated.

Production of Nucleic Acids and Polypeptides

The nucleic acids encoding sALPs and sALP fusion polypeptides of the invention (such as TNALP, for example the sALP polypeptide of SEQ ID NO: 1 or a polypeptide variant having at least 95% sequence identity to the sequence of SEQ ID NO: 1, e.g., asfotase alfa) can be produced by any method known in the art. Typically, a nucleic acid encoding the desired fusion polypeptide is generated using molecular cloning methods, and is generally placed within a vector, such as a plasmid or virus. The vector is used to transform the nucleic acid into a host cell appropriate for the expression of the fusion polypeptide. Representative methods are disclosed, for example, in Maniatis et al. (Cold Springs Harbor Laboratory, 1989). Many cell types can be used as appropriate host cells, although mammalian cells are preferable because they are able to confer appropriate post-translational modifications. Host cells of the present invention can include, e.g., Chinese Hamster Ovary (CHO) cell, L cell, C127 cell, 3T3 cell, BHK cell, COS-7 cell or any other suitable host cell known in the art. For example, the host cell is a Chinese Hamster Ovary (CHO) cell (e.g., a CHO-DG44 cell).

The sALPs and sALP fusion polypeptides (such as TNALP, for example the sALP polypeptide of SEQ ID NO: 1 or a polypeptide variant having at least 95% sequence identity to the sequence of SEQ ID NO: 1, e.g., asfotase alfa) can be produced under any conditions suitable to effect expression of the sALP polypeptide in the host cell. Such conditions include appropriate selection of a media prepared with components such as a buffer, bicarbonate and/or HEPES, ions like chloride, phosphate, calcium, sodium, potassium, magnesium, iron, carbon sources like simple sugars, amino acids, potentially lipids, nucleotides, vitamins and growth factors like insulin; regular commercially available media like alpha-MEM, DMEM, Ham's-F12, and IMDM supplemented with 2-4 mM L-glutamine and 5% Fetal bovine serum; regular commercially available animal protein free media like Hyclone™ SFM4CHO, Sigma CHO DHFR⁻, Cambrex POW ER™ CHO CD supplemented with 2-4 mM L-glutamine. These media are desirably prepared without thymidine, hypoxanthine and L-glycine to maintain selective pressure, allowing stable protein-product expression.

Pharmaceutical Compositions and Formulations

A composition of the present invention (e.g., including a sALP or sALP fusion polypeptide, such as TNALP, for example the sALP polypeptide of SEQ ID NO: 1 or a polypeptide variant having at least 95% sequence identity to the sequence of SEQ ID NO: 1, e.g., asfotase alfa) can be administered by a variety of methods known in the art. As will be appreciated by the skilled artisan, the route and/or mode of administration will vary depending upon the desired results. The route of administration can depend on a variety of factors, such as the environment and therapeutic goals. In particular, the polypeptides and fusion polypeptides described herein can be administration by any route known in the art, e.g., subcutaneous (e.g., by subcutaneous injection), intravenously, orally, nasally, intramuscularly, sublingually, intrathecally, or intradermally, or by combinations thereof. By way of example, pharmaceutical compositions of the invention can be in the form of a liquid, solution, suspension, pill, capsule, tablet, gelcap, powder, gel, ointment, cream, nebulae, mist, atomized vapor, aerosol, or phytosome.

Dosage

Any amount of a pharmaceutical composition (e.g., including a sALP or sALP fusion polypeptide, such as TNALP, for example the sALP polypeptide of SEQ ID NO: 1 or a polypeptide variant having at least 95% sequence identity to the sequence of SEQ ID NO: 1, e.g., asfotase alfa) can be administered to a child having HPP (e.g., a child of about 5 to about 12 years of age). The dosages will depend on many factors including the mode of administration and the age of the patient. Typically, the amount of the composition (e.g., a sALP or sALP fusion polypeptide, such as TNALP, for example the sALP polypeptide of SEQ ID NO: 1 or a polypeptide variant having at least 95% sequence identity to the sequence of SEQ ID NO: 1, e.g., asfotase alfa) contained within a single dose will be an amount that is effective to treat a condition (e.g., HPP) as described herein without inducing significant toxicity.

For example, the sALP polypeptides (such as TNALP, for example the sALP polypeptide of SEQ ID NO: 1 or a polypeptide variant having at least 95% sequence identity to the sequence of SEQ ID NO: 1, e.g., asfotase alfa) described herein can be administered to an HPP patient, such as a child having HPP (e.g., a child of about 5 to about 12 years of age) or an infant having HPP (e.g., an infant of about 3 years of age or less than 3 years of age), in individual doses ranging, e.g., from 0.01 mg/kg to 500 mg/kg (e.g., from 0.05 mg/kg to 500 mg/kg, from 0.1 mg/kg to 20 mg/kg, from 5 mg/kg to 500 mg/kg, from 0.1 mg/kg to 100 mg/kg, from 10 mg/kg to 100 mg/kg, from 0.1 mg/kg to 50 mg/kg, 0.5 mg/kg to 25 mg/kg, 1.0 mg/kg to 10 mg/kg, 1.5 mg/kg to 5 mg/kg, or 2.0 mg/kg to 3.0 mg/kg) or from 1 µg/kg to 1,000 µg/kg (e.g., from 5 µg/kg to 1,000 µg/kg, from 1 µg/kg to 750 µg/kg, from 5 µg/kg to 750 µg/kg, from 10 µg/kg to 750 µg/kg, from 1 µg/kg to 500 µg/kg, from 5 µg/kg to 500 µg/kg, from 10 µg/kg to 500 µg/kg, from 1 µg/kg to 100 µg/kg, from 5 µg/kg to 100 µg/kg, from 10 µg/kg to 100 µg/kg, from 1 µg/kg to 50 µg/kg, from 5 µg/kg to 50 µg/kg, or from 10 µg/kg to 50 µg/kg).

Exemplary doses of a sALP include, e.g., 0.01, 0.05, 0.1, 0.5, 1, 2, 2.5, 5, 10, 20, 25, 50, 100, 125, 150, 200, 250, or 500 mg/kg; or 1, 2, 2.5, 5, 10, 20, 25, 50, 100, 125, 150, 200, 250, 500, 750, 900, or 1,000 µg/kg. For all dosages or ranges recited herein, the term "about" can be used to modify these dosages by ±10% of the recited values or range endpoints. In particular, compositions (e.g., including sALP (such as TNALP, for example the sALP polypeptide of SEQ ID NO: 1 or a polypeptide variant having at least 95% sequence identity to the sequence of SEQ ID NO: 1, e.g., asfotase alfa)) in accordance with the present disclosure can be administered to patients in doses ranging from about 0.001 mg/kg/day to about 500 mg/kg/day, about 0.01 mg/kg/day to about 100 mg/kg/day, or about 0.01 mg/kg/day to about 20 mg/kg/day. For example, the sALP compositions (such as TNALP, for example the sALP polypeptide of SEQ ID NO: 1 or a polypeptide variant having at least 95% sequence identity to the sequence of SEQ ID NO: 1, e.g., asfotase alfa) can be administered to patients in a weekly dosage ranging, e.g., from about 0.5 mg/kg/week to about 140 mg/kg/week, e.g., about 0.8 mg/kg/week to about 50 mg/kg/week, or about 1 mg/kg/week to about 10 mg/kg/week (e.g., about 6 or about 9 mg/kg/week). In particular, the sALP (such as TNALP, for example the sALP polypeptide of SEQ ID NO: 1 or a polypeptide variant having at least 95% sequence identity to the sequence of SEQ ID NO: 1, e.g., asfotase alfa) can be administered at a dosage of 2 mg/kg three times a week (total dose 6 mg/kg/week), 1 mg/kg six times a week (total dose 6 mg/kg/week), 3 mg/kg three times a week (total dose 9 mg/kg/week), 0.5 mg/kg three times a week (total dose of 1.5 mg/kg/week), or 9.3 mg/kg three times a week (total dose 28 mg/kg/week). The dosage will be adapted by the clinician in accordance with conventional factors such as the extent of the disease and different parameters from the HPP patient, such as a child having HPP (e.g., a child of about 5 to about 12 years of age) or an infant having HPP (e.g., an infant of about 3 years of age or less than 3 years of age).

Dosages of compositions including sALPs and sALP fusion polypeptides (such as TNALP, for example the sALP polypeptide of SEQ ID NO: 1 or a polypeptide variant having at least 95% sequence identity to the sequence of SEQ ID NO: 1, e.g., asfotase alfa) can be provided in either a single or multiple dosage regimens. Doses can be administered, e.g., hourly, bihourly, daily, bidaily, twice a week, three times a week, four times a week, five times a week, six times a week, weekly, biweekly, monthly, bimonthly, or yearly. Alternatively, doses can be administered, e.g., twice, three times, four times, five times, six times, seven times, eight times, nine times, 10 times, 11 times, or 12 times per day. In particular, the dosing regimen is once weekly. The duration of the dosing regimen can be, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 day(s), week(s), or month(s), or even for the remaining lifespan of the HPP patient, such as a child having HPP (e.g., a child of about 5 to about 12 years of age) or an infant having HPP (e.g., an infant of about 3 years of age or less than 3 years of age). The amount, frequency, and duration of dosage will be adapted by the clinician in accordance with conventional factors such as the extent of the disease and different parameters from the HPP patient, such as a child having HPP (e.g., a child of about 5 to about 12 years of age) or an infant having HPP (e.g., an infant of about 3 years of age or less than 3 years of age).

For example, a sALP or sALP fusion polypeptide (such as TNALP, for example the sALP polypeptide of SEQ ID NO: 1 or a polypeptide variant having at least 95% sequence identity to the sequence of SEQ ID NO: 1, e.g., asfotase alfa) can be formulated as a solution for injection, which is a clear, colorless to slightly yellow, aqueous solution, pH 7.4. The sALP or sALP polypeptide (such as TNALP, for example the sALP polypeptide of SEQ ID NO: 1 or a polypeptide variant having at least 95% sequence identity to the sequence of SEQ ID NO: 1, e.g., asfotase alfa) may be formulated at a concentration of 12 mg/0.3 mL, 18 mg/0.45 mL, 28 mg/0.7 mL, 40 mg/1 ml, or 80 mg/0.8 mL. In particular, the composition can be formulated as a 40 mg/ml solution for injection, in which each ml of solution contains 40 mg of sALP or sALP polypeptide (e.g., each vial contains 0.3 ml solution and 12 mg of sALP (40 mg/ml), each vial contains 0.45 ml solution and 18 mg of sALP (40 mg/ml), each vial contains 0.7 ml solution and 28 mg of sALP (40 mg/ml), or each vial contains 1.0 ml solution and 40 mg of asfotase alfa (40 mg/ml)). A sALP or sALP polypeptide (such as TNALP, for example the sALP polypeptide of SEQ ID NO: 1 or a polypeptide variant having at least 95% sequence identity to the sequence of SEQ ID NO: 1, e.g., asfotase alfa) can be formulated as a solution for injection at a concentration of 100 mg/ml, in which each 1 ml of solution contains 100 mg of sALP or sALP polypeptide (e.g., each vial contains 0.8 ml solution and 80 mg of asfotase alfa (100 mg/ml)).

For example, the recommended dosage of a sALP or sALP fusion polypeptide ((such as TNALP, for example the sALP polypeptide of SEQ ID NO: 1 or a polypeptide variant having at least 95% sequence identity to the sequence of SEQ ID NO: 1, e.g., asfotase alfa) is 2 mg/kg of body weight administered subcutaneously three times per week, or a dosage regimen of 1 mg/kg of body weight administered subcutaneously six times per week. Additional dosage information is provided below (Table 1).

TABLE 1

Dosing of asfotase alfa.

| | If injecting 3x per week | | | If injecting 6 x per week | | |
|---|---|---|---|---|---|---|
| Body Weight (kg) | Dose to be injected | Volume to be injected | Vial type used for injection | Dose to be injected | Volume to be injected | Vial type used for injection |
| 3 | 6 mg | 0.15 ml | 0.3 ml | | | |
| 4 | 8 mg | 0.20 ml | 0.3 ml | | | |
| 5 | 10 mg | 0.25 ml | 0.3 ml | | | |
| 6 | 12 mg | 0.30 ml | 0.3 ml | 6 mg | 0.15 ml | 0.3 ml |
| 7 | 14 mg | 0.35 ml | 0.45 ml | 7 mg | 0.18 ml | 0.3 ml |
| 8 | 16 mg | 0.40 ml | 0.45 ml | 8 mg | 0.20 ml | 0.3 ml |
| 9 | 18 mg | 0.45 ml | 0.45 ml | 9 mg | 0.23 ml | 0.3 ml |
| 10 | 20 mg | 0.50 ml | 0.7 ml | 10 mg | 0.25 ml | 0.3 ml |
| 11 | 22 mg | 0.55 ml | 0.7 ml | 11 mg | 0.28 ml | 0.3 ml |
| 12 | 24 mg | 0.60 ml | 0.7 ml | 12 mg | 0.30 ml | 0.3 ml |
| 13 | 26 mg | 0.65 ml | 0.7 ml | 13 mg | 0.33 ml | 0.45 ml |
| 14 | 28 mg | 0.70 ml | 0.7 ml | 14 mg | 0.35 ml | 0.45 ml |
| 15 | 30 mg | 0.75 ml | 1 ml | 15 mg | 0.38 ml | 0.45 ml |
| 16 | 32 mg | 0.80 ml | 1 ml | 16 mg | 0.40 ml | 0.45 ml |
| 17 | 34 mg | 0.85 ml | 1 ml | 17 mg | 0.43 ml | 0.45 ml |

TABLE 1-continued

Dosing of asfotase alfa.

| Body Weight (kg) | If injecting 3x per week | | | If injecting 6 x per week | | |
|---|---|---|---|---|---|---|
| | Dose to be injected | Volume to be injected | Vial type used for injection | Dose to be injected | Volume to be injected | Vial type used for injection |
| 18 | 36 mg | 0.90 ml | 1 ml | 18 mg | 0.45 ml | 0.45 ml |
| 19 | 38 mg | 0.95 ml | 1 ml | 19 mg | 0.48 ml | 0.7 ml |
| 20 | 40 mg | 1.00 ml | 1 ml | 20 mg | 0.50 ml | 0.7 ml |
| 25 | 50 mg | 0.50 ml | 0.8 ml | 25 mg | 0.63 ml | 0.7 ml |
| 30 | 60 mg | 0.60 ml | 0.8 ml | 30 mg | 0.75 ml | 1 ml |
| 35 | 70 mg | 0.70 ml | 0.8 ml | 35 mg | 0.88 ml | 1 ml |
| 40 | 80 mg | 0.80 ml | 0.8 ml | 40 mg | 1.00 ml | 1 ml |
| 50 | | | | 50 mg | 0.50 ml | 0.8 ml |
| 60 | | | | 60 mg | 0.60 ml | 0.8 ml |
| 70 | | | | 70 mg | 0.70 ml | 0.8 ml |
| 80 | | | | 80 mg | 0.80 ml | 0.8 ml |
| 90 | | | | 90 mg | 0.90 ml | 0.8 ml (x2) |
| 100 | | | | 100 mg | 1.00 ml | 0.8 ml (x2) |

Formulations

The compositions including sALPs and sALP fusion polypeptides (such as TNALP, for example the sALP polypeptide of SEQ ID NO: 1 or a polypeptide variant having at least 95% sequence identity to the sequence of SEQ ID NO: 1, e.g., asfotase alfa) can be formulated according to standard methods. Pharmaceutical formulation is a well-established art, and is further described in, e.g., Gennaro (2000) "Remington: The Science and Practice of Pharmacy," 20$^{th}$ Edition, Lippincott, Williams & Wilkins (ISBN: 0683306472); Ansel et al. (1999) "Pharmaceutical Dosage Forms and Drug Delivery Systems," 7$^{th}$ Edition, Lippincott Williams & Wilkins Publishers (ISBN: 0683305727); and Kibbe (2000) "Handbook of Pharmaceutical Excipients American Pharmaceutical Association," 3$^{rd}$ Edition (ISBN: 091733096X). For instance, a sALP composition (such as TNALP, for example the sALP polypeptide of SEQ ID NO: 1 or a polypeptide variant having at least 95% sequence identity to the sequence of SEQ ID NO: 1, e.g., asfotase alfa) can be formulated, for example, as a buffered solution at a suitable concentration and suitable for storage at 2-8° C. (e.g., 4° C.). A composition can also be formulated for storage at a temperature below 0° C. (e.g., –20° C. or –80° C.). A composition can further be formulated for storage for up to 2 years (e.g., one month, two months, three months, four months, five months, six months, seven months, eight months, nine months, 10 months, 11 months, 1 year, 1½ years, or 2 years) at 2-8° C. (e.g., 4° C.). Thus, the compositions described herein can be stable in storage for at least 1 year at 2-8° C. (e.g., 4° C.).

The compositions including sALPs and sALP fusion polypeptides (such as TNALP, for example the sALP polypeptide of SEQ ID NO: 1 or a polypeptide variant having at least 95% sequence identity to the sequence of SEQ ID NO: 1, e.g., asfotase alfa) can be in a variety of forms. These forms include, e.g., liquid, semi-solid and solid dosage forms, such as liquid solutions (e.g., injectable and infusible solutions), dispersions or suspensions, tablets, pills, powders, liposomes and suppositories. The preferred form depends, in part, on the intended mode of administration and therapeutic application.

For example, compositions intended for systemic or local delivery can be in the form of injectable or infusible solutions. Accordingly, the compositions (such as TNALP, for example the sALP polypeptide of SEQ ID NO: 1 or a polypeptide variant having at least 95% sequence identity to the sequence of SEQ ID NO: 1, e.g., asfotase alfa) can be formulated for administration by a parenteral mode (e.g., subcutaneous, intravenous, intraperitoneal, or intramuscular injection). "Parenteral administration," "administered parenterally," and other grammatically equivalent phrases, as used herein, refer to modes of administration other than enteral and topical administration, usually by injection, and include, without limitation, subcutaneous, intradermal, intravenous, intranasal, intraocular, pulmonary, intramuscular, intra-arterial, intrathecal, intracapsular, intraorbital, intracardiac, intradermal, intrapulmonary, intraperitoneal, transtracheal, subcuticular, intraarticular, subcapsular, subarachnoid, intraspinal, epidural, intracerebral, intracranial, intracarotid, and intrasternal injection and infusion.

The compositions including sALPs and sALP fusion polypeptides (such as TNALP, for example the sALP polypeptide of SEQ ID NO: 1 or a polypeptide variant having at least 95% sequence identity to the sequence of SEQ ID NO: 1, e.g., asfotase alfa) can be formulated as a solution, microemulsion, dispersion, liposome, or other ordered structure suitable for stable storage at high concentration. Sterile injectable solutions can be prepared by incorporating a composition described herein in the required amount in an appropriate solvent with one or a combination of ingredients enumerated above, as required, followed by filter sterilization. Generally, dispersions are prepared by incorporating a composition described herein into a sterile vehicle that contains a basic dispersion medium and the required other ingredients from those enumerated above. In the case of sterile powders for the preparation of sterile injectable solutions, methods for preparation include vacuum drying and freeze-drying that yield a powder of a composition described herein plus any additional desired ingredient (see below) from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts, and gelatin.

The compositions described herein can also be formulated in immunoliposome compositions. Such formulations can be prepared by methods known in the art such as, e.g., the methods described in Epstein et al. (1985) *Proc Natl Acad Sci USA* 82:3688; Hwang et al. (1980) *Proc Natl Acad Sci*

USA 77:4030; and U.S. Pat. Nos. 4,485,045 and 4,544,545. Liposomes with enhanced circulation time are disclosed in, e.g., U.S. Pat. No. 5,013,556.

Compositions including sALPs and sALP fusion polypeptides (such as TNALP, for example the sALP polypeptide of SEQ ID NO: 1 or a polypeptide variant having at least 95% sequence identity to the sequence of SEQ ID NO: 1, e.g., asfotase alfa) can also be formulated with a carrier that will protect the composition (e.g., a sALP polypeptide or sALP fusion polypeptide) against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known in the art. See, e.g., J. R. Robinson (1978) "Sustained and Controlled Release Drug Delivery Systems," Marcel Dekker, Inc., New York.

When compositions are to be used in combination with a second active agent, the compositions can be co-formulated with the second agent, or the compositions can be formulated separately from the second agent formulation. For example, the respective pharmaceutical compositions can be mixed, e.g., just prior to administration, and administered together or can be administered separately, e.g., at the same or different times.

Compositions including sALPs and sALP fusion polypeptides (such as TNALP, for example the sALP polypeptide of SEQ ID NO: 1 or a polypeptide variant having at least 95% sequence identity to the sequence of SEQ ID NO: 1, e.g., asfotase alfa) can be formulated for administration to a patient or, if administered to a fetus, to a female carrying such fetus, along with intravenous gamma globulin therapy (IVIG), plasmapheresis, plasma replacement, or plasma exchange.

Carriers/Vehicles

Preparations containing a sALP or sALP fusion polypeptide (such as TNALP, for example the sALP polypeptide of SEQ ID NO: 1 or a polypeptide variant having at least 95% sequence identity to the sequence of SEQ ID NO: 1, e.g., asfotase alfa) can be provided to HPP patients, such as a child having HPP (e.g., a child of about 5 to about 12 years of age) or an infant having HPP (e.g., an infant of about 3 years of age or less than 3 years of age), in combination with pharmaceutically acceptable sterile aqueous or non-aqueous solvents, suspensions or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. For example, the pharmaceutically acceptable carrier can include sodium chloride and/or sodium phosphate, in which the composition includes, e.g., about 150 mM sodium chloride and/or about 25 mM sodium phosphate, pH 7.4.

Intravenous vehicles can include fluid and nutrient replenishers, electrolyte replenishers, such as those based upon Ringer's dextrose, and the like. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, can be present in such vehicles. A thorough discussion of pharmaceutically acceptable carriers is available in Remington's Pharmaceutical Sciences (Mack Pub. Co., N.J. 1991).

The following examples are intended to illustrate, rather than limit, the disclosure. These studies feature the administration of asfotase alfa (SEQ ID NO: 1) to children of about 5 to about 12 years of age to treat HPP, its symptoms, and physical impairments associated therewith for an extended period of time.

Example 1. Study Design for Treatment of HPP Children with Asfotase Alfa

Children with hypophosphatasia (HPP) of about 5 years to about 12 years of age participated in an initial phase study to determine the efficacy, safety, tolerability, and pharmacokinetics of treatment with a soluble alkaline phosphatase (sALP; asfotase alfa; SEQ ID NO: 1) for 6 months (Table 2). Inclusion criteria included radiographic skeletal features of hypophosphatasia-related rickets, serum ALP activity below age-adjusted lower limits of normal, and plasma PLP levels at least twice the upper limit of normal. Serum 25-hydroxyvitamin D had to be greater than or equal to 20 ng/ml (50 nM). Exclusion criteria included treatable rickets, hypocalcemia, hypophosphatemia, or bisphosphonate exposure.

TABLE 2

Baseline characteristics of historical control HPP patients and HPP patients treated with asfotase alfa.

|  | Historical Control HPP Patients | Treated Patients |
|---|---|---|
| n | 16 | 13 |
| Age (yrs) at enrollment | | |
| Mean ± SD | 6.0 ± 1.8 | 8.8 ± 2.2 |
| Median (min, max) | 5.5 (4, 11) | 8.6 (6, 12) |
| Sex, % (n) | | |
| Male | 69% (11) | 85% (11) |
| Ethnicity, % (n) | | |
| Not Hispanic or Latino | NA | 92% (12) |
| Race, % (n) | | |
| White | NA | 92% (12) |
| Form of hypophosphatasia, % (n) | | |
| Infantile | 44% (7) | 38% (5) |
| Childhood (≥6 mos to <18 yrs) | 56% (9) | 62% (8) |

TABLE 2-continued

Baseline characteristics of historical control HPP patients and HPP patients treated with asfotase alfa.

| | Historical Control HPP Patients | Treated Patients |
|---|---|---|
| Age (mos) at onset of hypophosphatasia symptoms | | |
| Mean ± SD | 7.4 ± 9.5 | 10.5 ± 7.0 |
| Median (min, max) | 6.0 (0, 40) | 12.0 (1, 22) |
| Baseline RSS (0 = normal, 10 = severe) | | |
| Mean ± SD | 1.44 ± 0.96 | 2.77 ± 1.33 |
| Median (min, max) | 1.0 (0.0, 3.5) | 3.0 (0.5, 6.0) |
| Baseline plasma PPi (µM) | | |
| Mean ± SD | NA | 5.01 ± 0.97 |
| Median (min, max [normal range]) | | 4.86 (3.74, 6.96 [0.75-5.71 µM]) |
| Baseline serum PLP (ng/ml) | | |
| Mean ± SD | 323 ± 178 | 214 ± 127 |
| Median (min, max [normal range]) | 328 (85, 726 [5.7-61.2 ng/ml]) | 218 (76, 527 [5.7-61.2 ng/ml]) |
| Baseline serum calciump (mmol/l) | | |
| Mean ± SD | ± | ± |
| Median (min, max [normal range]) | 2.52 (2.35, 2.78 [2.12-2.57 mmol/l]) | 2.50 (2.37, 2.67 [2.12-2.57 mmol/l]) |
| Hypophosphatasia-related disease history, % (n) | | |
| Unusual gait or running | NA | 100% (13) |
| Premature tooth loss | | 100% (13) |
| Delayed (≥15 mos) walking | | 85% (11) |
| Knock knees | | 77% (10) |
| Muscle weakness | | 62% (8) |
| Elevated serum phosphorous | | 54% (7) |
| Difficulty eating/swallowing | | 46% (6) |
| Difficulty gaining weight | | 46% (6) |
| Hypermobility | | 46% (6) |
| Joint pain | | 46% (6) |
| Muscle pain | | 46% (6) |
| Abnormally shaped chest | | 46% (6) |
| Bone pain severe enough to limit activities | | 46% (6) |
| Bone pain severe enough to require medication | | 39% (5) |
| Bowing of legs | | 39% (5) |

A total of 13 HPP patients treated with asfotase alfa (40 or 100 mg/ml concentration) were initially randomized to receive 2 mg/kg or 3 mg/kg three times weekly (i.e., 6 or 9 mg/kg/week) for 6 months (FIG. 1). In the extension study of at least 5 years, HPP patients initially received asfotase alfa administered via subcutaneous administration 3 mg/kg/week, either as 0.5 mg/kg six times weekly or 1 mg/kg three times weekly, until preliminary analysis led to a protocol amendment that doubled the dose to 6 mg/kg/week after three to nine months to maintain therapeutic efficacy. Since a separately identified historical control patient group was used for comparison, there was no randomization between the patients treated with asfotase alfa and historical control HPP patients.

Figure 2:
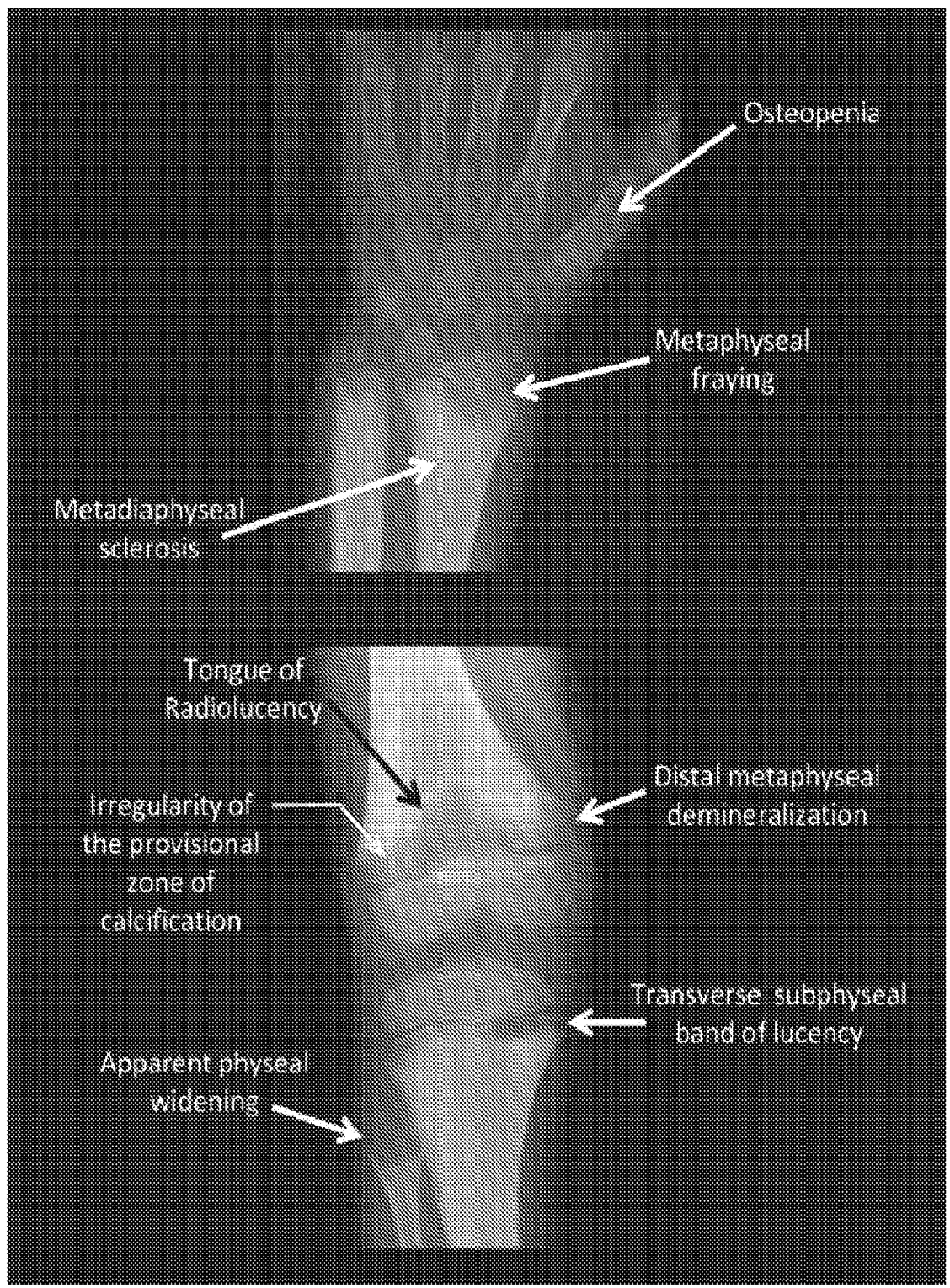
FIG. 2 is a radiographic image showing skeletal features of HPP in a child prior to treatment with asfotase alfa. Untreated, the radiographic features of hypophosphatasia in children include, as in the wrist pictured, osteopenia, metaphyseal fraying, metaphyseal flaring, and metadiaphyseal sclerosis, and as in the knee pictured, characteristic tongues of radiolucency, irregularity of the provisional zone of calcification, distal metaphyseal demineralization, transverse subphyseal band of lucency, and apparent physeal widening.

Skeletal abnormalities of HPP children at baseline included knock knees (77%), rachitic chest (46%), bowing of legs (39%), and craniosynostosis (31%) and were accompanied by muscle weakness in most patients and an unusual gait in all patients. Radiographic abnormalities observed in children with HPP at baseline included metaphyseal flaring, metadiaphyseal sclerosis, radiolucencies, apparent physical widening, irregularity of the provisional zone of calcification, and transverse subphyseal band of lucency (FIG. 2). Bone pain often limited activities (46%) and/or required analgesics (39%). Nearly half of the patients had poor weight gain and prior difficulty in feeding. Hypercalcemia occurred in 31% of patients. After 1 month of treatment, 1 boy withdrew for elective scoliosis surgery.

Patients treated with asfotase alfa were assessed for skeletal manifestations of HPP using the Radiographic Global Impression of Change (RGI-C) and Rickets Severity Score (RSS); changes in tissue-nonspecific alkaline phosphatase (TNALP) substrate levels (plasma PPi and PLP); growth (height, weight, and body mass index (BMI) Z-scores); strength of muscle groups that move the hips and knees, measured using a hand-held dynamometer; walking ability and endurance or speed using a Six Minute Walk Test (6MWT); physical function and strength using the Bruininks-Oseretsky Test of Motor Proficiency, 2nd Edition (BOT-2); global function, including pain and interference with normal activities, using the Pediatric Outcomes Data Collection Instrument (PODCI); and disability, using the Childhood Health Assessment Questionnaire (CHAQ).

An overview of the metrics used in this study to assess treatment of childhood HPP with asfotase alfa over an extended period (≥5 years of treatment) is shown in Table 3. In particular, physical function and impairments of HPP patients were assessed with the Bruininks-Oseretsky Test of Motor Proficiency, 2nd Edition (BOT-2). The BOT-2 was administered to capture body structure impairments and mobility restrictions important in HPP in the BOT-2 subtests of strength and running speed and agility, as compared to a normal age-matched population with a standard BOT-2 score of 15 (standard deviation of 5).

Ability to perform Activities of Daily Living (ADL) and pain of HPP patients were assessed with the Childhood Health Assessment Questionnaire (CHAQ) and the Pediatric Outcomes Data Collection Instrument (PODCI). The CHAQ has two scales: a Disability Index with 30 age-appropriate items in 8 subscales of ADL, and a Discomfort (pain) Index. CHAQ disability is scored from 0 to 3 (0=functional independence; 3=complete dependence on caregiver). For example, a decrease of ≥0.13 in a CHAQ index score is considered clinically meaningful in juvenile arthritis (see Dempster et al., Arthritis Rheum. 44(8): 1768-74, 2001; incorporated herein by reference). The PODCI has eight scales, including Upper Extremity and Physical Function, Transfer and Basic Mobility, Sports and Physical Functioning, and Global Functioning; each has a normative mean score for healthy patients of 50 (standard deviation of 10).

evaluated as close to 6 months or 1 to 2 years apart for comparison with the treatment group.

The Radiographic Global Impression of Change (RGI-C), a 7-point ordinal scale, assesses HPP skeletal disease in wrists and knees, including physeal widening, irregularity of the provisional zone of calcification, metaphyseal flaring, radiolucencies, patchy osteosclerosis, and recent fractures. The changes compared with baseline were quantified independently by 3 pediatric radiologists blinded to treatment time points and group assignments. For the RGI-C, +3 signifies complete or nearly complete healing, whereas −3 represents severe worsening. The scores per patient were averaged across radiologists at each time point. An RGI-C

TABLE 3

Metrics used to evaluate physical function, activities of daily living, and pain of HPP patients.

| Physical Function | Activities of Daily Living/Pain |
|---|---|
| BOT-2 Strength and Agility<br>Assesses motor ability in<br>4-21 year olds<br>Valid reliable, standardized<br>tool with normative data<br>Captures body structure<br>impairments and mobility<br>restrictions important in HPP<br>    Strength<br>    Running Speed and<br>    Agility<br>    Standard Score:<br>    Mean 15, SD 5<br>Scores compared with<br>normal age-matched<br>population | Childhood Health Assessment Questionnaire (CHAQ)<br>  Disability index, includes 8 sub-scales:<br>    Dressing/grooming<br>    Arising<br>    Eating<br>    Walking<br>    Hygiene<br>    Reach<br>    Grip<br>    Activities<br>    Score 0-3 where 0 = no difficulty and 3 = unable to do<br>  Discomfort (Pain) Index, visual analog sale (single question)<br>Pediatric Outcomes Data Collection Instrument (PODCI)<br>  8 scales:<br>    Transfer and basic mobility<br>    Sports and physical functioning<br>    Pain and comfort<br>    Upper extremity and physical function<br>    Treatment expectations<br>    Happiness<br>    Satisfaction with symptoms<br>    Global functioning scale<br>  Standardized scale from 0 to 100, 100 = less disability |

Example 2. Skeletal Changes in HPP Children Treated with Asfotase Alfa

Radiographic assessments of HPP patients were performed during the course of treatment as previously described (see Whyte et al. (*N Engl J Med* 366(10): 904-913, 2012); incorporated herein by reference), with 16 historical controls. Radiographic skeletal changes during the first 2 years of asfotase alfa treatment were compared to the historical control HPP patients. Bilateral wrist and/or knee radiographs, previously obtained at intervals spanning 6 months to 2 years between 5 and 12 years of age, were "responder" had a score greater than or equal to +2 (i.e., substantial or near/complete healing).

The Rickets Severity Score (RSS), which was developed to assess nutritional rickets, was scored by the same individual rater to: (i) evaluate the radiographs of patients treated with asfotase alfa throughout the study and (ii) evaluate the historical control radiographs representing 6 month, 1 year, and 2 year intervals. Knee and wrist growth-plate abnormalities and metaphyseal fraying and cupping were rated according to a 10-point scale (0=no rickets; 10=severe rickets), with scores for each radiograph determined in random order (Table 4).

TABLE 4

Rickets Severity Score (RSS) 10-point radiographic scoring method for rickets.

Wrist: score both radius and ulna separately

| Grade | Radiographic features |
|---|---|
| 0 | Normal growth plate without changes of rickets |
| 0.5 | Lucency of metaphyseal margin without fraying or irregularity |
| 1 | Widened growth plate, irregularity of metaphyseal margin but without concave cupping |

TABLE 4-continued

Rickets Severity Score (RSS) 10-point radiographic scoring method for rickets.

| | |
|---|---|
| 1.5 | Partial metaphyseal concavity or incomplete fraying of metaphyseal margin |
| 2 | Metaphyseal concavity with fraying of margins |

2 bones × 2 points = 4 points possible

Knee: score both femur and tibia separately
Multiply the grade in A by the multiplier in B for each bone, then add femur and tibia scores together

| A | Grade | Degree of lucency and widening of zone of provisional calcification |
|---|---|---|
| | 0 | Normal growth plate without changes of rickets |
| | 1 | Partial lucency, smooth margin of metaphysis visible |
| | 2 | Partial lucency, smooth margin of metaphysis NOT visible |
| | 3 | Complete lucency, epiphysis appears widely separated from distal met |
| B | Multiplier | Portion of growth plate affected |
| | 0.5 | ≤1 condyle or plateau |
| | 1 | 2 condyles or plateaus |

2 bones × 1 point × 3 points = 6 points possible
Total: 10 points possible that would indicate very severe rickets The RGI-C median scores were compared using Wilcoxon rank-sum test. Missing values were imputed with last observation carried forward (LOCF), and patients with no post-baseline assessment were assigned "no change" (e.g., RGI-C=0). Observed median and mean within-group changes were also assessed for difference from 0 using the Wilcoxon signed-rank test and paired t-test. All analyses were 2-sided, with significance defined as a P-value less than 0.05.

Figure 3:
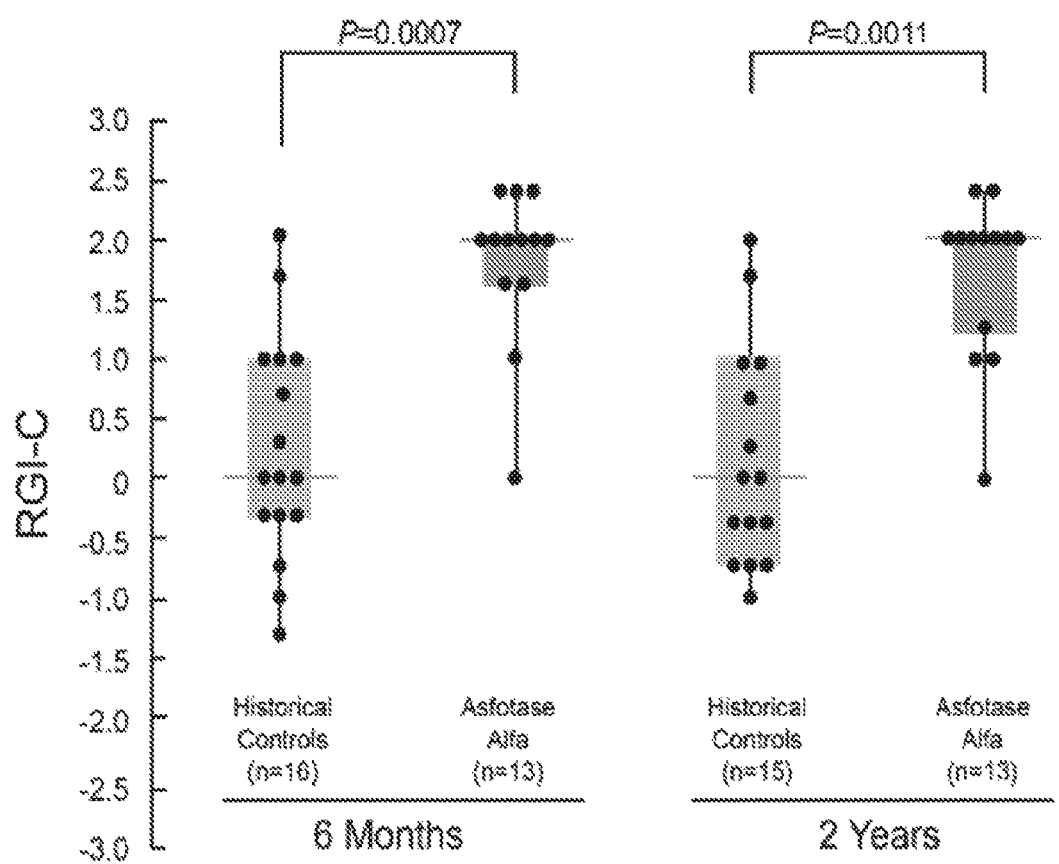
FIG. 3 is a graph showing changes in the Radiographic Global Impression of Change (RGI-C) scores of HPP children after administration of asfotase alfa over a treatment period of 6 months and 2 years relative to historical untreated controls. Individual dots illustrate the distribution of individual patient scores at each time point. Boxes represent the median RGI-C scores and first and third quartiles. Whisker lines above and below the boxes represent the end-range of patient scores. The RGI-C is scored on a scale ranging from −3 to +3, with 0 representing no change. Negative values represent worsening, and positive values represent improvement or healing. A score of +3 indicates nearly complete or complete healing. Median RGI-C scores for the historical controls and asfotase alfa were 0 and 2, respectively, at 6 months and 2 years. The number of patients assessed at each time point is shown below each bar. P≤0.0001 by Wilcoxon signed-rank test at all time points compared with no change.

After 6 weeks of treatment with asfotase alfa, the median RGI-C score had improved significantly (+1.0 [0.0, +2.0; min, max]; P=0.001). Further improvement occurred by 6 months and persisted through 5 years (+2.2 [+1.7, +2.7]; P=0.0005). In contrast, no significant change occurred in the RGI-C score of the historical controls spanning up to 2 years (FIG. 3).

Figure 4:
FIG. 4 is a series of images showing representative radiographic changes of a child with HPP at baseline and after 6 months, 3 years, and 5 years of treatment with asfotase alfa. The child was 6 years old at baseline. RGI-C and Rickets Severity Score (RSS) scores over time are also shown.

The RGI-C responder analysis showed 69% (9/13) of asfotase alfa-treated HPP patients achieved "responder" designation (RGI-C score≥2) at 6 months of therapy (LOCF data imputation applied) compared with 6% (1/16) of the historical controls (P=0.007). The percentage of asfotase alfa-treated HPP patients considered responders then further improved steadily; 75% at 2 years, 88% at 3 years, and 92% at 5 years (1 patient had withdrawn at month 1). Notably, improvements at 6 months of treatment with asfotase alfa persisted after 5 years of treatment, as evidenced by representative radiographic changes in a male patient with HPP that was 6 years of age at baseline (FIG. 4). Consistent with the RGI-C findings, the RSS analysis confirmed improvement of rickets after treatment of the HPP children with asfotase alfa with significantly decreased median RSS scores comparing the first eligible radiographs with all subsequent evaluated time points in comparison to the historical controls (Table 5).

TABLE 5

Change in Rickets Severity Score (RSS) scores with asfotase alfa treatment.

| Variable | Baseline | Month 6 | Year 1 | Year 2 | Year 3 | Year 4 | Year 5 |
|---|---|---|---|---|---|---|---|
| Historical Control Patients | | | | | | | |
| N | 16 | 16 | 16 | 15 | | | |
| RSS, mean (SD) | 1.44 (0.96) | 1.31 (1.05) | 1.19 (1.03) | 1.43 (1.19) | | | |
| RSS, median | 1.00 | 1.25 | 1.00 | 1.00 | | | |
| (min, max) | (0.0, 3.5) | (0.0, 4.0) | (0.0, 4.0) | (0.5, 5.0) | | | |
| RSS Change from baseline, median (min, max) | | 0.00 (−1.0, 1.5) | −0.50 (−1.0, 1.5) | 0.00 (−1.5, 1.5) | | | |
| $P^A$ | | | | | | | |
| Asfotase Alfa-treated Patients | | | | | | | |
| N | 12 | 12 | 12 | 12 | 8 | 10 | 10 |
| RSS, mean (SD) | 2.75 (1.39) | 1.04 (1.23) | 1.25 (1.25) | 1.04 (1.12) | 0.56 (0.68) | 0.40 (0.52) | 0.15 (0.34) |
| RSS, median | 2.75 | 0.75 | 1.00 | 0.50 | 0.50 | 0.25 | 0.00 |
| (min, max) | (0.5, 6.0) | (0.0, 4.5) | (0.0, 4.5) | (0.0, 4.0) | (0.0, 2.0) | (0.0, 1.5) | (0.0, 1.0) |
| RSS Change from baseline, median (min, max) | | −1.50 (−3.5, −0.5) | −1.25 (−3.0, 0.0) | −2.00 (−3.5, 0.5) | −2.50 (−4.0, 1.0) | −2.50 (−4.5, 0.0) | −2.75 (−5.0, −0.5) |
| $P^A$ | | 0.0005 | 0.001 | 0.002 | NA | NA | NA |
| $P^B$ | | 0.0008 | 0.007 | 0.0025 | | | |

$^A$P value based on within group Wilcoxon signed-rank test for change from baseline.
$^B$P value based on Willcoxon rank sum test comparing change from baseline of the treatment group with the historical control group.
NA, not available.

Example 3. Tissue-Nonspecific Alkaline Phosphatase (TNALP) Activity in HPP Children Treated with Asfotase Alfa Of the HPP children treated with asfotase alfa, 12 of the 13 treated children had at least 1 mutant TNSALP allele identified using PCR and DNA sequencing of all coding exons and splice sites (Table 6). One patient did not show a TNALP gene mutation despite extensive molecular investigations.

TABLE 6

TNALP gene mutation analysis by HPP patient treated with asfotase alfa.

| Patient Number | Gene Mutation Class | AA Change 1 AA Change 2 | Nuc Change 1 Nuc Change 2 |
|---|---|---|---|
| 1 | Compound heterozygote | ALA176THR ASP294ALA | C.526G > A C.881A > C |
| 2 | Compound heterozygote | ALA176THR ASP294ALA | C.526G > A C.881A > C |
| 3 | Heterozygous | ASP378VAL | C.1133A > T |
| 4 | Compound heterozygote | GLU191LYS ASP337GLY | C.571G > A C.1010A > G |
| 5 | Compound heterozygote | GLU191LYS ASN417SER | C.571G > A C.1250A > G |
| 6 | Compound heterozygote | GLU191LYS ASP294ALA | C.571G > A C.881A > C |
| 7 | Compound heterozygote | ALA176THR ALA179THR | C.526G > A C.535G > A |
| 8 | Compound heterozygote | GLU84ASP VAL459MET | C.252G > C C.1375G > A |
| 9 | Compound heterozygote | GLU191LYS GLY334ASP | C.571G > A C.1001G > A |
| 10 | Compound heterozygote | GLU191LYS ALA116THR | C.571 G > A C.346G > A |
| 11[4] | NA | NA | NA |
| 12 | Compound heterozygote | GLU191LYS P.327DELPHE | C.571G > A C.978 980DELCTT |
| 13 | Compound heterozygote | ALA114THR GLY455SER | C.340G > A C.1363G > A |

AA, amino acid; NA, not available; Nuc, nucleotide.
[4]No mutation was detected.

Figure 5A:
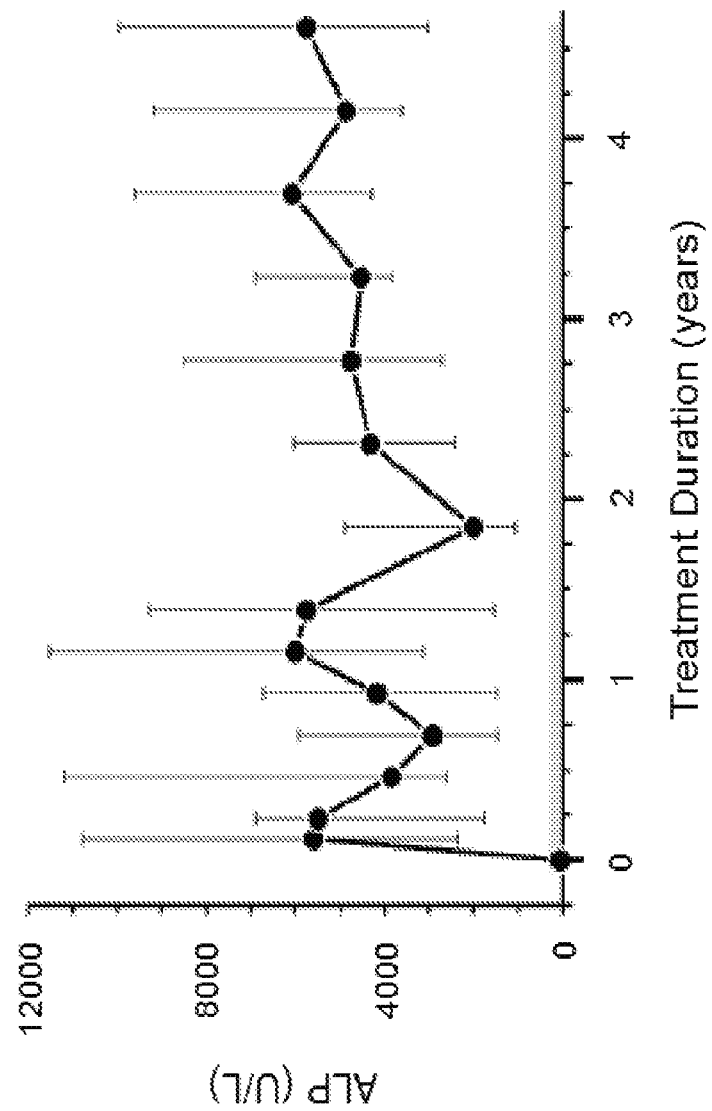
FIGS. 5A-5C are graphs showing alkaline phosphatase (ALP) activity (FIG. 5A), pyridoxal 5'-phosphate (PLP) concentrations (FIG. 5B), and inorganic pyrophosphate ($PP_i$) concentrations (FIG. 5C) in samples from HPP children after administration of asfotase alfa over a time period of 5 years. PLP and PPi concentrations are shown relative to the normal range for healthy children. Median, min, and max values are given below each panel.
Figure 5B:
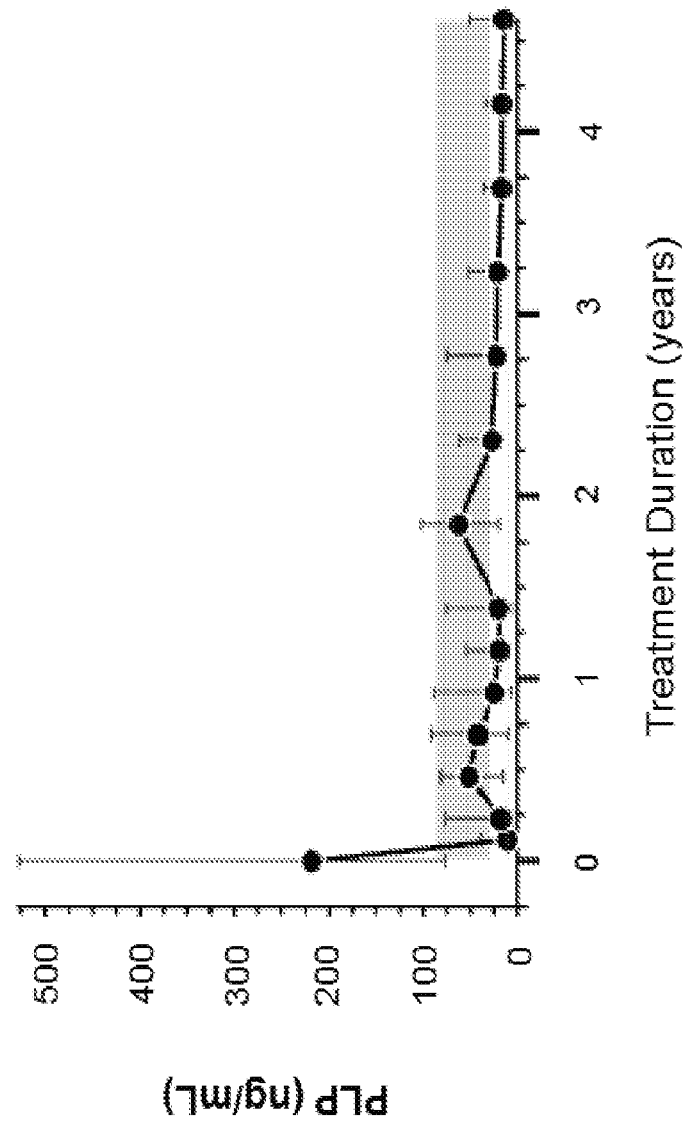
Figure 5C:
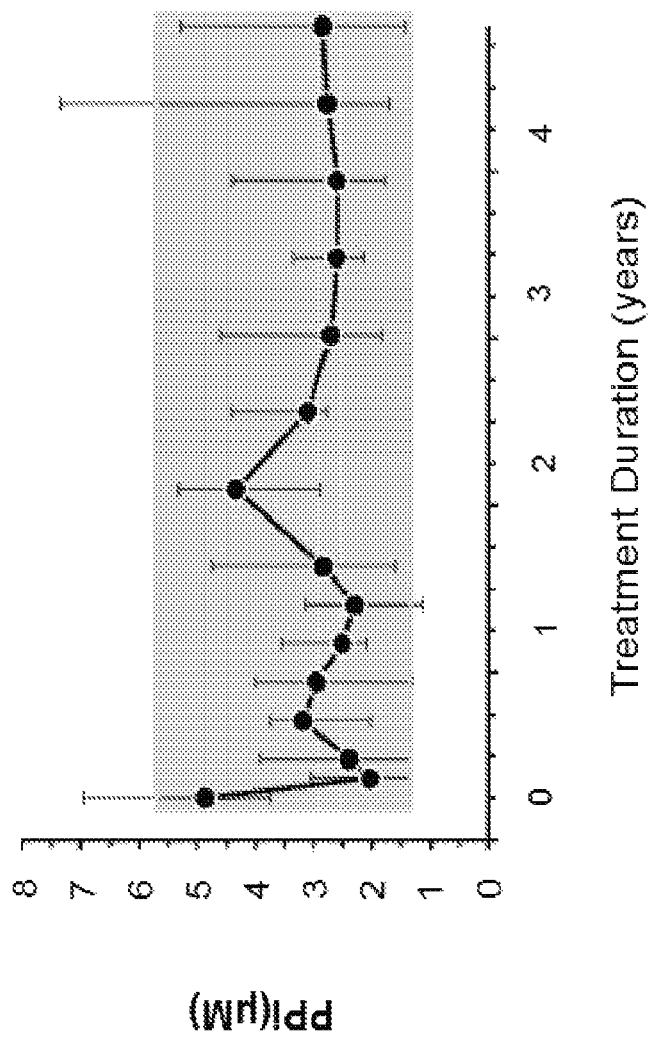

The median serum ALP activity of the treatment group at baseline was 49 IU/l (min, max: 27, 68) and then rapidly increased after treatment with asfotase alfa (FIG. 5A). After 5 years of therapy, serum ALP remained markedly elevated at 5747 IU/l (3,039, 9,959). Baseline plasma PPi median concentration, 4.9 µM (3.7, 7.0), was near the upper limit of the age-dependent reference range (0.75-5.71 µM). Baseline plasma PLP median concentration, 218 ng/ml (76, 527), was clearly elevated (normal 5.7-61.2 ng/ml) in the HPP children. At 6 weeks of treatment, the rapid and significant reduction of plasma PPi and PLP concentrations resulted in normal limits for most asfotase alfa-treated children (2.0 µM [1.3, 3.1] and 10.6 ng/ml [0.9, 40.3], respectively; FIG. 5B and FIG. 5C, respectively). Normal levels of PPi and PLP were sustained throughout the study for the HPP children treated with asfotase alfa.

Example 4. Growth and Strength of HPP Children Treated with Asfotase Alfa

Figure 6A:
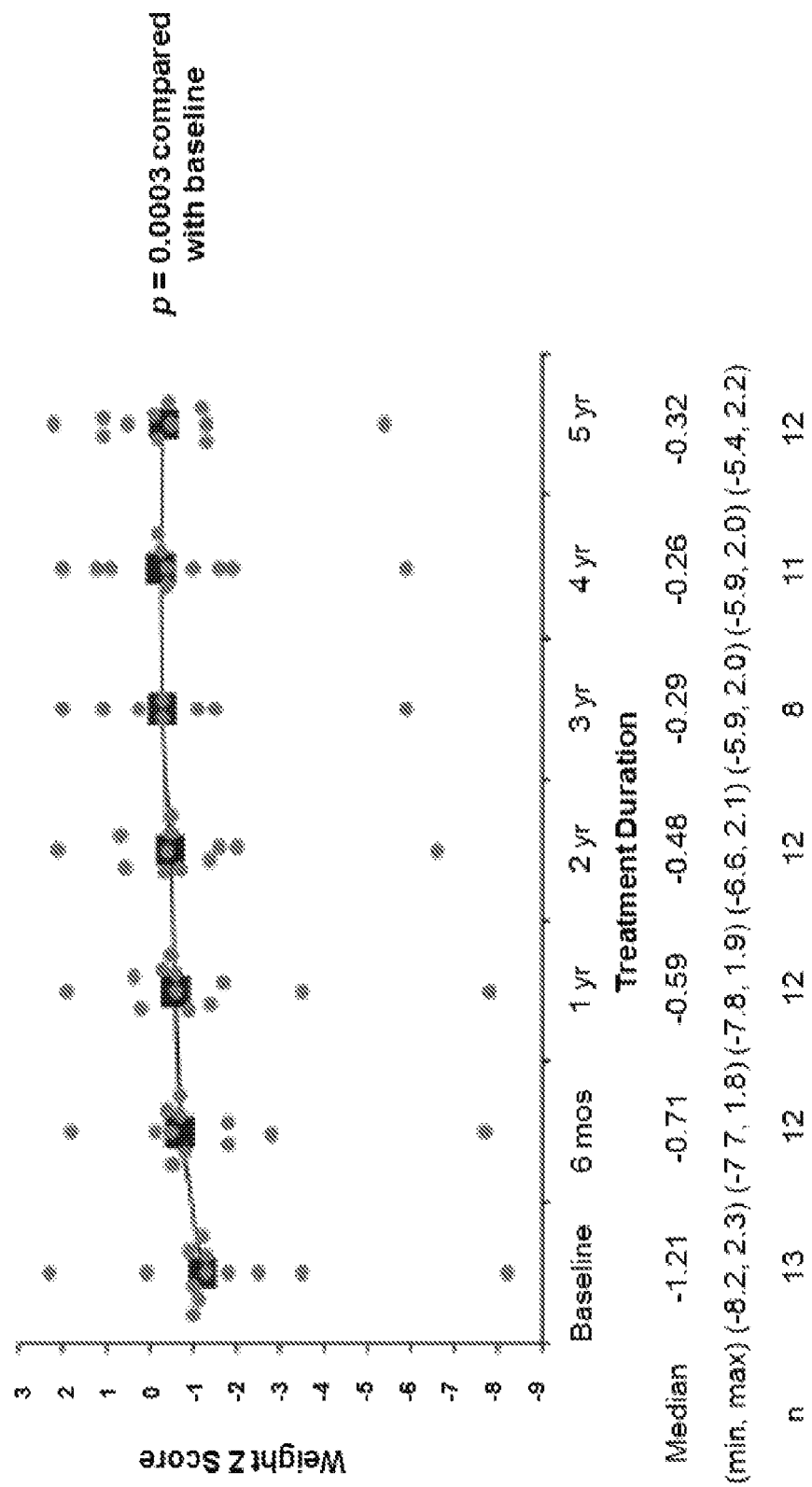
Figure 6B:
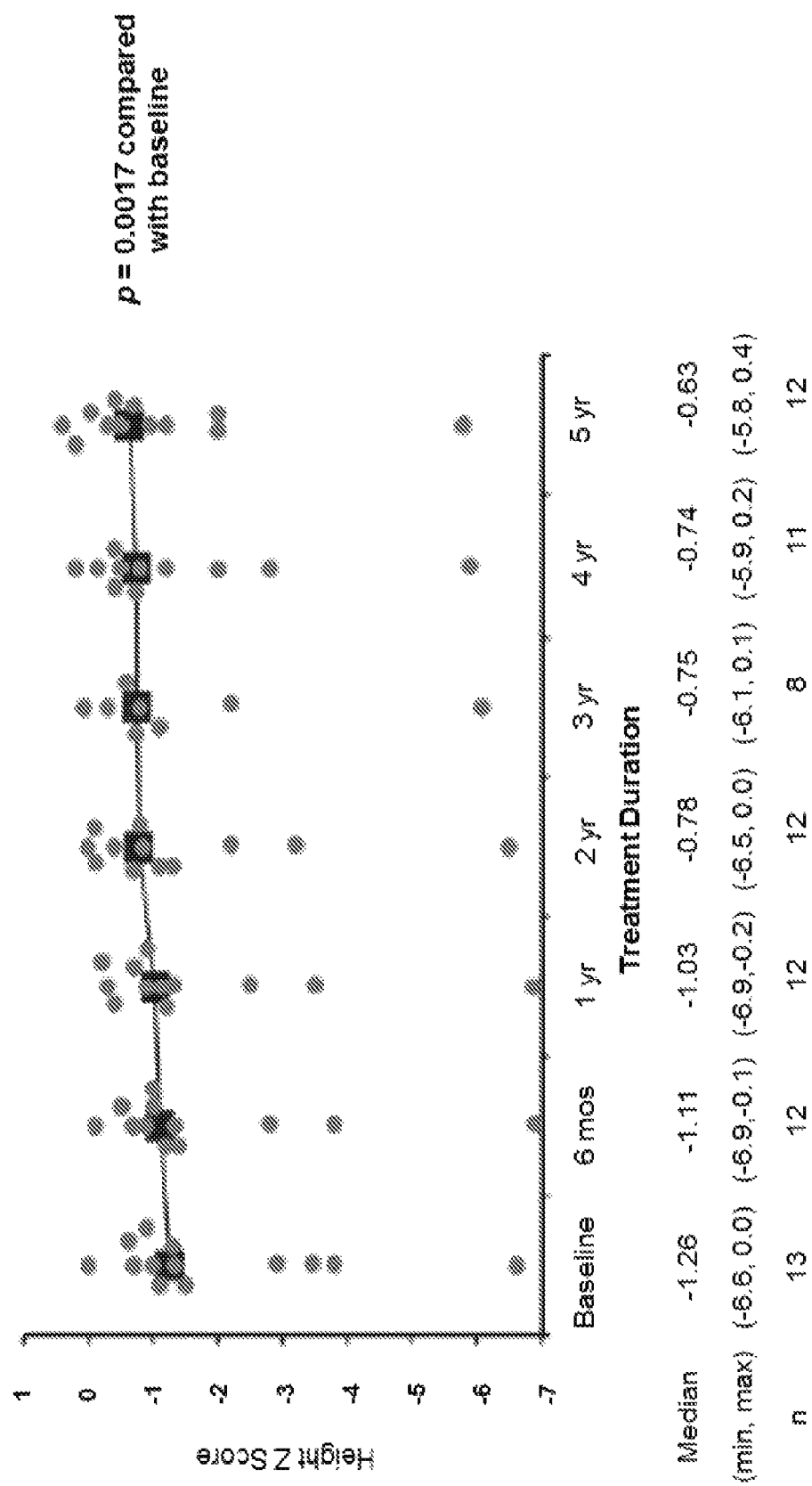
Figure 7A:
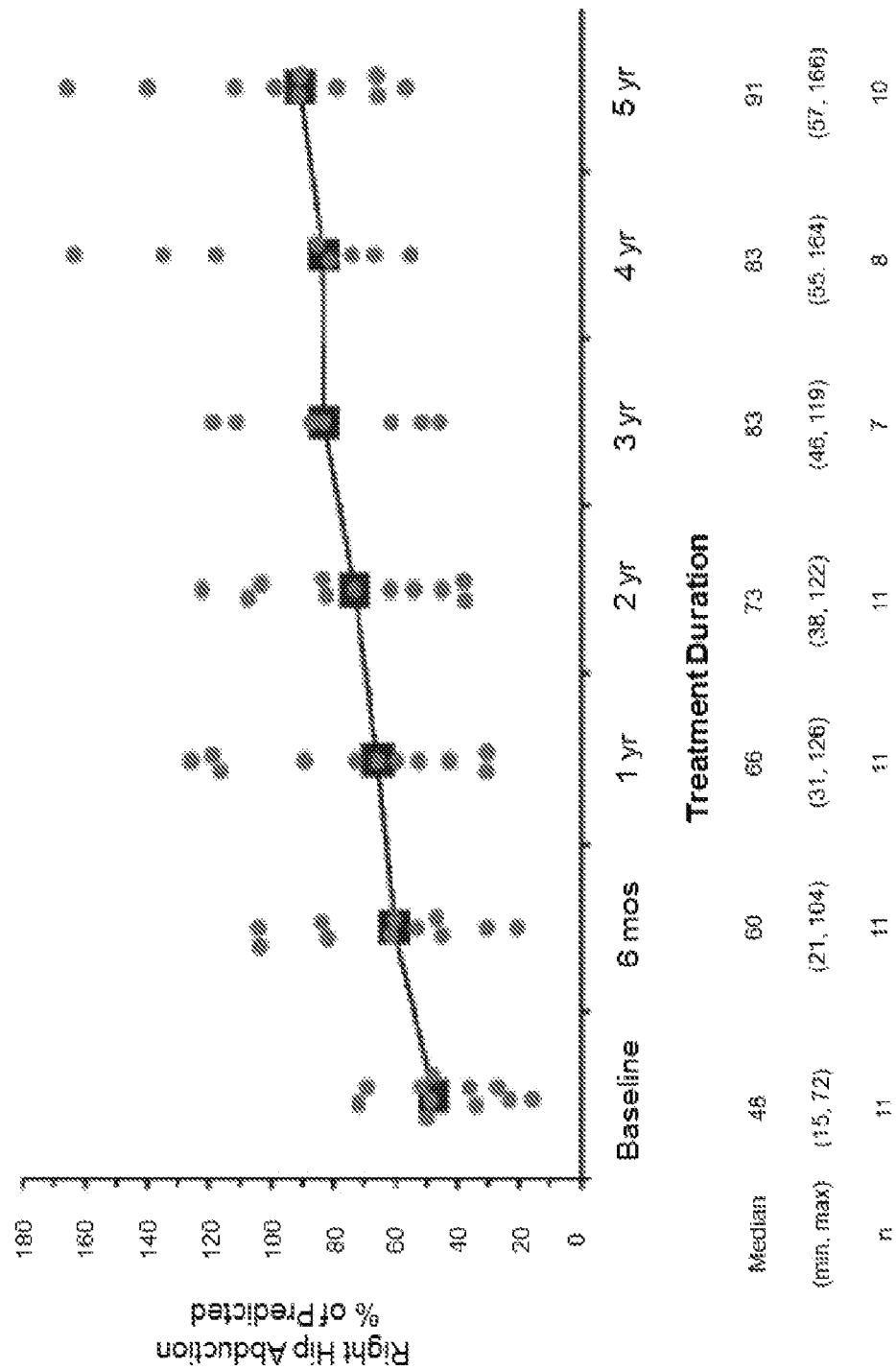
Figure 7C:
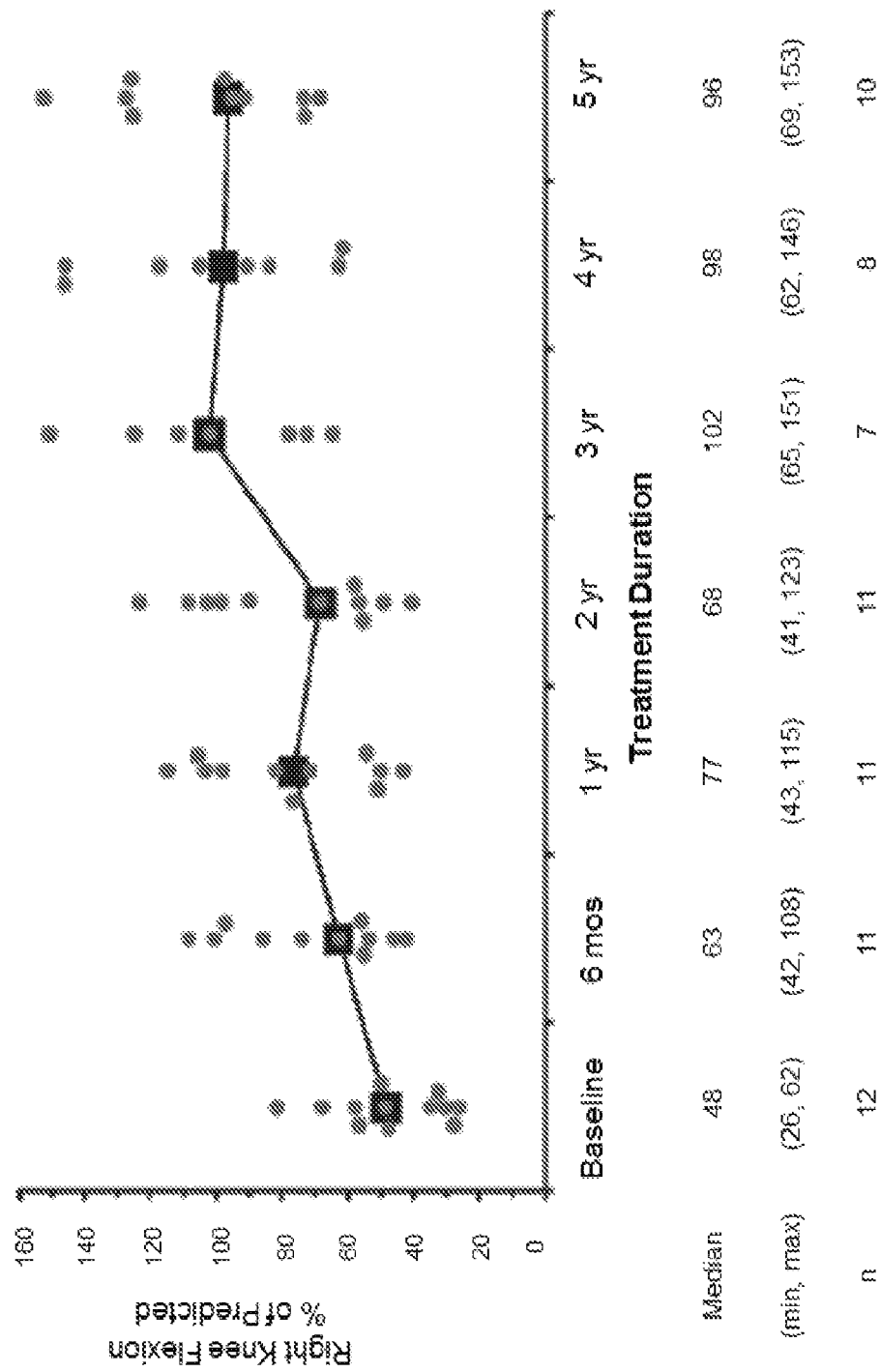

After treatment with asfotase alfa, the first significant increase in the weight Z-scores of the HPP patients was identified at 6 weeks (baseline: −1.21 [−8.2, 2.3]; 6 weeks: −0.92 [−8.0, 2.1], P=0.0048); FIG. 6A). The first significant increase in the height Z-scores of the HPP patients treated with asfotase alfa was noted after 1.5 years (baseline: −1.26 [−6.6, 0.0]; 1.5 years: −0.87 [−6.6, −0.3], P=0.0257; FIG. 6B). The median BMI Z-score of the HPP patients treated with asfotase alfa had increased 5 years of treatment (baseline: −0.57 [−1.4, 2.4]; 5 years: 0.05 [−1.0, 2.2], P=0.0077; FIG. 6C). Most asfotase alfa-treated patients became stronger for their age and sex; e.g., right hip abduction baseline median at 13.6 lbs was 7.3 and 22.1 (min, max, respectively). Right hip abduction of the HPP patients treated with asfotase alfa was 50% of the right hip abduction predicted for healthy peers at baseline (FIG. 7A). At 6 months and 18.3 pounds, minimum and maximum values were 8.4 and 28.2, respectively (P=0.0018 or 60% predicted). At 5 years and 30.7 pounds, minimum and maximum values were 19.5 and 84.4, respectively (P=0.0079 or 91% predicted). Significant improvements were similarly documented for hip and knee extensors and knee flexors of HPP children treated with asfotase alfa (FIG. 7B-7D).

Example 5. Physical Function of HPP Children Treated with Asfotase Alfa Assessed Using the Six Minute Walk Test (6MWT)

Physical function and impairments of the HPP children treated with asfotase alfa were assessed using the Six Minute Walk Test (6MWT). Before treatment, gross motor delays and functional disability were documented in most HPP patients; e.g., 9 of the 13 had a subnormal 6MWT (<80% predicted for of age- and sex-matched peers). Patients improved by a walking distance of at least 20 meters (e.g., a minimal clinically important difference (MCID)) after treatment with asfotase alfa. After 5 years of treatment, 7 of 9 children achieved or surpassed 80% of the predicted distance (±2 SD mean), indicating normal ambulation.

Figure 8B:
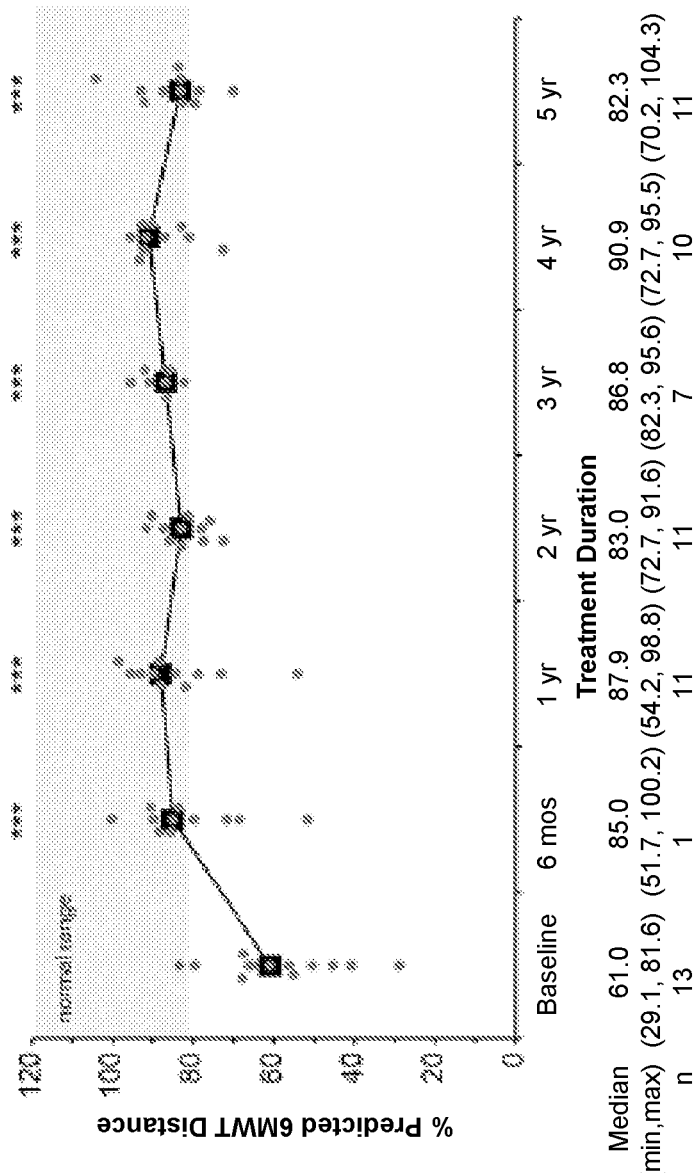

6MWT values improved for individual HPP patients and the median 6MWT value of the HPP patients treated with asfotase alfa increased from about 350 meters at baseline to about 550 meters after 5 years of treatment with asfotase alfa (FIG. 8A). The percent predicted 6MWT distance median of the HPP patients treated with asfotase was within the normal range after 6 months of treatment, which was sustained for at least 5 years of treatment with asfotase alfa (FIG. 8B). The median 6MWT distance of the HPP patients increased from 61% of the predicted 6MWT distance for healthy children (age- and sex-matched) at baseline to 83% of the predicted median 6MWT distance after 5 years of treatment with asfotase alfa (FIG. 8B).

Clinical relevance of the 6MWT value was assessed via Pearson correlations between 6MWT and measures of skeletal disease using the RGI-C scale, the RSS, and ability to perform ADL as assessed by the CHAQ Disability Index and PODCI Global Function, Transfer and Basic Mobility, and Sports and Physical Functioning scaled scores. Correlation analysis of 127 data points revealed significant (p<0.001), moderate-to-strong linear relationships between distance walked (percent predicted for age, gender, and height) and RSS (r=0.73), CHAQ Disability Index (r=−0.57), and PODCI subscales, including Global Function (r=0.76), Transfer and Basic Mobility (r=0.69), and Sports and Physical Functioning (r=0.78). Changes in 6MWT and RGI-C scores showed weaker correlation (r=0.32; 68 data points; p<0.01).

Additionally, all patients requiring the use of assistive devices to walk prior to treatment with asfotase alfa exhibited an improvement after treatment with asfotase alfa, such as treatment with asfotase alfa for one year. In particular, patients progressed from a wheelchair to crutches, from a walker to a cane, from a wheeled walker to independent ambulation, and from a cane to independent ambulation.

These results indicate that the 6MWT is a valid, clinically relevant measure of disability and treatment outcomes for patients with HPP, particularly HPP patients treated with asfotase alfa. Importantly, asfotase alfa effectively restores physical function and walking ability in children with HPP, as shown by the increase in the 6MWT distance after treatment with asfotase alfa.

Example 6. Physical Function of HPP Children Treated with Asfotase Alfa Assessed Using the Bruininks-Oseretsky Test of Motor Proficiency, Second Edition (BOT-2)

Figure 9A:
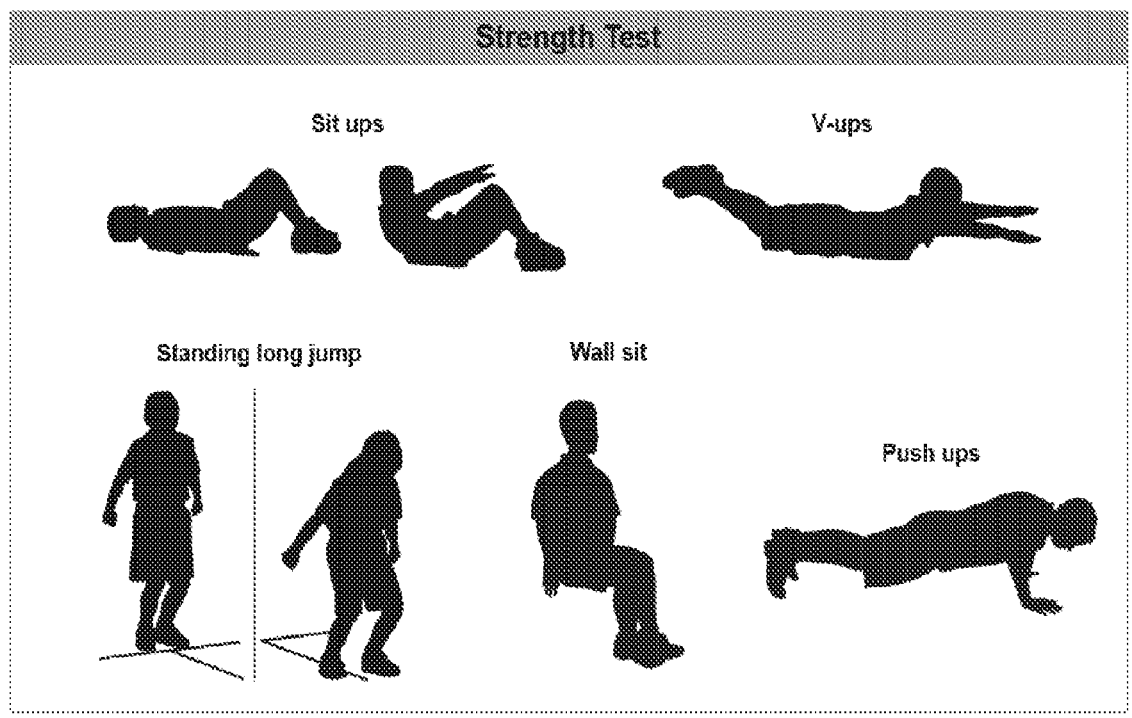
FIGS. 9A-9B are an image and graph, respectively, of the Bruininks-Oseretsky Test of Motor Proficiency, 2nd Edition (BOT-2) strength tests (FIG. 9A) and the average BOT-2 strength scaled scores of HPP patients administered asfotase alfa over a time period of 5 years (FIG. 9B). The mean±the standard deviation and median of the BOT-2 scores for each time interval (baseline, 6 months, 1 year, 2 years, 3 years, 4 years, and 5 years) are shown. Arrows indicate the initial phase and extension phase, respectively, of treatment with asfotase alfa.
Figure 9B:
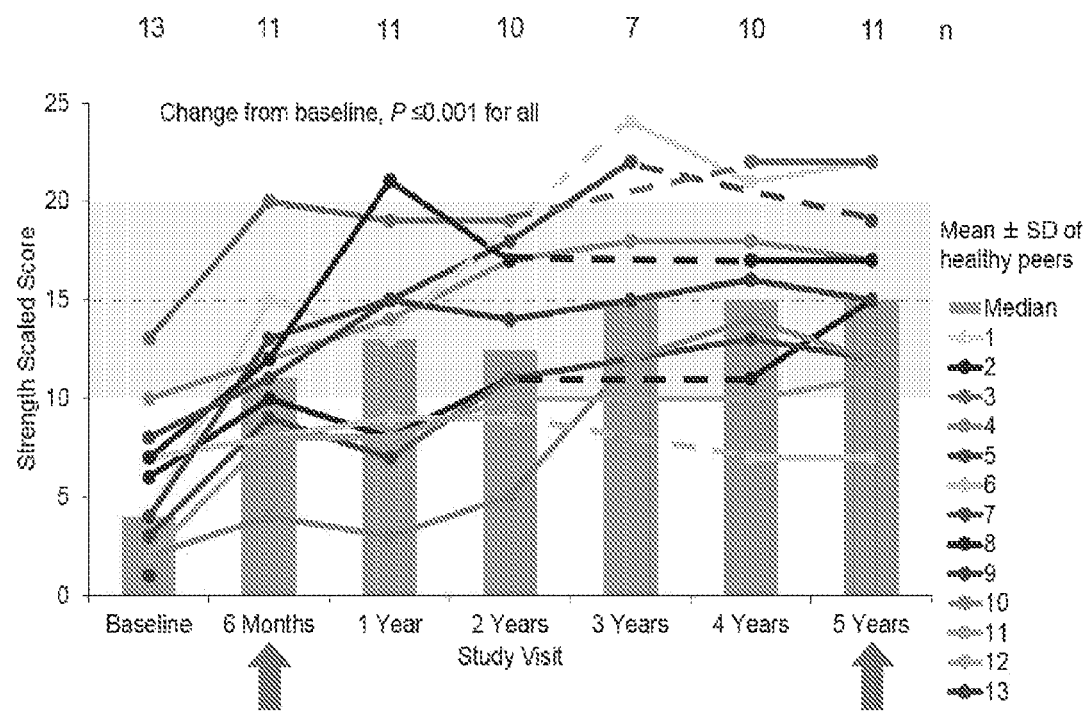

Physical function and impairments of the HPP patients treated with asfotase alfa were assessed using the Bruininks-Oseretsky Test of Motor Proficiency, Second Edition (BOT-2) strength test and the BOT-2 running speed and agility test. BOT-2 tests to assess strength of the HPP patients included sit-ups, v-ups, standing long jump, wall sit, and push-ups (FIG. 9A). Strength scores were converted to strength scaled scores relative to a healthy age and gender matched reference population for each time interval (baseline, 6 months, 1 year, 2 year, 3 years, 4 years, and 5 years) (FIG. 9B). The strength scaled score mean for age-matched healthy patients was 15 with a standard deviation (SD) of 5, resulting in a range of 10 to 20 for the healthy reference population. At baseline, patients had physical impairments compared with healthy peers with a BOT-2 Strength score of 4 (minimum score of 1, maximum score of 13). BOT-2 strength scores significantly improved by 6 months of treatment, resulting in a BOT-2 score within the range of healthy patients, which was sustained throughout at least 5 years of treatment with asfotase alfa.

Figure 10A:
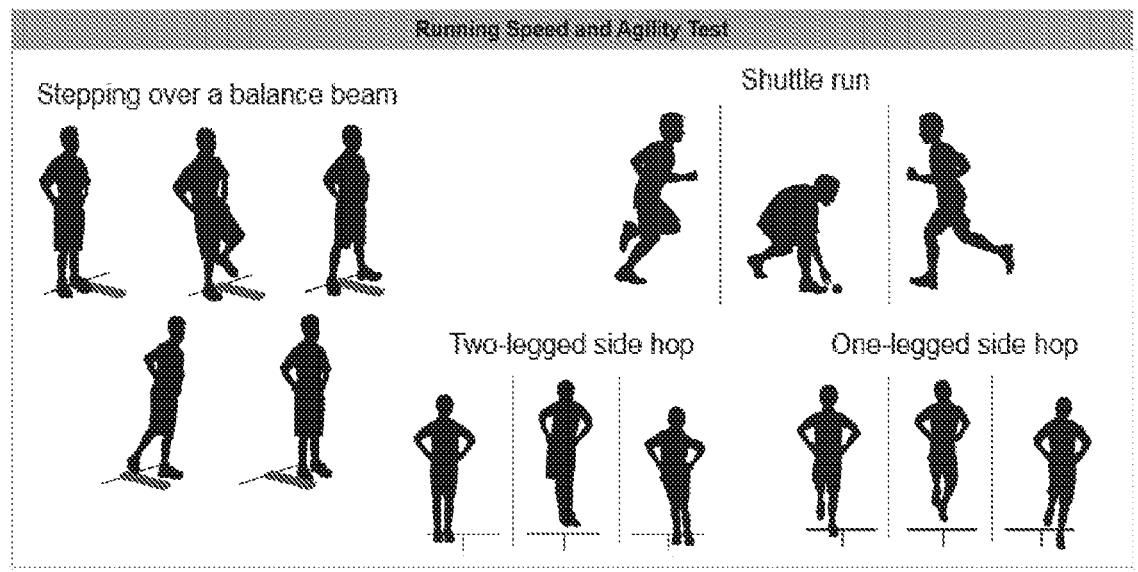
FIGS. 10A-10O are an image and graphs, respectively, of the BOT-2 running speed and agility tests (FIG. 10A) and BOT-2 running speed and agility scaled scores (FIG. 10B) and BOT-2 composite strength and agility standardized scores (FIG. 10C-10D) of HPP patients administered asfotase alfa over a time period of 5 years. The mean±the standard deviation and median of the BOT-2 scores for each time interval (baseline, 6 months, 1 year, 2 years, 3 years, 4 years, and 5 years) are shown. Arrows indicate the initial phase and extension phase, respectively, of treatment with asfotase alfa. Median, min, max, and n values are shown for FIG. 10D.
Figure 10B:
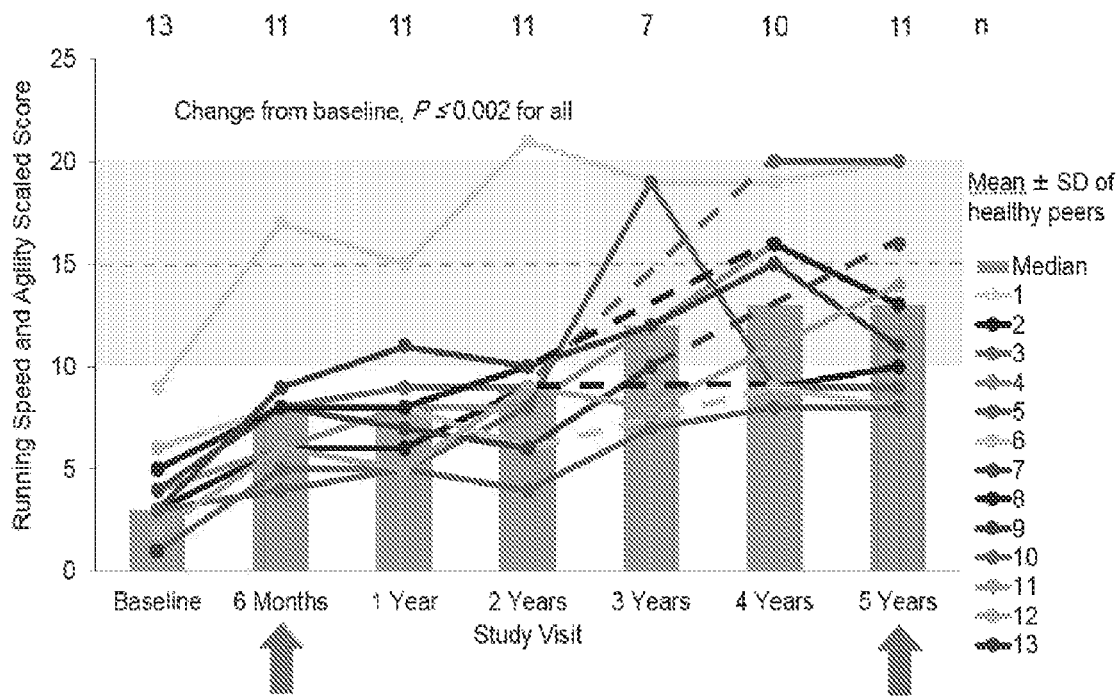

BOT-2 tests to assess running speed and agility of the HPP patients included the 50 foot shuttle run, sideways steps over balance beam, and one and two legged side hops (FIG. 10A). Running speed and agility scores were converted to running speed and agility scaled scores relative to all HPP patients in the study and the median score was determined at each time interval (baseline, 6 months, 1 year, 2 year, 3 years, 4 years, and 5 years). The scaled score mean for age-matched healthy patients was 15 with a standard deviation (SD) of 5, resulting in a range of 10 to 20 for healthy patients. At baseline, patients had physical impairments compared to healthy peers with a BOT-2 running speed and agility score of 3 (minimum score of 1, maximum score of 9). BOT-2 running speed and agility scores significantly improved by 6 months of treatment, resulting in a BOT-2 score within the range of healthy patients by 3 years, which was sustained throughout 5 years of treatment with asfotase alfa (FIG. 10B).

Figure 10C:
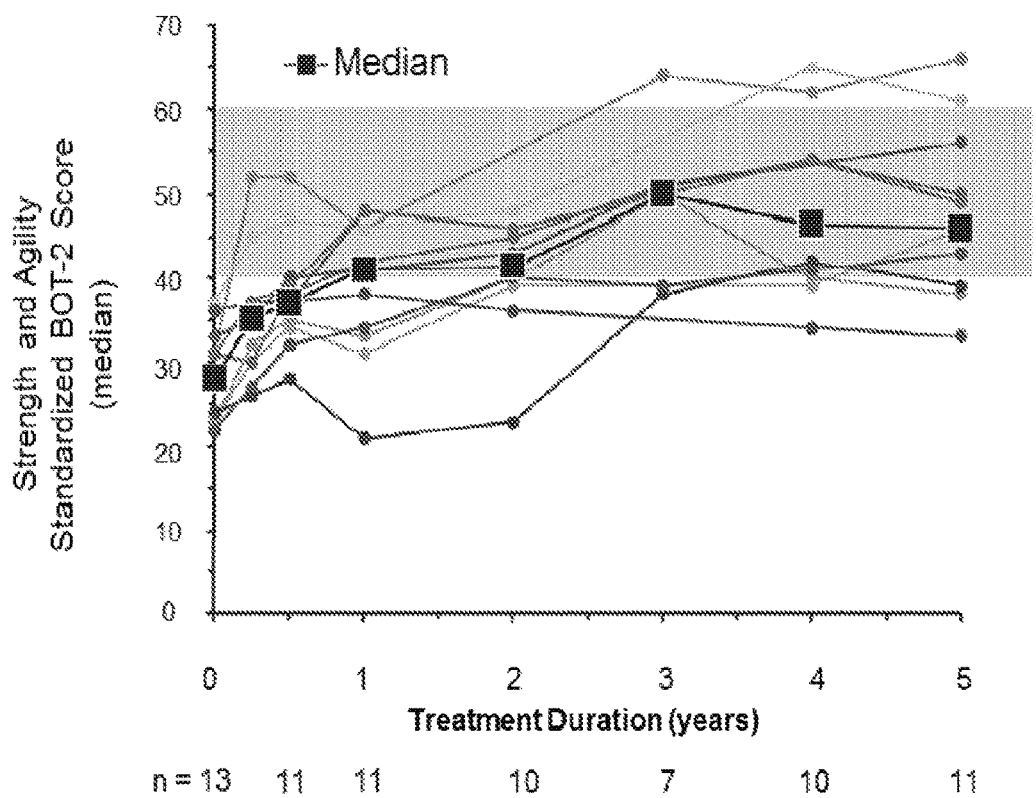
Figure 10D:
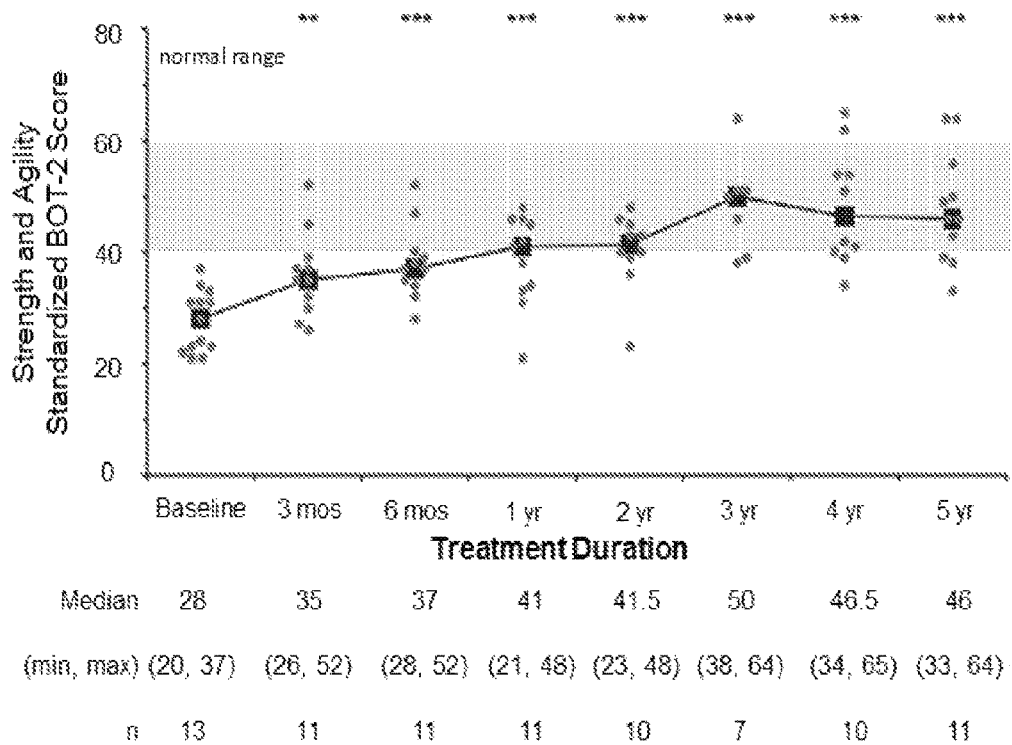

Composite strength and agility scaled scores were also determined from the BOT-2 strength and running speed and agility for the HPP children treated with asfotase alfa relative to healthy children (FIG. 10C). The median value for the BOT-2 strength and agility composite score at baseline (28.0 [20.0, 37.0]; percentile rank=1.0) was greater than 2 SD below the median score of 50 for healthy, age-matched peers. During treatment, the BOT-2 strength and agility composite score improved, reaching the normal range after 1 year, and was significantly better after 5 years (46.0 [33.0, 64.0]; P≤0.0001; percentile rank=35.0; FIG. 10D). The magnitude of change in the standard scores indicated gross motor function within the normal range (±1 SD mean).

Example 7. Ability to Perform Activities of Daily Living and Pain of HPP Children Treated with Asfotase Alfa The ability to perform activities of daily living (ADL) and pain of the HPP patients were reported by parents via the Childhood Health Assessment Questionnaire (CHAQ; Table 7). The CHAQ has a Disability Index with 30 age-appropriate items in 8 subscales (0-3, 0=no disability for the index) and a Discomfort (pain) Index (0-100, 0=no pain for the index).

TABLE 7

Description, scoring, and interpretation of CHAQ Disability and Discomfort tests.

| Component | Disability | Discomfort |
|---|---|---|
| Description | Covers major aspects of daily living (30 questions in 8 domains):<br>Dressing and grooming<br>Arising<br>Eating<br>Walking<br>Hygiene<br>Reach<br>Grip<br>Activities | Measures discomfort as determined by the presence of pain<br>Visual analog scale (single question) |
| Scoring | 0 = no difficulty<br>1 = some difficulty<br>2 = much difficulty<br>3 = unable to do | 0-100 (anchored by 0, no pain; 100, very severe pain) |
| Interpretation | Decreased score = reduced disability<br>MCID: decrease ≥0.13 | Decreased score = reduced pain<br>MCID not determined<br>Healthy children (no disability) score 0 |

Ability to perform ADL and pain of the HPP children treated with asfotase alfa were also reported by parents using the Pediatric Outcomes Data Collection Instrument (PODCI). The PODCI has 8 scales, including Transfer and Basic Mobility, Sports and Physical Function, and Pain and Comfort (Table 8). For the PODCI, the normative mean was 50 (standard deviation of 10).

TABLE 8

Description of measurements and exemplary tasks of PODCI Transfer and Basic Mobility, Sports and Physical Function, and Pain and Comfort scales.

| | Domain | Example tasks |
|---|---|---|
| Transfer and Basic Mobility Scale | Measures difficulty experienced in performing routine motion and motor activities in daily activities | Climb one flight of stairs<br>Walk one block<br>Get on and off a bus<br>Bend over from a standing position and pick up something off the floor |
| Sports/Physical Functioning Scale | Measures difficulty or limitations encountered in participating in more active activities or sports | Run short distances<br>Climb three flights of stairs<br>How often in the last week did your child participate in gym/recess? |
| Pain/Comfort Scale | Measures the level of pain experienced during the past week | Did pain or discomfort interfere with your child's activities?<br>During the last week, how much did pain interfere with your child's normal activities (including at home, outside of home, and at school)? |

Figure 11:
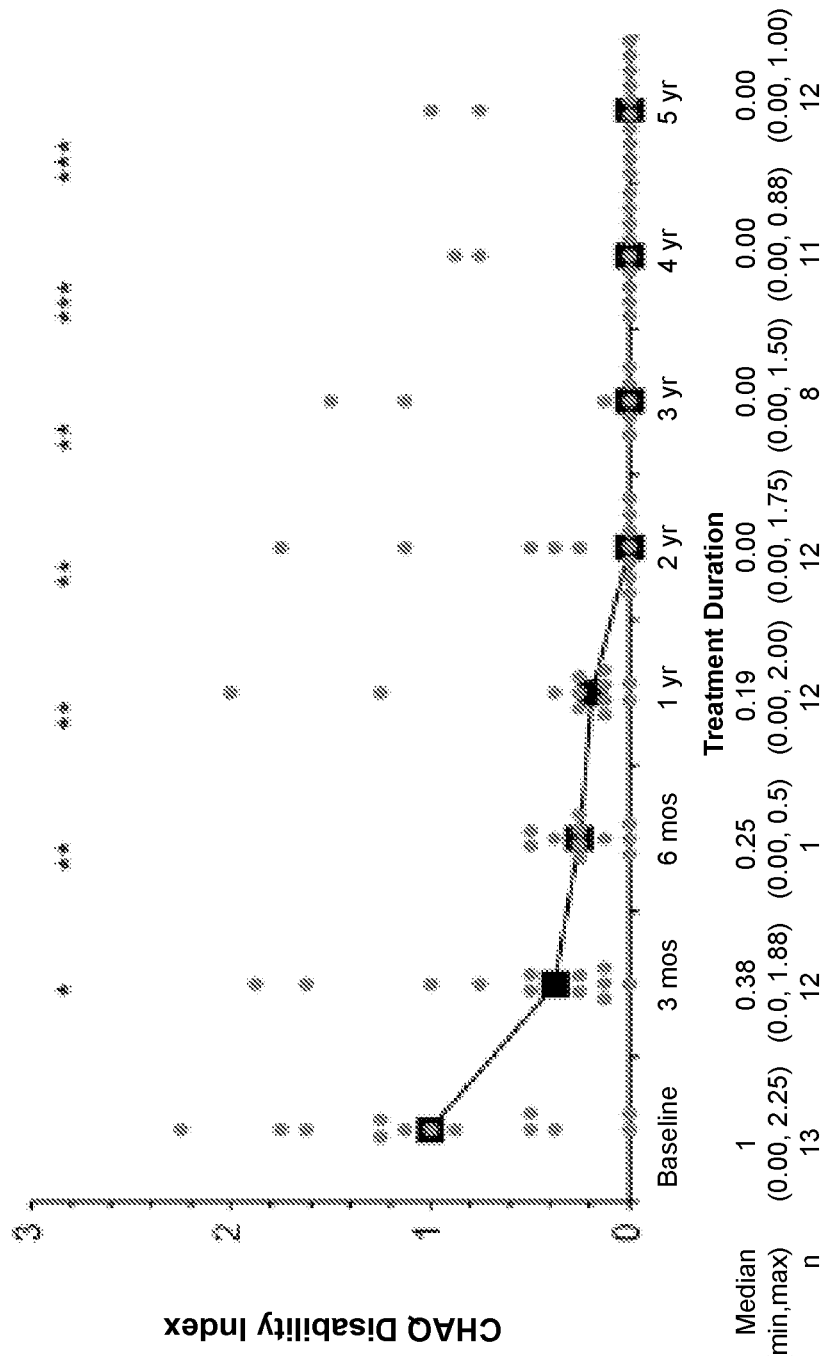
FIG. 11 is a graph of the Childhood Health Assessment Questionnaire (CHAQ) disability index scores of HPP patients administered asfotase alfa over a time period of 5 years. Average CHAQ disability index scores at baseline, 3 months, 6 months, 1 year, 2 years, 3 years, 4 years, and 5 years are shown. Median CHAQ disability index scores at each time interval are shown in bold. *P≤0.05, P≤0.01, and *P≤0.001 mean difference for each time point compared with baseline by paired t test. Median, min, max, and n values are shown. Individual dots indicate individual patient scores at each time point.

Pain experienced by the HPP patients decreased after administration of asfotase alfa with significant improvements observed by 2 years with an average CHAQ median disability index score of 0 (FIG. 11). This decrease in physical disability was sustained throughout 5 years with a CHAQ median disability index score of about 0. In particular, the elevated CHAQ pain (20.0 [0.0, 72.0]) and disability (1.0 [0.0, 2.3]) medians at baseline were 0 at 5 years of treatment with asfotase alfa, indicating no pain or disability for most of the HPP children (0.0 [0.0, 60.0], P=0.1125; 0.0 [0.0, 1.0], P=0.0002, respectively).

Figure 12B:
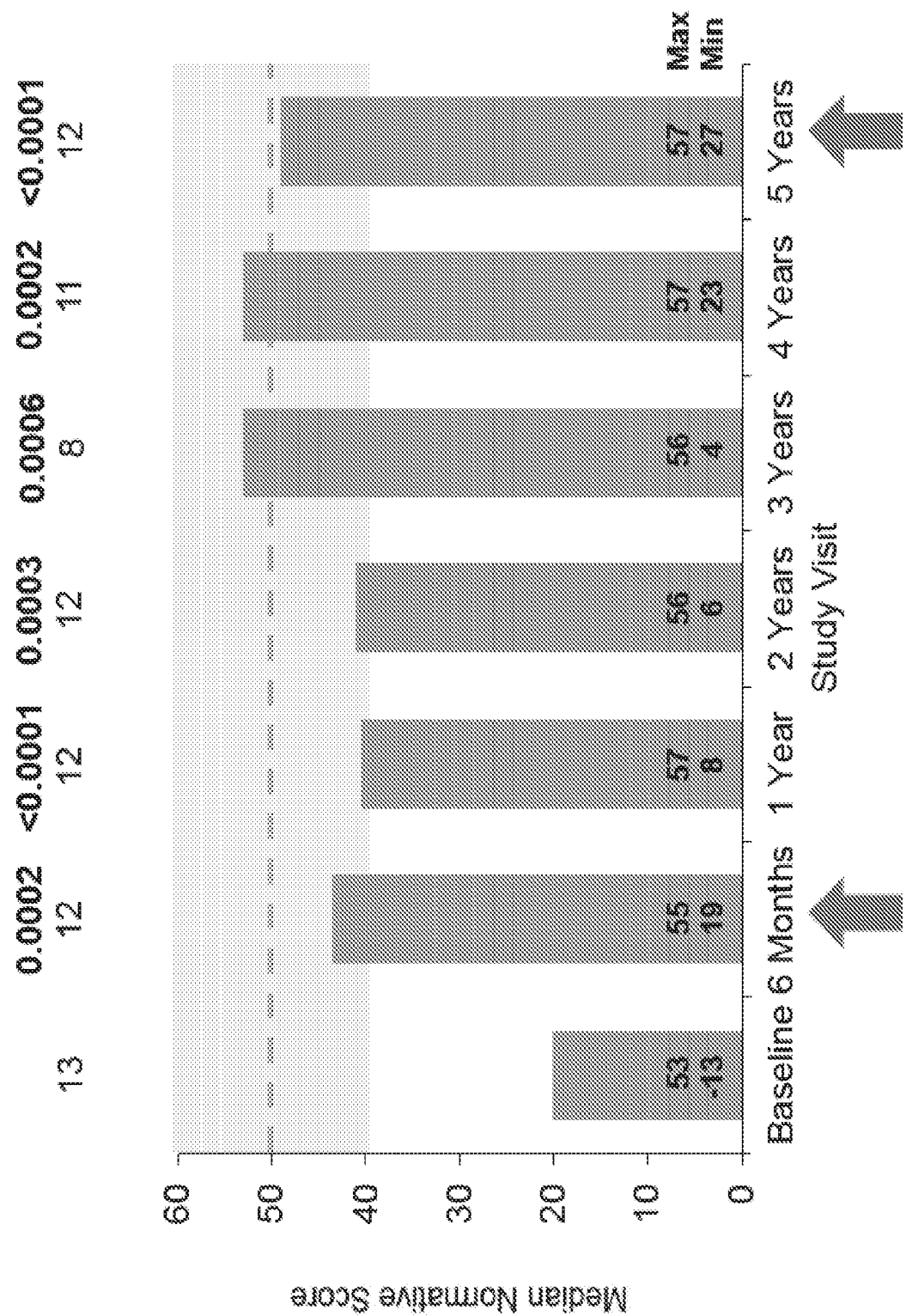
Figure 13B:
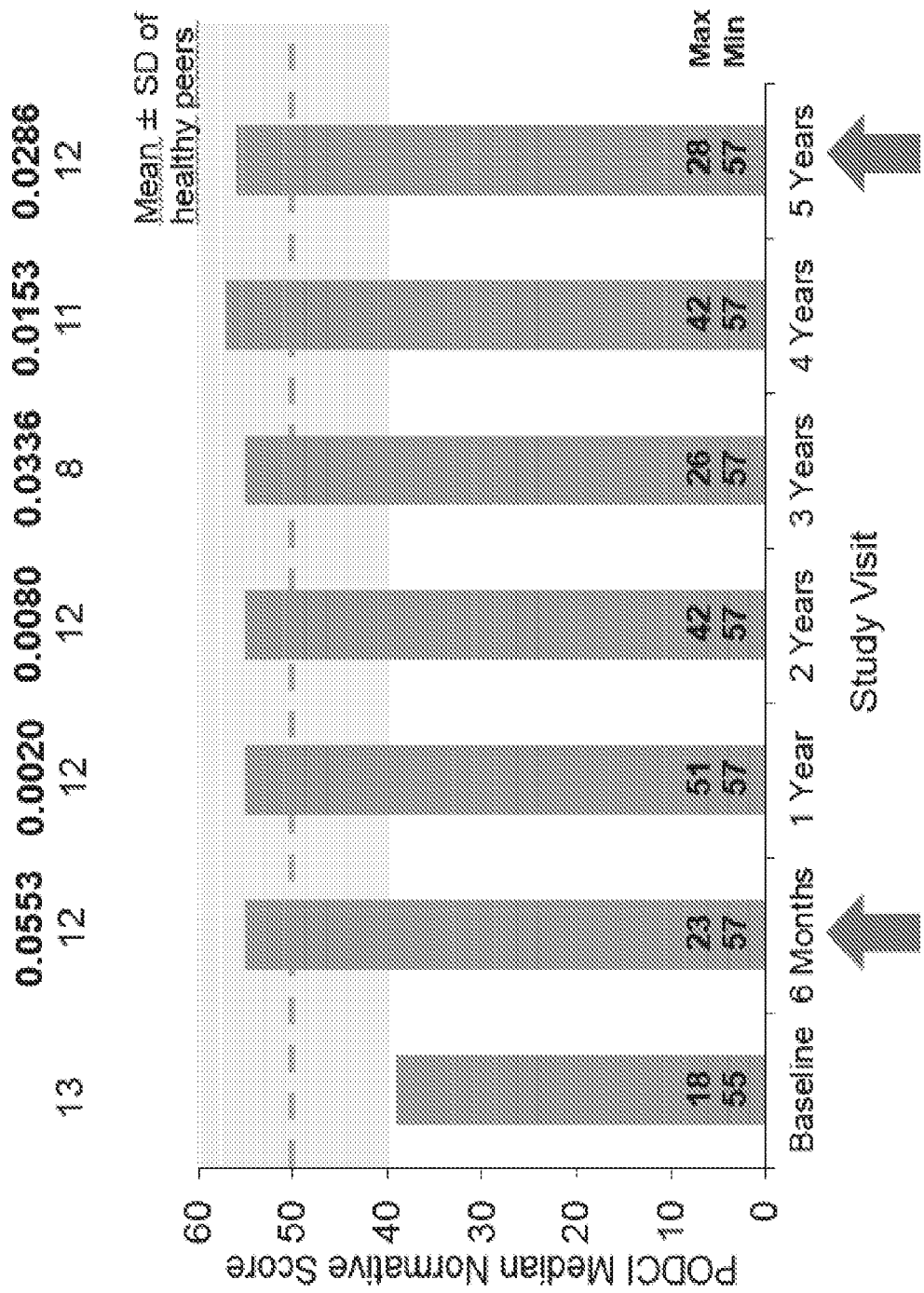

Likewise, physical disability of the HPP patients decreased after administration of asfotase alfa with significant improvements observed by 6 months in the PODCI Transfer and Basic Mobility Scale and PODCI Sports and Physical Functioning Scale, in which patients attained normal ranges by 6 months (FIG. 12A and FIG. 12B, respectively). The decrease in physical disability as assessed by the average PODCI scores was sustained throughout 5 years of treatment with asfotase alfa in both PODCI Transfer and Basic Mobility Scale and PODCI Sports and Physical Functioning Scales. In summary, decreased pain of the HPP children treated with asfotase alfa was apparent from CHAQ and PODCI discomfort median normative scores by 6 months, which was sustained throughout 5 years of treatment with asfotase alfa (FIGS. 13A and 13B, respectively). Thus, reduced pain and increased ability to perform ADL were sustained in this cohort of children with HPP throughout 5 years of treatment with asfotase alfa.

Example 8. Tolerability of HPP Children to Long-Term Treatment with Asfotase Alfa Generally, treatment with asfotase alfa was well-tolerated in children having HPP, with most adverse events (AEs) considered mild or moderate. There were no deaths, serious AEs, or withdrawals due to AEs. One patient receiving asfotase alfa at a dosage regimen of 9 mg/kg/week subcutaneously underwent a dose reduction for a low plasma PLP level. Four patients had injection-associated reactions (10 events) during the first month of treatment. All were injection site reactions (ISRs), with the exception of nausea and peripheral edema in 1 patient, and all were mild. Each patient experienced at least 1 treatment-emergent AE; 86% mild and 14% moderate in severity. Most AEs (53%) were considered by the investigators to be unrelated to the treatment. When ISRs were excluded, 2% of AEs were deemed treatment related. The most common AEs were mild injection site reactions (Table 9). For example, erythematous reaction, purple discoloration at 5 years, and abdominal lipohypertrophy at 4.5 years were noted in individual patients.

TABLE 9

Occurrence of injection site reactions in patients treated with asfotase alfa for 5 years.

| | Asfotase alfa, n = 13 | |
|---|---|---|
| Injection site reactions in ≥3 patients | Events, n | Patients, n (%) |
| Injection site reactions | 250 | 12 (92%) |
| Erythema | 71 | 11 (85%) |
| Hypertrophy | 26 | 8 (62) |
| Pruritus | 23 | 7 (54) |
| Pain | 18 | 6 (46) |
| Atrophy | 13 | 5 (38) |
| Discoloration | 17 | 5 (38) |
| Swelling | 12 | 3 (23) |
| Induration | 1 | 1 (8) |
| Nodule | 1 | 1 (8) |
| Papule | 1 | 1 (8) |
| Urticaria | 1 | 1 (8) |

In summary, a total of 250 injection site reactions occurred in 12 of the 13 patients (92% of total patients). In particular, 71 instances of erythema occurred in 11 patients (85% of total patients); 26 instances of hypertrophy occurred in 8 patients (62% of total patients); 23 instances of pruritus occurred in 7 patients (54% of total patients); 18 instances of pain occurred in 6 patients (46% of total patients); 13 instances of atrophy occurred in 5 (38% of total patients); 17 instances of discoloration occurred in 5 patients (38% of total patients); 12 instances of swelling occurred in 3 patients (23% of total patients); 1 instance of induration occurred in 1 patient (8% of total patients); 1 instance of a nodule occurred in 1 patient (8% of total patients); 1 instance of a papule occurred in 1 patient (8% of total patients); and 1 instance of a urticaria occurred in 1 patient (8% of total patients).

Surveillance of radiographs of the HPP children treated with asfotase alfa showed no evidence of ectopic calcification. On ophthalmoscopy, the retinal examinations were consistently unremarkable. Notably, 46% (6 of 13) of the patients showed small refractile deposits in the conjunctiva or cornea presumed to contain calcium. For 5 HPP patients, these were considered possibly or probably related to the treatment. No deposit was deemed clinically apparent or significant. No children developed nephrocalcinosis, although after approximately 2 years of treatment, renal sonography revealed "focal echogenicity" consistent with a small renal stone present for 6 months in 1 kidney of 1 child.

All 12 treated HPP children showed anti-asfotase alfa antibodies. A total of 5 of the 6 patients who began treatment in the 3 mg/kg dose group were antibody positive by Week 6, and all were antibody positive at Week 12 of treatment. In those starting in the 2 mg/kg dose group, 1 patient was antibody positive by Week 6, and 5 patients were positive by Week 48. In 5 of the 12 patients, the antibodies were neutralizing in vitro at 1 or more time points, but with no apparent compromise of therapeutic efficacy.

Example 9. Study Design of HPP Infants Treated with Asfotase Alfa

Infants aged ≤3 years with onset of HPP symptoms prior to 6 months of age were selected for treatment with asfotase alfa for a time period of at least 5 years (see Table 10).

TABLE 10

Characteristics of HPP infants treated with asfotase alfa for 5 years.

| Characteristic | asfotase alfa (N = 11) |
|---|---|
| Age (months) | 6.8 (0.7, 36.4) |
| Age at onset of HPP (months) | 1.0 (0.0, 5.8) |
| Female, n (%) | 7 (64) |
| White, n (%) | 10 (91) |
| Failure to thrive, n (%) | 10 (91) |
| Length/height, Z-score | −3.7 (−9.2, −0.7) |
| Weight, Z-score | −3.8 (−5.4, −0.5) |
| BSID-III | |
| Gross motor | 1 (1, 9) |
| Fine motor | 5 (1, 13) |

Inclusion criteria included low alkaline phosphatase (ALP) activity (total serum ALP ≥3 SDs below the age-adjusted mean of healthy patients); high pyridoxal 5'-phosphate (PLP) plasma concentrations (plasma PLP ≥4 times upper limit of healthy patients); radiographic evidence of skeletal deformities (i.e. flared and frayed metaphyses, severe generalized osteopenia, and/or widened growth plates); rachitic chest deformity; vitamin B6—responsive seizures; failure to thrive; a history of non-traumatic postnatal fracture or delayed fracture healing; history of elevated serum calcium; craniosynostosis; nephrocalcinosis; and/or respiratory compromise. Exclusion criteria included low serum calcium, phosphate, or 25-hydroxyvitamin D levels.

Figure 14:
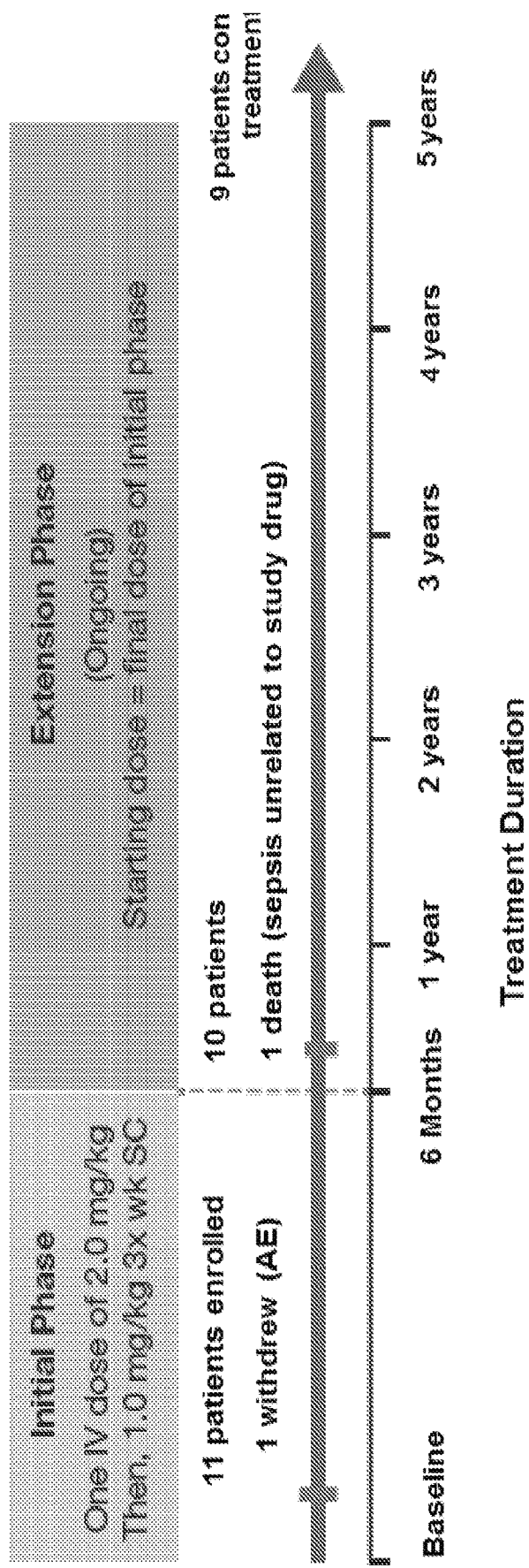
FIG. 14 is an image showing the study design for the treatment of infants with HPP over a period of 5 years with a asfotase alfa including an initial phase of treatment with asfotase alfa (from baseline to 6 months and an extension phase of treatment with asfotase alfa (from 6 months of treatment to 5 or more years of treatment).

Following the initial phase study, 10 of the 11 patients proceeded with an extension phase study of asfotase alfa administration for at least 5 years (one patient withdrew due to adverse events) (FIG. 14). In the extension phase, 9 out of 10 patients completed the study (one patient died due to septic shock unrelated to asfotase alfa administration). Asfotase alfa was administered via subcutaneous administration to patients at a dosage of 1.0 mg/kg three times weekly. Additional dose adjustments could be made for changes in weight and/or for safety concerns or for lack of efficacy after 1 month (e.g., increasing the dosage to 2 mg/kg three times weekly) and again after 3 months (e.g., increasing the dosage to 3 mg/kg three times weekly).

Example 10. Radiographic Assessments of HPP Infants Treated with Asfotase Alfa

Figure 15A:
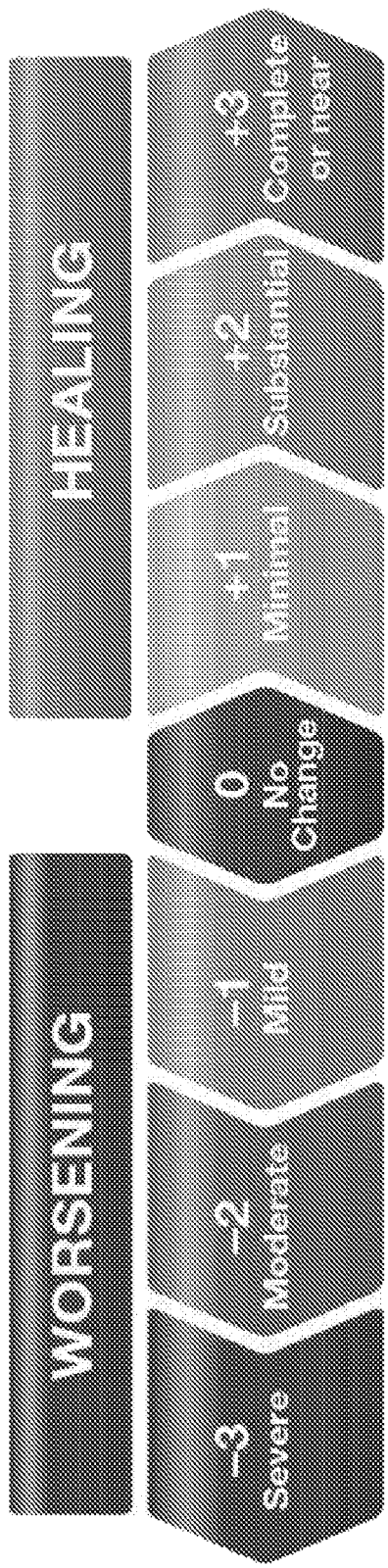
FIGS. 15A-15B are an image and a graph, respectively, showing the RGI-C assessment scale (FIG. 15A) and the average RGI-C scores (FIG. 15B) of HPP patients after administration of asfotase alfa over a time period of 5 years.

Radiographic assessments of HPP patients were performed during the course of treatment as previously described (see Whyte et al. (*N Engl J Med* 366(10): 904-913, 2012)). The Radiographic Global Impression of Change (RGI-C) assessment scale was utilized during treatment of HPP patients with asfotase alfa. Paired pre-treatment and on-treatment radiographs of bilateral wrists, knees, and, when available, chests, were evaluated for changes in the skeletal manifestations of HPP (−3=severe worsening; 0=no change; +3=near/complete healing; FIG. 15A).

Figure 15B:
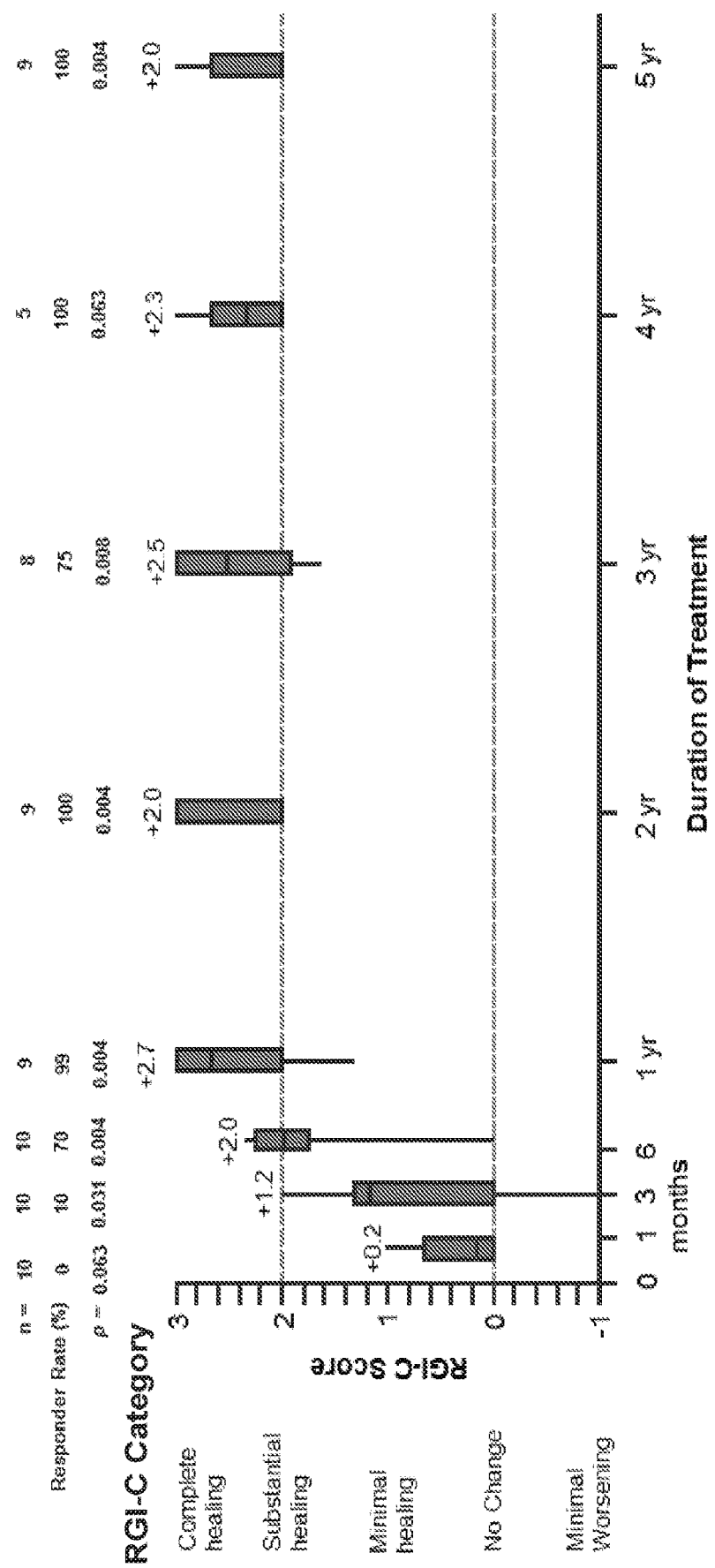

Evaluations were performed by three independent radiologists blinded to the post-baseline time point. The average RGI-C score was determined as the mean of the three RGI-C scores. A patient with a score of ≥+2 was considered a "responder" for that time point. RGI-C scores of the HPP patients demonstrated significant skeletal improvement by 6 months (primary endpoint), which was sustained throughout 5 years for the 9 remaining patients (FIG. 15B). For the primary endpoint analysis of RGI-C, a Wilcoxon signed-rank test with a two-sided alpha of 0.05 tested whether the median RGI-C at Week 24 differed from 0. If the P-value was <0.05 and the median RGI-C score was positive, significant positive change from baseline is shown. Missing RGI-C scores were imputed with last observation carried forward; patients with no post-baseline data were considered non-responders. Additionally, this responder analysis was repeated using the last assessment of RGI-C scores. From year 1, the majority of patients achieved RGI-C scores ≥2, corresponding to substantial healing of rickets.

Example 11. Growth Assessments of HPP Infants Treated with Asfotase Alfa

Figure 16A:
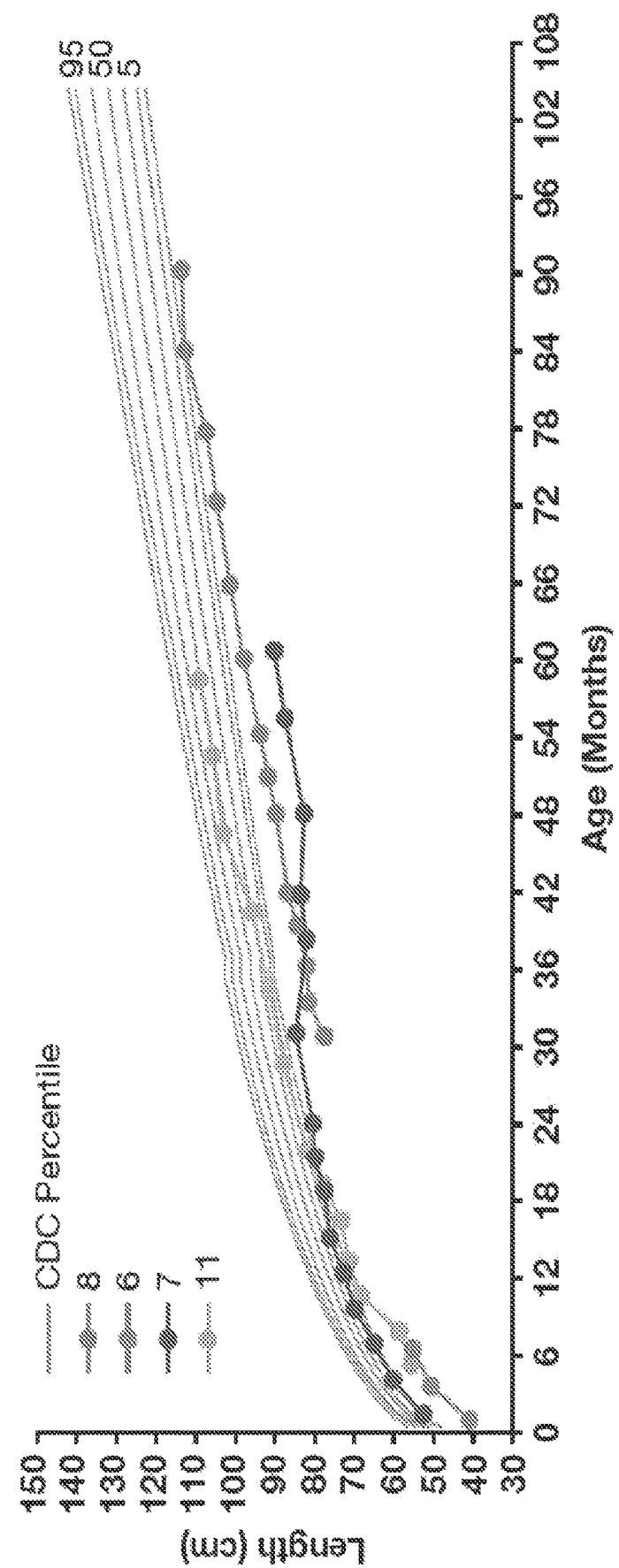
FIGS. 16A-16B are graphs showing length Z-scores of HPP patients after administration of asfotase alfa at 0 to 108 months. Male and female patients are shown (FIG. 16A and FIG. 16B, respectively).
Figure 16B:
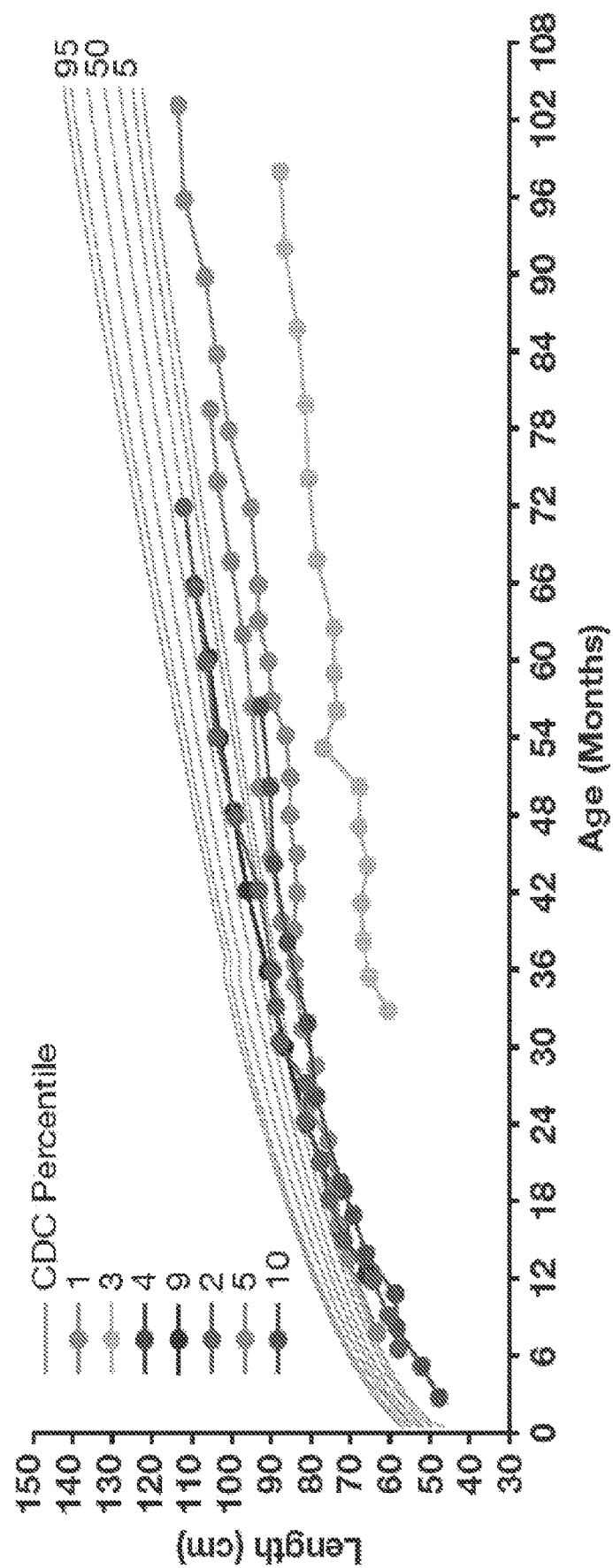
Figure 17A:
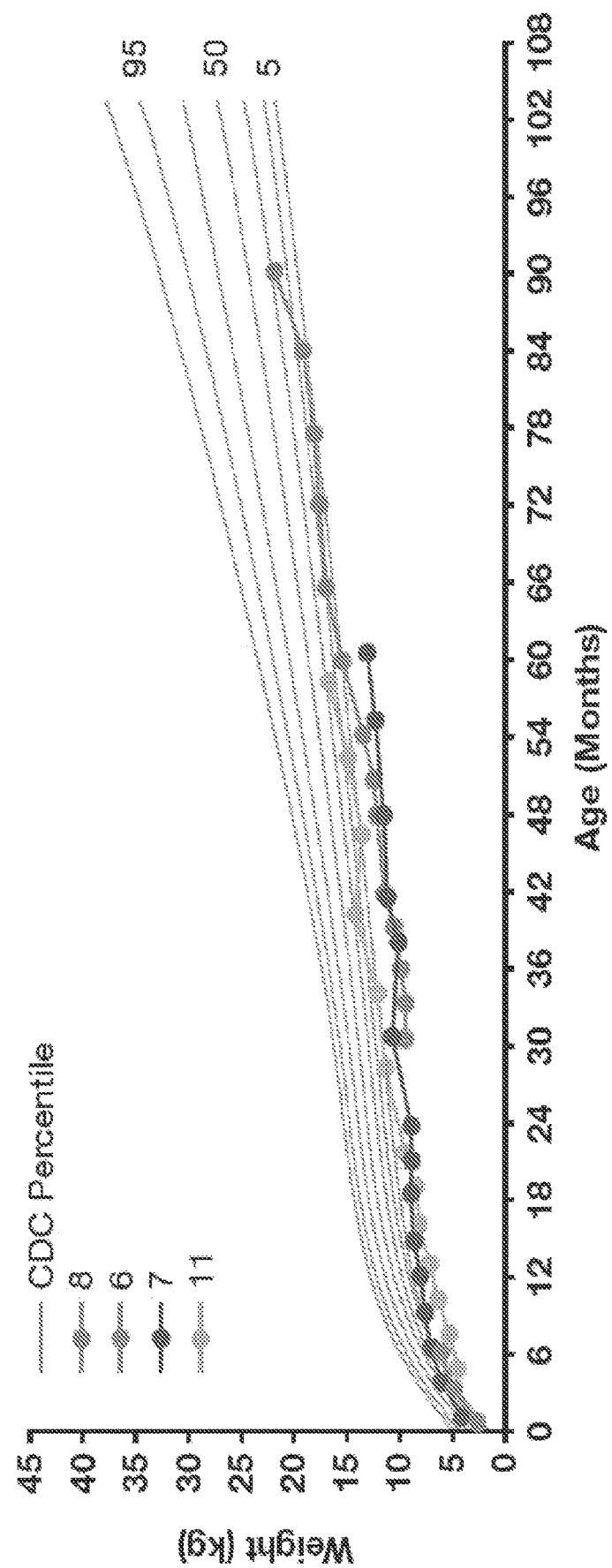
FIGS. 17A-17B are graphs showing weight Z-scores of HPP patients after administration of asfotase alfa at 0 to 108 months. Male and female patients are shown (FIG. 17A and FIG. 17B, respectively).
Figure 17B:
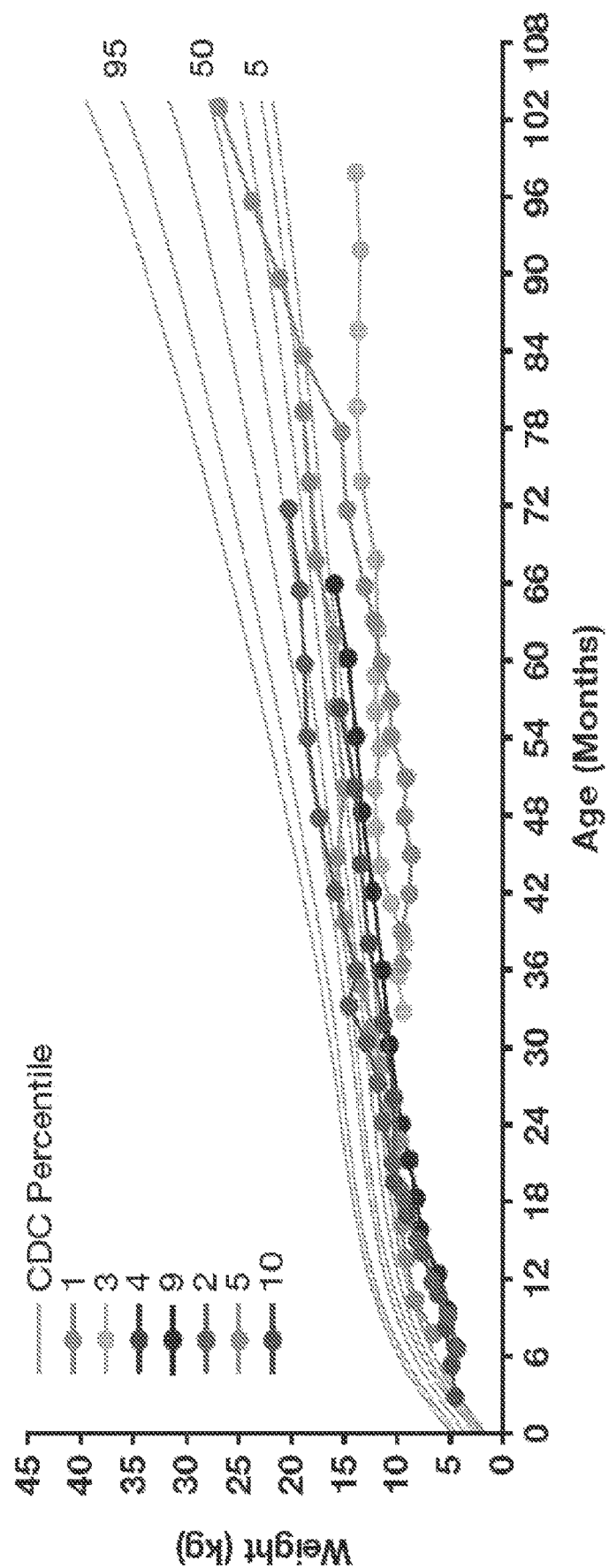
Figure 18:
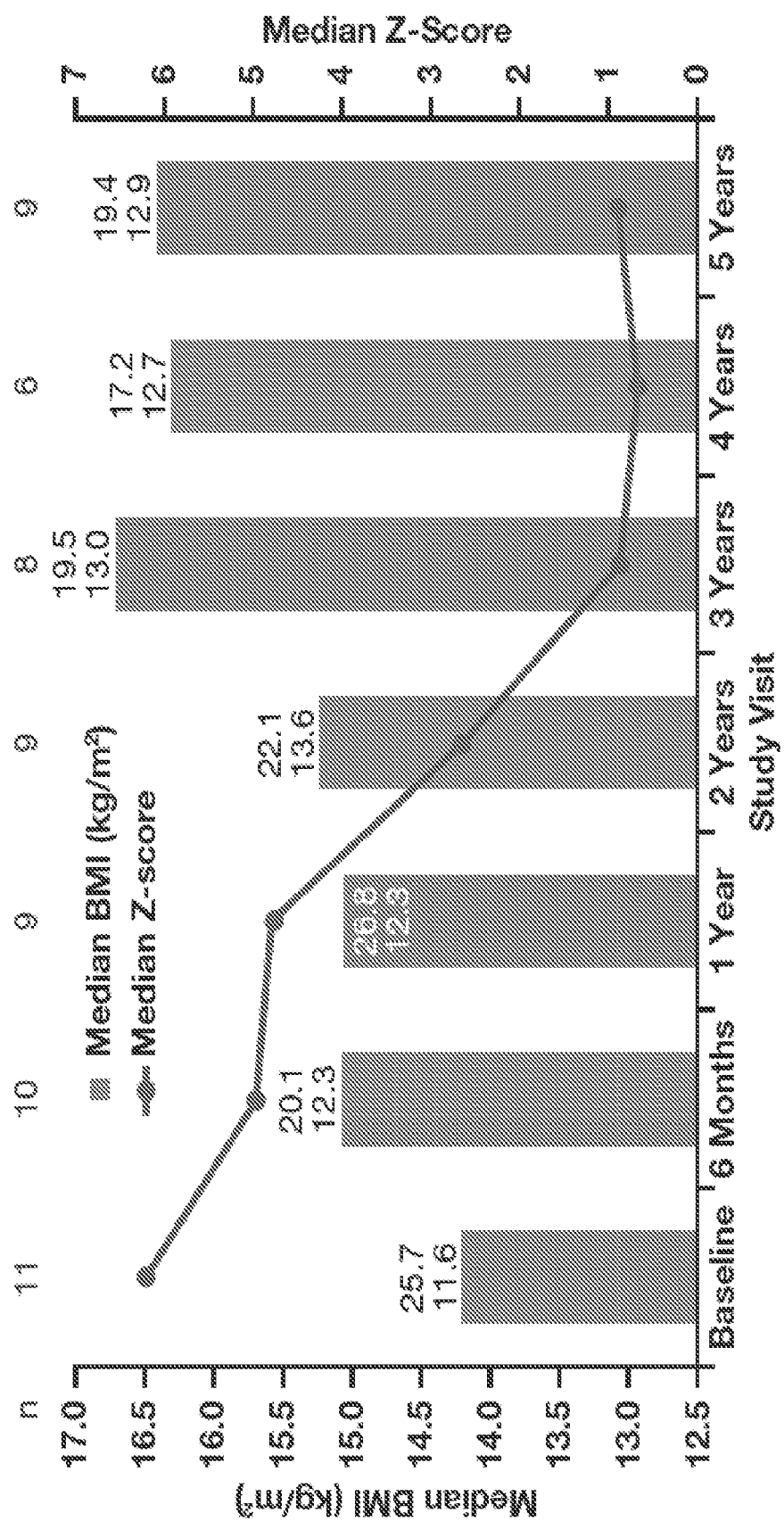
FIG. 18 is a graph showing the median BMI and Z-scores (length and width) of both female and male HPP patients after administration of asfotase alfa at 0 to 108 months.

Length and height of HPP patients at each time point were measured, and BMI was determined from the length and height measurements. The CDC percentiles were generated using the 2000 National Center for Health Statistics Growth Chart Equation, Length Z-scores improved from baseline to 5 years of treatment, with scores reflecting catch-up growth relative to healthy peers (male patients shown in FIG. 16A; female patients shown in FIG. 16B). Likewise, weight Z-scores improved from baseline to 5 years of treatment, with scores reflecting catch-up growth relative to healthy peers (male patients shown in FIG. 17A; female patients shown in FIG. 17B). The median BMI and Z-scores (length and width) also exhibited improvement from baseline to 5 years of treatment (FIG. 18). Statistical significance was defined as P≤0.05.

Example 12. Motor Development of HPP Infants Treated with Asfotase Alfa

Motor development of HPP patients treated with asfotase alfa was determined using the Infant and Toddler Development, 3rd Edition (BSID-III) scaled score for patients ≤42 months of age and using the Locomotion Subtest of the Peabody Developmental Motor Scales, 2nd Edition (PDMS-2) standard score for patients 43 to 71 months of age. Detailed protocols are described in BSID-III, Bayley Scales of Infant and Toddler Development, 3rd Edition and in Peabody Developmental Motor Scales, 2nd edition.

Figure 19:
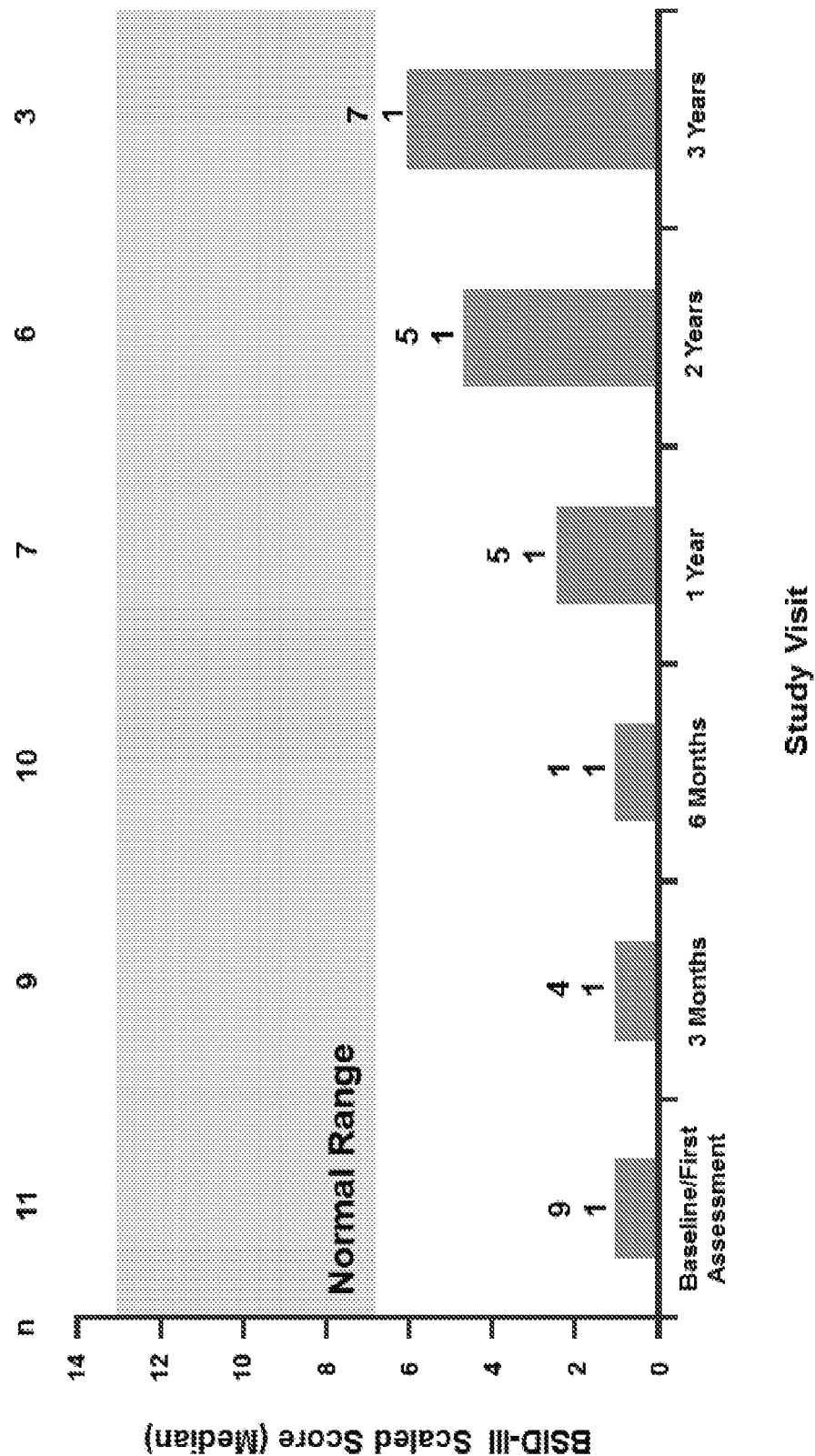
FIG. 19 is a graph showing the average Bayley Scales of Infant and Toddler Development, $3^{rd}$ Edition (BSID-III) scores of HPP patients after administration of asfotase alfa over a time period of 3 years. BSID-III scores at baseline, 3 months, 6 months, 1 year, 2 years, and 3 years are shown.
Figure 20:
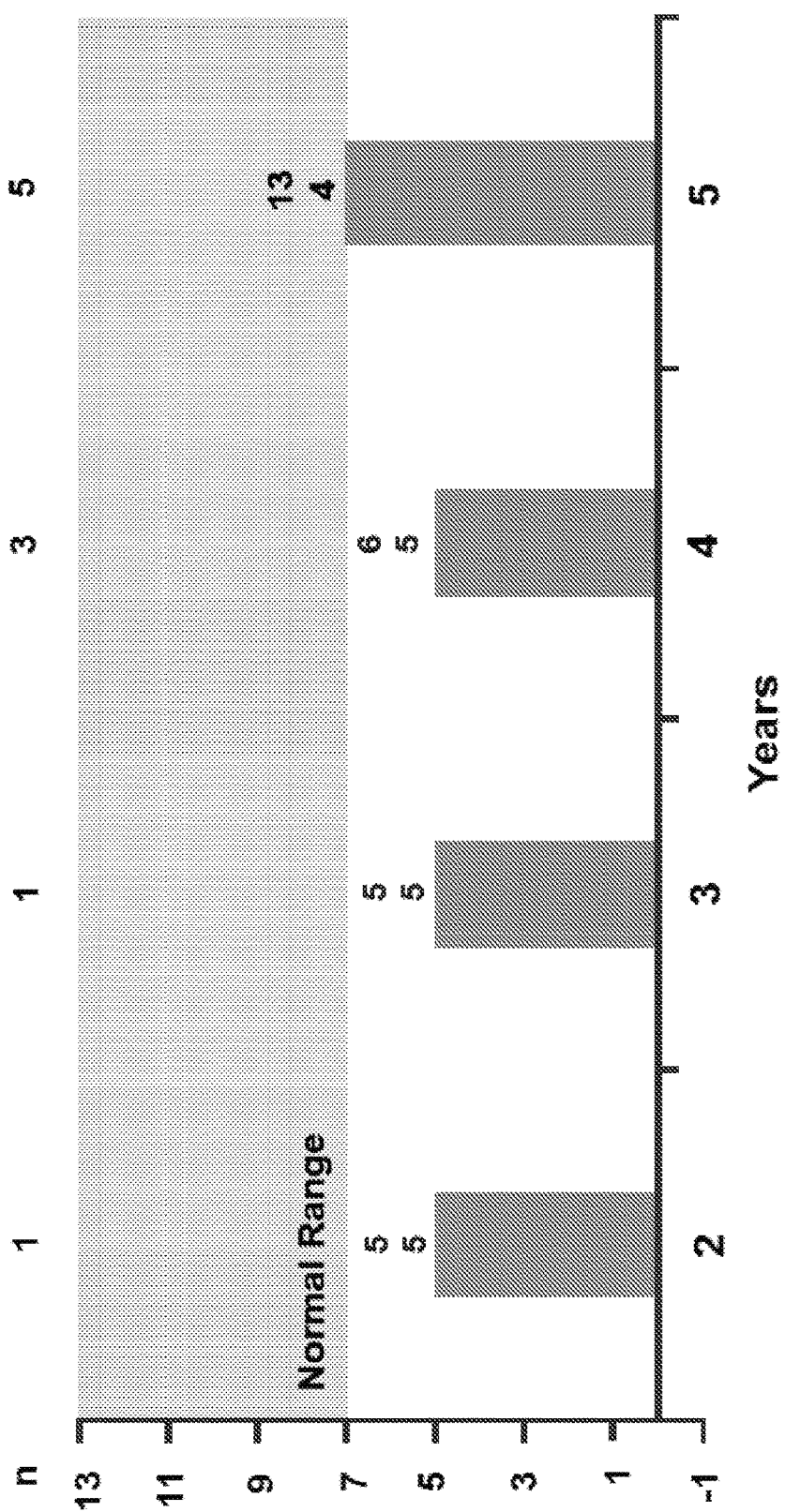
FIG. 20 is a graph showing the average Peabody Developmental Motor Scales, 2nd Edition (PDMS-2) scores of HPP patients after administration of asfotase alfa over a time period of 5 years. PDMS-2 scores at 2 years, 3 years, 4 years, and 5 years are shown.

BSID-III scaled score and PDMS-2 standard score both reflect the patient's performance relative to healthy, same-aged peers; the healthy age-matched mean for both scores was 10 (standard deviation of 3). At baseline or first assessment (FA), BSID-III median scaled scores indicated functional delay in all 11 patients (FIG. 19). BSID-III median scaled scores improved by 1 year of treatment, with continued improvement throughout asfotase alfa administration. The normal range of BSID-III scores was defined as described in Connolly et al. (*Pediatr Phys Ther.* 24(4):345-52, 2012; incorporated herein by reference). Five patients transitioned to PDMS-2 measurements by 5 years, the median scoring near the normal range for the PDMS-2 locomotion subtest (FIG. 20). Improvements in the PDMS-2 scaled score were noted through 5 years of therapy (median baseline score (min, max): 5 (1, 13). n=11; median score at year 2: 9.5 (7, 11), n=6; Year 3: 7 (7, 13), n=3). Calculation of the normal BSID-III range is described in Folio et al. *Peabody developmental motor scales*-2 (2nd ed.). Austin, Tex.; incorporated herein by reference. Substantial improvements in skeletal manifestations and motor function continued during 5 years of treatment for life-threatening perinatal and infantile HPP with asfotase alfa.

Example 13. Tolerability to Long-Term Treatment with Asfotase Alfa

Generally, treatment with asfotase alfa was well-tolerated in infants having HPP, with most adverse events (AEs) considered mild or moderate. The most common AEs of patients are described in Table 11. AH adverse events (AEs) were coded using the Medical Dictionary for Regulatory Activities (v. 13.0 or higher).

TABLE 11

Adverse events (AEs) of infants having HPP treated with asfotase alfa for 5 years.

| Preferred term | Events, n | Patients, n (%) |
|---|---|---|
| Upper respiratory tract infection | 67 | 7 (64%) |
| Pyrexia | 20 | 7 (64%) |
| Pneumonia | 14 | 7 (64%) |
| Craniosynostosis | 12 | 7 (64%) |
| Otitis media | 19 | 6 (55%) |
| Vomiting | 13 | 6 (55%) |
| Constipation | 7 | 6 (55%) |
| Injection site erythema | 29 | 5 (46%) |
| Hemoglobin decreased | 9 | 4 (36%) |
| Tooth loss | 8 | 4 (36%) |
| Diarrhea | 6 | 4 (36%) |
| Nasopharyngitis | 6 | 4 (36%) |
| Rash | 5 | 4 (36%) |

TABLE 11-continued

Adverse events (AEs) of infants having HPP treated with asfotase alfa for 5 years.

| Preferred term | Events, n | Patients, n (%) |
|---|---|---|
| Dental caries | 4 | 4 (36%) |
| Irritability | 4 | 4 (36%) |

Injection associated reactions were reported by a total of 7 patients. Examples of common injection site reactions are shown in Table 12. In total, 73 injection site reactions occurred in 7 HPP patients (64% of total HPP patients) treated with asfotase alfa for 5 years. In particular, 28 instances of erythema occurred in 4 patients (37% of total HPP patients); 8 instances of hypertrophy occurred in 2 patients (18% of total HPP patients); 5 instances of both hematoma and swelling occurred in 2 patients (18% of total HPP patients); and 3 instances of nodule and warmth at the injection site occurred in 2 patients (18% of total HPP patients) throughout treatment with asfotase alfa for 5 years.

TABLE 12

Injection site reactions of infants having HPP treated with asfotase alfa for 5 years.

| Preferred term | Events, n | Patients, n (%) |
|---|---|---|
| Injection Site Reactions | 73 | 7 (64%) |
| Erythema | 28 | 4 (37%) |
| Hypertrophy | 8 | 2 (18%) |
| Haematoma | 5 | 2 (18%) |
| Swelling | 5 | 2 (18%) |
| Nodule | 3 | 2 (18%) |
| Warmth | 3 | 2 (18%) |

Other Embodiments

All publications, patents, and patent applications mentioned in the above specification are hereby incorporated by reference to the same extent as if each individual publication, patent or patent application was specifically and individually indicated to be incorporated by reference in its entirety. Various modifications and variations of the described methods, pharmaceutical compositions, and kits of the invention will be apparent to those skilled in the art without departing from the scope and spirit of the claimed invention. Although the disclosure has been described in connection with specific embodiments, it will be understood that it is capable of further modifications and that the invention as claimed should not be unduly limited to such specific embodiments.

The invention claimed is:

1. A method of treating hypophosphatasia (HPP) in a child from about 5 to about 12 years of age, wherein the method comprises administering a soluble alkaline phosphatase (sALP) to the child at a dosage providing about 1 mg/kg/week to about 10 mg/kg/week for a treatment period comprising at least five years, wherein the sALP comprises an amino acid sequence having at least 95% sequence identity to the amino acid sequence of SEQ ID NO: 1, and wherein the method comprises:
   a) performing a Bruininks-Oseretsky Test of Motor Proficiency 2nd Edition (BOT-2) test, wherein the child has an average BOT-2 strength score of less than about 10 and administration of the sALP results in an average increase in the BOT-2 strength score to about 10 to about 20 after a period of at least five years;
   b) performing a BOT-2 test, wherein the child has an average BOT-2 running speed and agility score of less than 5 and administration of the sALP results in an average increase in the BOT-2 running speed and agility score to about 5 to about 20 after a period of at least five years;
   c) performing a Childhood Health Assessment Questionnaire (CHAQ), wherein the child has an average CHAQ disability index and/or discomfort score of greater than about 0.8 and administration of the sALP results in an average decrease in the CHAQ disability index score and/or discomfort score to about 0 to equal to or less than about 0.5 after a period of at least five years;
   d) performing a Pediatric Outcomes Data Collection Instrument (PODCI), wherein the child has an average PODCI transfer and mobility, sports and physical functioning, and/or pain score of less than about 40 and administration of the sALP results in an average increase in the PODCI score to about 40 to about 50 after a period of at least five years; and
   e) performing a Six Minute Walk Test (6MWT), wherein administration of the sALP for a treatment period of at least five years results in an average increase in a 6MWT distance of the child of about 20 m or greater or to greater than about 80% of a predicted 6MWT distance relative to the 6MWT distance of the child prior to administration of the sALP.

2. The method of claim 1, wherein at least one of:
   a) the average BOT-2 strength score of the child is determined relative to a BOT-2 strength score of a child without HPP;
   b) the average BOT-2 running speed and agility score of the child is determined relative to a BOT-2 running speed and agility score of a child without HPP;
   c) the average CHAQ disability index and/or discomfort score of the child is determined relative to a CHAQ index score of a child without HPP;
   d) the average PODCI transfer and mobility, sports and physical functioning, and/or pain score of the child is determined relative to a PODCI score of a child without HPP; and e) the 6MWT distance of the child is determined relative to the 6MWT distance of a healthy child or an untreated child having HPP.

3. The method of claim 2, wherein at least one of:
a) the child with an average BOT-2 strength score of less than about 10 exhibits physical impairments relative to the child without HPP;
b) the child with an average BOT-2 running speed and agility score of less than 5 exhibits physical impairments relative to the child without HPP;
c) the child with an average CHAQ disability index and/or discomfort score of greater than 0.5 exhibits disability in activities of daily living (ADL) and pain relative to the child without HPP; and
d) the child with an average PODCI transfer and mobility, sports and physical functioning, and pain score of less than 40 exhibits disability in ADL and pain relative to the child without HPP.

4. The method of claim 1, wherein at least one of:
a) the child exhibits a decrease in physical impairments after administration of the sALP, wherein the decrease in physical impairments is sustained throughout administration of the sALP to the child;
b) the average BOT-2 strength score of the child increases to about 12 to about 16; and
c) the average BOT-2 strength score of the child is determined from measurements selected from the group consisting of sit-ups, V-ups, standing long jump, wall sit, and push-ups.

5. The method of claim 1, wherein at least one of:
a) the child exhibits a decrease in physical impairments after administration of the sALP;
b) the decrease in physical impairments is sustained throughout administration of the sALP to the child;
c) the average BOT-2 running speed and agility score of the child increases to about 9 to about 13; and
d) the average BOT-2 running speed and agility score of the child is determined from measurements selected from the group consisting of stepping over a balance beam, shuttle run, two-legged side hop, and one-legged side hop.

6. The method of claim 1, wherein said method further comprises performing a Bayley Scales of Infant and Toddler Development, $3^{rd}$ Edition (BSID-III) test; and/or a Peabody Development Motor Scales, $2^{nd}$ Edition (PDMS-2) test.

7. The method of claim 1, wherein at least one of:
a) the child exhibits an increase in ADL after administration of the sALP, wherein the increase in ADL is sustained throughout administration of the sALP to the child;
b) the child exhibits a decrease in pain after administration of the sALP, wherein the decrease in pain is sustained throughout administration of the sALP to the child; and
c) the average CHAQ disability index score and/or CHAQ discomfort score of the child decreases to about 0 to equal to or less than about 0.25.

8. The method of claim 1, wherein at least one of:
a) the child exhibits an increase in ADL after administration of the sALP, wherein the increase in ADL is sustained throughout administration of the sALP to the child; and
b) the child exhibits a decrease in pain after administration of the sALP, wherein the decrease in pain is sustained throughout administration of the sALP to the child.

9. The method of claim 1, wherein at least one of:
a) the average increase in the 6MWT distance is about 25 meters or greater;
b) the average increase in the 6MWT value of the patient is sustained during a treatment period of at least five years;
c) the child exhibits an improvement in rickets as determined by the Rickets Severity Scale (RSS) after administration of the sALP; and
d) the child exhibits an increase in ADL after administration of the sALP, wherein the increase in ADL is determined by a at least one of CHAQ disability index score, PODCI global function scale score, PODCI transfer and mobility scale score, and PODCI sports and physical functioning scale score.

10. The method of claim 1, wherein the child of about 5 to about 12 years of age exhibited an average Bayley Scales of Infant and Toddler Development, $3^{rd}$ Edition (BSID-III) scaled score of less than about 2 at about 3 years of age or less than 3 years of age, wherein administration of the sALP results in an average increase in the BSID-III scaled score to greater than about 5 after a period of at least five years.

11. The method of claim 10, wherein at least one of:
a) the average BSID-III scaled score of the child is determined relative to an average BSID-III scaled score of a child without HPP, wherein the child with the average BSID-III scaled score of less than 2 exhibits delayed motor development relative to a child without HPP;
b) the child exhibits an increase in motor development after administration of the sALP, wherein the increase in motor development is sustained throughout administration of the sALP to the child and/or the average BSID-III scaled score increases to about 5, to about 6, or to about 7; and
c) the average BSID-III scaled score of the child is determined from measurements selected from the group consisting of prehension, perceptual-motor integration, motor planning and speed, visual tracking, reaching, object grasping, object manipulation, functional hand skills, responses to tactile information, movement of the limbs and torso, static positioning, dynamic movement, balance, and motor planning.

12. The method of claim 1, wherein the child of about 5 to about 12 years of age exhibited an average (PDMS-2) standard score of about 5 at about 5 years of age or less than 5 years of age, and wherein administration of the sALP results in an average increase in the PDMS-2 standard score to about 7 after a period of at least five years.

13. The method of claim 12, wherein at least one of:
a) the average PDMS-2 standard score of the child is determined relative to a PDMS-2 standard score of a child without HPP, wherein the child with the average PDMS-2 standard score of about 5 exhibits delayed motor development relative to the child without HPP;
b) the child exhibits an increase in motor development after administration of the sALP, wherein the increase in motor development is sustained throughout administration of the sALP to the child; and
c) the average PDMS-2 standard score of the child is determined from measurements selected from the group consisting of crawling, walking, running, hopping, jumping forward, reflexes, balance, object manipulation, grasping, and visual-motor integration.

14. The method of claim 1, wherein the sALP is at least one of:
   a) formulated for daily or weekly administration;
   b) formulated for administration twice a week, three times a week, four times a week, five times a week, six times a week, or seven times a week;
   c) formulated at a dosage of 2 mg/kg for administration three times a week;
   d) formulated at a dosage of 1 mg/kg for administration six times a week;
   e) formulated at a dosage of 3 mg/kg for administration two times a week;
   f) formulated at a dosage of 3 mg/kg for administration three times a week;
   g) administered for at least five years, at least six year, at least seven years, at least eight years, at least nine years, at least ten years, or more than ten years;
   h) comprises the amino acid sequence of SEQ ID NO: 1; and
   i) consists of the amino acid sequence of SEQ ID NO: 1.

15. The method of claim 1, wherein the method further comprises determining sALP activity of a child, wherein the determination of sALP activity comprises measuring at least one of phosphoethanolamine (PEA), inorganic pyrophosphate (PPi), and pyridoxal 5'-phosphate (PLP) in a serum and/or blood sample from the child.

16. The method of claim 1, wherein the sALP is administered in an amount that is therapeutically effective to treat at least one symptom of HPP, wherein the at least one symptom of HPP comprises at least one of rickets, premature loss of deciduous teeth, incomplete bone mineralization, elevated blood and/or urine levels of inorganic pyrophosphate ($PP_i$), elevated blood levels of phosphoethanolamine (PEA), elevated urine levels of PEA, elevated blood levels of pyridoxal 5'-phosphate (PLP), elevated urine levels of PLP, hypomineralization, rachitic ribs, hypercalciuria, short stature, skeletal deformity, waddling gait, bone pain, bone fracture, HPP-related seizure, inadequate weight gain, and calcium pyrophosphate dihydrate crystal deposition.

17. The method of claim 1, wherein the sALP is administered at an initial dosage of about 3 mg/kg/week and then increased to a dosage of about 6 mg/kg/week or at an initial dosage of about 6 mg/kg/week and then increased to a dosage of about 9 mg/kg/week or more.

18. The method of claim 1, wherein at least one of:
   a) symptoms of HPP are exhibited at birth;
   b) symptoms of HPP are not exhibited at birth;
   c) symptoms of HPP are exhibited at five years of age or older; and
   d) the child exhibits tolerability to administration of the sALP, wherein the tolerability comprises a lack or decreased incidence of adverse events selected from the group consisting of injection site erythema, decrease in hemoglobin, pyrexia, pneumonia, upper respiratory tract infection, craniosynostosis, otitis media, vomiting, constipation, diarrhea, tooth loss, nasopharyngitis, rash, dental caries, and irritability.

19. The method of claim 1, wherein at least one of:
   a) the child does not exhibit serum calcium and/or phosphorus levels below the age-adjusted normal range;
   b) the child does not exhibit symptoms of a treatable form of rickets; and
   c) the child has not previously received treatment with a bisphosphonate.

20. The method of claim 1, wherein the method further comprises performing radiographs of the child to determine an average Radiographic Global Impression of Change (RGI-C) score, wherein at least one of:
   a) the child exhibits an average RGI-C score of less than 2 prior to administration of the sALP;
   b) the average RGI-C score of the child is determined relative to an average RGI-C score of a child without HPP; and
   c) the child exhibits increased bone density after administration of the sALP, wherein the increase in bone density is sustained throughout administration of the sALP and/or the child exhibits an average RGI-C score of greater than 2.

21. The method of claim 1, wherein the method further comprises determining weight and/or length of the child, wherein a Z-score is determined from the weight and/or length of the child and wherein the child exhibits an improved Z-score for weight and/or length after administration of the sALP.

22. The method of claim 1, wherein the sALP is formulated in a pharmaceutical composition with at least one pharmaceutically acceptable carrier.

23. The method of claim 22, wherein the at least one pharmaceutically acceptable carrier is saline or comprises sodium chloride and sodium phosphate.

24. The method of claim 1, wherein at least one of:
   a) the sALP is physiologically active toward PEA, PPi, and PLP;
   b) the sALP is catalytically competent to improve skeletal mineralization in bone;
   c) the sALP is the soluble extracellular domain of an alkaline phosphatase; and
   d) the child has not previously been administered the sALP.

25. The method of claim 9, wherein the average increase in the 6MWT distance is about 30 meters, about 35 meters, about 40 meters, about 45 meters, about 50 meters, about 55 meters, about 60 meters, about 65 meters, about 70 meters, about 75 meters, about 80 meters, about 85 meters, about 90 meters, about 95 meters, or about 100 meters or greater.

26. The method of claim 22, wherein the pharmaceutical composition is formulated for subcutaneous administration.

27. The method of claim 23, wherein the pharmaceutically acceptable carrier comprises the sodium phosphate and about 150 mM of the sodium chloride.

\* \* \* \* \*

UNITED STATES PATENT AND TRADEMARK OFFICE
CERTIFICATE OF CORRECTION

PATENT NO. : 11,065,306 B2
APPLICATION NO. : 16/083186
DATED : July 20, 2021
INVENTOR(S) : Kenji Fujita et al.

Page 1 of 1

It is certified that error appears in the above-identified patent and that said Letters Patent is hereby corrected as shown below:

In the Claims

Column 116, Line 13, Claim 9, replace "by a at least" with --by at least--.

Signed and Sealed this
Second Day of November, 2021

Drew Hirshfeld
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 20

<210> SEQ ID NO 1
<211> LENGTH: 726
<212> TYPE: PRT
<213> ORGANISM: Artificial Sequence
<220> FEATURE:
<223> OTHER INFORMATION: Synthetic Construct

<400> SEQUENCE: 1

Leu Val Pro Glu Lys Glu Lys Asp Pro Lys Tyr Trp Arg Asp Gln Ala
1               5                   10                  15

Gln Glu Thr Leu Lys Tyr Ala Leu Glu Leu Gln Lys Leu Asn Thr Asn
            20                  25                  30
```

Val Ala Lys Asn Val Ile Met Phe Leu Gly Asp Gly Met Gly Val Ser
        35                  40                  45

Thr Val Thr Ala Ala Arg Ile Leu Lys Gly Gln Leu His His Asn Pro
 50                  55                  60

Gly Glu Glu Thr Arg Leu Glu Met Asp Lys Phe Pro Phe Val Ala Leu
 65                  70                  75                  80

Ser Lys Thr Tyr Asn Thr Asn Ala Gln Val Pro Asp Ser Ala Gly Thr
                 85                  90                  95

Ala Thr Ala Tyr Leu Cys Gly Val Lys Ala Asn Glu Gly Thr Val Gly
                100                 105                 110

Val Ser Ala Ala Thr Glu Arg Ser Arg Cys Asn Thr Thr Gln Gly Asn
                115                 120                 125

Glu Val Thr Ser Ile Leu Arg Trp Ala Lys Asp Ala Gly Lys Ser Val
                130                 135                 140

Gly Ile Val Thr Thr Thr Arg Val Asn His Ala Thr Pro Ser Ala Ala
145                 150                 155                 160

Tyr Ala His Ser Ala Asp Arg Asp Trp Tyr Ser Asp Asn Glu Met Pro
                165                 170                 175

Pro Glu Ala Leu Ser Gln Gly Cys Lys Asp Ile Ala Tyr Gln Leu Met
                180                 185                 190

His Asn Ile Arg Asp Ile Asp Val Ile Met Gly Gly Gly Arg Lys Tyr
                195                 200                 205

Met Tyr Pro Lys Asn Lys Thr Asp Val Glu Tyr Glu Ser Asp Glu Lys
                210                 215                 220

Ala Arg Gly Thr Arg Leu Asp Gly Leu Asp Leu Val Asp Thr Trp Lys
225                 230                 235                 240

Ser Phe Lys Pro Arg Tyr Lys His Ser His Phe Ile Trp Asn Arg Thr
                245                 250                 255

Glu Leu Leu Thr Leu Asp Pro His Asn Val Asp Tyr Leu Leu Gly Leu
                260                 265                 270

Phe Glu Pro Gly Asp Met Gln Tyr Glu Leu Asn Arg Asn Asn Val Thr
                275                 280                 285

Asp Pro Ser Leu Ser Glu Met Val Val Ala Ile Gln Ile Leu Arg
                290                 295                 300

Lys Asn Pro Lys Gly Phe Phe Leu Leu Val Glu Gly Gly Arg Ile Asp
305                 310                 315                 320

His Gly His His Glu Gly Lys Ala Lys Gln Ala Leu His Glu Ala Val
                325                 330                 335

Glu Met Asp Arg Ala Ile Gly Gln Ala Gly Ser Leu Thr Ser Ser Glu
                340                 345                 350

Asp Thr Leu Thr Val Val Thr Ala Asp His Ser His Val Phe Thr Phe
                355                 360                 365

Gly Gly Tyr Thr Pro Arg Gly Asn Ser Ile Phe Gly Leu Ala Pro Met
                370                 375                 380

Leu Ser Asp Thr Asp Lys Lys Pro Phe Thr Ala Ile Leu Tyr Gly Asn
385                 390                 395                 400

Gly Pro Gly Tyr Lys Val Val Gly Gly Glu Arg Glu Asn Val Ser Met
                405                 410                 415

Val Asp Tyr Ala His Asn Asn Tyr Gln Ala Gln Ser Ala Val Pro Leu
                420                 425                 430

Arg His Glu Thr His Gly Gly Glu Asp Val Ala Val Phe Ser Lys Gly
                435                 440                 445

```
Pro Met Ala His Leu Leu His Gly Val His Glu Gln Asn Tyr Val Pro
    450                 455                 460
His Val Met Ala Tyr Ala Ala Cys Ile Gly Ala Asn Leu Gly His Cys
465                 470                 475                 480
Ala Pro Ala Ser Ser Leu Lys Asp Lys Thr His Thr Cys Pro Pro Cys
                485                 490                 495
Pro Ala Pro Glu Leu Leu Gly Gly Pro Ser Val Phe Leu Phe Pro Pro
            500                 505                 510
Lys Pro Lys Asp Thr Leu Met Ile Ser Arg Thr Pro Glu Val Thr Cys
        515                 520                 525
Val Val Val Asp Val Ser His Glu Asp Pro Glu Val Lys Phe Asn Trp
530                 535                 540
Tyr Val Asp Gly Val Glu Val His Asn Ala Lys Thr Lys Pro Arg Glu
545                 550                 555                 560
Glu Gln Tyr Asn Ser Thr Tyr Arg Val Val Ser Val Leu Thr Val Leu
                565                 570                 575
His Gln Asp Trp Leu Asn Gly Lys Glu Tyr Lys Cys Lys Val Ser Asn
            580                 585                 590
Lys Ala Leu Pro Ala Pro Ile Glu Lys Thr Ile Ser Lys Ala Lys Gly
        595                 600                 605
Gln Pro Arg Glu Pro Gln Val Tyr Thr Leu Pro Pro Ser Arg Glu Glu
610                 615                 620
Met Thr Lys Asn Gln Val Ser Leu Thr Cys Leu Val Lys Gly Phe Tyr
625                 630                 635                 640
Pro Ser Asp Ile Ala Val Glu Trp Glu Ser Asn Gly Gln Pro Glu Asn
                645                 650                 655
Asn Tyr Lys Thr Thr Pro Pro Val Leu Asp Ser Asp Gly Ser Phe Phe
            660                 665                 670
Leu Tyr Ser Lys Leu Thr Val Asp Lys Ser Arg Trp Gln Gln Gly Asn
        675                 680                 685
Val Phe Ser Cys Ser Val Met His Glu Ala Leu His Asn His Tyr Thr
690                 695                 700
Gln Lys Ser Leu Ser Leu Ser Pro Gly Lys Asp Ile Asp Asp Asp Asp
705                 710                 715                 720
Asp Asp Asp Asp Asp Asp
                725

<210> SEQ ID NO 2
<211> LENGTH: 524
<212> TYPE: PRT
<213> ORGANISM: Homo sapiens

<400> SEQUENCE: 2

Met Ile Ser Pro Phe Leu Val Leu Ala Ile Gly Thr Cys Leu Thr Asn
1               5                   10                  15
Ser Leu Val Pro Glu Lys Glu Lys Asp Pro Lys Tyr Trp Arg Asp Gln
                20                  25                  30
Ala Gln Glu Thr Leu Lys Tyr Ala Leu Glu Leu Gln Lys Leu Asn Thr
            35                  40                  45
Asn Val Ala Lys Asn Val Ile Met Phe Leu Gly Asp Gly Met Gly Val
        50                  55                  60
Ser Thr Val Thr Ala Ala Arg Ile Leu Lys Gly Gln Leu His His Asn
65                  70                  75                  80
Pro Gly Glu Glu Thr Arg Leu Glu Met Asp Lys Phe Pro Phe Val Ala
                85                  90                  95
```

```
Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
    210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
            260                 265                 270

Thr Glu Leu Leu Thr Leu Asp Pro His Asn Val Asp Tyr Leu Leu Gly
        275                 280                 285

Leu Phe Glu Pro Gly Asp Met Gln Tyr Glu Leu Asn Arg Asn Asn Val
    290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Arg Ala Ile Gly Gln Ala Gly Ser Leu Thr Ser Ser
        355                 360                 365

Glu Asp Thr Leu Thr Val Val Thr Ala Asp His Ser His Val Phe Thr
    370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
            420                 425                 430

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Ser Lys
    450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Ala Gly Ser Leu Ala Ala Gly Pro Leu Leu
            500                 505                 510
```

Leu Ala Leu Ala Leu Tyr Pro Leu Ser Val Leu Phe
            515                 520

<210> SEQ ID NO 3
<211> LENGTH: 524
<212> TYPE: PRT
<213> ORGANISM: Homo sapiens

<400> SEQUENCE: 3

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
    210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg His Lys His Ser His Phe Ile Trp Asn Arg
            260                 265                 270

Thr Glu Leu Leu Thr Leu Asp Pro His Asn Val Asp Tyr Leu Leu Gly
        275                 280                 285

Leu Phe Glu Pro Gly Asp Met Gln Tyr Glu Leu Asn Arg Asn Asn Val
    290                 295                 300

Thr Asp Pro Ser Leu Ser Glu Met Val Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Arg Ala Ile Gly Gln Ala Gly Ser Leu Thr Ser Ser
        355                 360                 365

-continued

```
Glu Asp Thr Leu Thr Val Val Thr Ala Asp His Ser His Val Phe Thr
    370                 375                 380
Phe Gly Gly Tyr Thr Pro Arg Gly Asn Ser Ile Phe Gly Leu Ala Pro
385                 390                 395                 400
Met Leu Ser Asp Thr Asp Lys Lys Pro Phe Thr Ala Ile Leu Tyr Gly
                405                 410                 415
Asn Gly Pro Gly Tyr Lys Val Val Gly Gly Glu Arg Glu Asn Val Ser
                420                 425                 430
Met Val Asp Tyr Ala His Asn Asn Tyr Gln Ala Gln Ser Ala Val Pro
                435                 440                 445
Leu Arg His Glu Thr His Gly Gly Glu Asp Val Ala Val Phe Ser Lys
            450                 455                 460
Gly Pro Met Ala His Leu Leu His Gly Val His Glu Gln Asn Tyr Val
465                 470                 475                 480
Pro His Val Met Ala Tyr Ala Ala Cys Ile Gly Ala Asn Leu Gly His
                485                 490                 495
Cys Ala Pro Ala Ser Ser Ala Gly Ser Leu Ala Ala Gly Pro Leu Leu
                500                 505                 510
Leu Ala Leu Ala Leu Tyr Pro Leu Ser Val Leu Phe
            515                 520

<210> SEQ ID NO 4
<211> LENGTH: 524
<212> TYPE: PRT
<213> ORGANISM: Homo sapiens

<400> SEQUENCE: 4

Met Ile Ser Pro Phe Leu Val Leu Ala Ile Gly Thr Cys Leu Thr Asn
1               5                   10                  15
Ser Leu Val Pro Glu Lys Glu Lys Asp Pro Lys Tyr Trp Arg Asp Gln
                20                  25                  30
Ala Gln Glu Thr Leu Lys Tyr Ala Leu Glu Leu Gln Lys Leu Asn Thr
            35                  40                  45
Asn Val Ala Lys Asn Val Ile Met Phe Leu Gly Asp Gly Met Gly Val
        50                  55                  60
Ser Thr Val Thr Ala Ala Arg Ile Leu Lys Gly Gln Leu His His Asn
65                  70                  75                  80
Pro Gly Glu Glu Thr Arg Leu Glu Met Asp Lys Phe Pro Phe Val Ala
                85                  90                  95
Leu Ser Lys Thr Tyr Asn Thr Asn Ala Gln Val Pro Asp Ser Ala Gly
                100                 105                 110
Thr Ala Thr Ala Tyr Leu Cys Gly Val Lys Ala Asn Glu Gly Thr Val
            115                 120                 125
Gly Val Ser Ala Ala Thr Glu Arg Ser Arg Cys Asn Thr Thr Gln Gly
        130                 135                 140
Asn Glu Val Thr Ser Ile Leu Arg Trp Ala Lys Asp Ala Gly Lys Ser
145                 150                 155                 160
Val Gly Ile Val Thr Thr Thr Arg Val Asn His Ala Thr Pro Ser Ala
                165                 170                 175
Ala Tyr Ala His Ser Ala Asp Arg Asp Trp Tyr Ser Asp Asn Glu Met
                180                 185                 190
Pro Pro Glu Ala Leu Ser Gln Gly Cys Lys Asp Ile Ala Tyr Gln Leu
            195                 200                 205
Met His Asn Ile Arg Asp Ile Asp Val Ile Met Gly Gly Gly Arg Lys
```

```
            210                 215                 220
Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser Phe Ile Trp Asn Arg
                260                 265                 270

Thr Glu Leu Leu Thr Leu Asp Pro His Asn Val Asp Tyr Leu Leu Gly
                275                 280                 285

Leu Phe Glu Pro Gly Asp Met Gln Tyr Glu Leu Asn Arg Asn Asn Val
        290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
                340                 345                 350

Val Glu Met Asp Arg Ala Ile Gly Gln Ala Gly Ser Leu Thr Ser Ser
        355                 360                 365

Glu Asp Thr Leu Thr Val Val Thr Ala Asp His Ser His Val Phe Thr
370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
                420                 425                 430

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Ser Lys
        450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Ala Gly Ser Leu Ala Gly Pro Leu Leu
                500                 505                 510

Leu Ala Leu Ala Leu Tyr Pro Leu Ser Val Leu Phe
            515                 520

<210> SEQ ID NO 5
<211> LENGTH: 524
<212> TYPE: PRT
<213> ORGANISM: Homo sapiens

<400> SEQUENCE: 5

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
                20                  25                  30

Ala Gln Glu Thr Leu Lys Tyr Ala Leu Glu Leu Gln Lys Leu Asn Thr
            35                  40                  45

Asn Val Ala Lys Asn Val Ile Met Phe Leu Gly Asp Gly Met Gly Val
        50                  55                  60
```

```
Ser Thr Val Thr Ala Ala Arg Ile Leu Lys Gly Gln Leu His His Asn
 65                  70                  75                  80

Pro Gly Glu Glu Thr Arg Leu Glu Met Asp Lys Phe Pro Phe Val Ala
                 85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
    210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
            260                 265                 270

Thr Glu Leu Leu Thr Leu Asp Pro His Asn Val Asp Tyr Leu Leu Gly
        275                 280                 285

Leu Phe Glu Pro Gly Asp Met Gln Tyr Glu Leu Asn Arg Asn Asn Val
    290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Arg Ala Ile Gly Gln Ala Gly Ser Leu Thr Ser Ser
        355                 360                 365

Glu Asp Thr Leu Thr Val Val Thr Ala Asp His Ser His Val Phe Thr
    370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
            420                 425                 430

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Ser Lys
    450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
```

```
                    485                 490                 495
Cys Ala Pro Ala Ser Ser Ala Gly Ser Leu Ala Ala Gly Pro Leu Leu
                500                 505                 510
Leu Ala Leu Ala Leu Tyr Pro Leu Ser Val Leu Phe
                515                 520

<210> SEQ ID NO 6
<211> LENGTH: 524
<212> TYPE: PRT
<213> ORGANISM: Homo sapiens

<400> SEQUENCE: 6

Met Ile Ser Pro Phe Leu Val Leu Ala Ile Gly Thr Cys Leu Thr Asn
1               5                   10                  15
Ser Leu Val Pro Glu Lys Glu Lys Asp Pro Lys Tyr Trp Arg Asp Gln
                20                  25                  30
Ala Gln Glu Thr Leu Lys Tyr Ala Leu Glu Leu Gln Lys Leu Asn Thr
            35                  40                  45
Asn Val Ala Lys Asn Val Ile Met Phe Leu Gly Asp Gly Met Gly Val
        50                  55                  60
Ser Thr Val Thr Ala Ala Arg Ile Leu Lys Gly Gln Leu His His Asn
65                  70                  75                  80
Pro Gly Glu Glu Thr Arg Leu Glu Met Asp Lys Phe Pro Phe Val Ala
                85                  90                  95
Leu Ser Lys Thr Tyr Asn Thr Asn Ala Gln Val Pro Asp Ser Ala Gly
                100                 105                 110
Thr Ala Thr Ala Tyr Leu Cys Gly Val Lys Ala Asn Glu Gly Thr Val
            115                 120                 125
Gly Val Ser Ala Ala Thr Glu Arg Ser Arg Cys Asn Thr Thr Gln Gly
        130                 135                 140
Asn Glu Val Thr Ser Ile Leu Arg Trp Ala Lys Asp Ala Gly Lys Ser
145                 150                 155                 160
Val Gly Ile Val Thr Thr Thr Arg Val Asn His Ala Thr Pro Ser Ala
                165                 170                 175
Ala Tyr Ala His Ser Ala Asp Arg Asp Trp Tyr Ser Asp Asn Glu Met
                180                 185                 190
Pro Pro Glu Ala Leu Ser Gln Gly Cys Lys Asp Ile Ala Tyr Gln Leu
            195                 200                 205
Met His Asn Ile Arg Asp Ile Asp Val Ile Met Gly Gly Gly Arg Lys
        210                 215                 220
Tyr Met Tyr Pro Lys Asn Lys Thr Asp Val Glu Tyr Glu Ser Asp Glu
225                 230                 235                 240
Lys Ala Arg Gly Thr Arg Leu Asp Gly Leu Asp Leu Val Asp Thr Trp
                245                 250                 255
Lys Ser Phe Lys Pro Arg His Lys His Ser His Phe Ile Trp Asn Arg
                260                 265                 270
Thr Glu Leu Leu Thr Leu Asp Pro His Asn Val Asp Tyr Leu Leu Gly
            275                 280                 285
Leu Phe Glu Pro Gly Asp Met Gln Tyr Glu Leu Asn Arg Asn Asn Val
        290                 295                 300
Thr Asp Pro Ser Leu Ser Glu Met Val Val Ala Ile Gln Ile Leu
305                 310                 315                 320
Arg Lys Asn Pro Lys Gly Phe Phe Leu Leu Val Glu Gly Gly Arg Ile
                325                 330                 335
```

```
Asp His Gly His His Glu Gly Lys Ala Lys Gln Ala Leu His Glu Ala
            340                 345                 350

Val Glu Met Asp Arg Ala Ile Gly Gln Ala Gly Ser Leu Thr Ser Ser
        355                 360                 365

Glu Asp Thr Leu Thr Val Val Thr Ala Asp His Ser His Val Phe Thr
    370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
            405                 410                 415

Asn Gly Pro Gly Tyr Lys Val Val Gly Gly Glu Arg Glu Asn Val Ser
        420                 425                 430

Met Val Asp Tyr Ala His Asn Asn Tyr Gln Ala Gln Ser Ala Val Pro
    435                 440                 445

Leu Arg His Glu Thr His Gly Gly Glu Asp Val Ala Val Phe Ser Lys
450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
            485                 490                 495

Cys Ala Pro Ala Ser Ser Ala Gly Ser Leu Ala Ala Gly Pro Leu Leu
        500                 505                 510

Leu Ala Leu Ala Leu Tyr Pro Leu Ser Val Leu Phe
    515                 520

<210> SEQ ID NO 7
<211> LENGTH: 652
<212> TYPE: PRT
<213> ORGANISM: Macaca mulatta

<400> SEQUENCE: 7

Met Pro Thr Val Lys Thr Lys Gln Glu Ser His Ala Gly Ser Gly Ser
1               5                   10                  15

Gly Pro Arg Leu Ala Glu Arg Lys Gly Arg Val Gly Ala Ala Arg Arg
            20                  25                  30

Gln Ser Pro Arg Ala Pro Gly Gly Gly Leu Pro Gly Pro Arg Ser Gly
        35                  40                  45

Pro Ala Ala Ala Phe Ile Arg Arg Gly Arg Trp Pro Gly Pro Arg
    50                  55                  60

Cys Ala Pro Ala Thr Pro Arg Pro Arg Ser Arg Leu Cys Ala Pro Thr
65                  70                  75                  80

Arg Leu Cys Leu Asp Glu Pro Ser Ser Val Leu Cys Ala Gly Leu Glu
            85                  90                  95

His Gln Leu Thr Ser Asp His Cys Gln Pro Thr Pro Ser His Pro Arg
        100                 105                 110

Arg Ser His Leu Trp Ala Ser Gly Ile Lys Gln Val Leu Gly Cys Thr
    115                 120                 125

Met Ile Ser Pro Phe Leu Val Leu Ala Ile Gly Thr Cys Leu Thr Asn
130                 135                 140

Ser Leu Val Pro Glu Lys Glu Lys Asp Pro Lys Tyr Trp Arg Asp Gln
145                 150                 155                 160

Ala Gln Glu Thr Leu Lys Tyr Ala Leu Glu Leu Gln Lys Leu Asn Thr
            165                 170                 175

Asn Val Ala Lys Asn Val Ile Met Phe Leu Gly Asp Gly Met Gly Val
        180                 185                 190
```

```
Ser Thr Val Thr Ala Thr Arg Ile Leu Lys Gly Gln Leu His His Asn
        195                 200                 205

Pro Gly Glu Glu Thr Arg Leu Glu Met Asp Lys Phe Pro Phe Val Ala
    210                 215                 220

Leu Ser Lys Thr Tyr Asn Thr Asn Ala Gln Val Pro Asp Ser Ala Gly
225                 230                 235                 240

Thr Ala Thr Ala Tyr Leu Cys Gly Val Lys Ala Asn Glu Gly Thr Val
                245                 250                 255

Gly Val Ser Ala Ala Thr Glu Arg Ser Arg Cys Asn Thr Thr Gln Gly
                260                 265                 270

Asn Glu Val Thr Ser Ile Leu Arg Trp Ala Lys Asp Ala Gly Lys Ser
            275                 280                 285

Val Gly Ile Val Thr Thr Thr Arg Val Asn His Ala Thr Pro Ser Ala
        290                 295                 300

Ala Tyr Ala His Ser Ala Asp Arg Asp Trp Tyr Ser Asp Asn Glu Met
305                 310                 315                 320

Pro Pro Glu Ala Leu Ser Gln Gly Cys Lys Asp Ile Ala Tyr Gln Leu
                325                 330                 335

Val His Asn Ile Arg Asp Ile Asp Val Ile Met Gly Gly Gly Arg Lys
            340                 345                 350

Tyr Met Tyr Pro Lys Asn Lys Thr Asp Val Glu Tyr Glu Ile Asp Glu
        355                 360                 365

Lys Ala Arg Gly Thr Arg Leu Asp Gly Leu Asp Leu Val Asn Ile Trp
    370                 375                 380

Lys Ser Phe Lys Pro Arg His Lys His Ser His Phe Ile Trp Asn Arg
385                 390                 395                 400

Thr Glu Leu Leu Thr Leu Asp Pro His Asn Val Asp Tyr Leu Leu Gly
                405                 410                 415

Leu Phe Glu Pro Gly Asp Met Glu Tyr Glu Leu Asn Arg Asn Asn Val
            420                 425                 430

Thr Asp Pro Ser Leu Ser Glu Met Val Val Ala Ile Gln Ile Leu
        435                 440                 445

Arg Lys Asn Pro Lys Gly Phe Phe Leu Leu Val Glu Gly Gly Arg Ile
    450                 455                 460

Asp His Gly His His Glu Gly Lys Ala Lys Gln Ala Leu His Glu Ala
465                 470                 475                 480

Val Glu Met Asp Arg Ala Ile Gly Gln Ala Gly Ser Met Thr Ser Leu
                485                 490                 495

Glu Asp Thr Leu Thr Val Val Thr Ala Asp His Ser His Val Phe Thr
            500                 505                 510

Phe Gly Gly Tyr Thr Pro Arg Gly Asn Ser Ile Phe Gly Leu Ala Pro
        515                 520                 525

Met Leu Ser Asp Thr Asp Lys Lys Pro Phe Thr Ala Ile Leu Tyr Gly
    530                 535                 540

Asn Gly Pro Gly Tyr Lys Val Val Gly Gly Glu Arg Glu Asn Val Ser
545                 550                 555                 560

Met Val Asp Tyr Ala His Asn Asn Tyr Gln Ala Gln Ser Ala Val Pro
                565                 570                 575

Leu Arg His Glu Thr His Gly Gly Glu Asp Val Ala Val Phe Ser Lys
            580                 585                 590

Gly Pro Met Ala His Leu Leu His Gly Val His Glu Gln Asn Tyr Ile
        595                 600                 605
```

```
Pro His Val Met Ala Tyr Ala Ala Cys Ile Gly Ala Asn Leu Asp His
    610                 615                 620

Cys Ala Pro Ala Ser Ser Ala Gly Ser Leu Ala Ala Gly Pro Leu Leu
625                 630                 635                 640

Leu Pro Leu Ala Leu Phe Pro Leu Ser Ile Leu Phe
                645                 650

<210> SEQ ID NO 8
<211> LENGTH: 524
<212> TYPE: PRT
<213> ORGANISM: Rattus norvegicus

<400> SEQUENCE: 8

Met Ile Leu Pro Phe Leu Val Leu Ala Ile Gly Pro Cys Leu Thr Asn
1               5                   10                  15

Ser Phe Val Pro Glu Lys Glu Lys Asp Pro Ser Tyr Trp Arg Gln Gln
            20                  25                  30

Ala Gln Glu Thr Leu Lys Asn Ala Leu Lys Leu Gln Lys Leu Asn Thr
        35                  40                  45

Asn Val Ala Lys Asn Ile Ile Met Phe Leu Gly Asp Gly Met Gly Val
50                  55                  60

Ser Thr Val Thr Ala Ala Arg Ile Leu Lys Gly Gln Leu His His Asn
65                  70                  75                  80

Thr Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Thr Arg Cys Asn Thr Thr Gln Gly
130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Arg Pro Glu Ala Leu Ser Gln Gly Cys Lys Asp Ile Ala Tyr Gln Leu
        195                 200                 205

Met His Asn Ile Lys Asp Ile Asp Val Ile Met Gly Gly Gly Arg Lys
210                 215                 220

Tyr Met Tyr Pro Lys Asn Arg Thr Asp Val Glu Tyr Glu Leu Asp Glu
225                 230                 235                 240

Lys Ala Arg Gly Thr Arg Leu Asp Gly Leu Asp Leu Ile Ser Ile Trp
                245                 250                 255

Lys Ser Phe Lys Pro Arg His Lys His Ser His Tyr Val Trp Asn Arg
            260                 265                 270

Thr Glu Leu Leu Ala Leu Asp Pro Ser Arg Val Asp Tyr Leu Leu Gly
        275                 280                 285

Leu Phe Glu Pro Gly Asp Met Gln Tyr Glu Leu Asn Arg Asn Asn Leu
290                 295                 300

Thr Asp Pro Ser Leu Ser Glu Met Val Glu Val Ala Leu Arg Ile Leu
305                 310                 315                 320

Thr Lys Asn Pro Lys Gly Phe Phe Leu Leu Val Glu Gly Gly Arg Ile
                325                 330                 335
```

Asp His Gly His His Glu Gly Lys Ala Lys Gln Ala Leu His Glu Ala
            340                 345                 350

Val Glu Met Asp Glu Ala Ile Gly Lys Ala Gly Thr Met Thr Ser Gln
            355                 360                 365

Lys Asp Thr Leu Thr Val Val Thr Ala Asp His Ser His Val Phe Thr
        370                 375                 380

Phe Gly Gly Tyr Thr Pro Arg Gly Asn Ser Ile Phe Gly Leu Ala Pro
385                 390                 395                 400

Met Val Ser Asp Thr Asp Lys Lys Pro Phe Thr Ala Ile Leu Tyr Gly
            405                 410                 415

Asn Gly Pro Gly Tyr Lys Val Val Asp Gly Glu Arg Glu Asn Val Ser
            420                 425                 430

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Ala Lys
    450                 455                 460

Gly Pro Met Ala His Leu Leu His Gly Val His Glu Gln Asn Tyr Ile
465                 470                 475                 480

Pro His Val Met Ala Tyr Ala Ser Cys Ile Gly Ala Asn Leu Asp His
            485                 490                 495

Cys Ala Trp Ala Ser Ser Ala Ser Ser Pro Ser Pro Gly Ala Leu Leu
            500                 505                 510

Leu Pro Leu Ala Leu Phe Pro Leu Arg Thr Leu Phe
        515                 520

<210> SEQ ID NO 9
<211> LENGTH: 502
<212> TYPE: PRT
<213> ORGANISM: Canis lupus familiaris

<400> SEQUENCE: 9

Glu Lys Asp Pro Lys Tyr Trp Arg Asp Gln Ala Gln Gln Thr Leu Lys
1               5                   10                  15

Tyr Ala Leu Arg Leu Gln Asn Leu Asn Thr Asn Val Ala Lys Asn Val
            20                  25                  30

Ile Met Phe Leu Gly Asp Gly Met Gly Val Ser Thr Val Thr Ala Thr
        35                  40                  45

Arg Ile Leu Lys Gly Gln Leu His His Asn Pro Gly Glu Glu Thr Arg
    50                  55                  60

Leu Glu Met Asp Lys Phe Pro Tyr Val Ala Leu Ser Lys Thr Tyr Asn
65                  70                  75                  80

Thr Asn Ala Gln Val Pro Asp Ser Ala Gly Thr Ala Thr Ala Tyr Leu
            85                  90                  95

Cys Gly Val Lys Ala Asn Glu Gly Thr Val Gly Val Ser Ala Ala Thr
            100                 105                 110

Gln Arg Thr His Cys Asn Thr Thr Gln Gly Asn Glu Val Thr Ser Ile
        115                 120                 125

Leu Arg Trp Ala Lys Asp Ala Gly Lys Ser Val Gly Ile Val Thr Thr
    130                 135                 140

Thr Arg Val Asn His Ala Thr Pro Ser Ala Ala Tyr Ala His Ser Ala
145                 150                 155                 160

Asp Arg Asp Trp Tyr Ser Asp Asn Glu Met Pro Pro Glu Ala Leu Ser
                165                 170                 175

Gln Gly Cys Lys Asp Ile Ala Tyr Gln Leu Met His Asn Val Lys Asp

```
            180                 185                 190
Ile Glu Val Ile Met Gly Gly Arg Lys Tyr Met Phe Pro Lys Asn
            195                 200                 205

Arg Thr Asp Val Glu Tyr Glu Met Asp Glu Lys Ser Thr Gly Ala Arg
            210                 215                 220

Leu Asp Gly Leu Asn Leu Ile Asp Ile Trp Lys Asn Phe Lys Pro Arg
225                 230                 235                 240

His Lys His Ser His Tyr Val Trp Asn Arg Thr Glu Leu Leu Ala Leu
                    245                 250                 255

Asp Pro Tyr Thr Val Asp Tyr Leu Leu Gly Leu Phe Asp Pro Gly Asp
                260                 265                 270

Met Gln Tyr Glu Leu Asn Arg Asn Asn Val Thr Asp Pro Ser Leu Ser
            275                 280                 285

Glu Met Val Glu Ile Ala Ile Lys Ile Leu Ser Lys Lys Pro Arg Gly
            290                 295                 300

Phe Phe Leu Leu Val Glu Gly Gly Arg Ile Asp His Gly His His Glu
305                 310                 315                 320

Gly Lys Ala Lys Gln Ala Leu His Glu Ala Val Glu Met Asp Arg Ala
                    325                 330                 335

Ile Gly Lys Ala Gly Val Met Thr Ser Leu Glu Asp Thr Leu Thr Val
                340                 345                 350

Val Thr Ala Asp His Ser His Val Phe Thr Phe Gly Gly Tyr Thr Pro
            355                 360                 365

Arg Gly Asn Ser Ile Phe Gly Leu Ala Pro Met Val Ser Asp Thr Asp
            370                 375                 380

Lys Lys Pro Phe Thr Ala Ile Leu Tyr Gly Asn Gly Pro Gly Tyr Lys
385                 390                 395                 400

Val Val Gly Gly Glu Arg Glu Asn Val Ser Met Val Asp Tyr Ala His
                    405                 410                 415

Asn Asn Tyr Gln Ala Gln Ser Ala Val Pro Leu Arg His Glu Thr His
                420                 425                 430

Gly Gly Glu Asp Val Ala Val Phe Ala Lys Gly Pro Met Ala His Leu
            435                 440                 445

Leu His Gly Val His Glu Gln Asn Tyr Ile Pro His Val Met Ala Tyr
            450                 455                 460

Ala Ala Cys Ile Gly Ala Asn Gln Asp His Cys Ala Ser Ala Ser Ser
465                 470                 475                 480

Ala Gly Gly Pro Ser Pro Gly Pro Leu Leu Leu Leu Ala Leu Leu
                    485                 490                 495

Pro Val Gly Ile Leu Phe
            500

<210> SEQ ID NO 10
<211> LENGTH: 252
<212> TYPE: PRT
<213> ORGANISM: Sus scrofa

<400> SEQUENCE: 10

Ala Glu Leu Leu Ala Leu Asp Pro His Thr Val Asp Tyr Leu Leu Gly
1               5                   10                  15

Leu Phe Glu Pro Gly Asp Met Gln Tyr Glu Leu Asn Arg Asn Asn Val
            20                  25                  30

Thr Asp Pro Ser Leu Ser Glu Met Val Glu Met Ala Ile Arg Ile Leu
        35                  40                  45
```

```
Ile Lys Asn Pro Lys Gly Phe Phe Leu Leu Val Glu Gly Gly Arg Ile
 50                  55                  60

Asp His Gly His His Glu Gly Lys Ala Lys Gln Ala Leu His Glu Ala
 65                  70                  75                  80

Val Glu Met Asp Arg Ala Ile Glu Gln Ala Gly Ser Met Thr Ser Val
                 85                  90                  95

Glu Asp Thr Leu Thr Val Val Thr Ala Asp His Ser His Val Phe Thr
            100                 105                 110

Phe Gly Gly Tyr Thr Pro Arg Gly Asn Ser Ile Phe Gly Leu Ala Pro
            115                 120                 125

Met Val Ser Asp Thr Asp Lys Lys Pro Phe Thr Ala Ile Leu Tyr Gly
130                 135                 140

Asn Gly Pro Gly Tyr Lys Val Val Gly Gly Glu Arg Glu Asn Val Ser
145                 150                 155                 160

Met Val Asp Tyr Ala His Asp Asn Tyr Gln Ala Gln Ser Ala Val Pro
                165                 170                 175

Leu Arg His Glu Thr His Gly Gly Glu Asp Val Ala Ile Phe Ala Arg
            180                 185                 190

Gly Pro Met Ala His Leu Leu His Gly Val His Glu Gln Asn Tyr Ile
            195                 200                 205

Pro His Val Met Ala Tyr Ala Ala Cys Val Gly Ala Asn Arg Asp His
210                 215                 220

Cys Ala Ser Ala Ser Ser Gly Ser Pro Ser Pro Gly Pro Leu Leu
225                 230                 235                 240

Leu Leu Leu Ala Leu Leu Pro Leu Gly Ile Leu Phe
            245                 250
```

<210> SEQ ID NO 11
<211> LENGTH: 524
<212> TYPE: PRT
<213> ORGANISM: Mus musculus

<400> SEQUENCE: 11

```
Met Ile Ser Pro Phe Leu Val Leu Ala Ile Gly Thr Cys Leu Thr Asn
 1               5                  10                  15

Ser Phe Val Pro Glu Lys Glu Arg Asp Pro Ser Tyr Trp Arg Gln Gln
                20                  25                  30

Ala Gln Glu Thr Leu Lys Asn Ala Leu Lys Leu Gln Lys Leu Asn Thr
            35                  40                  45

Asn Val Ala Lys Asn Val Ile Met Phe Leu Gly Asp Gly Met Gly Val
 50                  55                  60

Ser Thr Val Thr Ala Ala Arg Ile Leu Lys Gly Gln Leu His His Asn
 65                  70                  75                  80

Thr Gly Glu Glu Thr Arg Leu Glu Met Asp Lys Phe Pro Phe Val Ala
                 85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
            115                 120                 125

Gly Val Ser Ala Ala Thr Glu Arg Thr Arg Cys Asn Thr Thr Gln Gly
130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175
```

```
Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Lys Asp Ile Asp Val Ile Met Gly Gly Gly Arg Lys
    210                 215                 220

Tyr Met Tyr Pro Lys Asn Arg Thr Asp Val Glu Tyr Glu Leu Asp Glu
225                 230                 235                 240

Lys Ala Arg Gly Thr Arg Leu Asp Gly Leu Asp Leu Ile Ser Ile Trp
                245                 250                 255

Lys Ser Phe Lys Pro Arg His Lys His Ser His Tyr Val Trp Asn Arg
            260                 265                 270

Thr Glu Leu Leu Ala Leu Asp Pro Ser Arg Val Asp Tyr Leu Leu Gly
        275                 280                 285

Leu Phe Glu Pro Gly Asp Met Gln Tyr Glu Leu Asn Arg Asn Asn Leu
    290                 295                 300

Thr Asp Pro Ser Leu Ser Glu Met Val Glu Val Ala Leu Arg Ile Leu
305                 310                 315                 320

Thr Lys Asn Leu Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Gln Ala Ile Gly Lys Ala Gly Ala Met Thr Ser Gln
        355                 360                 365

Lys Asp Thr Leu Thr Val Val Thr Ala Asp His Ser His Val Phe Thr
    370                 375                 380

Phe Gly Gly Tyr Thr Pro Arg Gly Asn Ser Ile Phe Gly Leu Ala Pro
385                 390                 395                 400

Met Val Ser Asp Thr Asp Lys Lys Pro Phe Thr Ala Ile Leu Tyr Gly
                405                 410                 415

Asn Gly Pro Gly Tyr Lys Val Val Asp Gly Glu Arg Glu Asn Val Ser
            420                 425                 430

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Ala Lys
    450                 455                 460

Gly Pro Met Ala His Leu Leu His Gly Val His Glu Gln Asn Tyr Ile
465                 470                 475                 480

Pro His Val Met Ala Tyr Ala Ser Cys Ile Gly Ala Asn Leu Asp His
                485                 490                 495

Cys Ala Trp Ala Gly Ser Gly Ser Ala Pro Ser Pro Gly Ala Leu Leu
            500                 505                 510

Leu Pro Leu Ala Val Leu Ser Leu Arg Thr Leu Phe
    515                 520

<210> SEQ ID NO 12
<211> LENGTH: 524
<212> TYPE: PRT
<213> ORGANISM: Bos taurus

<400> SEQUENCE: 12

Met Ile Ser Pro Phe Leu Leu Leu Ala Ile Gly Thr Cys Phe Ala Ser
1               5                   10                  15

Ser Leu Val Pro Glu Lys Glu Lys Asp Pro Lys Tyr Trp Arg Asp Gln
```

```
                 20                  25                  30
Ala Gln Gln Thr Leu Lys Asn Ala Leu Arg Leu Gln Thr Leu Asn Thr
             35                  40                  45
Asn Val Ala Lys Asn Val Ile Met Phe Leu Gly Asp Gly Met Gly Val
         50                  55                  60
Ser Thr Val Thr Ala Ala Arg Ile Leu Lys Gly Gln Leu His His Ser
 65                  70                  75                  80
Pro Gly Glu Glu Thr Lys Leu Glu Met Asp Lys Phe Pro Tyr Val Ala
                 85                  90                  95
Leu Ser Lys Thr Tyr Asn Thr Asn Ala Gln Val Pro Asp Ser Ala Gly
            100                 105                 110
Thr Ala Thr Ala Tyr Leu Cys Gly Val Lys Ala Asn Glu Gly Thr Val
            115                 120                 125
Gly Val Ser Ala Ala Thr Gln Arg Ser Gln Cys Asn Thr Thr Gln Gly
            130                 135                 140
Asn Glu Val Thr Ser Ile Leu Arg Trp Ala Lys Asp Ala Gly Lys Ser
145                 150                 155                 160
Val Gly Ile Val Thr Thr Thr Arg Val Asn His Ala Thr Pro Ser Ala
            165                 170                 175
Ser Tyr Ala His Ser Ala Asp Arg Asp Trp Tyr Ser Asp Asn Glu Met
            180                 185                 190
Pro Pro Glu Ala Leu Ser Gln Gly Cys Lys Asp Ile Ala Tyr Gln Leu
            195                 200                 205
Met His Asn Ile Lys Asp Ile Glu Val Ile Met Gly Gly Gly Arg Lys
            210                 215                 220
Tyr Met Phe Pro Lys Asn Arg Thr Asp Val Glu Tyr Glu Leu Asp Glu
225                 230                 235                 240
Lys Ala Arg Gly Thr Arg Leu Asp Gly Leu Asn Leu Ile Asp Ile Trp
            245                 250                 255
Lys Ser Phe Lys Pro Lys His Lys His Ser His Tyr Val Trp Asn Arg
            260                 265                 270
Thr Asp Leu Leu Ala Leu Asp Pro His Ser Val Asp Tyr Leu Leu Gly
            275                 280                 285
Leu Phe Glu Pro Gly Asp Met Gln Tyr Glu Leu Asn Arg Asn Asn Ala
            290                 295                 300
Thr Asp Pro Ser Leu Ser Glu Met Val Glu Met Ala Ile Arg Ile Leu
305                 310                 315                 320
Asn Lys Asn Pro Lys Gly Phe Phe Leu Leu Val Glu Gly Gly Arg Ile
            325                 330                 335
Asp His Gly His His Glu Gly Lys Ala Lys Gln Ala Leu His Glu Ala
            340                 345                 350
Val Glu Met Asp Gln Ala Ile Gly Gln Ala Gly Ala Met Thr Ser Val
            355                 360                 365
Glu Asp Thr Leu Thr Val Val Thr Ala Asp His Ser His Val Phe Thr
            370                 375                 380
Phe Gly Gly Tyr Thr Pro Arg Gly Asn Ser Ile Phe Gly Leu Ala Pro
385                 390                 395                 400
Met Val Ser Asp Thr Asp Lys Lys Pro Phe Thr Ala Ile Leu Tyr Gly
            405                 410                 415
Asn Gly Pro Gly Tyr Lys Val Val Gly Gly Glu Arg Glu Asn Val Ser
            420                 425                 430
Met Val Asp Tyr Ala His Asn Asn Tyr Gln Ala Gln Ser Ala Val Pro
            435                 440                 445
```

```
Leu Arg His Glu Thr His Gly Gly Glu Asp Val Ala Val Phe Ala Lys
    450                 455                 460

Gly Pro Met Ala His Leu His Gly Val His Glu Gln Asn Tyr Ile
465                 470                 475                 480

Pro His Val Met Ala Tyr Ala Ala Cys Ile Gly Ala Asn Arg Asp His
                    485                 490                 495

Cys Ala Ser Ala Ser Ser Gly Ser Pro Ser Pro Gly Pro Leu Leu
                500                 505                 510

Leu Leu Leu Ala Leu Leu Pro Leu Gly Ser Leu Phe
            515                 520

<210> SEQ ID NO 13
<211> LENGTH: 524
<212> TYPE: PRT
<213> ORGANISM: Bos taurus

<400> SEQUENCE: 13

Met Ile Ser Pro Phe Leu Leu Ala Ile Gly Thr Cys Phe Ala Ser
1               5                   10                  15

Ser Leu Val Pro Glu Lys Glu Lys Asp Pro Lys Tyr Trp Arg Asp Gln
                20                  25                  30

Ala Gln Gln Thr Leu Lys Asn Ala Leu Arg Leu Gln Thr Leu Asn Thr
            35                  40                  45

Asn Val Ala Lys Asn Val Ile Met Phe Leu Gly Asp Gly Met Gly Val
        50                  55                  60

Ser Thr Val Thr Ala Ala Arg Ile Leu Lys Gly Gln Leu His His Ser
65                  70                  75                  80

Pro Gly Glu Glu Thr Lys Leu Glu Met Asp Lys Phe Pro Tyr Val Ala
                85                  90                  95

Leu Ser Lys Thr Tyr Asn Thr Asn Ala Gln Val Pro Asp Ser Ala Gly
                100                 105                 110

Thr Ala Thr Ala Tyr Leu Cys Gly Val Lys Ala Asn Glu Gly Thr Val
            115                 120                 125

Gly Val Ser Ala Ala Thr Gln Arg Ser Gln Cys Asn Thr Thr Gln Gly
        130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ser Tyr Ala His Ser Ala Asp Arg Asp Trp Tyr Ser Asp Asn Glu Met
                180                 185                 190

Pro Pro Glu Ala Leu Ser Gln Gly Cys Lys Asp Ile Ala Tyr Gln Leu
            195                 200                 205

Met His Asn Ile Lys Asp Ile Glu Val Ile Met Gly Gly Gly Arg Lys
        210                 215                 220

Tyr Met Phe Pro Lys Asn Arg Thr Asp Val Glu Tyr Glu Leu Asp Glu
225                 230                 235                 240

Lys Ala Arg Gly Thr Arg Leu Asp Gly Leu Asn Leu Ile Asp Ile Trp
                245                 250                 255

Lys Ser Phe Lys Pro Lys His Lys His Ser His Tyr Val Trp Asn Arg
                260                 265                 270

Thr Asp Leu Leu Ala Leu Asp Pro His Ser Val Asp Tyr Leu Leu Gly
            275                 280                 285

Leu Phe Glu Pro Gly Asp Met Gln Tyr Glu Leu Asn Arg Asn Asn Ala
```

```
                    290                 295                 300
Thr Asp Pro Ser Leu Ser Glu Met Val Glu Met Ala Ile Arg Ile Leu
305                 310                 315                 320

Asn Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
                340                 345                 350

Val Glu Met Asp Gln Ala Ile Gly Gln Ala Gly Ala Met Thr Ser Val
                355                 360                 365

Glu Asp Thr Leu Thr Val Val Thr Ala Asp His Ser His Val Phe Thr
370                 375                 380

Phe Gly Gly Tyr Thr Pro Arg Gly Asn Ser Ile Phe Gly Leu Ala Pro
385                 390                 395                 400

Met Val Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
                420                 425                 430

Met Val Asp Tyr Ala His Asn Asn Tyr Gln Ala Gln Ser Ala Val Pro
                435                 440                 445

Leu Arg His Glu Thr His Gly Gly Glu Asp Val Ala Val Phe Ala Lys
                450                 455                 460

Gly Pro Met Ala His Leu Leu His Gly Val His Glu Gln Asn Tyr Ile
465                 470                 475                 480

Pro His Val Met Ala Tyr Ala Ala Cys Ile Gly Ala Asn Arg Asp His
                485                 490                 495

Cys Ala Ser Ala Ser Ser Ser Gly Ser Pro Ser Pro Gly Pro Leu Leu
                500                 505                 510

Leu Leu Leu Ala Leu Leu Pro Leu Gly Ser Leu Phe
                515                 520
```

<210> SEQ ID NO 14
<211> LENGTH: 124
<212> TYPE: PRT
<213> ORGANISM: Bos taurus

<400> SEQUENCE: 14

```
Asp Pro Lys Tyr Trp Arg Asp Gln Ala Gln Gln Thr Leu Lys Asn Ala
1               5                   10                  15

Leu Gly Leu Gln Lys Leu Asn Thr Lys Val Ala Lys Asn Val Ile Leu
                20                  25                  30

Phe Leu Gly Asp Gly Met Gly Val Ser Thr Val Thr Ala Ala Arg Ile
                35                  40                  45

Leu Lys Gly Gln Leu His His Asn Pro Gly Glu Glu Thr Arg Leu Glu
                50                  55                  60

Met Asp Lys Phe Pro Phe Val Ala Leu Ser Lys Thr Tyr Asn Thr Asn
65              70                  75                  80

Ala Gln Val Pro Asp Ser Ala Gly Thr Ala Pro His Pro Val Arg Val
                85                  90                  95

Lys Ala Met Arg Ala Pro Trp Gly Glu Pro His Gln Arg Gln Cys Asn
                100                 105                 110

Thr Arg Arg Ala Thr Ser Thr His Leu Leu Ala Gly
                115                 120
```

<210> SEQ ID NO 15
<211> LENGTH: 524

<212> TYPE: PRT
<213> ORGANISM: Felis catus

<400> SEQUENCE: 15

```
Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Gln Thr Leu Lys Asn Ala Leu Arg Leu Gln Lys Leu Asn Thr
        35                  40                  45

Asn Val Val Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Tyr Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Gln Arg Thr Gln Cys Asn Thr Thr Gln Gly
    130                 135                 140

Asn Glu Val Thr Ser Ile Leu Arg Trp Ala Lys Asp Ser Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Val Arg Asp Ile Glu Val Ile Met Gly Gly Gly Arg Lys
    210                 215                 220

Tyr Met Phe Pro Lys Asn Arg Thr Asp Val Glu Tyr Glu Met Asp Glu
225                 230                 235                 240

Lys Ala Arg Gly Thr Arg Leu Asp Gly Leu Asn Leu Val Asp Ile Trp
                245                 250                 255

Lys Ser Phe Lys Pro Arg His Lys His Ser His Tyr Val Trp Asn Arg
            260                 265                 270

Thr Glu Leu Leu Thr Leu Asp Pro Tyr Gly Val Asp Tyr Leu Leu Gly
        275                 280                 285

Leu Phe Glu Pro Gly Asp Met Gln Tyr Glu Leu Asn Arg Asn Ser Thr
    290                 295                 300

Thr Asp Pro Ser Leu Ser Glu Met Val Glu Ile Ala Ile Lys Ile Leu
305                 310                 315                 320

Ser Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Gln Ala Ile Gly Arg Ala Gly Ala Met Thr Ser Val
        355                 360                 365

Glu Asp Thr Leu Thr Ile Val Thr Ala Asp His Ser His Val Phe Thr
    370                 375                 380

Phe Gly Gly Tyr Thr Pro Arg Gly Asn Ser Ile Phe Gly Leu Ala Pro
385                 390                 395                 400
```

```
Met Val Ser Asp Thr Asp Lys Lys Pro Phe Thr Ser Ile Leu Tyr Gly
                405                 410                 415

Asn Gly Pro Gly Tyr Lys Val Val Gly Glu Arg Glu Asn Val Ser
            420                 425                 430

Met Val Asp Tyr Ala His Asn Asn Tyr Gln Ala Gln Ser Ala Val Pro
            435                 440                 445

Leu Arg His Glu Thr His Gly Gly Glu Asp Val Ala Val Phe Ala Lys
        450                 455                 460

Gly Pro Met Ala His Leu Leu His Gly Val His Glu Gln Asn Tyr Ile
465                 470                 475                 480

Pro His Val Met Ala Tyr Ala Ala Cys Ile Gly Ala Asn Leu Asp His
                485                 490                 495

Cys Ala Ser Ala Ser Ser Ala Gly Gly Pro Ser Pro Gly Pro Leu Phe
                500                 505                 510

Leu Leu Leu Ala Leu Pro Ser Leu Gly Ile Leu Phe
            515                 520

<210> SEQ ID NO 16
<211> LENGTH: 532
<212> TYPE: PRT
<213> ORGANISM: Homo sapiens

<400> SEQUENCE: 16

Met Gln Gly Pro Trp Val Leu Leu Leu Leu Gly Leu Arg Leu Gln Leu
1               5                   10                  15

Ser Leu Gly Ile Ile Pro Val Glu Glu Glu Asn Pro Asp Phe Trp Asn
            20                  25                  30

Arg Gln Ala Ala Glu Ala Leu Gly Ala Ala Lys Lys Leu Gln Pro Ala
        35                  40                  45

Gln Thr Ala Ala Lys Asn Leu Ile Ile Phe Leu Gly Asp Gly Met Gly
    50                  55                  60

Val Ser Thr Val Thr Ala Ala Arg Ile Leu Lys Gly Gln Lys Lys Asp
65                  70                  75                  80

Lys Leu Gly Pro Glu Thr Phe Leu Ala Met Asp Arg Phe Pro Tyr Val
                85                  90                  95

Ala Leu Ser Lys Thr Tyr Ser Val Asp Lys His Val Pro Asp Ser Gly
            100                 105                 110

Ala Thr Ala Thr Ala Tyr Leu Cys Gly Val Lys Gly Asn Phe Gln Thr
        115                 120                 125

Ile Gly Leu Ser Ala Ala Ala Arg Phe Asn Gln Cys Asn Thr Thr Arg
    130                 135                 140

Gly Asn Glu Val Ile Ser Val Met Asn Arg Ala Lys Lys Ala Gly Lys
145                 150                 155                 160

Ser Val Gly Val Val Thr Thr Thr Arg Val Gln His Ala Ser Pro Ala
                165                 170                 175

Gly Ala Tyr Ala His Thr Val Asn Arg Asn Trp Tyr Ser Asp Ala Asp
            180                 185                 190

Val Pro Ala Ser Ala Arg Gln Glu Gly Cys Gln Asp Ile Ala Thr Gln
        195                 200                 205

Leu Ile Ser Asn Met Asp Ile Asp Val Ile Leu Gly Gly Gly Arg Lys
    210                 215                 220

Tyr Met Phe Pro Met Gly Thr Pro Asp Pro Glu Tyr Pro Asp Asp Tyr
225                 230                 235                 240

Ser Gln Gly Gly Thr Arg Leu Asp Gly Lys Asn Leu Val Gln Glu Trp
```

245                 250                 255
Leu Ala Lys His Gln Gly Ala Arg Tyr Val Trp Asn Arg Thr Glu Leu
            260                 265                 270

Leu Gln Ala Ser Leu Asp Pro Ser Val Thr His Leu Met Gly Leu Phe
        275                 280                 285

Glu Pro Gly Asp Met Lys Tyr Glu Ile His Arg Asp Ser Thr Leu Asp
290                 295                 300

Pro Ser Leu Met Glu Met Thr Glu Ala Leu Leu Leu Leu Ser Arg
305                 310                 315                 320

Asn Pro Arg Gly Phe Phe Leu Phe Val Glu Gly Gly Arg Ile Asp His
                325                 330                 335

Gly His His Glu Ser Arg Ala Tyr Arg Ala Leu Thr Glu Thr Ile Met
            340                 345                 350

Phe Asp Asp Ala Ile Glu Arg Ala Gly Gln Leu Thr Ser Glu Glu Asp
        355                 360                 365

Thr Leu Ser Leu Val Thr Ala Asp His Ser His Val Phe Ser Phe Gly
370                 375                 380

Gly Tyr Pro Leu Arg Gly Ser Ser Ile Phe Gly Leu Ala Pro Gly Lys
385                 390                 395                 400

Ala Arg Asp Arg Lys Ala Tyr Thr Val Leu Leu Tyr Gly Asn Gly Pro
                405                 410                 415

Gly Tyr Val Leu Lys Asp Gly Ala Arg Pro Asp Val Thr Glu Ser Glu
            420                 425                 430

Ser Gly Ser Pro Glu Tyr Arg Gln Gln Ser Ala Val Pro Leu Asp Gly
        435                 440                 445

Glu Thr His Ala Gly Glu Asp Val Ala Val Phe Ala Arg Gly Pro Gln
450                 455                 460

Ala His Leu Val His Gly Val Gln Glu Gln Thr Phe Ile Ala His Val
465                 470                 475                 480

Met Ala Phe Ala Ala Cys Leu Glu Pro Tyr Thr Ala Cys Asp Leu Ala
                485                 490                 495

Pro Arg Ala Gly Thr Thr Asp Ala Ala His Pro Gly Pro Ser Val Val
            500                 505                 510

Pro Ala Leu Leu Pro Leu Leu Ala Gly Thr Leu Leu Leu Leu Gly Thr
        515                 520                 525

Ala Thr Ala Pro
        530

<210> SEQ ID NO 17
<211> LENGTH: 535
<212> TYPE: PRT
<213> ORGANISM: Homo sapiens

<400> SEQUENCE: 17

Met Leu Gly Pro Cys Met Leu Leu Leu Leu Leu Leu Leu Gly Leu Arg
1               5                   10                  15

Leu Gln Leu Ser Leu Gly Ile Ile Pro Val Glu Glu Asn Pro Asp
            20                  25                  30

Phe Trp Asn Arg Glu Ala Ala Glu Ala Leu Gly Ala Ala Lys Lys Leu
        35                  40                  45

Gln Pro Ala Gln Thr Ala Ala Lys Asn Leu Ile Ile Phe Leu Gly Asp
    50                  55                  60

Gly Met Gly Val Ser Thr Val Thr Ala Ala Arg Ile Leu Lys Gly Gln
65                  70                  75                  80

```
Lys Lys Asp Lys Leu Gly Pro Glu Ile Pro Leu Ala Met Asp Arg Phe
            85                  90                  95

Pro Tyr Val Ala Leu Ser Lys Thr Tyr Asn Val Asp Lys His Val Pro
            100                 105                 110

Asp Ser Gly Ala Thr Ala Thr Ala Tyr Leu Cys Gly Val Lys Gly Asn
            115                 120                 125

Phe Gln Thr Ile Gly Leu Ser Ala Ala Arg Phe Asn Gln Cys Asn
            130                 135             140

Thr Thr Arg Gly Asn Glu Val Ile Ser Val Met Asn Arg Ala Lys Lys
145             150                 155                 160

Ala Gly Lys Ser Val Gly Val Val Thr Thr Arg Val Gln His Ala
            165                 170                 175

Ser Pro Ala Gly Thr Tyr Ala His Thr Val Asn Arg Asn Trp Tyr Ser
            180                 185                 190

Asp Ala Asp Val Pro Ala Ser Ala Arg Gln Glu Gly Cys Gln Asp Ile
            195                 200                 205

Ala Thr Gln Leu Ile Ser Asn Met Asp Ile Asp Val Ile Leu Gly Gly
            210                 215                 220

Gly Arg Lys Tyr Met Phe Arg Met Gly Thr Pro Asp Pro Glu Tyr Pro
225             230                 235                 240

Asp Asp Tyr Ser Gln Gly Gly Thr Arg Leu Asp Gly Lys Asn Leu Val
            245                 250                 255

Gln Glu Trp Leu Ala Lys Arg Gln Gly Ala Arg Tyr Val Trp Asn Arg
            260                 265                 270

Thr Glu Leu Met Gln Ala Ser Leu Asp Pro Ser Val Thr His Leu Met
            275                 280                 285

Gly Leu Phe Glu Pro Gly Asp Met Lys Tyr Glu Ile His Arg Asp Ser
            290                 295                 300

Thr Leu Asp Pro Ser Leu Met Glu Met Thr Glu Ala Ala Leu Arg Leu
305             310                 315                 320

Leu Ser Arg Asn Pro Arg Gly Phe Phe Leu Phe Val Glu Gly Gly Arg
            325                 330                 335

Ile Asp His Gly His His Glu Ser Arg Ala Tyr Arg Ala Leu Thr Glu
            340                 345                 350

Thr Ile Met Phe Asp Asp Ala Ile Glu Arg Ala Gly Gln Leu Thr Ser
            355                 360                 365

Glu Glu Asp Thr Leu Ser Leu Val Thr Ala Asp His Ser His Val Phe
            370                 375                 380

Ser Phe Gly Gly Tyr Pro Leu Arg Gly Ser Ser Ile Phe Gly Leu Ala
385             390                 395                 400

Pro Gly Lys Ala Arg Asp Arg Lys Ala Tyr Thr Val Leu Leu Tyr Gly
            405                 410                 415

Asn Gly Pro Gly Tyr Val Leu Lys Asp Gly Ala Arg Pro Asp Val Thr
            420                 425                 430

Glu Ser Glu Ser Gly Ser Pro Glu Tyr Arg Gln Gln Ser Ala Val Pro
            435                 440                 445

Leu Asp Glu Glu Thr His Ala Gly Glu Asp Val Ala Val Phe Ala Arg
            450                 455                 460

Gly Pro Gln Ala His Leu Val His Gly Val Gln Glu Gln Thr Phe Ile
465             470                 475                 480

Ala His Val Met Ala Phe Ala Ala Cys Leu Glu Pro Tyr Thr Ala Cys
            485                 490                 495

Asp Leu Ala Pro Pro Ala Gly Thr Thr Asp Ala Ala His Pro Gly Arg
```

```
              500                 505                 510
Ser Val Val Pro Ala Leu Leu Pro Leu Leu Ala Gly Thr Leu Leu Leu
            515                 520                 525

Leu Glu Thr Ala Thr Ala Pro
        530                 535

<210> SEQ ID NO 18
<211> LENGTH: 532
<212> TYPE: PRT
<213> ORGANISM: Homo sapiens

<400> SEQUENCE: 18

Met Gln Gly Pro Trp Val Leu Leu Leu Leu Gly Leu Arg Leu Gln Leu
1               5                   10                  15

Ser Leu Gly Ile Ile Pro Val Glu Glu Glu Asn Pro Asp Phe Trp Asn
            20                  25                  30

Arg Gln Ala Ala Glu Ala Leu Gly Ala Ala Lys Lys Leu Gln Pro Ala
        35                  40                  45

Gln Thr Ala Ala Lys Asn Leu Ile Ile Phe Leu Gly Asp Gly Met Gly
    50                  55                  60

Val Ser Thr Val Thr Ala Ala Arg Ile Leu Lys Gly Gln Lys Lys Asp
65                  70                  75                  80

Lys Leu Gly Pro Glu Thr Phe Leu Ala Met Asp Arg Phe Pro Tyr Val
                85                  90                  95

Ala Leu Ser Lys Thr Tyr Ser Val Asp Lys His Val Pro Asp Ser Gly
            100                 105                 110

Ala Thr Ala Thr Ala Tyr Leu Cys Gly Val Lys Gly Asn Phe Gln Thr
        115                 120                 125

Ile Gly Leu Ser Ala Ala Ala Arg Phe Asn Gln Cys Asn Thr Thr Arg
    130                 135                 140

Gly Asn Glu Val Ile Ser Val Met Asn Arg Ala Lys Lys Ala Gly Lys
145                 150                 155                 160

Ser Val Gly Val Val Thr Thr Thr Arg Val Gln His Ala Ser Pro Ala
                165                 170                 175

Gly Ala Tyr Ala His Thr Val Asn Arg Asn Trp Tyr Ser Asp Ala Asp
            180                 185                 190

Val Pro Ala Ser Ala Arg Gln Glu Gly Cys Gln Asp Ile Ala Thr Gln
        195                 200                 205

Leu Ile Ser Asn Met Asp Ile Asp Val Ile Leu Gly Gly Gly Arg Lys
    210                 215                 220

Tyr Met Phe Pro Met Gly Thr Pro Asp Pro Glu Tyr Pro Asp Asp Tyr
225                 230                 235                 240

Ser Gln Gly Gly Thr Arg Leu Asp Gly Lys Asn Leu Val Gln Glu Trp
                245                 250                 255

Leu Ala Lys His Gln Gly Ala Arg Tyr Val Trp Asn Arg Thr Glu Leu
            260                 265                 270

Leu Gln Ala Ser Leu Asp Pro Ser Val Thr His Leu Met Gly Leu Phe
        275                 280                 285

Glu Pro Gly Asp Met Lys Tyr Glu Ile His Arg Asp Ser Thr Leu Asp
    290                 295                 300

Pro Ser Leu Met Glu Met Thr Glu Ala Ala Leu Leu Leu Leu Ser Arg
305                 310                 315                 320

Asn Pro Arg Gly Phe Phe Leu Phe Val Glu Gly Gly Arg Ile Asp His
                325                 330                 335
```

```
Gly His His Glu Ser Arg Ala Tyr Arg Ala Leu Thr Glu Thr Ile Met
            340                 345                 350

Phe Asp Asp Ala Ile Glu Arg Ala Gly Gln Leu Thr Ser Glu Glu Asp
        355                 360                 365

Thr Leu Ser Leu Val Thr Ala Asp His Ser His Val Phe Ser Phe Gly
    370                 375                 380

Gly Tyr Pro Leu Arg Gly Ser Ser Ile Phe Gly Leu Ala Pro Gly Lys
385                 390                 395                 400

Ala Arg Asp Arg Lys Ala Tyr Thr Val Leu Leu Tyr Gly Asn Gly Pro
                405                 410                 415

Gly Tyr Val Leu Lys Asp Gly Ala Arg Pro Asp Val Thr Glu Ser Glu
            420                 425                 430

Ser Gly Ser Pro Glu Tyr Arg Gln Gln Ser Ala Val Pro Leu Asp Gly
        435                 440                 445

Glu Thr His Ala Gly Glu Asp Val Ala Val Phe Ala Arg Gly Pro Gln
    450                 455                 460

Ala His Leu Val His Gly Val Gln Glu Gln Thr Phe Ile Ala His Val
465                 470                 475                 480

Met Ala Phe Ala Ala Cys Leu Glu Pro Tyr Thr Ala Cys Asp Leu Ala
                485                 490                 495

Pro Arg Ala Gly Thr Thr Asp Ala Ala His Pro Gly Pro Ser Val Val
            500                 505                 510

Pro Ala Leu Leu Pro Leu Leu Ala Gly Thr Leu Leu Leu Gly Thr
        515                 520                 525

Ala Thr Ala Pro
    530

<210> SEQ ID NO 19
<211> LENGTH: 528
<212> TYPE: PRT
<213> ORGANISM: Homo sapiens

<400> SEQUENCE: 19

Met Gln Gly Pro Trp Val Leu Leu Leu Gly Leu Arg Leu Gln Leu
1               5                   10                  15

Ser Leu Gly Val Ile Pro Ala Glu Glu Asn Pro Ala Phe Trp Asn
                20                  25                  30

Arg Gln Ala Ala Glu Ala Leu Asp Ala Ala Lys Lys Leu Gln Pro Ile
            35                  40                  45

Gln Lys Val Ala Lys Asn Leu Ile Leu Phe Leu Gly Asp Gly Leu Gly
        50                  55                  60

Val Pro Thr Val Thr Ala Thr Arg Ile Leu Lys Gly Gln Lys Asn Gly
65                  70                  75                  80

Lys Leu Gly Pro Glu Thr Pro Leu Ala Met Asp Arg Phe Pro Tyr Leu
                85                  90                  95

Ala Leu Ser Lys Thr Tyr Asn Val Asp Arg Gln Val Pro Asp Ser Ala
            100                 105                 110

Ala Thr Ala Thr Ala Tyr Leu Cys Gly Val Lys Ala Asn Phe Gln Thr
        115                 120                 125

Ile Gly Leu Ser Ala Ala Ala Arg Phe Asn Gln Cys Asn Thr Thr Arg
    130                 135                 140

Gly Asn Glu Val Ile Ser Val Met Asn Arg Ala Lys Gln Ala Gly Lys
145                 150                 155                 160

Ser Val Gly Val Val Thr Thr Thr Arg Val Gln His Ala Ser Pro Ala
                165                 170                 175
```

Gly Thr Tyr Ala His Thr Val Asn Arg Asn Trp Tyr Ser Asp Ala Asp
            180                 185                 190

Met Pro Ala Ser Ala Arg Gln Glu Gly Cys Gln Asp Ile Ala Thr Gln
            195                 200                 205

Leu Ile Ser Asn Met Asp Ile Asp Val Ile Leu Gly Gly Arg Lys
210                 215                 220

Tyr Met Phe Pro Met Gly Thr Pro Asp Pro Glu Tyr Pro Ala Asp Ala
225                 230                 235                 240

Ser Gln Asn Gly Ile Arg Leu Asp Gly Lys Asn Leu Val Gln Glu Trp
            245                 250                 255

Leu Ala Lys His Gln Gly Ala Trp Tyr Val Trp Asn Arg Thr Glu Leu
            260                 265                 270

Met Gln Ala Ser Leu Asp Gln Ser Val Thr His Leu Met Gly Leu Phe
            275                 280                 285

Glu Pro Gly Asp Thr Lys Tyr Glu Ile His Arg Asp Pro Thr Leu Asp
            290                 295                 300

Pro Ser Leu Met Glu Met Thr Glu Ala Ala Leu Arg Leu Leu Ser Arg
305                 310                 315                 320

Asn Pro Arg Gly Phe Tyr Leu Phe Val Glu Gly Gly Arg Ile Asp His
            325                 330                 335

Gly His His Glu Gly Val Ala Tyr Gln Ala Leu Thr Glu Ala Val Met
            340                 345                 350

Phe Asp Asp Ala Ile Glu Arg Ala Gly Gln Leu Thr Ser Glu Glu Asp
            355                 360                 365

Thr Leu Thr Leu Val Thr Ala Asp His Ser His Val Phe Ser Phe Gly
            370                 375                 380

Gly Tyr Thr Leu Arg Gly Ser Ser Ile Phe Gly Leu Ala Pro Ser Lys
385                 390                 395                 400

Ala Gln Asp Ser Lys Ala Tyr Thr Ser Ile Leu Tyr Gly Asn Gly Pro
            405                 410                 415

Gly Tyr Val Phe Asn Ser Gly Val Arg Pro Asp Val Asn Glu Ser Glu
            420                 425                 430

Ser Gly Ser Pro Asp Tyr Gln Gln Gln Ala Ala Val Pro Leu Ser Ser
            435                 440                 445

Glu Thr His Gly Gly Glu Asp Val Ala Val Phe Ala Arg Gly Pro Gln
            450                 455                 460

Ala His Leu Val His Gly Val Gln Glu Gln Ser Phe Val Ala His Val
465                 470                 475                 480

Met Ala Phe Ala Ala Cys Leu Glu Pro Tyr Thr Ala Cys Asp Leu Ala
            485                 490                 495

Pro Pro Ala Cys Thr Thr Asp Ala Ala His Pro Val Ala Ala Ser Leu
            500                 505                 510

Pro Leu Leu Ala Gly Thr Leu Leu Leu Gly Ala Ser Ala Ala Pro
            515                 520                 525

<210> SEQ ID NO 20
<211> LENGTH: 227
<212> TYPE: PRT
<213> ORGANISM: Artificial Sequence
<220> FEATURE:
<223> OTHER INFORMATION: Synthetic Construct

<400> SEQUENCE: 20

Asp Lys Thr His Thr Cys Pro Pro Cys Pro Ala Pro Glu Leu Leu Gly
1               5                   10                  15

-continued

```
Gly Pro Ser Val Phe Leu Phe Pro Pro Lys Pro Lys Asp Thr Leu Met
            20              25              30

Ile Ser Arg Thr Pro Glu Val Thr Cys Val Val Val Asp Val Ser His
        35              40              45

Glu Asp Pro Glu Val Lys Phe Asn Trp Tyr Val Asp Gly Val Glu Val
    50              55              60

His Asn Ala Lys Thr Lys Pro Arg Glu Glu Gln Tyr Asn Ser Thr Tyr
65              70              75              80

Arg Val Val Ser Val Leu Thr Val Leu His Gln Asp Trp Leu Asn Gly
            85              90              95

Lys Glu Tyr Lys Cys Lys Val Ser Asn Lys Ala Leu Pro Ala Pro Ile
            100             105             110

Glu Lys Thr Ile Ser Lys Ala Lys Gly Gln Pro Arg Glu Pro Gln Val
        115             120             125

Tyr Thr Leu Pro Pro Ser Arg Glu Glu Met Thr Lys Asn Gln Val Ser
    130             135             140

Leu Thr Cys Leu Val Lys Gly Phe Tyr Pro Ser Asp Ile Ala Val Glu
145             150             155             160

Trp Glu Ser Asn Gly Gln Pro Glu Asn Asn Tyr Lys Thr Thr Pro Pro
            165             170             175

Val Leu Asp Ser Asp Gly Ser Phe Phe Leu Tyr Ser Lys Leu Thr Val
            180             185             190

Asp Lys Ser Arg Trp Gln Gln Gly Asn Val Phe Ser Cys Ser Val Met
        195             200             205

His Glu Ala Leu His Asn His Tyr Thr Gln Lys Ser Leu Ser Leu Ser
    210             215             220

Pro Gly Lys
225
```